US012448415B2

(12) United States Patent
Diamond et al.

(10) Patent No.: US 12,448,415 B2
(45) **Date of Patent: *Oct. 21, 2025**

(54) COMPOSITIONS AND METHODS FOR INHIBITION OF ALPHAVIRUS INFECTION

(71) Applicant: Washington University, St. Louis, MO (US)

(72) Inventors: Michael Diamond, St. Louis, MO (US); Daved Fremont, St. Louis, MO (US); Rong Zhang, St. Louis, MO (US); Arthur Kim, St. Louis, MO (US); Larissa Thackray, St. Louis, MO (US); Katherine Basore, St. Louis, MO (US); Christopher A. Nelson, St. Louis, MO (US)

(73) Assignee: Washington University, St. Louis, MO (US)

( * ) Notice: Subject to any disclaimer, the term of this patent is extended or adjusted under 35 U.S.C. 154(b) by 437 days.

This patent is subject to a terminal disclaimer.

(21) Appl. No.: 16/959,867

(22) PCT Filed: Jan. 4, 2019

(86) PCT No.: PCT/US2019/012435

§ 371 (c)(1),
(2) Date: Jul. 2, 2020

(87) PCT Pub. No.: WO2019/136316

PCT Pub. Date: Jul. 11, 2019

(65) Prior Publication Data

US 2020/0407401 A1 Dec. 31, 2020

Related U.S. Application Data

(60) Provisional application No. 62/672,080, filed on May 16, 2018, provisional application No. 62/671,680, filed on May 15, 2018, provisional application No. 62/613,658, filed on Jan. 4, 2018.

(51) Int. Cl.

| | |
|---|---|
| ***C07K 14/005*** | (2006.01) |
| ***A61K 38/46*** | (2006.01) |
| ***A61K 45/06*** | (2006.01) |
| ***C07K 16/08*** | (2006.01) |
| ***C12N 15/113*** | (2010.01) |

(52) U.S. Cl.

CPC .......... *C07K 14/005* (2013.01); *A61K 38/465* (2013.01); *C07K 16/08* (2013.01); *C12N 15/113* (2013.01); *A61K 45/06* (2013.01); *C07K 2319/02* (2013.01); *C07K 2319/30* (2013.01); *C07K 2319/50* (2013.01); *C12N 2310/20* (2017.05); *C12Y 301/00* (2013.01)

(58) Field of Classification Search

CPC .......... C07K 2319/30; C07K 14/70503; C07K 14/70546; C07K 2319/02; C07K 2319/32; C07K 2319/00; C12N 2770/36122; C12N 15/1138

See application file for complete search history.

(56) References Cited

U.S. PATENT DOCUMENTS

| | | | |
|---|---|---|---|
| 2004/0102410 A1 | 5/2004 | Meruelo | |
| 2016/0303221 A1 | 10/2016 | Nabel et al. | |
| 2017/0095531 A1 | 4/2017 | Schreiber et al. | |

FOREIGN PATENT DOCUMENTS

| | | | |
|---|---|---|---|
| KR | 20090124439 A * | 12/2009 | ... G01N 2333/70546 |
| WO | WO-2008065543 A2 * | 6/2008 | ............ A61K 38/17 |
| WO | WO 2016/095046 | 6/2016 | |

OTHER PUBLICATIONS

Cunningham et al (The Journal of Biological Chemistry, 2002, vol. 277, pp. 27589-27592) (Year: 2002).*

Translation of KR20090124439A, EPO and Google, downloaded Sep. 24, 2024 (Year: 2024).*

Zhang et al., The Journal of Gene Medicine, 2005, vol. 7, pp. 354-365 (Year: 2005).*

Von Heijne (Nucleic Acids Research, 1986, vol. 14, pp. 4683-4690) (Year: 1986).*

Afonine, P.V., Grosse-Kunstleve, R.W., Echols, N., Headd, J.J., Moriarty, N.W., Mustyakimov, M., Terwilliger, T.C., Urzhumtsev, A., Zwart, P.H., and Adams, P.D. (2012). Towards automated crystallographic structure refinement with phenix.refine. Acta Crystallogr D Biol Crystallogr 68, 352-367.

Akahata, W. et al. A virus-like particle vaccine for epidemic Chikungunya virus protects nonhuman primates against infection. *Nat. Med.* 16, 334-338 (2010).

Ashbrook, A. W. et al. Residue 82 of the Chikungunya virus E2 attachment protein modulates viral dissemination and arthritis in mice. *J. Virol.* 88, 12180-12192 (2014).

Barton, E. S. et al. Junction adhesion molecule is a receptor for reovirus. *Cell* 104, 441-451 (2001).

Bramucci, E., Paiardini, A., Bossa, F., and Pascarella, S. (2012). PyMod: sequence similarity searches, multiple sequence-structure alignments, and homology modeling within PyMOL. BMC Bioinformatics 13 Suppl 4, S2.

Brien, J.D., Lazear, H.M., and Diamond, M.S. (2013). Propagation, quantification, detection, and storage of West Nile virus. Curr Protoc Microbiol 31, 15D 13 11-15D 13 18.

Carleton, M., Lee, H., Mulvey, M., and Brown, D.T. (1997). Role of glycoprotein PE2 in formation and maturation of the Sindbis virus spike. J Virol 71, 1558-1566.

Chang, L.J., Dowd, K.A., Mendoza, F.H., Saunders, J.G., Sitar, S. Plummer, S.H., Yamshchikov, G., Sarwar, U.N., Hu, Z., Enama, M.E., et al. (2014). Safety and tolerability of chikungunya virus-like particle vaccine in healthy adults: a phase 1 dose-escalation trial. Lancet 384, 2046-2052.

(Continued)

*Primary Examiner* — Karen A. Canella

(57) ABSTRACT

Among the various aspects of the present disclosure is the provision of compositions and methods of treating arthritogenic alphavirus infection and methods of screening.

20 Claims, 37 Drawing Sheets
(36 of 37 Drawing Sheet(s) Filed in Color)
Specification includes a Sequence Listing.

(56) References Cited

OTHER PUBLICATIONS

Cheng, R.H., Kuhn, R.J., Olson, N.H., Rossmann, M.G., Choi, H.K., Smith, T.J., and Baker, T.S. (1995). Nucleocapsid and glycoprotein organization in an enveloped virus. Cell 80, 621-630.
Cong, L. et al. Multiplex genome engineering using CRISPR/Cas systems. *Science* 339, 819-823 (2013).
Couderc, T. & Lecuit, M. Chikungunya virus pathogenesis: From bedside to bench. *Antiviral Res.* 121, 120-131 (2015).
DeTulleo, L., and Kirchhausen, T. (1998). The clathrin endocytic pathway in viral infection. Embo j 17, 4585-4593.
Doranz, B. J., Berson, J. F., Rucker, J. & Doms, R. W. Chemokine receptors as fusion cofactors for human immunodeficiency virus type 1 (HIV-1). *Immunol. Res.* 16, 15-28 (1997).
Emsley, P., Lohkamp, B., Scott, W.G., and Cowtan, K. (2010). Features and development of Coot. Acta Crystallogr D Biol Crystallogr 66, 486-501.
Esko, J. D., Stewart, T. E. & Taylor, W. H. Animal cell mutants defective in glycosaminoglycan biosynthesis. *Proc. Natl Acad. Sci. USA* 82, 3197-3201 (1985).
Fox, J. M. et al. Broadly neutralizing alphavirus antibodies bind an epitope on E2 and inhibit entry and egress. *Cell* 163, 1095-1107 (2015).
Gardner, C. L., Burke, C. W., Higgs, S. T., Klimstra, W. B. & Ryman, K. D. Interferon-alpha/beta deficiency greatly exacerbates arthritogenic disease in mice infected with wild-type chikungunya virus but not with the cell culture-adapted live-attenuated 181/25 vaccine candidate. *Virology* 425, 103-112 (2012).
Grant, T., Rohou, A., and Grigorieff, N. (2018). cisTEM, user-friendly software for single-particle image processing. Elife 7, 52 pages.
Han, S. W. et al. DICAM inhibits angiogenesis via suppression of AKT and p38 MAP kinase signalling. *Cardiovasc. Res.* 98, 73-82 (2013).
Hawman, D. W et al. Chronic joint disease caused by persistent chikungunya virus infection is controlled by the adaptive immune response. *J. Virol.* 87, 13878-13888 (2013).
Heidner, H.W., Knott, T.A., and Johnston, R.E. (1996). Differential processing of sindbis virus glycoprotein PE2 in cultured vertebrate and arthropod cells. J Virol 70, 2069-2073.
Hoornweg, T.E., van Duijl-Richter, M.K.S., Ayala Nunez, N.V., Albulescu, I.C., van Hemert, M.J., and Smit, J.M. (2016). Dynamics of Chikungunya Virus Cell Entry Unraveled by Single-Virus Tracking in Living Cells. J Virol 90, 4745-4756.
Huang, I. C. et al. SARS coronavirus, but not human coronavirus NL63, utilizes cathepsin L to infect ACE2-expressing cells. *J. Biol. Chem.* 281, 3198-3203 (2006).
International Search Report and Written Opinion dated May 1, 2019 in corresponding International Application No. PCT/US19/12435 filed Jan. 4, 2019, 11 pages.
Jemielity, S et al. TIM-family proteins promote infection of multiple enveloped viruses through virion-associated phosphatidylserine. *PLoS Pathog.* 9, e1003232 (2013).
Jin, J. et al. Neutralizing monoclonal antibodies block chikungunya virus entry and release by targeting an epitope critical to viral pathogenesis. *Cell Reports* 13, 2553-2564 (2015).
Jinek, M. et al. RNA-programmed genome editing in human cells. *eLife* 2, e00471 (2013).
Joung, J. et al. Genome-scale CRISPR-Cas9 knockout and transcriptional activation screening. *Nat. Protocols* 12, 828-863 (2017).
Jung, Y. K. et al. DICAM inhibits osteoclast differentiation through attenuation of the integrin αVβ3 pathway. *J. Bone Miner. Res.* 27, 2024-2034 (2012).
Jung, Y. K. et al. DICAM, a novel dual immunoglobulin domain containing cell adhesion molecule interacts with αvβ3 integrin. *J. Cell. Physiol.* 216, 603-614 (2008).
Klimstra, W. B., Ryman, K. D. & Johnston, R. E. Adaptation of Sindbis virus to BHK cells selects for use of heparan sulfate as an attachment receptor. *J. Virol.* 72, 7357-7366 (1998).
Kostyuchenko, V.A., Jakana, J., Liu, X., Haddow, A.D., Aung, M., Weaver, S.C., Chiu, W., and Lok, S.M. (2011). The structure of barmah forest virus as revealed by cryo-electron microscopy at a 6-angstrom resolution has detailed transmembrane protein architecture and interactions. J Virol 85, 9327-9333.
Lee, J. et al. Structure of the Ebola virus envelope protein MPER/TM domain and its interaction with the fusion loop explains their fusion activity. *Proc. Natl Acad. Sci. USA* 114, E7987-E7996 (2017).
Lee, R.C., Hapuarachchi, H.C., Chen, K.C., Hussain, K.M., Chen, H., Low, S.L., Ng, L.C., Lin, R., Ng, M.M., and Chu, J.J. (2013). Mosquito cellular factors and functions in mediating the infectious entry of chikungunya virus. PLoS neglected tropical diseases 7, e2050.
Lee, S., Kuhn, R.J., and Rossmann, M.G. (1998). Probing the potential glycoprotein binding site of sindbis virus capsid protein with dioxane and model building. Proteins 33, 311-317.
Lescar, J., Roussel, A., Wien, M.W., Navaza, J., Fuller, S.D., Wengler, G., and Rey, F.A. (2001). The Fusion glycoprotein shell of Semliki Forest virus: an icosahedral assembly primed for fusogenic activation at endosomal pH. Cell 105, 137-148.
Levitt, N. H. et al. Development of an attenuated strain of chikungunya virus for use in vaccine production. *Vaccine* 4, 157-162 (1986).
Li, L., Jose, J., Xiang, Y., Kuhn, R.J., and Rossmann, M.G. (2010). Structural changes of envelope proteins during alphavirus fusion. Nature 468, 705-708.
Li, W. et al. MAGeCK enables robust identification of essential genes from genome-scale CRISPR/Cas9 knockout screens. *Genome Biol.* 15, 554 (2014).
Loh, J. et al. Identification and sequencing of a novel rodent gammaherpesvirus that establishes acute and latent infection in laboratory mice. *J. Virol.* 85, 2642-2656 (2011).
Long, F., Fong, R.H., Austin, S.K., Chen, Z., Klose, T., Fokine, A., Liu, Y., Porta, J., Sapparapu, G., Akahata, W., et al. (2015). Cryo-EM structures elucidate neutralizing mechanisms of anti-chikungunya human monoclonal antibodies with therapeutic activity. Proc Natl Acad Sci U S A 112, 13898-13903.
Lubman, O. Y. et al. Rodent herpesvirus Peru encodes a secreted chemokine decoy receptor. *J. Virol.* 88, 538-546 (2014).
Martiny et al. (2013) In SIlico Mechanistic Profiling to Probe Small Molecule Binding to Sulfotransferases. PLOSOne. vol. 8, Issue 9, e73587.
ModBase : Database of comparative protein structure Models (created Dec. 6, 2016) downloaded from the internet Apr. 14, 2019 from https://modbase.compbio.ucsf.edu/modbase-cgi/model_details.cgi?queryfile=1555360562_4966&searchmode=default&displaymode=moddetail&referer=yes&snpfiag=& (3 pages).
Mukherjee, S., Sirohi, D., Dowd, K.A., Chen, Z., Diamond, M.S., Kuhn, R.J., and Pierson, T.C. (2016). Enhancing dengue virus maturation using a stable furin over-expressing cell line. Virology 497, 33-40.
Mulvey, M., and Brown, D.T. (1995). Involvement of the molecular chaperone BiP in maturation of Sindbis virus envelope glycoproteins. J Virol 69, 1621-1627.
Oliphant, T et al. Development of a humanized monoclonal antibody with therapeutic potential against West Nile virus. *Nat. Med.* 11, 522-530 (2005).
Ooi, Y.S., Stiles, K.M., Liu, C.Y., Taylor, G.M., and Kielian, M. (2013). Genome-wide RNAi screen identifies novel host proteins required for alphavirus entry. PLoS Pathog 9, e1003835.
Pal, P. et al. Development of a highly protective combination monoclonal antibody therapy against Chikungunya virus. PLoS Pathog. 9, e1003312 (2013).
Papadopoulos, J.S., and Agarwala, R. (2007). COBALT: constraint-based alignment tool for multiple protein sequences. Bioinformatics 23, 1073-1079.
Paredes, A.M., Brown, D.T., Rothnagel, R., Chiu, W., Schoepp, R.J., Johnston, R.E., and Prasad, B.V. (1993). Three-dimensional structure of a membrane-containing virus. Proc Natl Acad Sci U S A 90, 9095-9099.
Pletnev, S.V., Zhang, W., Mukhopadhyay, S., Fisher, B.R., Hernandez, R., Brown, D.T., Baker, T.S., Rossmann, M.G., and Kuhn, R.J. (2001). Locations of carbohydrate sites on alphavirus glycoproteins show that E1 forms an icosahedral scaffold. Cell 105, 127-136.

(56) References Cited

OTHER PUBLICATIONS

Pokidysheva, E., Zhang, Y., Battisti, A.J., Bator-Kelly, C.M., Chipman, P.R., Xiao, C., Gregorio, G.G., Hendrickson, W.A., Kuhn, R.J., and Rossmann, M.G. (2006). Cryo-EM reconstruction of dengue virus in complex with the carbohydrate recognition domain of DC-SIGN. Cell 124, 485-493.

Powers, A.M., Brault, A.C., Shirako, Y., Strauss, E.G., Kang, W., Strauss, J.H., and Weaver, S.C. (2001). Evolutionary relationships and systematics of the alphaviruses. J Virol 75, 10118-10131.

Robert, X., and Gouet, P. (2014). Deciphering key features in protein structures with the new ENDscript server. Nucleic Acids Res 42, W320-324.

Rohou, A., and Grigorieff, N. (2015). CTFFIND4: Fast and accurate defocus estimation from electron micrographs. J Struct Biol 192, 216-221.

Rose, P. P. et al. Natural resistance-associated macrophage protein is a cellular receptor for sindbis virus in both insect and mammalian hosts. *Cell Host Microbe* 10, 97-104 (2011).

Roussel, A., Lescar, J., Vaney, M.C., Wengler, G., Wengler, G., and Rey, F.A. (2006). Structure and interactions at the viral surface of the envelope protein E1 of Semliki Forest virus. Structure 14, 75-86.

Sanjana, N. E., Shalem, O. & Zhang, F. Improved vectors and genome-wide libraries for CRISPR screening. *Nat Methods* 11, 783-784 (2014).

Selvarajah, S. et al. A neutralizing monoclonal antibody targeting the acid-sensitive region in chikungunya virus E2 protects from disease. *PLoS Negl. Trop. Dis.* 7, e2423 (2013).

Shalem, O. et al. Genome-scale CRISPR-Cas9 knockout screening in human cells. *Science* 343, 84-87 (2014).

Smith, S. A. et al. Isolation and characterization of broad and ultrapotent human monoclonal antibodies with therapeutic activity against Chikungunya virus. *Cell Host Microbe* 18, 86-95 (2015).

Smith, T.J., Cheng, R.H., Olson, N.H., Peterson, P., Chase, E., Kuhn, R.J., and Baker, T.S. (1995). Putative receptor binding sites on alphaviruses as visualized by cryoelectron microscopy. Proc Natl Acad Sci U S A 92, 10648-10652.

Strauss, J.H., Wang, K.S., Schmaljohn, A.L., Kuhn, R.J., and Strauss, E.G. (1994). Host-cell receptors for Sindbis virus. Arch Virol Suppl 9, 473-484.

Sun, S. et al. Structural analyses at pseudo atomic resolution of Chikungunya virus and antibodies show mechanisms of neutralization. *eLife* 2, e00435 (2013).

Taube, S. et al. High-resolution x-ray structure and functional analysis of the murine norovirus 1 capsid protein protruding domain. *J. Virol.* 84, 5695-5705 (2010).

Tucker, P.C., and Griffin, D.E. (1991). Mechanism of altered Sindbis virus neurovirulence associated with a single-amino-acid change in the E2 Glycoprotein. *J Virol* 65, 1551-1557.

Uchime, O., Fields, W., and Kielian, M. (2013). The role of E3 in pH protection during alphavirus assembly and exit. J Virol 87, 10255-10262.

Vancini, R., Hernandez, R. & Brown, D. Alphavirus entry into host cells. *Prog. Mol. Biol. Transl. Sci.* 129, 33-62 (2015).

Voss, J. E. et al. Glycoprotein organization of Chikungunya virus particles revealed by X-ray crystallography. *Nature* 468, 709-712 (2010).

Weaver, S. C., Charlier, C., Vasilakis, N. & Lecuit, M. Zika, Chikungunya, and other emerging vector-borne viral diseases. *Annu. Rev. Med.* 69, 395-408 (2018).

Yap, M.L., Klose, T., Urakami, A., Hasan, S.S., Akahata, W., and Rossmann, M.G. (2017). Structural studies of Chikungunya virus maturation. Proc Natl Acad Sci U S A 114, 13703-13707.

Yonezawa, T. et al. Limitrin, a novel immunoglobulin superfamily protein localized to glia limitans formed by astrocyte endfeet. *Glia* 44, 190-204 (2003).

Zhang, R., Hryc, C.F., Cong, Y., Liu, X., Jakana, J., Gorchakov, R., Baker, M.L., Weaver, S.C., and Chiu, W. (2011). 4.4 A cryo-EM structure of an enveloped alphavirus Venezuelan equine encephalitis virus. Embo J 30, 3854-3863.

Zhang, R., Kim, A.S., Fox, J.M., Nair, S., Basore, K., Klimstra, W.B., Rimkunas, R., Fong, R.H., Lin, H., Poddar, S., et al. (2018). Mxra8 is a receptor for multiple arthritogenic alphaviruses. Nature 557, 570-574.

Zhang, W., Heil, M., Kuhn, R.J., and Baker, T.S. (2005). Heparin binding sites on Ross River virus revealed by electron cryo-microscopy. Virology 332, 511-518.

Zhang, W., Mukhopadhyay, S., Pletnev, S.V., Baker, T.S., Kuhn, R.J., and Rossmann, M.G. (2002). Placement of the structural proteins in Sindbis virus. J Virol 76, 11645-11658.

Zheng, S.Q., Palovcak, E., Armache, J.P., Verba, K.A., Cheng, Y., and Agard, D.A. (2017). MotionCor2: anisotropic correction of beam-induced motion for improved cryo-electron microscopy. Nat Methods 14, 331-332.

Ziemiecki, A., and Garoff, H. (1978). Subunit composition of the membrane glycoprotein complex of Semliki Forest virus. J Mol Biol 122, 259-269.

Zivanov, J., Nakane, T., Forsberg, B.O., Kimanius, D., Hagen, W.J., Lindahl, E., and Scheres, S.H. (2018). New tools for automated high-resolution cryo-EM structure determination in RELION-3. Elife 7.

* cited by examiner

FIG. 6

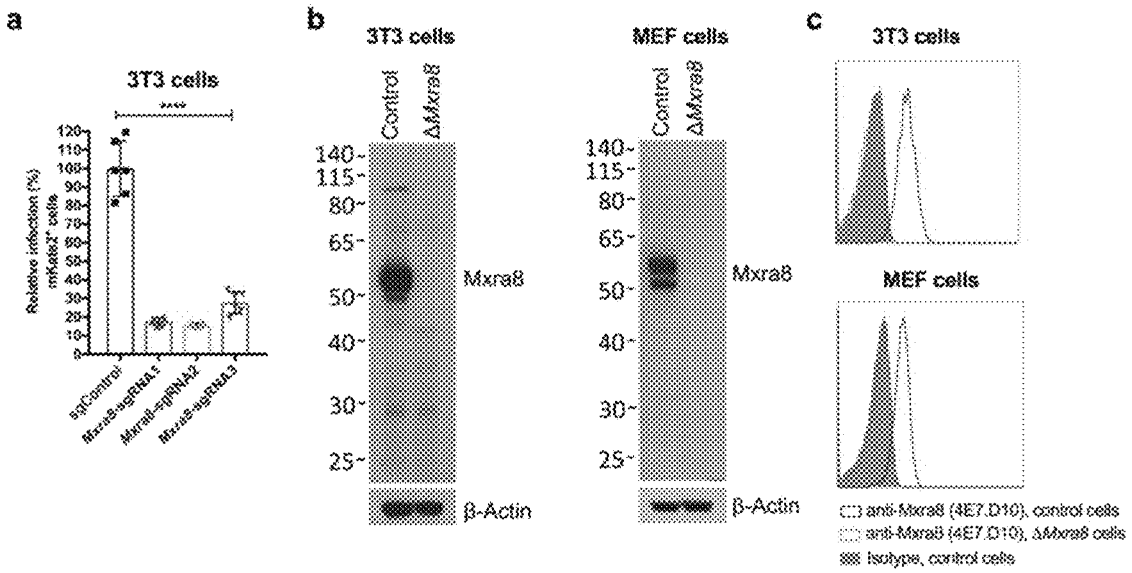

**3T3 Δ*Mxra8* cells:**

GCCAACGGCGCCGACTTGTGGATATGTATTCGGCGGGTGAACAGCGCGTGTACGAGCCGCGCGA wild-type allele
GCCAACGGCGCCGACTTGTGGATATGT-----------GAACAGCGCGTGTACGAGCCGCGCGA mutant allele (11 bp deletion)
GCCAACGGCGCCGACTTGTGGATATGTAT--GGCGGGTGAACAGCGCGTGTACGAGCCGCGCGA mutant allele (2 bp deletion)

wild-type allele (SEQ ID NO: 55); mutant allele 11 bp deletion (SEQ ID NO: 56); mutant allele 2 bp deletion (SEQ ID NO: 57)

**MEF Δ*Mxra8* cells:**

GCCAACGGCGCCGACTTGTGGATATGTATTC-GGCGGGTGAACAGCGCGTGTACGAGCCGCGCGA wild-type allele
GCCAACGGCGCCGACTTGTGGATATGTAT---GGCGGGTGAACAGCGCGTGTACGAGCCGCGCGA mutant allele (2 bp deletion)
GCCAACGGCGCCGACTTGTGGATATGT-----GGCGGGTGAACAGCGCGTGTACGAGCCGCGCGA mutant allele (4 bp deletion)
GCCAACGGCGCCGACTTGTGGATATGTATTCTGGCGGGTGAACAGCGCGTGTACGAGCCGCGCGA mutant allele (1 bp insertion)

wild-type allele (SEQ ID NO: 58); mutant allele 2 bp deletion (SEQ ID NO: 59); mutant allele 4 bp deletion (SEQ ID NO: 60); mutant allele 1 bp deletion (SEQ ID NO: 61)

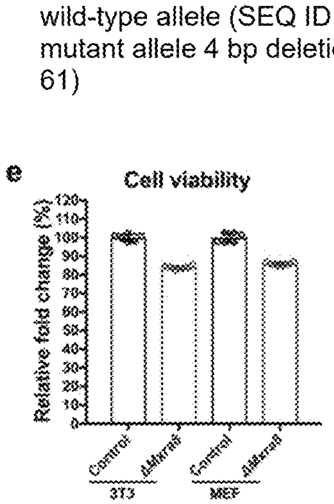

FIG. 16

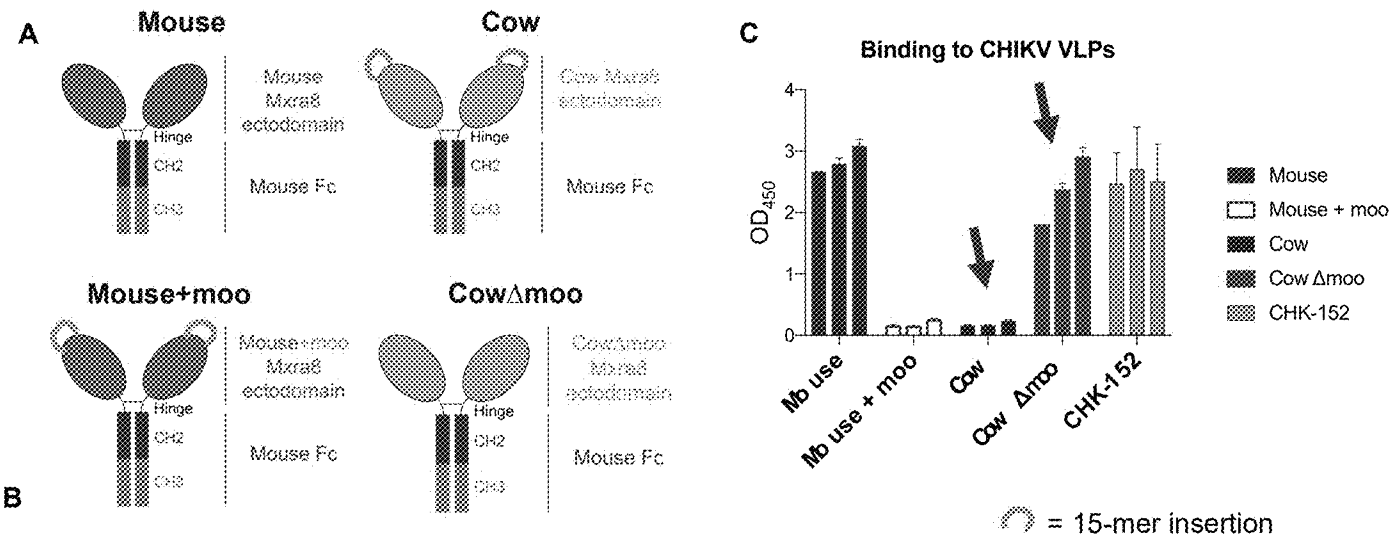

B

```
SEQ ID NO: 62   sp|Q9DBV4|MXRA8_MOUSE       WTQDRLHDRQRVVHWDLSGGP-GSQRRRLVDMYSAGE---------------QRVYEPRD
SEQ ID NO: 63   sp|Q9DBV4|MXRA8_MOUSE+MOO   WTQDRLHDRQRVVHWDLSGGP-GSQRRRLVDMYSAGEQRVGEQRLGEQRVGEQRVYEPRD
SEQ ID NO: 64   sp|Q148M6|MXRA8_BOVIN       WTQDRLHDRQRVVHWDLSGSKAGGPARRLVDMYSTGEQRVGEQRLGEQRVGEQRVYEPRD
SEQ ID NO: 65   sp|Q148M6|MXRA8_BOVIN∆MOO   WTQDRLHDRQRVVHWDLSGSKAGGPARRLVDMYSTGE---------------QRVYEPRD
                                            *******************.  *.  ********:**               ********
```

FIG. 18

A

```
Majority           TGATGAGGGCATCTATTCCTGCCACCTGCACCATCACTACTGTGGCCTCCACGAGCGCCGAGTCTT       SEQ ID NO: 66
                            10        20        30        40        50        60
Mxra8.seq          TGATGAGGGCATCTATTCCTGCCACCTGCACCATCACTACTGTGGCCTCCACGAGCGCCGAGTCTT 66    SEQ ID NO: 67
Mxra8-del8.seq     TGATGAGGGCATCTATTCCTGCCACCTGCACCATCACTACTGTGGCCTCCACGAGCGCCGAGTCTT 66    SEQ ID NO: 68
Mxra8-del97.seq    TGATGAGGGCATCTATTCCTGCCACCTGCACCATCACTACTGTGGCCTCC---------------- 50    SEQ ID NO: 69

Majority           CCACCTACAGGTCACAGAGCCTGCCTTTGAGCCACCAGCTCGTGCTTCTCCTG--------TCTGG
                      70        80        90        100       110       120       130
Mxra8.seq          CCACCTACAGGTCACAGAGCCTGCCTTTGAGCCACCAGCTCGTGCTTCTCCTGGCAATGGGTCTGG 132
Mxra8-del8.seq     CCACCTACAGGTCACAGAGCCTGCCTTTGAGCCACCAGCTCGTGCTTCTCCTG--------TCTGG 124
Mxra8-del97.seq    ------------------------------------------------------------------ 50

Majority           TCACAGCAGTGCTCCTAGCCCAGGTGTGTGTGTAGCCTGCCGGCCTGAGAAGAGGTCCTGTTGTG
                         140       150       160       170       180       190
Mxra8.seq          TCACAGCAGTGCTCCTAGCCCAGGTGTGTGTGTAGCCTGCCGGCCTGAGAAGAGGTCCTGTTGTG  197
Mxra8-del8.seq     TCACAGCAGTGCTCCTAGCCCAGGTGTGTGTGTAGCCTGCCGGCCTGAGAAGAGGTCCTGTTGTG  189
Mxra8-del97.seq    ---------------TAGCCCAGGTGTGTGTGTAGCCTGCCGGCCTGAGAAGAGGTCCTGTTGTG  100
```

B

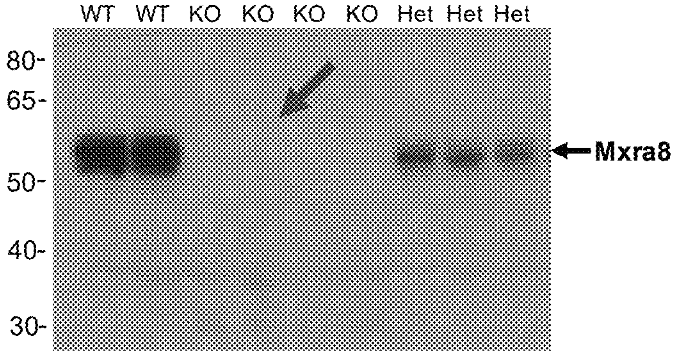

Left calf muscle

FIG. 34A

| Binding Reactivity (% WT (Range)) | | | | | | |
|---|---|---|---|---|---|---|
| Mutation | Fc-mMxra8 | MAb 84 | MAb 88 | IM-CKV063 | IM-CKV065 | MAb C9 |
| | | Domain B | Domain A | Domain A | A and B | Arch 1 |
| DOMAIN A | | | | | | |
| V32A | 47.1 (10) | 36.6 (3) | 84.8 (21) | 44.1 (4) | 33.3 (4) | 44 (0) |
| A33S | 85.3 (0) | 75.8 (6) | 122.7 (26) | 99.4 (2) | 122.9 (28) | 86 (18) |
| L34A | 28.3 (3) | 23.5 (0) | 58.3 (4) | 29.4 (1) | 16.3 (1) | 34.4 (1) |
| E35A | 11 (2) | 99.1 (6) | 55.9 (9) | 19.1 (2) | 11.7 (0) | 22.2 (2) |
| R36A | 68.3 (3) | 104 (2) | 83.8 (16) | 76.5 (13) | 119.2 (1) | 75.4 (4) |
| I37A | 36.2 (0) | 20.7 (1) | 63.2 (15) | 26 (3) | 12.1 (3) | 30.4 (6) |
| R38A | 90.7 (24) | 153 (25) | 99.6 (5) | 94.7 (14) | 132.9 (23) | 86.3 (11) |
| N39A | 91.9 (18) | 71.5 (4) | 123.9 (21) | 119.5 (4) | 120.1 (6) | 107.8 (24) |
| E40A | 86.2 (12) | 74.9 (2) | 107.5 (7) | 106.3 (37) | 124.1 (3) | 106.7 (7) |
| A41S | 4.9 (2) | 79.9 (5) | 89.8 (29) | 51.1 (23) | 33.8 (4) | 70.7 (15) |
| T42A | 95.7 (5) | 64.3 (14) | 111.8 (33) | 110.9 (52) | 104 (3) | 102.4 (30) |
| D43A | 36.2 (1) | 4.5 (1) | 37.5 (5) | 8.3 (2) | 3.7 (1) | 11.1 (1) |
| G44A | 72.2 (10) | 43.8 (5) | 98.1 (7) | 68.2 (7) | 50.4 (10) | 72.5 (8) |
| T45A | 81.2 (9) | 48 (4) | 85.7 (28) | 62.1 (6) | 62.4 (4) | 71.7 (8) |
| L46A | 4.8 (1) | 3.4 (3) | 23.6 (3) | 2.7 (1) | -2.7 (1) | 1.7 (1) |
| K47A | 102.3 (21) | 66.1 (18) | 100.4 (26) | 72.1 (7) | 85.5 (16) | 84 (30) |
| I48A | 11.1 (2) | 6.4 (0) | 39.6 (6) | 7.9 (0) | 0.3 (0) | 10.7 (1) |
| Q49A | 56.8 (8) | 88.8 (12) | 87.1 (5) | 55.4 (1) | 37.3 (7) | 47 (7) |
| V50A | 67.8 (5) | 43.2 (3) | 78.6 (15) | 64.1 (2) | 48.2 (4) | 76.7 (23) |
| S51A | 99.2 (15) | 97 (19) | 96.9 (8) | 89.8 (0) | 85.6 (0) | 85.3 (0) |
| L52A | 86.8 (3) | 83.6 (8) | 100.5 (19) | 106.7 (33) | 141.6 (0) | 84.7 (2) |
| Q53A | 26.3 (5) | 120.5 (29) | 85 (10) | 37.3 (1) | 43.3 (4) | 39.6 (9) |
| I54A | 104.4 (13) | 86.9 (3) | 115.5 (21) | 102.2 (1) | 80.8 (8) | 110.4 (29) |
| G55A | 101.2 (29) | 87.5 (41) | 111.4 (16) | 83.3 (30) | 86.2 (25) | 75.9 (11) |
| I56A | 91.7 (15) | 106.3 (29) | 115.5 (3) | 111.3 (11) | 101.6 (6) | 113.7 (18) |
| G57A | 106.1 (1) | 101.7 (11) | 133.8 (10) | 96.5 (10) | 108 (16) | 109.1 (28) |
| T58A | 94.1 (8) | 114.3 (5) | 81.2 (14) | 88.7 (9) | 93.5 (21) | 98.6 (23) |
| D59A | 78.9 (12) | 73.2 (9) | 86.1 (15) | 81.1 (17) | 72.8 (7) | 71.8 (9) |
| D60A | 101.8 (18) | 70.2 (23) | 56.5 (1) | 64.8 (9) | 114 (23) | 74 (5) |
| S61A | 115.6 (19) | 105.8 (13) | 105 (15) | 100.4 (20) | 112.4 (16) | 93.1 (0) |
| H62A | 102.1 (15) | 105.1 (2) | 101.2 (14) | 79.6 (1) | 88.5 (10) | 93.1 (17) |
| D63A | 85 (2) | 52.1 (10) | 85 (16) | 65.8 (7) | 64.8 (9) | 71.8 (15) |
| W64A | 17.7 (4) | 121.7 (12) | 125.5 (46) | 69.1 (5) | 86.3 (11) | 60.6 (14) |
| T65A | 68.9 (2) | 76.6 (7) | 87.9 (17) | 70.1 (4) | 98.4 (25) | 71.1 (1) |
| K66A | 93.1 (10) | 66.8 (5) | 103 (26) | 84.2 (4) | 99.6 (4) | 85.7 (2) |
| L67A | 77.4 (12) | 38.7 (0) | 84.6 (4) | 62.1 (3) | 54.1 (7) | 60.9 (0) |
| R68A | 66.1 (8) | 76.5 (5) | 74.7 (16) | 67.1 (6) | 88.1 (1) | 64.8 (3) |
| Y69A | 105.8 (4) | 4.2 (1) | 95.4 (0) | 60.7 (3) | 46.3 (1) | 55.3 (12) |

FIG. 34B

| Binding Reactivity (% WT (Range)) | | | | | | |
|---|---|---|---|---|---|---|
| Mutation | Fc-mMxra8 | MAb 84 | MAb 88 | IM-CKV063 | IM-CKV065 | MAb C9 |
| | | Domain B | Domain A | Domain A | A and B | Arch 1 |
| **DOMAIN A (continued)** | | | | | | |
| M70A | 109.5 (20) | 60.1 (8) | 93.7 (2) | 81.7 (0) | 103.9 (6) | 81 (6) |
| N72A | 127.6 (31) | 4.6 (1) | 108.8 (8) | 114.3 (29) | 102.7 (15) | 111.8 (19) |
| H73A | 101.9 (7) | 72.8 (5) | 91.8 (4) | 84.2 (26) | -0.9 (3) | 89.6 (7) |
| I74A | 44.8 (9) | 131.6 (8) | 106.2 (27) | 106.1 (17) | 0.3 (0) | 108.3 (25) |
| P75A | 86.7 (8) | 85.5 (11) | 114.9 (26) | 96.4 (12) | 84.9 (6) | 98.5 (0) |
| A76S | 85 (6) | 128.8 (8) | 122 (13) | 106.6 (14) | 125.3 (2) | 107.3 (3) |
| D77A | 83.7 (11) | 73.4 (6) | 94.7 (41) | 92.2 (1) | 61.2 (16) | 93.3 (5) |
| A78S | 105.6 (17) | 63.1 (5) | 126.4 (14) | 99.1 (6) | 107.3 (3) | 84.1 (11) |
| G79A | 94.6 (19) | 116.2 (21) | 121.2 (11) | 86.9 (5) | 98.5 (6) | 81.4 (6) |
| R80A | 130.9 (28) | 100.9 (25) | 127.9 (2) | 86.3 (16) | 125.2 (16) | 68.8 (8) |
| A81S | 85.2 (13) | 119.8 (3) | 82.3 (1) | 93 (13) | 96.6 (12) | 86.6 (8) |
| G82A | 122.6 (12) | 80.9 (4) | 91.5 (2) | 91.1 (7) | 103.5 (18) | 90.2 (10) |
| L83A | 17.3 (2) | 5.2 (0) | 38.8 (4) | 18.7 (2) | 6.2 (2) | 18.7 (2) |
| F84A | 77.6 (8) | 38.9 (6) | 83.9 (7) | 61.7 (1) | 51.6 (5) | 76.2 (15) |
| V85A | 84.6 (3) | 59.7 (6) | 75.9 (2) | 74.5 (2) | 88.1 (2) | 77.8 (11) |
| R86A | 91.5 (3) | 84.7 (22) | 109.6 (18) | 127.3 (1) | 102 (6) | 120.8 (15) |
| T87A | 23.5 (7) | 11.8 (1) | 52.9 (7) | 18.8 (3) | 7.6 (3) | 20.7 (3) |
| S88A | 94 (22) | 101.2 (2) | 110.8 (30) | 89.5 (13) | 100.9 (2) | 122.1 (25) |
| A89S | 102.4 (23) | 93.2 (8) | 117.7 (4) | 84 (15) | 111.4 (16) | 108.6 (11) |
| P90A | 113.5 (10) | 103.2 (19) | 119.4 (22) | 95.3 (9) | 108.5 (7) | 100.2 (18) |
| C91A | 1 (0) | 1.1 (2) | 4 (5) | 1.5 (2) | -2 (0) | 0.6 (1) |
| T92A | 98.6 (11) | 99.3 (14) | 109.4 (21) | 84.5 (24) | 93.2 (12) | 96 (2) |
| I93A | 14.6 (6) | 1.7 (0) | 29.1 (5) | 8.4 (1) | -0.9 (0) | 10.4 (3) |
| T94A | 99.7 (19) | 83.1 (6) | 109.1 (12) | 95.5 (5) | 101.5 (5) | 115.6 (18) |
| G95A | 94.6 (32) | 81.8 (24) | 89 (7) | 88.9 (25) | 92.6 (23) | 86.2 (2) |
| T96A | 95.6 (6) | 110.6 (3) | 102.8 (13) | 111.2 (10) | 113.2 (12) | 99.2 (10) |
| M97A | 95.1 (20) | 85.3 (9) | 85.1 (10) | 69.9 (9) | 65.7 (3) | 76.3 (3) |
| G98A | 102.5 (1) | 68 (15) | 106.1 (27) | 99.9 (42) | 111.6 (3) | 101.5 (13) |
| H99A | 58.1 (0) | 55.3 (5) | 85.6 (23) | 63.8 (14) | 27.5 (1) | 57.4 (5) |
| F100A | 26.2 (0) | 26.6 (0) | 69.1 (3) | 33.6 (0) | 15.1 (3) | 34.2 (3) |
| I101A | 23.7 (2) | 9.9 (1) | 44.5 (4) | 19.8 (2) | 6.3 (3) | 26.6 (9) |
| L102A | 22.8 (1) | 33 (1) | 61.4 (9) | 24.1 (1) | 4.7 (0) | 31.2 (5) |
| A103S | 91.3 (4) | 65.4 (6) | 85 (6) | 65.8 (5) | 46.8 (7) | 69.7 (7) |
| R104A | 49.9 (15) | 70 (16) | 76 (8) | 75.7 (5) | 66.9 (7) | 91.6 (0) |
| C105A | -0.1 (0) | -1.6 (0) | -0.1 (0) | 0.4 (1) | -2.9 (0) | -0.2 (1) |
| P106A | 91.2 (24) | 66.7 (8) | 105.1 (1) | 94.3 (7) | 98.1 (4) | 88.9 (9) |
| K107A | 84.6 (13) | 97.2 (13) | 99.2 (12) | 86.8 (19) | 95.2 (13) | 95.6 (32) |

FIG. 34C

| Binding Reactivity (% WT (Range)) | | | | | | |
|---|---|---|---|---|---|---|
| **Mutation** | **Fc-mMxra8** | **MAb 84** | **MAb 88** | **IM-CKV063** | **IM-CKV065** | **MAb C9** |
| | | **Domain B** | **Domain A** | **Domain A** | **A and B** | **Arch 1** |
| **DOMAIN A (continued)** | | | | | | |
| G108A | 76.7 (15) | 35.9 (10) | 71.1 (9) | 59 (2) | 34.8 (2) | 71.9 (3) |
| E109A | 97.4 (3) | 40.9 (9) | 123.8 (29) | 76.6 (1) | 82.6 (10) | 108.9 (22) |
| T110A | 99.6 (8) | 89.4 (3) | 107.3 (11) | 88.1 (17) | 72.1 (2) | 88 (1) |
| L111A | 25.7 (6) | 13.9 (2) | 50.9 (4) | 20.3 (0) | 6.6 (1) | 23.2 (5) |
| T112A | 44.2 (6) | 22.2 (9) | 71.6 (3) | 43.1 (1) | 16.2 (3) | 50.5 (5) |
| V113A | 78 (18) | 61.8 (2) | 112.4 (2) | 79.8 (0) | 70.4 (11) | 81.8 (11) |
| G114A | 79.1 (6) | 31.8 (5) | 65.3 (10) | 58.4 (6) | 35.2 (8) | 67.5 (5) |
| F115A | 3.3 (1) | -0.2 (0) | 25.1 (1) | 3.6 (1) | -0.2 (0) | 4.3 (0) |
| T116A | 31.2 (0) | 84.1 (4) | 110 (9) | 104.2 (16) | 103.3 (29) | 98.2 (2) |
| D117A | -0.3 (0) | 6 (0) | 102.8 (16) | 74.2 (25) | 70.9 (4) | 74.4 (27) |
| S118A | 89.6 (8) | 107.7 (19) | 117.2 (17) | 93.1 (7) | 86 (13) | 97.4 (4) |
| R119A | 0 (1) | 20 (2) | 99.5 (14) | 72 (4) | 119.5 (5) | 88 (11) |
| K120A | 1.8 (1) | 171.7 (16) | 82.3 (8) | 13.1 (2) | 0.4 (2) | 15.4 (1) |
| I121A | 12.1 (1) | 96.3 (4) | 110.7 (22) | 108.6 (42) | 111.4 (5) | 96.7 (22) |
| S122A | 101.4 (8) | 99 (3) | 84.3 (3) | 82.8 (4) | 91.1 (31) | 98.7 (7) |
| H123A | 33.6 (1) | 25.6 (3) | 61.5 (0) | 44.2 (3) | 30.8 (1) | 53.6 (2) |
| S124A | 92.8 (1) | 80.4 (3) | 111.6 (35) | 97.8 (31) | 97.3 (23) | 115.9 (22) |
| C125A | -0.2 (0) | -1 (0) | 3.7 (2) | 0.5 (1) | -2.9 (0) | 0 (0) |
| T126A | 76 (5) | 51.2 (16) | 95.1 (11) | 83.4 (3) | 67.2 (11) | 106.1 (12) |
| H127A | 78 (7) | 92.5 (8) | 91 (0) | 96.1 (12) | 81.9 (4) | 92.4 (23) |
| P128A | 122.5 (23) | 103.3 (6) | 101.8 (6) | 86 (2) | 80.3 (0) | 112.2 (6) |
| F129A | 4.1 (2) | 2.6 (1) | 25.1 (1) | 3.9 (0) | -1.1 (1) | 6.7 (2) |
| H130A | 101 (24) | 56.3 (13) | 109.9 (5) | 91 (13) | 103.8 (7) | 105.6 (13) |
| H131A | 15.7 (1) | 8.4 (0) | 56.3 (5) | 16.5 (1) | 3.2 (3) | 24.4 (5) |
| D132A | 104.6 (27) | 93.5 (18) | 120.1 (15) | 116.4 (5) | 125.8 (16) | 94.4 (23) |
| P133A | 81.3 (5) | 52.5 (9) | 92.3 (5) | 73.9 (7) | 66.6 (5) | 87.2 (11) |

FIG. 34D

| Binding Reactivity (% WT (Range)) | | | | | | |
|---|---|---|---|---|---|---|
| **Mutation** | **Fc-mMxra8** | **MAb 84** | **MAb 88** | **IM-CKV063** | **IM-CKV065** | **MAb C9** |
| | | **Domain B** | **Domain A** | **Domain A** | **A and B** | **Arch 1** |
| **DOMAIN B** | | | | | | |
| L180A | 57.0 (18) | 86.7 (3) | 85.9 (1) | 114.1 (35) | 226.7 (36) | 125.5 (8) |
| L181A | 53.2 (11) | 96.3 (8) | 92.2 (7) | 87.9 (15) | 57.9 (14) | 110.3 (33) |
| S182A | 70.9 (5) | 91.7 (20) | 123.3 (27) | 120.8 (33) | 75.8 (11) | 131.9 (3) |
| Q183A | 96.1 (29) | 100.2 (36) | 118.9 (23) | 101.3 (4) | 60.6 (11) | 176.3 (27) |
| Q184A | 130.5 (3) | 76.5 (13) | 100.3 (6) | 120.7 (11) | 123.8 (15) | 134.6 (45) |
| S185A | 88.1 (8) | 95.7 (18) | 1.5 (0.6) | 108.2 (18) | 114.0 (0.7) | 104.8 (8) |
| G186A | 108.2 (11) | 85.8 (3) | 113.0 (27) | 95.4 (3) | 69.7 (1) | 101.0 (3) |
| N187A | 90.5 (8) | 78.1 (17) | 93.4 (4) | 113.8 (18) | 135.6 (1) | 123.3 (11) |
| -, V188A | 55.2 (5) | 163.6 (4) | 67.2 (4) | 114.3 (27) | 124.8 (51) | 140.7 (11) |
| K189A | 156.5 (19) | 97.2 (18) | 60.2 (7) | 109.1 (0.1) | 96.9 (0.5) | 128.7 (19)_ |
| I190A | 9.4 (0.8) | 109.2 (9) | 24.4 (0.4) | 56.1 (17) | 25.0 (2) | 81.8 (9) |
| T191A | 87.4 (25) | 88.6 (2) | 121.5 (31) | 94.8 (5) | 72.1 (17) | 117.7 (7) |
| V192A | 56.9 (19) | 71.8 (8) | 85.6 (5) | 98.3 (34) | 34.9 (9) | 114.3 (0.5) |
| N193A | 120.2 (9) | 66.6 (12) | 76.0 (4) | 85.7 (23) | 128.4 (9) | 112.8 (14) |
| S194A | 87.0 (15) | 65.9 (25) | 92.3 (2) | 94.0 (18) | 105.0 (9) | 118.6 (26) |
| Q195A | 82.4 (30) | 106.2 (7) | 102.4 (2) | 78.6 (9) | 0.9 (0.7) | 128.8 (12) |
| T196A | 86.6 (26) | 77.8 (7) | 95.3 (10) | 83.0 (17) | 0.3 (0.07) | 99.8 (11) |
| V197A | 33.9 (10) | 85.9 (14) | 48.8 (7) | 67.4 (8) | 78.6 (8) | 83.8 (27) |
| R198A | 74.0 (17) | 80.4 (45) | 83.5 (13) | 98.2 (12) | 10.2 (0.9) | 121.6 (49) |
| Y199A | 15.9 (8) | 73.3 (57) | 42.1 (5) | 79.8 (14) | 20.8 (4) | 122.4 (12) |
| K200A | 75.5 (5) | 101.9 (17) | 136.1 (48) | 119.31 (14) | 56.8 (27) | 143.6 (17) |
| C201A | 9.6 (0.9) | 66.2 (0.3) | 28.2 (7) | 47.7 (16) | 12.3 (0.7) | 65.0 (6) |
| N202A | 80.6 (16) | 65.4 (4) | 83.8 (7) | 92.8 (4) | 42.7 (5) | 96.2 (3) |
| C203A | 10.4 (1) | 72.0 (18) | 30.3 (3) | 45.1 (3) | 24.5 (1) | 58.3 (12) |
| G204A | 76.7 (17) | 87.2 (16) | 102.6 (47) | 91.5 (9) | 29.1 (9) | 105.6 (29) |
| G205A | 78.9 (3) | 85.8 (9) | 73.7 (11) | 62.0 (22) | 41.7 | 110.8 (17) |
| S206A | 52.2 (57) | 87.3 (20) | 113.1 (31) | 119.3 (30) | 65.9 (3) | 96.0 (84) |
| G209A | 77.9 (22) | 71.3 (7) | 117.3 (4) | 99.8 (6) | 34.8 (9) | 108.35 (30) |
| L210A | 70.1 (3) | 92.56 (6) | 76.9 (2) | 86.3 (9) | 36.2 (4) | 104.9 (15) |
| I211A | 81.1 (64) | 68.0 (72) | 87.7 (33) | 77.2 (82) | 21.9 (4) | 125.9 (7) |
| T212A | 94.6 (27) | 86.4 (4) | 95.4 (4) | 107.81 (26) | 3.05 (1) | 125.4 (0.4) |
| K215A | 106.4 (14) | 86.9 (34) | 137.1 (14) | 102.3 (41) | 44.2 (9) | 142.8 (79) |
| V216A | 82.9 (36) | 100.4 (38) | 72.9 (1) | 97.7 (7) | 66.5 (8) | 112.5 (29) |
| I217A | 12.3 (9) | 97.5 (23) | 48.5 (4) | 69.7 (21) | 32.0 (7) | 110.5 (13) |
| N218A | 56.5 (14) | 71.6 (15) | 86.5 (28) | 97.6 (26) | 53.5 (27) | 72.0 (41) |
| N219A | 66.6 (0.3) | 83.2 (24) | 94.7 (8) | 98.0 (9) | 47.5 (5) | 117.4 (14) |
| C220A | 60.2 (8) | 48.6 (2) | 73.0 (6) | 95.2 (16) | 32.5 (0.4) | 103.6 (6) |

SEQUENCE LISTING

```
<160> NUMBER OF SEQ ID NOS: 92

<210> SEQ ID NO 1
<211> LENGTH: 954
<212> TYPE: DNA
```

<213> ORGANISM: homo sapiens

<400> SEQUENCE: 1

```
gtcctgttgc atagcggctc ctctgtcccg gccgcagcgg gatcaagcgt agtgagcgag     60
tcagcagttt cctgggaagc gggggcaagg gctgttctga ggtgtcagag cccaaggatg    120
gtgtggacgc aagaccggct ccacgacagg caaagagtgc ttcactggga cctcagggga    180
cccggtggtg gcccagcacg ccggctcctg gacctctata gcgcgggaga acaacgagta    240
tacgaagcta gggacagagg aagactggag ctttcagcca gtgcgttcga tgatggaaat    300
ttttcacttc tgatccgggc tgtggaagaa actgatgctg gactgtatac ttgtaatctc    360
caccatcact actgccacct ctatgagtca ttggctgtca gactggaagt taccgatggc    420
ccgcccgcca caccagctta ctgggatggc gaaaaagaag tacttgctgt cgcgcgaggt    480
gcccctgcgc tcctgacatg cgtcaacagg ggtcacgttt ggactgatcg gcacgtcgaa    540
gaggctcagc aagtagttca ctgggaccgc cagccgcctg gcgtacctca cgatagggcc    600
gaccgcctct tggacctcta cgcctccggt gaaaggaggg cctatgggcc tctgttcctc    660
agagataggg ttgcggtggg cgcagatgcc tttgaacgag gcgatttcag cctccgcatt    720
gagcccctgg aggtagccga tgagggcacc tactcctgtc atctgcatca tcattattgc    780
ggattgcacg agaggagggt cttccacttg actgtagctg aaccgcatgc tgaaccgcca    840
cctcgcggat cacccggaaa cggtagcagt cattccgggg ctcccgggcc ggatccgaca    900
ttggcacgag ggcataacgt aataaatgtc atcgttcccg agtcacgcgc tcat          954
```

<210> SEQ ID NO 2
<211> LENGTH: 318
<212> TYPE: PRT
<213> ORGANISM: homo sapiens

<400> SEQUENCE: 2

```
Val Leu Leu His Ser Gly Ser Ser Val Pro Ala Ala Ala Gly Ser Ser
1               5                   10                  15

Val Val Ser Glu Ser Ala Val Ser Trp Glu Ala Gly Ala Arg Ala Val
            20                  25                  30

Leu Arg Cys Gln Ser Pro Arg Met Val Trp Thr Gln Asp Arg Leu His
        35                  40                  45

Asp Arg Gln Arg Val Leu His Trp Asp Leu Arg Gly Pro Gly Gly Gly
    50                  55                  60

Pro Ala Arg Arg Leu Leu Asp Leu Tyr Ser Ala Gly Glu Gln Arg Val
65                  70                  75                  80

Tyr Glu Ala Arg Asp Arg Gly Arg Leu Glu Leu Ser Ala Ser Ala Phe
                85                  90                  95

Asp Asp Gly Asn Phe Ser Leu Leu Ile Arg Ala Val Glu Glu Thr Asp
            100                 105                 110

Ala Gly Leu Tyr Thr Cys Asn Leu His His His Tyr Cys His Leu Tyr
        115                 120                 125

Glu Ser Leu Ala Val Arg Leu Glu Val Thr Asp Gly Pro Pro Ala Thr
    130                 135                 140

Pro Ala Tyr Trp Asp Gly Glu Lys Glu Val Leu Ala Val Ala Arg Gly
145                 150                 155                 160

Ala Pro Ala Leu Leu Thr Cys Val Asn Arg Gly His Val Trp Thr Asp
                165                 170                 175

Arg His Val Glu Glu Ala Gln Gln Val Val His Trp Asp Arg Gln Pro
            180                 185                 190
```

```
Pro Gly Val Pro His Asp Arg Ala Asp Arg Leu Leu Asp Leu Tyr Ala
        195                 200                 205

Ser Gly Glu Arg Arg Ala Tyr Gly Pro Leu Phe Leu Arg Asp Arg Val
    210                 215                 220

Ala Val Gly Ala Asp Ala Phe Glu Arg Gly Asp Phe Ser Leu Arg Ile
225                 230                 235                 240

Glu Pro Leu Glu Val Ala Asp Glu Gly Thr Tyr Ser Cys His Leu His
                245                 250                 255

His His Tyr Cys Gly Leu His Glu Arg Arg Val Phe His Leu Thr Val
            260                 265                 270

Ala Glu Pro His Ala Glu Pro Pro Pro Arg Gly Ser Pro Gly Asn Gly
        275                 280                 285

Ser Ser His Ser Gly Ala Pro Gly Pro Asp Pro Thr Leu Ala Arg Gly
    290                 295                 300

His Asn Val Ile Asn Val Ile Val Pro Glu Ser Arg Ala His
305                 310                 315


<210> SEQ ID NO 3
<211> LENGTH: 942
<212> TYPE: DNA
<213> ORGANISM: Mus musculus

<400> SEQUENCE: 3

tctggcccga gcggtactgc tgccgcaagc tcaagcctcg tctctgaatc agttgtgtct      60

ctcgcggccg gaactcaggc ggtcctgagg tgtcaaagtc caaggatggt ttggacccaa     120

gatcgcttgc atgatcgaca aagagttgtg cactgggacc tcagcggtgg tcctggatca     180

caacgaagaa ggctggtgga catgtactca gccggagaac agcgcgttta cgagccacga     240

gaccgagatc gactcctttt gtcaccttct gcgttccatg acggcaactt ttctttgttg     300

ataagagccg tagatcgcgg agatgaagga gtttatacgt gtaaccttca ccaccattac     360

tgccatctcg atgaaagtct cgccgtacgg ctggaagtta cggaggaccc acttctttca     420

cgggcatatt gggatggcga gaaggaggtc ctggtcgttg ctcacggcgc accagccctg     480

atgacatgca tcaacagagc ccatgtttgg accgacaggc accttgaaga agcacaacaa     540

gttgtccatt gggaccgaca gctcccaggt gttagccatg atcgggccga tcgcttgctt     600

gacttgtatg ccagcgggga acggagggca tacggcccgc cttttcttcg ggatcgagtt     660

agcgtaaaca ctaacgcctt tgcacgcggt gacttcagcc ttcgcataga tgaactcgaa     720

cgagcagatg aaggaatata ctcctgccat ttgcatcatc attattgcgg cctgcatgag     780

cgaagggtat ttcacctcca agtgactgaa cctgcattcg agccaccagc gagggcctca     840

ccgggaaacg gctccggcca cagcagcgca ccgtctccgg acccgacttt gacacggggc     900

catagtataa taaacgtaat agttcctgag gaccataccc ac                        942


<210> SEQ ID NO 4
<211> LENGTH: 314
<212> TYPE: PRT
<213> ORGANISM: Mus musculus

<400> SEQUENCE: 4

Ser Gly Pro Ser Gly Thr Ala Ala Ala Ser Ser Ser Leu Val Ser Glu
1               5                   10                  15

Ser Val Val Ser Leu Ala Ala Gly Thr Gln Ala Val Leu Arg Cys Gln
            20                  25                  30
```

```
Ser Pro Arg Met Val Trp Thr Gln Asp Arg Leu His Asp Arg Gln Arg
        35                  40                  45

Val Val His Trp Asp Leu Ser Gly Gly Pro Gly Ser Gln Arg Arg Arg
    50                  55                  60

Leu Val Asp Met Tyr Ser Ala Gly Glu Gln Arg Val Tyr Glu Pro Arg
65                  70                  75                  80

Asp Arg Asp Arg Leu Leu Leu Ser Pro Ser Ala Phe His Asp Gly Asn
                85                  90                  95

Phe Ser Leu Leu Ile Arg Ala Val Asp Arg Gly Asp Glu Gly Val Tyr
            100                 105                 110

Thr Cys Asn Leu His His His Tyr Cys His Leu Asp Glu Ser Leu Ala
        115                 120                 125

Val Arg Leu Glu Val Thr Glu Asp Pro Leu Leu Ser Arg Ala Tyr Trp
    130                 135                 140

Asp Gly Glu Lys Glu Val Leu Val Val Ala His Gly Ala Pro Ala Leu
145                 150                 155                 160

Met Thr Cys Ile Asn Arg Ala His Val Trp Thr Asp Arg His Leu Glu
                165                 170                 175

Glu Ala Gln Gln Val Val His Trp Asp Arg Gln Leu Pro Gly Val Ser
            180                 185                 190

His Asp Arg Ala Asp Arg Leu Leu Asp Leu Tyr Ala Ser Gly Glu Arg
        195                 200                 205

Arg Ala Tyr Gly Pro Pro Phe Leu Arg Asp Arg Val Ser Val Asn Thr
    210                 215                 220

Asn Ala Phe Ala Arg Gly Asp Phe Ser Leu Arg Ile Asp Glu Leu Glu
225                 230                 235                 240

Arg Ala Asp Glu Gly Ile Tyr Ser Cys His Leu His His His Tyr Cys
                245                 250                 255

Gly Leu His Glu Arg Arg Val Phe His Leu Gln Val Thr Glu Pro Ala
            260                 265                 270

Phe Glu Pro Pro Ala Arg Ala Ser Pro Gly Asn Gly Ser Gly His Ser
        275                 280                 285

Ser Ala Pro Ser Pro Asp Pro Thr Leu Thr Arg Gly His Ser Ile Ile
    290                 295                 300

Asn Val Ile Val Pro Glu Asp His Thr His
305                 310
```

<210> SEQ ID NO 5
<211> LENGTH: 933
<212> TYPE: DNA
<213> ORGANISM: Mus musculus

<400> SEQUENCE: 5

```
cccagcgggc ccatttcaac aatcaacccc tgtcctccat gcaaggagtg tcacaaatgc     60

ccaggtaagt cactaccaga gctccactcc caggagaatg gtaagtgctg taaaaatccc    120

tgtaatggag gataagccat gtacaaatcc atttccatct ctcctcatca gctcctaacc    180

tcgagggtgg accatccgtc ttcatcttcc ctccaaatat caaggatgta ctcatgatct    240

ccctgacacc caaggtcacg tgtgtggtgg tggatgtgag cgaggatgac ccagacgtcc    300

agatcagctg gtttgtgaac aacgtggaag tacacacagc tcagacacaa acccatagag    360

aggattacaa cagtactatc cgggtggtca gcaccctccc catccagcac caggactgga    420

tgagtggcaa ggagttcaaa tgcaaggtca acaacaaaga cctcccatca cccatcgaga    480

gaaccatctc aaaaattaaa ggtgggacct gcaggacaac tgcatggggg ctgggatggg    540
```

```
cataagaata aatgtctatg tggacagcct tccacttcag ccatgacctc tatgtatgtt    600

tctaacccca cagggctagt cagagctcca caagtataca tcttgccgcc accagcagag    660

cagttgtcca ggaaagatgt cagtctcact tgcctggtcg tgggcttcaa ccctggagac    720

atcagtgtgg agtggaccag caatgggcat acagaggaga actacaagga caccgcacca    780

gtcctggact ctgacggttc ttacttcata tatagcaagc tcaatatgaa aacaagcaag    840

tgggagaaaa cagattcctt ctcatgcaac gtgagacacg agggtctgaa aaattactac    900

ctgaagaaga ccatctcccg gtctccgggt aaa                                 933
```

<210> SEQ ID NO 6
<211> LENGTH: 238
<212> TYPE: PRT
<213> ORGANISM: Mus musculus

<400> SEQUENCE: 6

```
Pro Ser Gly Pro Ile Ser Thr Ile Asn Pro Cys Pro Pro Cys Lys Glu
1               5                   10                  15

Cys His Lys Cys Pro Ala Pro Asn Leu Glu Gly Gly Pro Ser Val Phe
            20                  25                  30

Ile Phe Pro Pro Asn Ile Lys Asp Val Leu Met Ile Ser Leu Thr Pro
        35                  40                  45

Lys Val Thr Cys Val Val Val Asp Val Ser Glu Asp Asp Pro Asp Val
    50                  55                  60

Gln Ile Ser Trp Phe Val Asn Asn Val Glu Val His Thr Ala Gln Thr
65                  70                  75                  80

Gln Thr His Arg Glu Asp Tyr Asn Ser Thr Ile Arg Val Val Ser Thr
                85                  90                  95

Leu Pro Ile Gln His Gln Asp Trp Met Ser Gly Lys Glu Phe Lys Cys
            100                 105                 110

Lys Val Asn Asn Lys Asp Leu Pro Ser Pro Ile Glu Arg Thr Ile Ser
        115                 120                 125

Lys Ile Lys Gly Leu Val Arg Ala Pro Gln Val Tyr Ile Leu Pro Pro
    130                 135                 140

Pro Ala Glu Gln Leu Ser Arg Lys Asp Val Ser Leu Thr Cys Leu Val
145                 150                 155                 160

Val Gly Phe Asn Pro Gly Asp Ile Ser Val Glu Trp Thr Ser Asn Gly
                165                 170                 175

His Thr Glu Glu Asn Tyr Lys Asp Thr Ala Pro Val Leu Asp Ser Asp
            180                 185                 190

Gly Ser Tyr Phe Ile Tyr Ser Lys Leu Asn Met Lys Thr Ser Lys Trp
        195                 200                 205

Glu Lys Thr Asp Ser Phe Ser Cys Asn Val Arg His Glu Gly Leu Lys
    210                 215                 220

Asn Tyr Tyr Leu Lys Lys Thr Ile Ser Arg Ser Pro Gly Lys
225                 230                 235
```

<210> SEQ ID NO 7
<211> LENGTH: 681
<212> TYPE: DNA
<213> ORGANISM: homo sapiens

<400> SEQUENCE: 7

```
gacaaaaccc atacatgccc accttgtcca gcaccagagc tgctgggagg accaagcgtg     60

ttcctgtttc cacccaagcc caaagatacc ctgatgatct cccggactcc cgaagtcacc    120
```

```
tgcgtggtcg tggacgtgtc tcacgaggac cccgaagtca agttcaactg gtacgtggac    180

ggggtcgagg tgcataatgc caagacaaaa cccagagagg aacagtacaa cagtacctat    240

agagtcgtgt cagtcctgac agtgctgcat caggattggc tgaacgggaa agagtataag    300

tgcaaagtga gtaataaggc tctgcctgca ccaatcgaga aaactatttc caaggccaaa    360

ggacagccca gggaacctca ggtgtacacc ctgcctccat cacgcgagga aatgacaaag    420

aaccaggtca gcctgacttg tctggtgaaa ggcttctatc cttctgacat cgctgtggag    480

tgggaaagta atgggcagcc agagaacaat tacaagacaa ctccccctgt cctggactct    540

gatggaagtt tctttctgta tagcaagctg accgtggata aatcccggtg gcagcagggc    600

aatgtcttta gctgttccgt gatgcacgaa gccctgcaca accactacac ccagaagagc    660

ctgagcctgt cacccggcaa a                                              681
```

```
<210> SEQ ID NO 8
<211> LENGTH: 227
<212> TYPE: PRT
<213> ORGANISM: homo sapiens

<400> SEQUENCE: 8

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 9
<211> LENGTH: 681
<212> TYPE: DNA
<213> ORGANISM: homo sapiens
```

<400> SEQUENCE: 9

```
gacaaaaccc atacatgccc accttgtcca gcaccagagc tgctgggagg accaagcgtg      60
ttcctgtttc cacccaagcc caaagatacc ctgatgatct cccggactcc cgaagtcacc     120
tgcgtggtcg tggacgtgtc tcacgaggac cccgaagtca agttcaactg gtacgtggac     180
ggggtcgagg tgcataatgc caagacaaaa cccagagagg aacagtacca gagtacctat     240
agagtcgtgt cagtcctgac agtgctgcat caggattggc tgaacgggaa agagtataag     300
tgcaaagtga gtaataaggc tctgcctgca ccaatcgaga aaactatttc caaggccaaa     360
ggacagccca gggaacctca ggtgtacacc ctgcctccat cacgcgagga aatgacaaag     420
aaccaggtca gcctgacttg tctggtgaaa ggcttctatc cttctgacat cgctgtggag     480
tgggaaagta atgggcagcc agagaacaat tacaagacaa ctcccccctgt cctggactct    540
gatggaagtt tctttctgta tagcaagctg accgtggata aatcccggtg gcagcagggc     600
aatgtcttta gctgttccgt gatgcacgaa gccctgcaca accactacac ccagaagagc     660
ctgagcctgt cacccggcaa a                                               681
```

<210> SEQ ID NO 10
<211> LENGTH: 227
<212> TYPE: PRT
<213> ORGANISM: homo sapiens

<400> SEQUENCE: 10

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Gln Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 11
<211> LENGTH: 60
<212> TYPE: DNA
<213> ORGANISM: Artificial Sequence
<220> FEATURE:
<223> OTHER INFORMATION: IL-2 signal peptide

<400> SEQUENCE: 11
atgtacagga tgcaactcct gtcttgcatt gcactaagtc ttgcacttgt cacgaattcg 60

<210> SEQ ID NO 12
<211> LENGTH: 20
<212> TYPE: PRT
<213> ORGANISM: Artificial Sequence
<220> FEATURE:
<223> OTHER INFORMATION: IL-2 signal peptide

<400> SEQUENCE: 12

Met Tyr Arg Met Gln Leu Leu Ser Cys Ile Ala Leu Ser Leu Ala Leu
1 5 10 15

Val Thr Asn Ser
20

<210> SEQ ID NO 13
<211> LENGTH: 27
<212> TYPE: DNA
<213> ORGANISM: Artificial Sequence
<220> FEATURE:
<223> OTHER INFORMATION: GS linker

<400> SEQUENCE: 13
tcaagcggca gcagcggcag ttcaggg 27

<210> SEQ ID NO 14
<211> LENGTH: 9
<212> TYPE: PRT
<213> ORGANISM: Artificial Sequence
<220> FEATURE:
<223> OTHER INFORMATION: GS linker

<400> SEQUENCE: 14

Ser Ser Gly Ser Ser Gly Ser Ser Gly
1 5

<210> SEQ ID NO 15
<211> LENGTH: 84
<212> TYPE: DNA
<213> ORGANISM: Artificial Sequence
<220> FEATURE:
<223> OTHER INFORMATION: Signal peptide

<400> SEQUENCE: 15
atggggatcc ttcccagccc tgggatgcct gcgctgctct ccctcgtgag ccttctctcc 60
gtgctgctga tgggttgcgt agct 84

<210> SEQ ID NO 16
<211> LENGTH: 28
<212> TYPE: PRT
<213> ORGANISM: Artificial Sequence
<220> FEATURE:
<223> OTHER INFORMATION: Signal peptide

<400> SEQUENCE: 16

Met Gly Ile Leu Pro Ser Pro Gly Met Pro Ala Leu Leu Ser Leu Val

```
1               5                   10                  15

Ser Leu Leu Ser Val Leu Leu Met Gly Cys Val Ala
            20                  25


<210> SEQ ID NO 17
<211> LENGTH: 1968
<212> TYPE: DNA
<213> ORGANISM: Artificial Sequence
<220> FEATURE:
<223> OTHER INFORMATION: mIgG2b_human_Mxra8_iso1

<400> SEQUENCE: 17

atgtacagga tgcaactcct gtcttgcatt gcactaagtc ttgcacttgt cacgaattcg     60

atatcggtcc tgttgcatag cggctcctct gtcccggccg cagcgggatc aagcgtagtg    120

agcgagtcag cagtttcctg ggaagcgggg gcaagggctg ttctgaggtg tcagagccca    180

aggatggtgt ggacgcaaga ccggctccac gacaggcaaa gagtgcttca ctgggacctc    240

aggggacccg gtggtggccc agcacgccgg ctcctggacc tctatagcgc gggagaacaa    300

cgagtatacg aagctaggga cagaggaaga ctggagcttt cagccagtgc gttcgatgat    360

ggaaattttt cacttctgat ccgggctgtg gaagaaactg atgctggact gtatacttgt    420

aatctccacc atcactactg ccacctctat gagtcattgg ctgtcagact ggaagttacc    480

gatggcccgc ccgccacacc agcttactgg gatggcgaaa aagaagtact tgctgtcgcg    540

cgaggtgccc ctgcgctcct gacatgcgtc aacaggggtc acgtttggac tgatcggcac    600

gtcgaagagg ctcagcaagt agttcactgg gaccgccagc cgcctggcgt acctcacgat    660

agggccgacc gcctcttgga cctctacgcc tccggtgaaa ggagggccta tgggcctctg    720

ttcctcagag atagggttgc ggtgggcgca gatgcctttg aacgaggcga tttcagcctc    780

cgcattgagc ccctggaggt agccgatgag ggcacctact cctgtcatct gcatcatcat    840

tattgcggat tgcacgagag gagggtcttc cacttgactg tagctgaacc gcatgctgaa    900

ccgccacctc gcggatcacc cggaaacggt agcagtcatt ccggggctcc cgggccggat    960

ccgacattgg cacgagggca taacgtaata aatgtcatcg ttcccgagtc acgcgctcat   1020

gctagcgtta gatctcccag cgggcccatt tcaacaatca acccctgtcc tccatgcaag   1080

gagtgtcaca aatgcccagg taagtcacta ccagagctcc actcccagga gaatggtaag   1140

tgctgtaaaa atccctgtaa tggaggataa gccatgtaca aatccatttc catctctcct   1200

catcagctcc taacctcgag ggtggaccat ccgtcttcat cttccctcca aatatcaagg   1260

atgtactcat gatctccctg acacccaagg tcacgtgtgt ggtggtggat gtgagcgagg   1320

atgacccaga cgtccagatc agctggtttg tgaacaacgt ggaagtacac acagctcaga   1380

cacaaaccca tagagaggat tacaacagta ctatccgggt ggtcagcacc ctccccatcc   1440

agcaccagga ctggatgagt ggcaaggagt tcaaatgcaa ggtcaacaac aaagacctcc   1500

catcacccat cgagagaacc atctcaaaaa ttaaaggtgg gacctgcagg acaactgcat   1560

gggggctggg atgggcataa gaataaatgt ctatgtggac agccttccac ttcagccatg   1620

acctctatgt atgtttctaa ccccacaggg ctagtcagag ctccacaagt atacatcttg   1680

ccgccaccag cagagcagtt gtccaggaaa gatgtcagtc tcacttgcct ggtcgtgggc   1740

ttcaaccctg gagacatcag tgtggagtgg accagcaatg ggcatacaga ggagaactac   1800

aaggacaccg caccagtcct ggactctgac ggttcttact tcatatatag caagctcaat   1860

atgaaaacaa gcaagtggga gaaaacagat tccttctcat gcaacgtgag acacgagggt   1920
```

```
ctgaaaaatt actacctgaa gaagaccatc tcccggtctc cgggtaaa              1968


<210> SEQ ID NO 18
<211> LENGTH: 583
<212> TYPE: PRT
<213> ORGANISM: Artificial Sequence
<220> FEATURE:
<223> OTHER INFORMATION: mIgG2b_human_Mxra8_iso1

<400> SEQUENCE: 18

Met Tyr Arg Met Gln Leu Leu Ser Cys Ile Ala Leu Ser Leu Ala Leu
1               5                   10                  15

Val Thr Asn Ser Ile Ser Val Leu Leu His Ser Gly Ser Ser Val Pro
            20                  25                  30

Ala Ala Ala Gly Ser Ser Val Val Ser Glu Ser Ala Val Ser Trp Glu
        35                  40                  45

Ala Gly Ala Arg Ala Val Leu Arg Cys Gln Ser Pro Arg Met Val Trp
    50                  55                  60

Thr Gln Asp Arg Leu His Asp Arg Gln Arg Val Leu His Trp Asp Leu
65                  70                  75                  80

Arg Gly Pro Gly Gly Gly Pro Ala Arg Arg Leu Leu Asp Leu Tyr Ser
                85                  90                  95

Ala Gly Glu Gln Arg Val Tyr Glu Ala Arg Asp Arg Gly Arg Leu Glu
            100                 105                 110

Leu Ser Ala Ser Ala Phe Asp Asp Gly Asn Phe Ser Leu Leu Ile Arg
        115                 120                 125

Ala Val Glu Glu Thr Asp Ala Gly Leu Tyr Thr Cys Asn Leu His His
    130                 135                 140

His Tyr Cys His Leu Tyr Glu Ser Leu Ala Val Arg Leu Glu Val Thr
145                 150                 155                 160

Asp Gly Pro Pro Ala Thr Pro Ala Tyr Trp Asp Gly Glu Lys Glu Val
                165                 170                 175

Leu Ala Val Ala Arg Gly Ala Pro Ala Leu Leu Thr Cys Val Asn Arg
            180                 185                 190

Gly His Val Trp Thr Asp Arg His Val Glu Glu Ala Gln Gln Val Val
        195                 200                 205

His Trp Asp Arg Gln Pro Pro Gly Val Pro His Asp Arg Ala Asp Arg
    210                 215                 220

Leu Leu Asp Leu Tyr Ala Ser Gly Glu Arg Arg Ala Tyr Gly Pro Leu
225                 230                 235                 240

Phe Leu Arg Asp Arg Val Ala Val Gly Ala Asp Ala Phe Glu Arg Gly
                245                 250                 255

Asp Phe Ser Leu Arg Ile Glu Pro Leu Glu Val Ala Asp Glu Gly Thr
            260                 265                 270

Tyr Ser Cys His Leu His His His Tyr Cys Gly Leu His Glu Arg Arg
        275                 280                 285

Val Phe His Leu Thr Val Ala Glu Pro His Ala Glu Pro Pro Pro Arg
    290                 295                 300

Gly Ser Pro Gly Asn Gly Ser Ser His Ser Gly Ala Pro Gly Pro Asp
305                 310                 315                 320

Pro Thr Leu Ala Arg Gly His Asn Val Ile Asn Val Ile Val Pro Glu
                325                 330                 335

Ser Arg Ala His Ala Ser Val Arg Ser Pro Ser Gly Pro Ile Ser Thr
            340                 345                 350

Ile Asn Pro Cys Pro Pro Cys Lys Glu Cys His Lys Cys Pro Ala Pro
```

```
        355                 360                 365

Asn Leu Glu Gly Gly Pro Ser Val Phe Ile Phe Pro Pro Asn Ile Lys
    370                 375                 380

Asp Val Leu Met Ile Ser Leu Thr Pro Lys Val Thr Cys Val Val Val
385                 390                 395                 400

Asp Val Ser Glu Asp Asp Pro Asp Val Gln Ile Ser Trp Phe Val Asn
                405                 410                 415

Asn Val Glu Val His Thr Ala Gln Thr Gln Thr His Arg Glu Asp Tyr
            420                 425                 430

Asn Ser Thr Ile Arg Val Val Ser Thr Leu Pro Ile Gln His Gln Asp
        435                 440                 445

Trp Met Ser Gly Lys Glu Phe Lys Cys Lys Val Asn Asn Lys Asp Leu
    450                 455                 460

Pro Ser Pro Ile Glu Arg Thr Ile Ser Lys Ile Lys Gly Leu Val Arg
465                 470                 475                 480

Ala Pro Gln Val Tyr Ile Leu Pro Pro Pro Ala Glu Gln Leu Ser Arg
                485                 490                 495

Lys Asp Val Ser Leu Thr Cys Leu Val Val Gly Phe Asn Pro Gly Asp
            500                 505                 510

Ile Ser Val Glu Trp Thr Ser Asn Gly His Thr Glu Glu Asn Tyr Lys
        515                 520                 525

Asp Thr Ala Pro Val Leu Asp Ser Asp Gly Ser Tyr Phe Ile Tyr Ser
    530                 535                 540

Lys Leu Asn Met Lys Thr Ser Lys Trp Glu Lys Thr Asp Ser Phe Ser
545                 550                 555                 560

Cys Asn Val Arg His Glu Gly Leu Lys Asn Tyr Tyr Leu Lys Lys Thr
                565                 570                 575

Ile Ser Arg Ser Pro Gly Lys
            580
```

<210> SEQ ID NO 19
<211> LENGTH: 1956
<212> TYPE: DNA
<213> ORGANISM: Artificial Sequence
<220> FEATURE:
<223> OTHER INFORMATION: mIgG2b_mouse_Mxra8

<400> SEQUENCE: 19

```
atgtacagga tgcaactcct gtcttgcatt gcactaagtc ttgcacttgt cacgaattcg     60

atatcgtctg gcccgagcgg tactgctgcc gcaagctcaa gcctcgtctc tgaatcagtt    120

gtgtctctcg cggccggaac tcaggcggtc ctgaggtgtc aaagtccaag gatggtttgg    180

acccaagatc gcttgcatga tcgacaaaga gttgtgcact gggacctcag cggtggtcct    240

ggatcacaac gaagaaggct ggtggacatg tactcagccg gagaacagcg cgtttacgag    300

ccacgagacc gagatcgact ccttttgtca ccttctgcgt tccatgacgg caacttttct    360

ttgttgataa gagccgtaga tcgcggagat gaaggagttt atacgtgtaa ccttcaccac    420

cattactgcc atctcgatga aagtctcgcc gtacggctgg aagttacgga ggacccactt    480

ctttcacggg catattggga tggcgagaag gaggtcctgg tcgttgctca cggcgcacca    540

gccctgatga catgcatcaa cagagcccat gtttggaccg acaggcacct tgaagaagca    600

caacaagttg tccattggga ccgacagctc ccaggtgtta gccatgatcg ggccgatcgc    660

ttgcttgact tgtatgccag cggggaacgg agggcatacg gcccgccttt tcttcgggat    720

cgagttagcg taaacactaa cgcctttgca cgcggtgact tcagccttcg catagatgaa    780
```

```
ctcgaacgag cagatgaagg aatatactcc tgccatttgc atcatcatta ttgcggcctg    840

catgagcgaa gggtatttca cctccaagtg actgaacctg cattcgagcc accagcgagg    900

gcctcaccgg gaaacggctc cggccacagc agcgcaccgt ctccggaccc gactttgaca    960

cggggccata gtataataaa cgtaatagtt cctgaggacc atacccacgc tagcgttaga   1020

tctcccagcg ggcccatttc aacaatcaac ccctgtcctc catgcaagga gtgtcacaaa   1080

tgcccaggta agtcactacc agagctccac tcccaggaga atggtaagtg ctgtaaaaat   1140

ccctgtaatg gaggataagc catgtacaaa tccatttcca tctctcctca tcagctccta   1200

acctcgaggg tggaccatcc gtcttcatct tccctccaaa tatcaaggat gtactcatga   1260

tctccctgac acccaaggtc acgtgtgtgg tggtggatgt gagcgaggat gacccagacg   1320

tccagatcag ctggtttgtg aacaacgtgg aagtacacac agctcagaca caaacccata   1380

gagaggatta caacagtact atccgggtgg tcagcaccct ccccatccag caccaggact   1440

ggatgagtgg caaggagttc aaatgcaagg tcaacaacaa agacctccca tcacccatcg   1500

agagaaccat ctcaaaaatt aaaggtggga cctgcaggac aactgcatgg gggctgggat   1560

gggcataaga ataaatgtct atgtggacag ccttccactt cagccatgac ctctatgtat   1620

gtttctaacc ccacagggct agtcagagct ccacaagtat acatcttgcc gccaccagca   1680

gagcagttgt ccaggaaaga tgtcagtctc acttgcctgg tcgtgggctt caaccctgga   1740

gacatcagtg tggagtggac cagcaatggg catacagagg agaactacaa ggacaccgca   1800

ccagtcctgg actctgacgg ttcttacttc atatatagca agctcaatat gaaaacaagc   1860

aagtgggaga aaacagattc cttctcatgc aacgtgagac acgagggtct gaaaaattac   1920

tacctgaaga agaccatctc ccggtctccg ggtaaa                             1956
```

<210> SEQ ID NO 20
<211> LENGTH: 579
<212> TYPE: PRT
<213> ORGANISM: Artificial Sequence
<220> FEATURE:
<223> OTHER INFORMATION: Synthetic sequence

<400> SEQUENCE: 20

```
Met Tyr Arg Met Gln Leu Leu Ser Cys Ile Ala Leu Ser Leu Ala Leu
1               5                   10                  15

Val Thr Asn Ser Ile Ser Ser Gly Pro Ser Gly Thr Ala Ala Ala Ser
            20                  25                  30

Ser Ser Leu Val Ser Glu Ser Val Val Ser Leu Ala Ala Gly Thr Gln
        35                  40                  45

Ala Val Leu Arg Cys Gln Ser Pro Arg Met Val Trp Thr Gln Asp Arg
    50                  55                  60

Leu His Asp Arg Gln Arg Val Val His Trp Asp Leu Ser Gly Gly Pro
65                  70                  75                  80

Gly Ser Gln Arg Arg Arg Leu Val Asp Met Tyr Ser Ala Gly Glu Gln
                85                  90                  95

Arg Val Tyr Glu Pro Arg Asp Arg Asp Arg Leu Leu Leu Ser Pro Ser
            100                 105                 110

Ala Phe His Asp Gly Asn Phe Ser Leu Leu Ile Arg Ala Val Asp Arg
        115                 120                 125

Gly Asp Glu Gly Val Tyr Thr Cys Asn Leu His His His Tyr Cys His
    130                 135                 140

Leu Asp Glu Ser Leu Ala Val Arg Leu Glu Val Thr Glu Asp Pro Leu
```

-continued

```
145                 150                 155                 160

Leu Ser Arg Ala Tyr Trp Asp Gly Glu Lys Glu Val Leu Val Val Ala
                165                 170                 175

His Gly Ala Pro Ala Leu Met Thr Cys Ile Asn Arg Ala His Val Trp
            180                 185                 190

Thr Asp Arg His Leu Glu Glu Ala Gln Gln Val Val His Trp Asp Arg
        195                 200                 205

Gln Leu Pro Gly Val Ser His Asp Arg Ala Asp Arg Leu Leu Asp Leu
    210                 215                 220

Tyr Ala Ser Gly Glu Arg Arg Ala Tyr Gly Pro Pro Phe Leu Arg Asp
225                 230                 235                 240

Arg Val Ser Val Asn Thr Asn Ala Phe Ala Arg Gly Asp Phe Ser Leu
                245                 250                 255

Arg Ile Asp Glu Leu Glu Arg Ala Asp Glu Gly Ile Tyr Ser Cys His
            260                 265                 270

Leu His His His Tyr Cys Gly Leu His Glu Arg Arg Val Phe His Leu
        275                 280                 285

Gln Val Thr Glu Pro Ala Phe Glu Pro Pro Ala Arg Ala Ser Pro Gly
    290                 295                 300

Asn Gly Ser Gly His Ser Ser Ala Pro Ser Pro Asp Pro Thr Leu Thr
305                 310                 315                 320

Arg Gly His Ser Ile Ile Asn Val Ile Val Pro Glu Asp His Thr His
                325                 330                 335

Ala Ser Val Arg Ser Pro Ser Gly Pro Ile Ser Thr Ile Asn Pro Cys
            340                 345                 350

Pro Pro Cys Lys Glu Cys His Lys Cys Pro Ala Pro Asn Leu Glu Gly
        355                 360                 365

Gly Pro Ser Val Phe Ile Phe Pro Pro Asn Ile Lys Asp Val Leu Met
    370                 375                 380

Ile Ser Leu Thr Pro Lys Val Thr Cys Val Val Val Asp Val Ser Glu
385                 390                 395                 400

Asp Asp Pro Asp Val Gln Ile Ser Trp Phe Val Asn Asn Val Glu Val
                405                 410                 415

His Thr Ala Gln Thr Gln Thr His Arg Glu Asp Tyr Asn Ser Thr Ile
            420                 425                 430

Arg Val Val Ser Thr Leu Pro Ile Gln His Gln Asp Trp Met Ser Gly
        435                 440                 445

Lys Glu Phe Lys Cys Lys Val Asn Asn Lys Asp Leu Pro Ser Pro Ile
    450                 455                 460

Glu Arg Thr Ile Ser Lys Ile Lys Gly Leu Val Arg Ala Pro Gln Val
465                 470                 475                 480

Tyr Ile Leu Pro Pro Pro Ala Glu Gln Leu Ser Arg Lys Asp Val Ser
                485                 490                 495

Leu Thr Cys Leu Val Val Gly Phe Asn Pro Gly Asp Ile Ser Val Glu
            500                 505                 510

Trp Thr Ser Asn Gly His Thr Glu Glu Asn Tyr Lys Asp Thr Ala Pro
        515                 520                 525

Val Leu Asp Ser Asp Gly Ser Tyr Phe Ile Tyr Ser Lys Leu Asn Met
    530                 535                 540

Lys Thr Ser Lys Trp Glu Lys Thr Asp Ser Phe Ser Cys Asn Val Arg
545                 550                 555                 560

His Glu Gly Leu Lys Asn Tyr Tyr Leu Lys Lys Thr Ile Ser Arg Ser
                565                 570                 575
```

Pro Gly Lys

<210> SEQ ID NO 21
<211> LENGTH: 1743
<212> TYPE: DNA
<213> ORGANISM: Artificial Sequence
<220> FEATURE:
<223> OTHER INFORMATION: Synthetic sequence

<400> SEQUENCE: 21
atggggatcc ttcccagccc tgggatgcct gcgctgctct ccctcgtgag ccttctctcc 60
gtgctgctga tgggttgcgt agctgaaacc ggttctggcc cgagcggtac tgctgccgca 120
agctcaagcc tcgtctctga atcagttgtg tctctcgcgg ccggaactca ggcggtcctg 180
aggtgtcaaa gtccaaggat ggtttggacc caagatcgct tgcatgatcg acaaagagtt 240
gtgcactggg acctcagcgg tggtcctgga tcacaacgaa gaaggctggt ggacatgtac 300
tcagccggag aacagcgcgt ttacgagcca cgagaccgag atcgactcct tttgtcacct 360
tctgcgttcc atgacggcaa cttttctttg ttgataagag ccgtagatcg cggagatgaa 420
ggagtttata cgtgtaacct tcaccaccat tactgccatc tcgatgaaag tctcgccgta 480
cggctggaag ttacggagga cccacttctt tcacgggcat attgggatgg cgagaaggag 540
gtcctggtcg ttgctcacgg cgcaccagcc ctgatgacat gcatcaacag agcccatgtt 600
tggaccgaca ggcaccttga agaagcacaa caagttgtcc attgggaccg acagctccca 660
ggtgttagcc atgatcgggc cgatcgcttg cttgacttgt atgccagcgg ggaacggagg 720
gcatacggcc cgccttttct tcgggatcga gttagcgtaa acactaacgc ctttgcacgc 780
ggtgacttca gccttcgcat agatgaactc gaacgagcag atgaaggaat atactcctgc 840
catttgcatc atcattattg cggcctgcat gagcgaaggg tatttcacct ccaagtgact 900
gaacctgcat tcgagccacc agcgagggcc tcaccgggaa acggctccgg ccacagcagc 960
gcaccgtctc cggacccgac tttgacacgg ggccatagta taataaacgt aatagttcct 1020
gaggaccata cccactcaag cggcagcagc ggcagttcag gggacaaaac ccatacatgc 1080
ccaccttgtc cagcaccaga gctgctggga ggaccaagcg tgttcctgtt tccacccaag 1140
cccaaagata ccctgatgat ctcccggact cccgaagtca cctgcgtggt cgtggacgtg 1200
tctcacgagg accccgaagt caagttcaac tggtacgtgg acggggtcga ggtgcataat 1260
gccaagacaa aacccagaga ggaacagtac aacagtacct atagagtcgt gtcagtcctg 1320
acagtgctgc atcaggattg gctgaacggg aaagagtata agtgcaaagt gagtaataag 1380
gctctgcctg caccaatcga gaaaactatt tccaaggcca aaggacagcc cagggaacct 1440
caggtgtaca ccctgcctcc atcacgcgag gaaatgacaa agaaccaggt cagcctgact 1500
tgtctggtga aaggcttcta tccttctgac atcgctgtgg agtgggaaag taatgggcag 1560
ccagagaaca attacaagac aactccccct gtcctggact ctgatggaag tttctttctg 1620
tatagcaagc tgaccgtgga taaatcccgg tggcagcagg gcaatgtctt tagctgttcc 1680
gtgatgcacg aagccctgca caaccactac acccagaaga gcctgagcct gtcacccggc 1740
aaa 1743

<210> SEQ ID NO 22
<211> LENGTH: 581
<212> TYPE: PRT
<213> ORGANISM: Artificial Sequence
<220> FEATURE:

<223> OTHER INFORMATION: Synthetic sequence

<400> SEQUENCE: 22

```
Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Ser
            20                  25                  30

Gly Pro Ser Gly Thr Ala Ala Ala Ser Ser Ser Leu Val Ser Glu Ser
        35                  40                  45

Val Val Ser Leu Ala Ala Gly Thr Gln Ala Val Leu Arg Cys Gln Ser
    50                  55                  60

Pro Arg Met Val Trp Thr Gln Asp Arg Leu His Asp Arg Gln Arg Val
65                  70                  75                  80

Val His Trp Asp Leu Ser Gly Gly Pro Gly Ser Gln Arg Arg Arg Leu
                85                  90                  95

Val Asp Met Tyr Ser Ala Gly Glu Gln Arg Val Tyr Glu Pro Arg Asp
            100                 105                 110

Arg Asp Arg Leu Leu Leu Ser Pro Ser Ala Phe His Asp Gly Asn Phe
        115                 120                 125

Ser Leu Leu Ile Arg Ala Val Asp Arg Gly Asp Glu Gly Val Tyr Thr
    130                 135                 140

Cys Asn Leu His His His Tyr Cys His Leu Asp Glu Ser Leu Ala Val
145                 150                 155                 160

Arg Leu Glu Val Thr Glu Asp Pro Leu Leu Ser Arg Ala Tyr Trp Asp
                165                 170                 175

Gly Glu Lys Glu Val Leu Val Val Ala His Gly Ala Pro Ala Leu Met
            180                 185                 190

Thr Cys Ile Asn Arg Ala His Val Trp Thr Asp Arg His Leu Glu Glu
        195                 200                 205

Ala Gln Gln Val Val His Trp Asp Arg Gln Leu Pro Gly Val Ser His
    210                 215                 220

Asp Arg Ala Asp Arg Leu Leu Asp Leu Tyr Ala Ser Gly Glu Arg Arg
225                 230                 235                 240

Ala Tyr Gly Pro Pro Phe Leu Arg Asp Arg Val Ser Val Asn Thr Asn
                245                 250                 255

Ala Phe Ala Arg Gly Asp Phe Ser Leu Arg Ile Asp Glu Leu Glu Arg
            260                 265                 270

Ala Asp Glu Gly Ile Tyr Ser Cys His Leu His His His Tyr Cys Gly
        275                 280                 285

Leu His Glu Arg Arg Val Phe His Leu Gln Val Thr Glu Pro Ala Phe
    290                 295                 300

Glu Pro Pro Ala Arg Ala Ser Pro Gly Asn Gly Ser Gly His Ser Ser
305                 310                 315                 320

Ala Pro Ser Pro Asp Pro Thr Leu Thr Arg Gly His Ser Ile Ile Asn
                325                 330                 335

Val Ile Val Pro Glu Asp His Thr His Ser Ser Gly Ser Ser Gly Ser
            340                 345                 350

Ser Gly Asp Lys Thr His Thr Cys Pro Pro Cys Pro Ala Pro Glu Leu
        355                 360                 365

Leu Gly Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400
```

```
Ser His Glu Asp Pro Glu Val Lys Phe Asn Trp Tyr Val Asp Gly Val
                405                 410                 415

Glu Val His Asn Ala Lys Thr Lys Pro Arg Glu Glu Gln Tyr Asn Ser
            420                 425                 430

Thr Tyr Arg Val Val Ser Val Leu Thr Val Leu His Gln Asp Trp Leu
        435                 440                 445

Asn Gly Lys Glu Tyr Lys Cys Lys Val Ser Asn Lys Ala Leu Pro Ala
    450                 455                 460

Pro Ile Glu Lys Thr Ile Ser Lys Ala Lys Gly Gln Pro Arg Glu Pro
465                 470                 475                 480

Gln Val Tyr Thr Leu Pro Pro Ser Arg Glu Glu Met Thr Lys Asn Gln
                485                 490                 495

Val Ser Leu Thr Cys Leu Val Lys Gly Phe Tyr Pro Ser Asp Ile Ala
            500                 505                 510

Val Glu Trp Glu Ser Asn Gly Gln Pro Glu Asn Asn Tyr Lys Thr Thr
        515                 520                 525

Pro Pro Val Leu Asp Ser Asp Gly Ser Phe Phe Leu Tyr Ser Lys Leu
    530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Pro Gly Lys
            580
```

<210> SEQ ID NO 23
<211> LENGTH: 1743
<212> TYPE: DNA
<213> ORGANISM: Artificial Sequence
<220> FEATURE:
<223> OTHER INFORMATION: Synthetic sequence

<400> SEQUENCE: 23

```
atggggatcc ttcccagccc tgggatgcct gcgctgctct ccctcgtgag ccttctctcc      60

gtgctgctga tgggttgcgt agctgaaacc ggttctggcc cgagcggtac tgctgccgca     120

agctcaagcc tcgtctctga atcagttgtg tctctcgcgg ccggaactca ggcggtcctg     180

aggtgtcaaa gtccaaggat ggtttggacc caagatcgct tgcatgatcg acaaagagtt     240

gtgcactggg acctcagcgg tggtcctgga tcacaacgaa gaaggctggt ggacatgtac     300

tcagccggag aacagcgcgt ttacgagcca cgagaccgag atcgactcct tttgtcacct     360

tctgcgttcc atgacggcaa cttttctttg ttgataagag ccgtagatcg cggagatgaa     420

ggagtttata cgtgtaacct tcaccaccat tactgccatc tcgatgaaag tctcgccgta     480

cggctggaag ttacggagga cccacttctt tcacgggcat attgggatgg cgagaaggag     540

gtcctggtcg ttgctcacgg cgcaccagcc ctgatgacat gcatcaacag agcccatgtt     600

tggaccgaca ggcaccttga agaagcacaa caagttgtcc attgggaccg acagctccca     660

ggtgttagcc atgatcgggc cgatcgcttg cttgacttgt atgccagcgg ggaacggagg     720

gcatacggcc cgccttttct tcgggatcga gttagcgtaa acactaacgc ctttgcacgc     780

ggtgacttca gccttcgcat agatgaactc gaacgagcag atgaaggaat atactcctgc     840

catttgcatc atcattattg cggcctgcat gagcgaaggg tatttcacct ccaagtgact     900

gaacctgcat tcgagccacc agcgagggcc tcaccgggaa acggctccgg ccacagcagc     960

gcaccgtctc cggacccgac tttgacacgg ggccatagta taataaacgt aatagttcct    1020
```

```
gaggaccata cccactcaag cggcagcagc ggcagttcag gggacaaaac ccatacatgc   1080

ccaccttgtc cagcaccaga gctgctggga ggaccaagcg tgttcctgtt tccacccaag   1140

cccaaagata ccctgatgat ctcccggact cccgaagtca cctgcgtggt cgtggacgtg   1200

tctcacgagg accccgaagt caagttcaac tggtacgtgg acggggtcga ggtgcataat   1260

gccaagacaa aacccagaga ggaacagtac cagagtacct atagagtcgt gtcagtcctg   1320

acagtgctgc atcaggattg gctgaacggg aaagagtata agtgcaaagt gagtaataag   1380

gctctgcctg caccaatcga gaaaactatt tccaaggcca aaggacagcc cagggaacct   1440

caggtgtaca ccctgcctcc atcacgcgag gaaatgacaa agaaccaggt cagcctgact   1500

tgtctggtga aaggcttcta tccttctgac atcgctgtgg agtgggaaag taatgggcag   1560

ccagagaaca attacaagac aactccccct gtcctggact ctgatggaag tttctttctg   1620

tatagcaagc tgaccgtgga taaatcccgg tggcagcagg gcaatgtctt tagctgttcc   1680

gtgatgcacg aagccctgca caaccactac acccagaaga gcctgagcct gtcacccggc   1740

aaa                                                                 1743
```

<210> SEQ ID NO 24
<211> LENGTH: 581
<212> TYPE: PRT
<213> ORGANISM: Artificial Sequence
<220> FEATURE:
<223> OTHER INFORMATION: Synthetic Sequence

<400> SEQUENCE: 24

```
Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Ser
            20                  25                  30

Gly Pro Ser Gly Thr Ala Ala Ala Ser Ser Ser Leu Val Ser Glu Ser
        35                  40                  45

Val Val Ser Leu Ala Ala Gly Thr Gln Ala Val Leu Arg Cys Gln Ser
    50                  55                  60

Pro Arg Met Val Trp Thr Gln Asp Arg Leu His Asp Arg Gln Arg Val
65                  70                  75                  80

Val His Trp Asp Leu Ser Gly Gly Pro Gly Ser Gln Arg Arg Arg Leu
                85                  90                  95

Val Asp Met Tyr Ser Ala Gly Glu Gln Arg Val Tyr Glu Pro Arg Asp
            100                 105                 110

Arg Asp Arg Leu Leu Leu Ser Pro Ser Ala Phe His Asp Gly Asn Phe
        115                 120                 125

Ser Leu Leu Ile Arg Ala Val Asp Arg Gly Asp Glu Gly Val Tyr Thr
    130                 135                 140

Cys Asn Leu His His His Tyr Cys His Leu Asp Glu Ser Leu Ala Val
145                 150                 155                 160

Arg Leu Glu Val Thr Glu Asp Pro Leu Leu Ser Arg Ala Tyr Trp Asp
                165                 170                 175

Gly Glu Lys Glu Val Leu Val Val Ala His Gly Ala Pro Ala Leu Met
            180                 185                 190

Thr Cys Ile Asn Arg Ala His Val Trp Thr Asp Arg His Leu Glu Glu
        195                 200                 205

Ala Gln Gln Val Val His Trp Asp Arg Gln Leu Pro Gly Val Ser His
    210                 215                 220
```

Asp Arg Ala Asp Arg Leu Leu Asp Leu Tyr Ala Ser Gly Glu Arg Arg
225 230 235 240

Ala Tyr Gly Pro Pro Phe Leu Arg Asp Arg Val Ser Val Asn Thr Asn
245 250 255

Ala Phe Ala Arg Gly Asp Phe Ser Leu Arg Ile Asp Glu Leu Glu Arg
260 265 270

Ala Asp Glu Gly Ile Tyr Ser Cys His Leu His His His Tyr Cys Gly
275 280 285

Leu His Glu Arg Arg Val Phe His Leu Gln Val Thr Glu Pro Ala Phe
290 295 300

Glu Pro Pro Ala Arg Ala Ser Pro Gly Asn Gly Ser Gly His Ser Ser
305 310 315 320

Ala Pro Ser Pro Asp Pro Thr Leu Thr Arg Gly His Ser Ile Ile Asn
325 330 335

Val Ile Val Pro Glu Asp His Thr His Ser Ser Gly Ser Ser Gly Ser
340 345 350

Ser Gly Asp Lys Thr His Thr Cys Pro Pro Cys Pro Ala Pro Glu Leu
355 360 365

Leu Gly Gly Pro Ser Val Phe Leu Phe Pro Pro Lys Pro Lys Asp Thr
370 375 380

Leu Met Ile Ser Arg Thr Pro Glu Val Thr Cys Val Val Val Asp Val
385 390 395 400

Ser His Glu Asp Pro Glu Val Lys Phe Asn Trp Tyr Val Asp Gly Val
405 410 415

Glu Val His Asn Ala Lys Thr Lys Pro Arg Glu Glu Gln Tyr Gln Ser
420 425 430

Thr Tyr Arg Val Val Ser Val Leu Thr Val Leu His Gln Asp Trp Leu
435 440 445

Asn Gly Lys Glu Tyr Lys Cys Lys Val Ser Asn Lys Ala Leu Pro Ala
450 455 460

Pro Ile Glu Lys Thr Ile Ser Lys Ala Lys Gly Gln Pro Arg Glu Pro
465 470 475 480

Gln Val Tyr Thr Leu Pro Pro Ser Arg Glu Glu Met Thr Lys Asn Gln
485 490 495

Val Ser Leu Thr Cys Leu Val Lys Gly Phe Tyr Pro Ser Asp Ile Ala
500 505 510

Val Glu Trp Glu Ser Asn Gly Gln Pro Glu Asn Asn Tyr Lys Thr Thr
515 520 525

Pro Pro Val Leu Asp Ser Asp Gly Ser Phe Phe Leu Tyr Ser Lys Leu
530 535 540

Thr Val Asp Lys Ser Arg Trp Gln Gln Gly Asn Val Phe Ser Cys Ser
545 550 555 560

Val Met His Glu Ala Leu His Asn His Tyr Thr Gln Lys Ser Leu Ser
565 570 575

Leu Ser Pro Gly Lys
580

<210> SEQ ID NO 25
<211> LENGTH: 343
<212> TYPE: PRT
<213> ORGANISM: homo sapiens

<400> SEQUENCE: 25

Met Ala Leu Pro Ser Arg Ile Leu Leu Trp Lys Leu Val Leu Leu Gln
1 5 10 15

```
Ser Ser Ala Val Leu Leu His Ser Ala Val Glu Glu Thr Asp Ala Gly
            20                  25                  30

Leu Tyr Thr Cys Asn Leu His His His Tyr Cys His Leu Tyr Glu Ser
        35                  40                  45

Leu Ala Val Arg Leu Glu Val Thr Asp Gly Pro Pro Ala Thr Pro Ala
    50                  55                  60

Tyr Trp Asp Gly Glu Lys Glu Val Leu Ala Val Ala Arg Gly Ala Pro
65                  70                  75                  80

Ala Leu Leu Thr Cys Val Asn Arg Gly His Val Trp Thr Asp Arg His
                85                  90                  95

Val Glu Glu Ala Gln Gln Val Val His Trp Asp Arg Gln Pro Pro Gly
            100                 105                 110

Val Pro His Asp Arg Ala Asp Arg Leu Leu Asp Leu Tyr Ala Ser Gly
        115                 120                 125

Glu Arg Arg Ala Tyr Gly Pro Leu Phe Leu Arg Asp Arg Val Ala Val
    130                 135                 140

Gly Ala Asp Ala Phe Glu Arg Gly Asp Phe Ser Leu Arg Ile Glu Pro
145                 150                 155                 160

Leu Glu Val Ala Asp Glu Gly Thr Tyr Ser Cys His Leu His His His
                165                 170                 175

Tyr Cys Gly Leu His Glu Arg Arg Val Phe His Leu Thr Val Ala Glu
            180                 185                 190

Pro His Ala Glu Pro Pro Pro Arg Gly Ser Pro Gly Asn Gly Ser Ser
        195                 200                 205

His Ser Gly Ala Pro Gly Pro Asp Pro Thr Leu Ala Arg Gly His Asn
    210                 215                 220

Val Ile Asn Val Ile Val Pro Glu Ser Arg Ala His Phe Phe Gln Gln
225                 230                 235                 240

Leu Gly Tyr Val Leu Ala Thr Leu Leu Leu Phe Ile Leu Leu Leu Val
                245                 250                 255

Thr Val Leu Leu Ala Ala Arg Arg Arg Arg Gly Gly Tyr Glu Tyr Ser
            260                 265                 270

Asp Gln Lys Ser Gly Lys Ser Lys Gly Lys Asp Val Asn Leu Ala Glu
        275                 280                 285

Phe Ala Val Ala Ala Gly Asp Gln Met Leu Tyr Arg Ser Glu Asp Ile
    290                 295                 300

Gln Leu Asp Tyr Lys Asn Asn Ile Leu Lys Glu Arg Ala Glu Leu Ala
305                 310                 315                 320

His Ser Pro Leu Pro Ala Lys Tyr Ile Asp Leu Asp Lys Asp Pro Ser
                325                 330                 335

Gly Leu Cys Pro Leu Gly Ala
            340


<210> SEQ ID NO 26
<211> LENGTH: 444
<212> TYPE: PRT
<213> ORGANISM: homo sapiens

<400> SEQUENCE: 26

Met Ala Leu Pro Ser Arg Ile Leu Leu Trp Lys Leu Val Leu Leu Gln
1               5                   10                  15

Ser Ser Ala Val Leu Leu His Ser Gly Ser Ser Val Pro Ala Ala Ala
            20                  25                  30

Gly Ser Ser Val Val Ser Glu Ser Ala Val Ser Trp Glu Ala Gly Ala
```

```
        35                  40                  45

Arg Ala Val Leu Arg Cys Gln Ser Pro Arg Met Val Trp Thr Gln Asp
    50                  55                  60

Arg Leu His Asp Arg Gln Arg Val Leu His Trp Asp Leu Arg Gly Pro
65                  70                  75                  80

Gly Gly Gly Pro Ala Arg Arg Leu Leu Asp Leu Tyr Ser Ala Gly Glu
                85                  90                  95

Gln Arg Val Tyr Glu Ala Arg Asp Arg Gly Arg Leu Glu Leu Ser Ala
            100                 105                 110

Ser Ala Phe Asp Asp Gly Asn Phe Ser Leu Leu Ile Arg Ala Val Glu
        115                 120                 125

Glu Thr Asp Ala Gly Leu Tyr Thr Cys Asn Leu His His His Tyr Cys
    130                 135                 140

His Leu Tyr Glu Ser Leu Ala Val Arg Leu Glu Val Thr Asp Gly Pro
145                 150                 155                 160

Pro Ala Thr Pro Ala Tyr Trp Asp Gly Glu Lys Glu Val Leu Ala Val
                165                 170                 175

Ala Arg Gly Ala Pro Ala Leu Leu Thr Cys Val Asn Arg Gly His Val
            180                 185                 190

Trp Thr Asp Arg His Val Glu Glu Ala Gln Gln Val Val His Trp Asp
        195                 200                 205

Arg Gln Pro Pro Gly Val Pro His Asp Arg Ala Asp Arg Leu Leu Asp
    210                 215                 220

Leu Tyr Ala Ser Gly Glu Arg Arg Ala Tyr Gly Pro Leu Phe Leu Arg
225                 230                 235                 240

Asp Arg Val Ala Val Gly Ala Asp Ala Phe Glu Arg Gly Asp Phe Ser
                245                 250                 255

Leu Arg Ile Glu Pro Leu Glu Val Ala Asp Glu Gly Thr Tyr Ser Cys
            260                 265                 270

His Leu His His His Tyr Cys Gly Leu His Glu Arg Arg Val Phe His
        275                 280                 285

Leu Thr Val Ala Glu Pro His Ala Glu Pro Pro Pro Arg Gly Ser Pro
    290                 295                 300

Gly Asn Gly Ser Ser His Ser Gly Ala Pro Gly Pro Asp Pro Thr Leu
305                 310                 315                 320

Ala Arg Gly His Asn Val Ile Asn Val Ile Val Pro Glu Ser Arg Ala
                325                 330                 335

His Phe Phe Gln Gln Leu Gly Tyr Val Leu Ala Thr Leu Leu Leu Phe
            340                 345                 350

Ile Leu Leu Leu Val Thr Val Leu Leu Ala Ala Arg Arg Arg Arg Gly
        355                 360                 365

Gly Tyr Glu Tyr Ser Asp Gln Lys Ser Gly Lys Ser Lys Gly Lys Asp
    370                 375                 380

Val Asn Leu Ala Glu Phe Ala Val Ala Ala Gly Asp Gln Met Leu Tyr
385                 390                 395                 400

Arg Ser Glu Asp Ile Gln Leu Asp Tyr Lys Asn Asn Ile Leu Lys Glu
                405                 410                 415

Arg Ala Glu Leu Ala His Ser Pro Leu Pro Ala Lys Tyr Ile Asp Leu
            420                 425                 430

Asp Lys Asp Pro Ser Gly Leu Cys Pro Leu Gly Ala
        435                 440
```

<210> SEQ ID NO 27

<211> LENGTH: 442
<212> TYPE: PRT
<213> ORGANISM: homo sapiens

<400> SEQUENCE: 27

```
Met Ala Leu Pro Ser Arg Ile Leu Leu Trp Lys Leu Val Leu Leu Gln
1               5                   10                  15

Ser Ser Ala Val Leu Leu His Ser Gly Ser Ser Val Pro Ala Ala Ala
            20                  25                  30

Gly Ser Ser Val Val Ser Glu Ser Ala Val Ser Trp Glu Ala Gly Ala
        35                  40                  45

Arg Ala Val Leu Arg Cys Gln Ser Pro Arg Met Val Trp Thr Gln Asp
    50                  55                  60

Arg Leu His Asp Arg Gln Arg Val Leu His Trp Asp Leu Arg Gly Pro
65                  70                  75                  80

Gly Gly Gly Pro Ala Arg Arg Leu Leu Asp Leu Tyr Ser Ala Gly Glu
                85                  90                  95

Gln Arg Val Tyr Glu Ala Arg Asp Arg Gly Arg Leu Glu Leu Ser Ala
            100                 105                 110

Ser Ala Phe Asp Asp Gly Asn Phe Ser Leu Leu Ile Arg Ala Val Glu
        115                 120                 125

Glu Thr Asp Ala Gly Leu Tyr Thr Cys Asn Leu His His His Tyr Cys
    130                 135                 140

His Leu Tyr Glu Ser Leu Ala Val Arg Leu Glu Val Thr Asp Gly Pro
145                 150                 155                 160

Pro Ala Thr Pro Ala Tyr Trp Asp Gly Glu Lys Glu Val Leu Ala Val
                165                 170                 175

Ala Arg Gly Ala Pro Ala Leu Leu Thr Cys Val Asn Arg Gly His Val
            180                 185                 190

Trp Thr Asp Arg His Val Glu Glu Ala Gln Gln Val Val His Trp Asp
        195                 200                 205

Arg Gln Pro Pro Gly Val Pro His Asp Arg Ala Asp Arg Leu Leu Asp
    210                 215                 220

Leu Tyr Ala Ser Gly Glu Arg Arg Ala Tyr Gly Pro Leu Phe Leu Arg
225                 230                 235                 240

Asp Arg Val Ala Val Gly Ala Asp Ala Phe Glu Arg Gly Asp Phe Ser
                245                 250                 255

Leu Arg Ile Glu Pro Leu Glu Val Ala Asp Glu Gly Thr Tyr Ser Cys
            260                 265                 270

His Leu His His His Tyr Cys Gly Leu His Glu Arg Arg Val Phe His
        275                 280                 285

Leu Thr Val Ala Glu Pro His Ala Glu Pro Pro Pro Arg Gly Ser Pro
    290                 295                 300

Gly Asn Gly Ser Ser His Ser Gly Ala Pro Gly Pro Asp Pro Thr Leu
305                 310                 315                 320

Ala Arg Gly His Asn Val Ile Asn Val Ile Val Pro Glu Ser Arg Ala
                325                 330                 335

His Phe Phe Gln Gln Leu Gly Tyr Val Leu Ala Thr Leu Leu Leu Phe
            340                 345                 350

Ile Leu Leu Leu Val Thr Val Leu Leu Ala Ala Arg Arg Arg Arg Gly
        355                 360                 365

Gly Tyr Glu Tyr Ser Asp Gln Lys Ser Gly Lys Ser Lys Gly Lys Asp
    370                 375                 380

Val Asn Leu Ala Glu Phe Ala Val Ala Ala Gly Asp Gln Met Leu Tyr
```

```
385                 390                 395                 400

Arg Ser Glu Asp Ile Gln Leu Asp Tyr Lys Asn Asn Ile Leu Lys Glu
                405                 410                 415

Arg Ala Glu Leu Ala His Ser Pro Leu Pro Ala Lys Tyr Ile Asp Leu
            420                 425                 430

Asp Lys Gly Phe Arg Lys Glu Asn Cys Lys
        435                 440


<210> SEQ ID NO 28
<211> LENGTH: 433
<212> TYPE: PRT
<213> ORGANISM: homo sapiens

<400> SEQUENCE: 28

Met Ile Arg Cys Ala Ala Thr Gly Ser Ala Val Leu Leu His Ser Gly
1               5                   10                  15

Ser Ser Val Pro Ala Ala Ala Gly Ser Ser Val Val Ser Glu Ser Ala
            20                  25                  30

Val Ser Trp Glu Ala Gly Ala Arg Ala Val Leu Arg Cys Gln Ser Pro
        35                  40                  45

Arg Met Val Trp Thr Gln Asp Arg Leu His Asp Arg Gln Arg Val Leu
    50                  55                  60

His Trp Asp Leu Arg Gly Pro Gly Gly Gly Pro Ala Arg Arg Leu Leu
65                  70                  75                  80

Asp Leu Tyr Ser Ala Gly Glu Gln Arg Val Tyr Glu Ala Arg Asp Arg
                85                  90                  95

Gly Arg Leu Glu Leu Ser Ala Ser Ala Phe Asp Asp Gly Asn Phe Ser
            100                 105                 110

Leu Leu Ile Arg Ala Val Glu Glu Thr Asp Ala Gly Leu Tyr Thr Cys
        115                 120                 125

Asn Leu His His His Tyr Cys His Leu Tyr Glu Ser Leu Ala Val Arg
    130                 135                 140

Leu Glu Val Thr Asp Gly Pro Pro Ala Thr Pro Ala Tyr Trp Asp Gly
145                 150                 155                 160

Glu Lys Glu Val Leu Ala Val Ala Arg Gly Ala Pro Ala Leu Leu Thr
                165                 170                 175

Cys Val Asn Arg Gly His Val Trp Thr Asp Arg His Val Glu Glu Ala
            180                 185                 190

Gln Gln Val Val His Trp Asp Arg Gln Pro Pro Gly Val Pro His Asp
        195                 200                 205

Arg Ala Asp Arg Leu Leu Asp Leu Tyr Ala Ser Gly Glu Arg Arg Ala
    210                 215                 220

Tyr Gly Pro Leu Phe Leu Arg Asp Arg Val Ala Val Gly Ala Asp Ala
225                 230                 235                 240

Phe Glu Arg Gly Asp Phe Ser Leu Arg Ile Glu Pro Leu Glu Val Ala
                245                 250                 255

Asp Glu Gly Thr Tyr Ser Cys His Leu His His His Tyr Cys Gly Leu
            260                 265                 270

His Glu Arg Arg Val Phe His Leu Thr Val Ala Glu Pro His Ala Glu
        275                 280                 285

Pro Pro Pro Arg Gly Ser Pro Gly Asn Gly Ser Ser His Ser Gly Ala
    290                 295                 300

Pro Gly Pro Asp Pro Thr Leu Ala Arg Gly His Asn Val Ile Asn Val
305                 310                 315                 320
```

```
Ile Val Pro Glu Ser Arg Ala His Phe Phe Gln Gln Leu Gly Tyr Val
                325                 330                 335

Leu Ala Thr Leu Leu Leu Phe Ile Leu Leu Leu Val Thr Val Leu Leu
            340                 345                 350

Ala Ala Arg Arg Arg Arg Gly Gly Tyr Glu Tyr Ser Asp Gln Lys Ser
        355                 360                 365

Gly Lys Ser Lys Gly Lys Asp Val Asn Leu Ala Glu Phe Ala Val Ala
    370                 375                 380

Ala Gly Asp Gln Met Leu Tyr Arg Ser Glu Asp Ile Gln Leu Asp Tyr
385                 390                 395                 400

Lys Asn Asn Ile Leu Lys Glu Arg Ala Glu Leu Ala His Ser Pro Leu
                405                 410                 415

Pro Ala Lys Tyr Ile Asp Leu Asp Lys Gly Phe Arg Lys Glu Asn Cys
            420                 425                 430

Lys


<210> SEQ ID NO 29
<211> LENGTH: 341
<212> TYPE: PRT
<213> ORGANISM: homo sapiens

<400> SEQUENCE: 29

Met Ala Leu Pro Ser Arg Ile Leu Leu Trp Lys Leu Val Leu Leu Gln
1               5                   10                  15

Ser Ser Ala Val Leu Leu His Ser Ala Val Glu Glu Thr Asp Ala Gly
            20                  25                  30

Leu Tyr Thr Cys Asn Leu His His His Tyr Cys His Leu Tyr Glu Ser
        35                  40                  45

Leu Ala Val Arg Leu Glu Val Thr Asp Gly Pro Pro Ala Thr Pro Ala
    50                  55                  60

Tyr Trp Asp Gly Glu Lys Glu Val Leu Ala Val Ala Arg Gly Ala Pro
65                  70                  75                  80

Ala Leu Leu Thr Cys Val Asn Arg Gly His Val Trp Thr Asp Arg His
                85                  90                  95

Val Glu Glu Ala Gln Gln Val Val His Trp Asp Arg Gln Pro Pro Gly
            100                 105                 110

Val Pro His Asp Arg Ala Asp Arg Leu Leu Asp Leu Tyr Ala Ser Gly
        115                 120                 125

Glu Arg Arg Ala Tyr Gly Pro Leu Phe Leu Arg Asp Arg Val Ala Val
    130                 135                 140

Gly Ala Asp Ala Phe Glu Arg Gly Asp Phe Ser Leu Arg Ile Glu Pro
145                 150                 155                 160

Leu Glu Val Ala Asp Glu Gly Thr Tyr Ser Cys His Leu His His His
                165                 170                 175

Tyr Cys Gly Leu His Glu Arg Arg Val Phe His Leu Thr Val Ala Glu
            180                 185                 190

Pro His Ala Glu Pro Pro Pro Arg Gly Ser Pro Gly Asn Gly Ser Ser
        195                 200                 205

His Ser Gly Ala Pro Gly Pro Asp Pro Thr Leu Ala Arg Gly His Asn
    210                 215                 220

Val Ile Asn Val Ile Val Pro Glu Ser Arg Ala His Phe Phe Gln Gln
225                 230                 235                 240

Leu Gly Tyr Val Leu Ala Thr Leu Leu Leu Phe Ile Leu Leu Leu Val
                245                 250                 255
```

```
Thr Val Leu Leu Ala Ala Arg Arg Arg Arg Gly Gly Tyr Glu Tyr Ser
            260                 265                 270

Asp Gln Lys Ser Gly Lys Ser Lys Gly Lys Asp Val Asn Leu Ala Glu
        275                 280                 285

Phe Ala Val Ala Ala Gly Asp Gln Met Leu Tyr Arg Ser Glu Asp Ile
    290                 295                 300

Gln Leu Asp Tyr Lys Asn Asn Ile Leu Lys Glu Arg Ala Glu Leu Ala
305                 310                 315                 320

His Ser Pro Leu Pro Ala Lys Tyr Ile Asp Leu Asp Lys Gly Phe Arg
                325                 330                 335

Lys Glu Asn Cys Lys
            340


<210> SEQ ID NO 30
<211> LENGTH: 450
<212> TYPE: PRT
<213> ORGANISM: homo sapiens

<400> SEQUENCE: 30

Met Ala Leu Pro Ser Arg Ile Leu Leu Trp Lys Leu Val Leu Leu Gln
1               5                   10                  15

Ser Ser Ala Val Leu Leu His Ser Gly Ser Ser Val Pro Ala Ala Ala
            20                  25                  30

Gly Ser Ser Val Val Ser Glu Ser Ala Val Ser Trp Glu Ala Gly Ala
        35                  40                  45

Arg Ala Val Leu Arg Cys Gln Ser Pro Arg Met Val Trp Thr Gln Asp
    50                  55                  60

Arg Leu His Asp Arg Gln Arg Val Leu His Trp Asp Leu Arg Gly Pro
65                  70                  75                  80

Gly Gly Gly Pro Ala Arg Arg Leu Leu Asp Leu Tyr Ser Ala Gly Glu
                85                  90                  95

Gln Arg Val Tyr Glu Ala Arg Asp Arg Gly Arg Leu Glu Leu Ser Ala
            100                 105                 110

Ser Ala Phe Asp Asp Gly Asn Phe Ser Leu Leu Ile Arg Ala Val Glu
        115                 120                 125

Glu Thr Asp Ala Gly Leu Tyr Thr Cys Asn Leu His His His Tyr Cys
    130                 135                 140

His Leu Tyr Glu Ser Leu Ala Val Arg Leu Glu Val Thr Asp Gly Pro
145                 150                 155                 160

Pro Ala Thr Pro Ala Tyr Trp Asp Gly Glu Lys Glu Val Leu Ala Val
                165                 170                 175

Ala Arg Gly Ala Pro Ala Leu Leu Thr Cys Val Asn Arg Gly His Val
            180                 185                 190

Trp Thr Asp Arg His Val Glu Glu Ala Gln Gln Val Val His Trp Asp
        195                 200                 205

Arg Gln Pro Pro Gly Val Pro His Asp Arg Ala Asp Arg Leu Leu Asp
    210                 215                 220

Leu Tyr Ala Ser Gly Glu Arg Arg Ala Tyr Gly Pro Leu Phe Leu Arg
225                 230                 235                 240

Asp Arg Val Ala Val Gly Ala Asp Ala Phe Glu Arg Gly Asp Phe Ser
                245                 250                 255

Leu Arg Ile Glu Pro Leu Glu Val Ala Asp Glu Gly Thr Tyr Ser Cys
            260                 265                 270

His Leu His His His Tyr Cys Gly Leu His Glu Arg Arg Val Phe His
        275                 280                 285
```

Leu Thr Val Ala Glu Pro His Ala Glu Pro Pro Pro Arg Gly Ser Pro
290 295 300

Gly Asn Gly Ser Ser His Ser Gly Ala Pro Gly Pro Asp Pro Thr Leu
305 310 315 320

Ala Arg Gly His Asn Val Ile Asn Val Ile Val Pro Glu Ser Arg Ala
325 330 335

His Phe Phe Gln Gln Leu Gly Tyr Val Leu Ala Thr Leu Leu Leu Phe
340 345 350

Ile Leu Leu Leu Val Thr Val Leu Leu Ala Ala Arg Arg Arg Arg Gly
355 360 365

Gly Tyr Glu Tyr Ser Asp Gln Lys Ser Gly Lys Ser Lys Gly Lys Asp
370 375 380

Val Asn Leu Ala Glu Phe Ala Val Ala Ala Gly Asp Gln Met Leu Tyr
385 390 395 400

Arg Ser Glu Asp Ile Gln Leu Ala Ser Ser Pro Pro Thr Asp Tyr Lys
405 410 415

Asn Asn Ile Leu Lys Glu Arg Ala Glu Leu Ala His Ser Pro Leu Pro
420 425 430

Ala Lys Tyr Ile Asp Leu Asp Lys Asp Pro Ser Gly Leu Cys Pro Leu
435 440 445

Gly Ala
450

<210> SEQ ID NO 31
<211> LENGTH: 442
<212> TYPE: PRT
<213> ORGANISM: homo sapiens

<400> SEQUENCE: 31

Met Ala Leu Pro Ser Arg Ile Leu Leu Trp Lys Leu Val Leu Leu Gln
1 5 10 15

Ser Ser Ala Val Leu Leu His Ser Gly Ser Ser Val Pro Ala Ala Ala
20 25 30

Gly Ser Ser Val Val Ser Glu Ser Ala Val Ser Trp Glu Ala Gly Ala
35 40 45

Arg Ala Val Leu Arg Cys Gln Ser Pro Arg Met Val Trp Thr Gln Asp
50 55 60

Arg Leu His Asp Arg Gln Arg Val Leu His Trp Asp Leu Arg Gly Pro
65 70 75 80

Gly Gly Gly Pro Ala Arg Arg Leu Leu Asp Leu Tyr Ser Ala Gly Glu
85 90 95

Gln Arg Val Tyr Glu Ala Arg Asp Arg Gly Arg Leu Glu Leu Ser Ala
100 105 110

Ser Ala Phe Asp Asp Gly Asn Phe Ser Leu Leu Ile Arg Ala Val Glu
115 120 125

Glu Thr Asp Ala Gly Leu Tyr Thr Cys Asn Leu His His His Tyr Cys
130 135 140

His Leu Tyr Glu Ser Leu Ala Val Arg Leu Glu Val Thr Asp Gly Pro
145 150 155 160

Pro Ala Thr Pro Ala Tyr Trp Asp Gly Glu Lys Glu Val Leu Ala Val
165 170 175

Ala Arg Gly Ala Pro Ala Leu Leu Thr Cys Val Asn Arg Gly His Val
180 185 190

Trp Thr Asp Arg His Val Glu Glu Ala Gln Gln Val Val His Trp Asp

```
        195                 200                 205

Arg Gln Pro Pro Gly Val Pro His Asp Arg Ala Asp Arg Leu Leu Asp
    210                 215                 220

Leu Tyr Ala Ser Gly Glu Arg Arg Ala Tyr Gly Pro Leu Phe Leu Arg
225                 230                 235                 240

Asp Arg Val Ala Val Gly Ala Asp Ala Phe Glu Arg Gly Asp Phe Ser
                245                 250                 255

Leu Arg Ile Glu Pro Leu Glu Val Ala Asp Glu Gly Thr Tyr Ser Cys
            260                 265                 270

His Leu His His His Tyr Cys Gly Leu His Glu Arg Arg Val Phe His
        275                 280                 285

Leu Thr Val Ala Glu Pro His Ala Glu Pro Pro Pro Arg Gly Ser Pro
    290                 295                 300

Gly Asn Gly Ser Ser His Ser Gly Ala Pro Gly Pro Asp Pro Thr Leu
305                 310                 315                 320

Ala Arg Gly His Asn Val Ile Asn Val Ile Val Pro Glu Ser Arg Ala
                325                 330                 335

His Phe Phe Gln Gln Leu Gly Tyr Val Leu Ala Thr Leu Leu Leu Phe
            340                 345                 350

Ile Leu Leu Leu Val Thr Val Leu Leu Ala Ala Arg Arg Arg Arg Gly
        355                 360                 365

Gly Tyr Glu Tyr Ser Asp Gln Lys Ser Gly Lys Ser Lys Gly Lys Asp
    370                 375                 380

Val Asn Leu Ala Glu Phe Ala Val Ala Ala Gly Asp Gln Met Leu Tyr
385                 390                 395                 400

Arg Ser Glu Asp Ile Gln Leu Asp Tyr Lys Asn Asn Ile Leu Lys Glu
                405                 410                 415

Arg Ala Glu Leu Ala His Ser Pro Leu Pro Ala Lys Tyr Ile Asp Leu
            420                 425                 430

Asp Lys Gly Phe Arg Lys Glu Asn Cys Lys
        435                 440
```

<210> SEQ ID NO 32
<211> LENGTH: 2280
<212> TYPE: DNA
<213> ORGANISM: Mus musculus

<400> SEQUENCE: 32

```
agtcaagatg ggggaggcca agcagttgag cagcgcagtg ggcggggccc agacccggcc     60

cagggctccg tgatgtcagc gggtgctggc agggagaggg ggtcggctgt ttttctggag    120

agttagagct gagtaagaca aagcacgtcc cccgcaggcg ccatggagct gctgtcccgc    180

gtcctgctgt ggaaactgct gcttcttcag agctctgcag tcctgtcctc agggccttca    240

gggaccgcag cagccagcag ctctctggtg tctgagtctg tggtgagctt ggcagccgga    300

acccaggctg tgctacgctg ccagagcccc cgcatggtgt ggacccaaga ccggctgcat    360

gatcgccagc gcgtggtcca ctgggacctc agcgggggcc cgggcagcca acggcgccga    420

cttgtggata tgtattcggc gggtgaacag cgcgtgtacg agccgcgcga tcgcgaccgc    480

ctcctgctgt cgccttctgc tttccacgac ggcaacttct cgctgctcat tcgcgctgtg    540

gacagaggcg atgaaggggt gtacacctgc aacctgcacc atcactactg ccacctcgat    600

gagagcctgg ctgtgcgcct cgaggttaca gaggatcccc tattaagtcg cgcatactgg    660

gacggtgaga aggaagtgtt ggtggtggcc catggcgcgc cggcactgat gacctgcatc    720
```

aaccgtgcgc acgtgtggac tgaccgccat ttagaggagg cgcagcaggt ggtccattgg 780
gaccgacagc tacctggggt gtcacacgac cgcgccgacc gcctgcttga cctgtatgca 840
tctggcgagc gccgcgccta tgggccaccc ttcctgcgtg atcgcgtgtc agtgaacacc 900
aacgcttttg cacgcggtga cttctcccta cgcatcgatg agctggagcg agctgatgag 960
ggcatctatt cctgccacct gcaccatcac tactgtggcc tccacgagcg ccgagtcttc 1020
cacctacagg tcacagagcc tgcctttgag ccaccagctc gtgcttctcc tggcaatggg 1080
tctggtcaca gcagtgctcc tagcccagat cccaccctga cccgaggcca cagcatcatc 1140
aatgtcattg tcccagagga ccacacacat ttcttccagc aactgggcta tgtgttggcc 1200
acgctgctgc tcttcatctt gctgctcatc actgtagtcc tggctacacg atatcgtcac 1260
agcggaggat gcaagacgtc ggacaaaaaa gctgggaagt caaaggggaa ggatgtgaac 1320
atggtggagt ttgctgtagc cacaagggat caggctccat ataggactga ggacatccag 1380
ctagattaca aaaacaacat cctgaaggag agggctgagc tggcccatag tcctctgcct 1440
gccaaggatg tggatctgga taaagagttc aggaaggagt actgcaaata aatggaccct 1500
gagcttctgg ctgggccagc agctctgtat caaaggacat ctccctgacc ctcctgcggt 1560
attcctggct cttctcagcg gctggtccga cttacctaga aacttggcag agcagctgcc 1620
tgtactttgc ccttcctaga atcgccaccc ctcatcttgg tgagcaactg tgggttccct 1680
agagactctg gtatagtacg attgctgccc ttcacctgtg cccactgatg gttgtacccc 1740
caacttaaac acaacaaaga tcccttgtta atatccacca aatgcaaagt ccctcgtggc 1800
ctcttactgc tagggtcagg aagacactta aaaattccag ttaagactcc ctagccacca 1860
gttaaacaca ttagccattg tcctgggggg tcttcctgag ctgcattgtg cctgtgtact 1920
gttcagagcc ctgctgttat aggttctgac tcatgggccc gccttgctgc tttgggcaac 1980
ttgaggctag cccagggccc tttctctgct tctgattcct ttctgccgaa tgcctcccaa 2040
gagctacacc agcagttact gggtaccgta tgactcttgg ccttgacatc cctccctagg 2100
ctggagtctg gggttggggc cccatttgtc ctctgttttg gctgaagatg gggcgaagat 2160
ttggctgagt ggcctatgct gtcacatcaa acagctatca tttactccta cttgggaagt 2220
tttcatgtga caataaaaga tacatctgat ttttagtctt ggaaaaaaaa aaaaaaaaaa 2280

<210> SEQ ID NO 33
<211> LENGTH: 2534
<212> TYPE: DNA
<213> ORGANISM: homo sapiens

<400> SEQUENCE: 33
atgtcctcgg accttcttgt ccctccaagg gtgcggtcac caccccctccc caggcctgac 60 cggtgagggg ctgggcctct gctcccacac tgcccctccc cagcaggcca gcaacgatgg 120
gggaggccaa ggggcccggc aggagccaga gggggcggtc cccagaccgt agacaggccc 180
aggcctccgt gatgtcaccg cgggtgctaa ggagggggag ggggtagggc tgtttttctg 240
gagagagact tagagccgag tgggacaaag cctggggctg ggcgggggcc atggcgctgc 300
catcccgaat cctgctttgg aaacttgtgc ttctgcagag ctctgctgtt ctcctgcact 360
cagggtcctc ggtacccgcc gctgctggca gctccgtggt gtccgagtcc gcggtgagct 420
gggaggcggg cgcccgggcg gtgctgcgct gccagagccc gcgcatggtg tggacccagg 480
accggctgca cgaccgccag cgcgtgctcc actgggacct gcgcggcccc gggggtggcc 540
ccgcgcggcg cctgctggac ttgtactcgg cgggcgagca gcgcgtgtac gaggcgcggg 600
accgcggccg cctggagctc tcggcctcgg ccttcgacga cggcaacttc tcgctgctca 660
tccgcgcggt ggaggagacg gacgcggggc tgtacacctg caacctgcac catcactact 720
gccacctcta cgagagcctg gccgtccgcc tggaggtcac cgacggcccc ccggccaccc 780
ccgcctactg ggacggcgag aaggaggtgc tggcggtggc gcgcggcgca cccgcgcttc 840
tgacctgcgt gaaccgcggg cacgtgtgga ccgaccggca cgtggaggag gctcaacagg 900
tggtgcactg ggaccggcag ccgcccgggg tcccgcacga ccgcgcggac cgcctgctgg 960
acctctacgc gtcgggcgag cgccgcgcct acgggcccct tttctgcgc gaccgcgtgg 1020 ctgtgggcgc ggatgccttt gagcgcggtg acttctcact gcgtatcgag ccgctggagg 1080
tcgccgacga gggcacctac tcctgccacc tgcaccacca ttactgtggc ctgcacgaac 1140
gccgcgtctt ccacctgacg gtcgccgaac cccacgcgga gccgcccccc cggggctctc 1200
cgggcaacgg ctccagccac agcggcgccc caggcccaga ccccacactg gcgcgcggcc 1260
acaacgtcat caatgtcatc gtccccgaga gccgagccca cttcttccag cagctgggct 1320
acgtgctggc cacgctgctg ctcttcatcc tgctactggt cactgtcctc ctggccgccc 1380
gcaggcgccg cggaggctac gaatactcgg accagaagtc gggaaagtca aaggggaagg 1440
atgttaactt ggcggagttc gctgtggctg caggggacca gatgctttac aggagtgagg 1500
acatccagct agattacaaa aacaacatcc tgaaggagag ggcggagctg gcccacagcc 1560
ccctgcctgc caagtacatc gacctagaca aagggttccg gaaggagaac tgcaaatagg 1620
gaggccctgg gctcctggct gggccagcag ctgcacctct cctgtctgtg ctcctcgggg 1680
catctcctga tgctccgggg ctcacccccc ttccagcggc tggtcccgct ttcctggaat 1740
ttggcctggg cgtatgcaga ggccgcctcc acacccctct cccaggggct tggtggcagc 1800
atagccccca cccctgcggc ctttgctcac gggtggccct gcccacccct ggcacaacca 1860
aaatcccact gatgcccatc atgccctcag acccttctgg gctctgcccg ctgggggcct 1920
gaagacattc ctggaggaca ctcccatcag aacctggcag ccccaaaact ggggtcagcc 1980
tcagggcagg agtcccactc ctccagggct ctgctcgtcc ggggctggga gatgttcctg 2040
gaggaggaca ctcccatcag aacttggcag ccttgaagtt ggggtcagcc tcggcaggag 2100
tcccactcct cctggggtgc tgcctgccac cgagagctcc cccacctgta ccaccatgtg 2160
ggactccagg caccatctgt tctccccagg gacctgctga cttgaatgcc agcccttgct 2220
cctctgtgtt gctttgggcc acctggggct gcaccccctg ccctttctct gccccatccc 2280
taccctagcc ttgctctcag ccaccttgat agtcactggg ctccctgtga cttctgaccc 2340
tgacacccct cccttggact ctgcctgggc tggagtctag ggctggggct acatttggct 2400
tctgtactgg ctgaggacag gggagggagt gaagttggtt tggggtggcc tgtgttgcca 2460
ctctcagcac cccacatttg catctgctgg tggacctgcc accatcacaa taaagtcccc 2520
atctgatttt taga 2534

<210> SEQ ID NO 34
<211> LENGTH: 20
<212> TYPE: DNA
<213> ORGANISM: Artificial Sequence
<220> FEATURE:
<223> OTHER INFORMATION: synthetic RNA

<400> SEQUENCE: 34
cttgtggata tgtattcggc 20

<210> SEQ ID NO 35
<211> LENGTH: 20
<212> TYPE: DNA
<213> ORGANISM: Artificial Sequence
<220> FEATURE:
<223> OTHER INFORMATION: synthetic RNA

<400> SEQUENCE: 35
tgtgcgcctc gaggttacag 20

<210> SEQ ID NO 36
<211> LENGTH: 20
<212> TYPE: DNA
<213> ORGANISM: Artificial Sequence
<220> FEATURE:
<223> OTHER INFORMATION: synthetic RNA

<400> SEQUENCE: 36
gctgcatgat cgccagcgcg 20

<210> SEQ ID NO 37
<211> LENGTH: 20
<212> TYPE: DNA
<213> ORGANISM: Artificial Sequence
<220> FEATURE:
<223> OTHER INFORMATION: Synthetic RNA

<400> SEQUENCE: 37
ggcgcggatg cctttgagcg 20

<210> SEQ ID NO 38
<211> LENGTH: 20
<212> TYPE: DNA
<213> ORGANISM: Artificial Sequence
<220> FEATURE:
<223> OTHER INFORMATION: Synthetic RNA

<400> SEQUENCE: 38
gtccgcctgg aggtcaccga 20

<210> SEQ ID NO 39
<211> LENGTH: 21
<212> TYPE: DNA
<213> ORGANISM: Artificial Sequence
<220> FEATURE:
<223> OTHER INFORMATION: Mxra8 sgRNA target sequence

<400> SEQUENCE: 39
cttgtggata tgtattcggc g 21

<210> SEQ ID NO 40
<211> LENGTH: 21
<212> TYPE: DNA
<213> ORGANISM: Artificial Sequence
<220> FEATURE:
<223> OTHER INFORMATION: Mxra8 sgRNA mutated target sequence

<400> SEQUENCE: 40
ctggtcgaca tgtacagcgc g 21

<210> SEQ ID NO 41
<211> LENGTH: 114
<212> TYPE: DNA
<213> ORGANISM: Artificial Sequence
<220> FEATURE:
<223> OTHER INFORMATION: PLAP

<400> SEQUENCE: 41
ctggcgcccc ccgccggcac caccgacgcc gcgcacccgg ggcggtccgt ggtccccgcg 60
ttgcttcctc tgctggccgg gaccctgctg ctgctggaga cggccactgc tccc 114

<210> SEQ ID NO 42
<211> LENGTH: 105
<212> TYPE: DNA
<213> ORGANISM: Mus musculus

<400> SEQUENCE: 42
tacccatacg atgttccaga ttacgctacg tcctcaccat ccattggcgg cccaaacatg 60
actttactat tggccatgat catgtttgcg ttaaagatag ggtcg 105

<210> SEQ ID NO 43
<211> LENGTH: 2534
<212> TYPE: DNA
<213> ORGANISM: Homo Sapiens

<400> SEQUENCE: 43
atgtcctcgg accttcttgt ccctccaagg gtgcggtcac cacccctccc caggcctgac 60
cggtgagggg ctgggcctct gctcccacac tgcccctccc cagcaggcca gcaacgatgg 120
gggaggccaa ggggcccggc aggagccaga gggggcggtc cccagaccgt agacaggccc 180
aggcctccgt gatgtcaccg cgggtgctaa ggagggggag ggggtagggc tgtttttctg 240
gagagagact tagagccgag tgggacaaag cctggggctg ggcgggggcc atggcgctgc 300
catcccgaat cctgctttgg aaacttgtgc ttctgcagag ctctgctgtt ctcctgcact 360
cagggtcctc ggtacccgcc gctgctggca gctccgtggt gtccgagtcc gcggtgagct 420
gggaggcggg cgcccgggcg gtgctgcgct gccagagccc gcgcatggtg tggacccagg 480
accggctgca cgaccgccag cgcgtgctcc actgggacct gcgcggcccc gggggtggcc 540
ccgcgcggcg cctgctggac ttgtactcgg cgggcgagca gcgcgtgtac gaggcgcggg 600
accgcggccg cctggagctc tcggcctcgg ccttcgacga cggcaacttc tcgctgctca 660
tccgcgcggt ggaggagacg gacgcggggc tgtacacctg caacctgcac catcactact 720
gccacctcta cgagagcctg gccgtccgcc tggaggtcac cgacggcccc ccggccaccc 780
ccgcctactg ggacggcgag aaggaggtgc tggcggtggc gcgcggcgca cccgcgcttc 840
tgacctgcgt gaaccgcggg cacgtgtgga ccgaccggca cgtggaggag gctcaacagg 900
tggtgcactg ggaccggcag ccgcccgggg tcccgcacga ccgcgcggac cgcctgctgg 960
acctctacgc gtcgggcgag cgccgcgcct acgggcccct ttttctgcgc gaccgcgtgg 1020
ctgtgggcgc ggatgccttt gagcgcggtg acttctcact gcgtatcgag ccgctggagg 1080
tcgccgacga gggcacctac tcctgccacc tgcaccacca ttactgtggc ctgcacgaac 1140
gccgcgtctt ccacctgacg gtcgccgaac cccacgcgga gccgcccccc cggggctctc 1200
cgggcaacgg ctccagccac agcggcgccc caggcccaga ccccacactg gcgcgcggcc 1260
acaacgtcat caatgtcatc gtccccgaga gccgagccca cttcttccag cagctgggct 1320
acgtgctggc cacgctgctg ctcttcatcc tgctactggt cactgtcctc ctggccgccc 1380
gcaggcgccg cggaggctac gaatactcgg accagaagtc gggaaagtca aaggggaagg 1440
atgttaactt ggcggagttc gctgtggctg caggggacca gatgctttac aggagtgagg 1500
acatccagct agattacaaa aacaacatcc tgaaggagag ggcggagctg gcccacagcc 1560

```
ccctgcctgc caagtacatc gacctagaca aagggttccg gaaggagaac tgcaaatagg   1620
gaggccctgg gctcctggct gggccagcag ctgcacctct cctgtctgtg ctcctcgggg   1680
catctcctga tgctccgggg ctcacccccc ttccagcggc tggtcccgct ttcctggaat   1740
ttggcctggg cgtatgcaga ggccgcctcc acacccctct cccaggggct tggtggcagc   1800
atagccccca cccctgcggc ctttgctcac gggtggccct gcccacccct ggcacaacca   1860
aaatcccact gatgcccatc atgccctcag acccttctgg gctctgcccg ctggggggcct   1920
gaagacattc ctggaggaca ctcccatcag aacctggcag ccccaaaact ggggtcagcc   1980
tcagggcagg agtcccactc ctccagggct ctgctcgtcc ggggctggga gatgttcctg   2040
gaggaggaca ctcccatcag aacttggcag ccttgaagtt ggggtcagcc tcggcaggag   2100
tcccactcct cctggggtgc tgcctgccac cgagagctcc cccacctgta ccaccatgtg   2160
ggactccagg caccatctgt tctccccagg gacctgctga cttgaatgcc agcccttgct   2220
cctctgtgtt gctttgggcc acctggggct gcacccccctg ccctttctct gccccatccc   2280
taccctagcc ttgctctcag ccaccttgat agtcactggg ctccctgtga cttctgaccc   2340
tgacacccct cccttggact ctgcctgggc tggagtctag ggctggggct acatttggct   2400
tctgtactgg ctgaggacag gggagggagt gaagttggtt tggggtggcc tgtgttgcca   2460
ctctcagcac cccacatttg catctgctgg tggacctgcc accatcacaa taaagtcccc   2520
atctgatttt taga                                                     2534
```

<210> SEQ ID NO 44
<211> LENGTH: 2008
<212> TYPE: DNA
<213> ORGANISM: Homo Sapiens

<400> SEQUENCE: 44

```
acttagagcc gagtgggaca aagcctgggg ctgggcgggg gccatggcgc tgccatcccg     60
aatcctgctt tggaaacttg tgcttctgca gagctctgct gttctcctgc actcagggtc    120
ctcggtaccc gccgctgctg gcagctccgt ggtgtccgag tccgcggtga gctgggaggc    180
gggcgcccgg gcggtgctgc gctgccagag cccgcgcatg gtgtggaccc aggaccggct    240
gcacgaccgc cagcgcgtgc tccactggga cctgcgcggc cccgggggtg gccccgcgcg    300
gcgcctgctg gacttgtact cggcgggcga gcagcgcgtg tacgaggcgc gggaccgcgg    360
ccgcctggag ctctcggcct cggccttcga cgacggcaac ttctcgctgc tcatccgcgc    420
ggtggaggag acggacgcgg ggctgtacac ctgcaacctg caccatcact actgccacct    480
ctacgagagc ctggccgtcc gcctggaggt caccgacggc cccccggcca cccccgccta    540
ctgggacggc gagaaggagg tgctggcggt ggcgcgcggc gcacccgcgc ttctgacctg    600
cgtgaaccgc gggcacgtgt ggaccgaccg gcacgtggag gaggctcaac aggtggtgca    660
ctgggaccgg cagccgcccg gggtcccgca cgaccgcgcg gaccgcctgc tggacctcta    720
cgcgtcgggc gagcgccgcg cctacgggcc cctttttctg cgcgaccgcg tggctgtggg    780
cgcggatgcc tttgagcgcg gtgacttctc actgcgtatc gagccgctgg aggtcgccga    840
cgagggcacc tactcctgcc acctgcacca ccattactgt ggcctgcacg aacgccgcgt    900
cttccacctg acggtcgccg aaccccacgc ggagccgccc ccccggggct ctccgggcaa    960
cggctccagc cacagcggcg ccccaggccc agaccccaca ctggcgcgcg gccacaacgt   1020
catcaatgtc atcgtccccg agagccgagc ccacttcttc cagcagctgg gctacgtgct   1080
ggccacgctg ctgctcttca tcctgctact ggtcactgtc ctcctggccg cccgcaggcg   1140
```

ccgcggaggc tacgaatact cggaccagaa gtcgggaaag tcaaagggga aggatgttaa 1200
cttggcggag ttcgctgtgg ctgcagggga ccagatgctt tacaggagtg aggacatcca 1260
gctagcctcc tctcctccca cagattacaa aaacaacatc ctgaaggaga gggcggagct 1320
ggcccacagc cccctgcctg ccaagtacat cgacctagac aaagaccctt ctgggctctg 1380
cccgctgggg gcctgaagac attcctggag gacactccca tcagaacctg gcagccccaa 1440
aactggggtc agcctcaggg caggagtccc actcctccag ggctctgctc gtccggggct 1500
gggagatgtt cctggaggag gacactccca tcagaacttg gcagccttga agttggggtc 1560
agcctcggca ggagtcccac tcctcctggg gtgctgcctg ccaccgagag ctcccccacc 1620
tgtaccacca tgtgggactc caggcaccat ctgttctccc cagggacctg ctgacttgaa 1680
tgccagccct tgctcctctg tgttgctttg ggccacctgg ggctgcaccc cctgcccttt 1740
ctctgcccca tccctaccct agccttgctc tcagccacct tgatagtcac tgggctccct 1800
gtgacttctg accctgacac ccctcccttg gactctgcct gggctggagt ctagggctgg 1860
ggctacattt ggcttctgta ctggctgagg acaggggagg gagtgaagtt ggtttggggt 1920
ggcctgtgtt gccactctca gcaccccaca tttgcatctg ctggtggacc tgccaccatc 1980
acaataaagt ccccatctga tttttaga 2008

<210> SEQ ID NO 45
<211> LENGTH: 2231
<212> TYPE: DNA
<213> ORGANISM: Homo sapiens

<400> SEQUENCE: 45
atgtcctcgg accttcttgt ccctccaagg gtgcggtcac cacccctccc caggcctgac 60
cggtgagggg ctgggcctct gctcccacac tgcccctccc cagcaggcca gcaacgatgg 120
gggaggccaa ggggcccggc aggagccaga gggggcggtc cccagaccgt agacaggccc 180
aggcctccgt gatgtcaccg cgggtgctaa ggagggggag ggggtagggc tgtttttctg 240
gagagagact tagagccgag tgggacaaag cctggggctg ggcgggggcc atggcgctgc 300
catcccgaat cctgctttgg aaacttgtgc ttctgcagag ctctgctgtt ctcctgcact 360
cagcggtgga ggagacggac gcggggctgt acacctgcaa cctgcaccat cactactgcc 420
acctctacga gagcctggcc gtccgcctgg aggtcaccga cggccccccg gccacccccg 480
cctactggga cggcgagaag gaggtgctgg cggtggcgcg cggcgcaccc gcgcttctga 540
cctgcgtgaa ccgcgggcac gtgtggaccg accggcacgt ggaggaggct caacaggtgg 600
tgcactggga ccggcagccg cccggggtcc cgcacgaccg cgcggaccgc ctgctggacc 660
tctacgcgtc gggcgagcgc cgcgcctacg ggcccctttt tctgcgcgac cgcgtggctg 720
tgggcgcgga tgcctttgag cgcggtgact tctcactgcg tatcgagccg ctggaggtcg 780
ccgacgaggg cacctactcc tgccacctgc accaccatta ctgtggcctg cacgaacgcc 840
gcgtcttcca cctgacggtc gccgaacccc acgcggagcc gcccccccgg ggctctccgg 900
gcaacggctc cagccacagc ggcgccccag gcccagaccc cacactggcg cgcggccaca 960
acgtcatcaa tgtcatcgtc cccgagagcc gagcccactt cttccagcag ctgggctacg 1020
tgctggccac gctgctgctc ttcatcctgc tactggtcac tgtcctcctg gccgcccgca 1080
ggcgccgcgg aggctacgaa tactcggacc agaagtcggg aaagtcaaag gggaaggatg 1140
ttaacttggc ggagttcgct gtggctgcag gggaccagat gctttacagg agtgaggaca 1200

```
tccagctaga ttacaaaaac aacatcctga aggagagggc ggagctggcc cacagccccc   1260
tgcctgccaa gtacatcgac ctagacaaag ggttccggaa ggagaactgc aaatagggag   1320
gccctgggct cctggctggg ccagcagctg cacctctcct gtctgtgctc ctcggggcat   1380
ctcctgatgc tccggggctc acccccccttc cagcggctgg tcccgctttc ctggaatttg   1440
gcctgggcgt atgcagaggc cgcctccaca cccctctccc aggggcttgg tggcagcata   1500
gcccccaccc ctgcggcctt tgctcacggg tggccctgcc cacccctggc acaaccaaaa   1560
tcccactgat gcccatcatg ccctcagacc cttctgggct ctgcccgctg gggggcctgaa   1620
gacattcctg gaggacactc ccatcagaac ctggcagccc caaaactggg gtcagcctca   1680
gggcaggagt cccactcctc cagggctctg ctcgtccggg gctgggagat gttcctggag   1740
gaggacactc ccatcagaac ttggcagcct tgaagttggg gtcagcctcg gcaggagtcc   1800
cactcctcct ggggtgctgc ctgccaccga gagctccccc acctgtacca ccatgtggga   1860
ctccaggcac catctgttct ccccagggac ctgctgactt gaatgccagc ccttgctcct   1920
ctgtgttgct ttgggccacc tggggctgca ccccctgccc tttctctgcc ccatccctac   1980
cctagccttg ctctcagcca ccttgatagt cactgggctc cctgtgactt ctgaccctga   2040
cacccctccc ttggactctg cctgggctgg agtctagggc tggggctaca tttggcttct   2100
gtactggctg aggacagggg agggagtgaa gttggtttgg ggtggcctgt gttgccactc   2160
tcagcacccc acatttgcat ctgctggtgg acctgccacc atcacaataa agtccccatc   2220
tgatttttag a                                                        2231
```

<210> SEQ ID NO 46
<211> LENGTH: 2731
<212> TYPE: DNA
<213> ORGANISM: Homo sapiens

<400> SEQUENCE: 46

```
aagaaggctg gcggtgtttc ctcttagagg ggagaaactc agcctgggta ggagacccag     60
ccccacgcag ggaaaactgt gctaacgctt ccgatgtgcg tggcaggtgc ggcggcggcg    120
aatacggttt gtcctcgagc ctaaccctgt ctgtgttggt gtcagcagtg gcccccctac    180
cacacacaca gggtccctgg cgtcccaaga ccactcctgg cagccccgcc actggctgcg    240
cctggaagcc gcgtcctcag gcctcgcctg gcatttgctg tcacagaggt tgcttccttg    300
ggtccgtccg tcctcgcccc tccagcctgg gcgccccccg accccctgtct cattccctcc    360
accacatgca gcacagtcca ggaggctggg gtccaagagg gccatggctg gcacccggct    420
tagtgctgag tccccagtgc ccagcaagcc tggcacccag gaggtggtca gcaaacgctt    480
ctgaacgaca ggaagtggga ctcttcagcc atcgatgatc cgctgtgcgg ccacaggctc    540
tgctgttctc ctgcactcag ggtcctcggt acccgccgct gctggcagct ccgtggtgtc    600
cgagtccgcg gtgagctggg aggcgggcgc ccgggcggtg ctgcgctgcc agagcccgcg    660
catggtgtgg acccaggacc ggctgcacga ccgccagcgc gtgctccact gggacctgcg    720
cggccccggg ggtggccccg cgcggcgcct gctggacttg tactcggcgg gcgagcagcg    780
cgtgtacgag gcgcgggacc gcggccgcct ggagctctcg gcctcggcct tcgacgacgg    840
caacttctcg ctgctcatcc gcgcggtgga ggagacggac gcggggctgt acacctgcaa    900
cctgcaccat cactactgcc acctctacga gagcctggcc gtccgcctgg aggtcaccga    960
cggcccccccg gccacccccg cctactggga cggcgagaag gaggtgctgg cggtggcgcg   1020
cggcgcaccc gcgcttctga cctgcgtgaa ccgcgggcac gtgtggaccg accggcacgt   1080
```

```
ggaggaggct caacaggtgg tgcactggga ccggcagccg cccggggtcc cgcacgaccg   1140

cgcggaccgc ctgctggacc tctacgcgtc gggcgagcgc cgcgcctacg ggccccttt    1200

tctgcgcgac cgcgtggctg tgggcgcgga tgcctttgag cgcggtgact tctcactgcg   1260

tatcgagccg ctggaggtcg ccgacgaggg cacctactcc tgccacctgc accaccatta   1320

ctgtggcctg cacgaacgcc gcgtcttcca cctgacggtc gccgaacccc acgcggagcc   1380

gcccccccgg ggctctccgg gcaacggctc cagccacagc ggcgccccag gcccagaccc   1440

cacactggcg cgcggccaca acgtcatcaa tgtcatcgtc cccgagagcc gagcccactt   1500

cttccagcag ctgggctacg tgctggccac gctgctgctc ttcatcctgc tactggtcac   1560

tgtcctcctg gccgcccgca ggcgccgcgg aggctacgaa tactcggacc agaagtcggg   1620

aaagtcaaag gggaaggatg ttaacttggc ggagttcgct gtggctgcag gggaccagat   1680

gctttacagg agtgaggaca tccagctaga ttacaaaaac aacatcctga aggagagggc   1740

ggagctggcc cacagccccc tgcctgccaa gtacatcgac ctagacaaag ggttccggaa   1800

ggagaactgc aaatagggag gccctgggct cctggctggg ccagcagctg cacctctcct   1860

gtctgtgctc ctcggggcat ctcctgatgc tccggggctc acccccttc cagcggctgg    1920

tcccgctttc ctggaatttg gcctgggcgt atgcagaggc cgcctccaca cccctctccc   1980

aggggcttgg tggcagcata gcccccaccc ctgcggcctt tgctcacggg tggccctgcc   2040

cacccctggc acaaccaaaa tcccactgat gcccatcatg ccctcagacc cttctgggct   2100

ctgcccgctg ggggcctgaa gacattcctg gaggacactc ccatcagaac ctggcagccc   2160

caaaactggg gtcagcctca gggcaggagt cccactcctc cagggctctg ctcgtccggg   2220

gctgggagat gttcctggag gaggacactc ccatcagaac ttggcagcct tgaagttggg   2280

gtcagcctcg gcaggagtcc cactcctcct ggggtgctgc ctgccaccga gagctccccc   2340

acctgtacca ccatgtggga ctccaggcac catctgttct ccccagggac ctgctgactt   2400

gaatgccagc ccttgctcct ctgtgttgct ttgggccacc tggggctgca ccccctgccc   2460

tttctctgcc ccatccctac cctagccttg ctctcagcca ccttgatagt cactgggctc   2520

cctgtgactt ctgaccctga cacccctccc ttggactctg cctgggctgg agtctagggc   2580

tggggctaca tttggcttct gtactggctg aggacagggg agggagtgaa gttggtttgg   2640

ggtggcctgt gttgccactc tcagcacccc acatttgcat ctgctggtgg acctgccacc   2700

atcacaataa agtccccatc tgatttttag a                                  2731
```

<210> SEQ ID NO 47
<211> LENGTH: 18
<212> TYPE: DNA
<213> ORGANISM: Artificial Sequence
<220> FEATURE:
<223> OTHER INFORMATION: synthetic primer

<400> SEQUENCE: 47

```
tcgacgcgcc atctttaa                                                   18
```

<210> SEQ ID NO 48
<211> LENGTH: 19
<212> TYPE: DNA
<213> ORGANISM: Artificial Sequence
<220> FEATURE:
<223> OTHER INFORMATION: synthetic primer

<400> SEQUENCE: 48
atcgaatgca ccgcacact 19

<210> SEQ ID NO 49
<211> LENGTH: 25
<212> TYPE: DNA
<213> ORGANISM: Artificial Sequence
<220> FEATURE:
<223> OTHER INFORMATION: synthetic sequence

<400> SEQUENCE: 49
accagcctgc acccactcct cagac 25

<210> SEQ ID NO 50
<211> LENGTH: 24
<212> TYPE: DNA
<213> ORGANISM: Artificial Sequence
<220> FEATURE:
<223> OTHER INFORMATION: synthetic sequence

<400> SEQUENCE: 50
gtggagtcat actggaacat gtag 24

<210> SEQ ID NO 51
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 51
tgcaaatggc agccctggtg 20

<210> SEQ ID NO 52
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 52

Leu Glu Val Leu Phe Gln Gly Pro
1               5

<210> SEQ ID NO 53
<211> LENGTH: 44
<212> TYPE: PRT
<213> ORGANISM: Mus musculus

<400> SEQUENCE: 53

Trp Thr Gln Asp Arg Leu His Asp Arg Gln Arg Val Val His Trp Asp
1               5                   10                  15

Leu Ser Gly Gly Pro Gly Ser Gln Arg Arg Arg Leu Val Asp Met Tyr
            20                  25                  30

Ser Ala Gly Glu Gln Arg Val Tyr Glu Pro Arg Asp
        35                  40

<210> SEQ ID NO 54
<211> LENGTH: 60
<212> TYPE: PRT
<213> ORGANISM: Artificial Sequence
<220> FEATURE:
<223> OTHER INFORMATION: Bovine

<400> SEQUENCE: 54

Trp Thr Gln Asp Arg Leu His Asp Arg Gln Arg Val Val His Trp Asp

```
1               5                   10                  15

Leu Ser Gly Ser Lys Ala Gly Gly Pro Ala Arg Arg Leu Val Asp Met
            20                  25                  30

Tyr Ser Thr Gly Glu Gln Arg Val Gly Glu Gln Arg Leu Gly Glu Gln
        35                  40                  45

Arg Val Gly Glu Gln Arg Val Tyr Glu Pro Arg Asp
    50                  55                  60


<210> SEQ ID NO 55
<211> LENGTH: 64
<212> TYPE: DNA
<213> ORGANISM: Mus musculus

<400> SEQUENCE: 55

gccaacggcg ccgacttgtg gatatgtatt cggcgggtga acagcgcgtg tacgagccgc     60

gcga                                                                  64


<210> SEQ ID NO 56
<211> LENGTH: 53
<212> TYPE: DNA
<213> ORGANISM: Artificial Sequence
<220> FEATURE:
<223> OTHER INFORMATION: mutant Mxra8 allele

<400> SEQUENCE: 56

gccaacggcg ccgacttgtg gatatgtgaa cagcgcgtgt acgagccgcg cga            53


<210> SEQ ID NO 57
<211> LENGTH: 62
<212> TYPE: DNA
<213> ORGANISM: Artificial Sequence
<220> FEATURE:
<223> OTHER INFORMATION: mutant Mxra8 allele

<400> SEQUENCE: 57

gccaacggcg ccgacttgtg gatatgtatg gcgggtgaac agcgcgtgta cgagccgcgc     60

ga                                                                    62


<210> SEQ ID NO 58
<211> LENGTH: 64
<212> TYPE: DNA
<213> ORGANISM: Mus musculus

<400> SEQUENCE: 58

gccaacggcg ccgacttgtg gatatgtatt cggcgggtga acagcgcgtg tacgagccgc     60

gcga                                                                  64


<210> SEQ ID NO 59
<211> LENGTH: 58
<212> TYPE: DNA
<213> ORGANISM: Artificial Sequence
<220> FEATURE:
<223> OTHER INFORMATION: mutant Mxra8 allele

<400> SEQUENCE: 59

gccaacggcg ccgacttgtg gatatggcgg gtgaacagcg cgtgtacgag ccgcgcga       58


<210> SEQ ID NO 60
<211> LENGTH: 60
<212> TYPE: DNA
<213> ORGANISM: Artificial Sequence
<220> FEATURE:
```

<223> OTHER INFORMATION: mutant Mxra8 allele

<400> SEQUENCE: 60
gccaacggcg ccgacttgtg gatatgtggc gggtgaacag cgcgtgtacg agccgcgcga 60

<210> SEQ ID NO 61
<211> LENGTH: 65
<212> TYPE: DNA
<213> ORGANISM: mutant Mxra8 allele

<400> SEQUENCE: 61
gccaacggcg ccgacttgtg gatatgtatt ctggcgggtg aacagcgcgt gtacgagccg 60
cgcga 65

<210> SEQ ID NO 62
<211> LENGTH: 44
<212> TYPE: PRT
<213> ORGANISM: Mus musculus

<400> SEQUENCE: 62

Trp Thr Gln Asp Arg Leu His Asp Arg Gln Arg Val Val His Trp Asp
1 5 10 15

Leu Ser Gly Gly Pro Gly Ser Gln Arg Arg Arg Leu Val Asp Met Tyr
20 25 30

Ser Ala Gly Glu Gln Arg Val Tyr Glu Pro Arg Asp
35 40

<210> SEQ ID NO 63
<211> LENGTH: 59
<212> TYPE: PRT
<213> ORGANISM: Artificial Sequence
<220> FEATURE:
<223> OTHER INFORMATION: mouse Mxra8 + moo

<400> SEQUENCE: 63

Trp Thr Gln Asp Arg Leu His Asp Arg Gln Arg Val Val His Trp Asp
1 5 10 15

Leu Ser Gly Gly Pro Gly Ser Gln Arg Arg Arg Leu Val Asp Met Tyr
20 25 30

Ser Ala Gly Glu Gln Arg Val Gly Glu Gln Arg Leu Gly Glu Gln Arg
35 40 45

Val Gly Glu Gln Arg Val Tyr Glu Pro Arg Asp
50 55

<210> SEQ ID NO 64
<211> LENGTH: 60
<212> TYPE: PRT
<213> ORGANISM: Bos taurus

<400> SEQUENCE: 64

Trp Thr Gln Asp Arg Leu His Asp Arg Gln Arg Val Val His Trp Asp
1 5 10 15

Leu Ser Gly Ser Lys Ala Gly Gly Pro Ala Arg Arg Leu Val Asp Met
20 25 30

Tyr Ser Thr Gly Glu Gln Arg Val Gly Glu Gln Arg Leu Gly Glu Gln
35 40 45

Arg Val Gly Glu Gln Arg Val Tyr Glu Pro Arg Asp
50 55 60

<210> SEQ ID NO 65

<211> LENGTH: 45
<212> TYPE: PRT
<213> ORGANISM: Artificial Sequence
<220> FEATURE:
<223> OTHER INFORMATION: cow Mxra8 delta moo

<400> SEQUENCE: 65

Trp Thr Gln Asp Arg Leu His Asp Arg Gln Arg Val Val His Trp Asp
1 5 10 15

Leu Ser Gly Ser Lys Ala Gly Gly Pro Ala Arg Arg Leu Val Asp Met
20 25 30

Tyr Ser Thr Gly Glu Gln Arg Val Tyr Glu Pro Arg Asp
35 40 45

<210> SEQ ID NO 66
<211> LENGTH: 196
<212> TYPE: DNA
<213> ORGANISM: Artificial Sequence
<220> FEATURE:
<223> OTHER INFORMATION: Mxra8 mutant

<400> SEQUENCE: 66
tgatgagggc atctattcct gccacctgcc acctgcacca tcactactgt ggcctccacg 60
agcgccgagt cttccaccta caggtcacag agcctgcctt tgagccacca gctcgtgctt 120
ctcctgtctg gtcacagcag tgctcctagc ccaggtgtgt gtgtagcctg ccggcctgag 180
aagaggtcct gttgtg 196

<210> SEQ ID NO 67
<211> LENGTH: 204
<212> TYPE: DNA
<213> ORGANISM: Mus musculus

<400> SEQUENCE: 67
tgatgagggc atctattcct gccacctgcc acctgcacca tcactactgt ggcctccacg 60
agcgccgagt cttccaccta caggtcacag agcctgcctt tgagccacca gctcgtgctt 120
ctcctggcaa tgggtctggt cacagcagtg ctcctagccc aggtgtgtgt gtagcctgcc 180
ggcctgagaa gaggtcctgt tgtg 204

<210> SEQ ID NO 68
<211> LENGTH: 196
<212> TYPE: DNA
<213> ORGANISM: Artificial Sequence
<220> FEATURE:
<223> OTHER INFORMATION: Mxra8 del 8 mutant

<400> SEQUENCE: 68
tgatgagggc atctattcct gccacctgcc acctgcacca tcactactgt ggcctccacg 60
agcgccgagt cttccaccta caggtcacag agcctgcctt tgagccacca gctcgtgctt 120
ctcctgtctg gtcacagcag tgctcctagc ccaggtgtgt gtgtagcctg ccggcctgag 180
aagaggtcct gttgtg 196

<210> SEQ ID NO 69
<211> LENGTH: 107
<212> TYPE: DNA
<213> ORGANISM: Artificial Sequence
<220> FEATURE:
<223> OTHER INFORMATION: Mxra8 del 97 mutant

<400> SEQUENCE: 69

```
tgatgagggc atctattcct gccacctgcc acctgcacca tcactactgt ggcctcctag      60

cccaggtgtg tgtgtagcct gccggcctga gaagaggtcc tgttgtg                   107


<210> SEQ ID NO 70
<211> LENGTH: 311
<212> TYPE: PRT
<213> ORGANISM: Mus musculus

<400> SEQUENCE: 70

Ser Gly Pro Ser Gly Thr Ala Ala Ala Ser Ser Ser Leu Val Ser Glu
1               5                   10                  15

Ser Val Val Ser Leu Ala Ala Gly Thr Gln Ala Val Leu Arg Cys Gln
            20                  25                  30

Ser Pro Arg Met Val Trp Thr Gln Asp Arg Leu His Asp Arg Gln Arg
        35                  40                  45

Val Val His Trp Asp Leu Ser Gly Gly Pro Gly Ser Gln Arg Arg Arg
    50                  55                  60

Leu Val Asp Met Tyr Ser Ala Gly Glu Gln Arg Val Tyr Glu Pro Arg
65                  70                  75                  80

Asp Arg Asp Arg Leu Leu Leu Ser Pro Ser Ala Phe His Asp Gly Asn
                85                  90                  95

Phe Ser Leu Leu Ile Arg Ala Val Asp Arg Gly Asp Glu Gly Val Tyr
            100                 105                 110

Thr Cys Asn Leu His His His Tyr Cys His Leu Asp Glu Ser Leu Ala
        115                 120                 125

Val Arg Leu Glu Val Thr Glu Asp Pro Leu Leu Ser Arg Ala Tyr Trp
    130                 135                 140

Asp Gly Glu Lys Glu Val Leu Val Val Ala His Gly Ala Pro Ala Leu
145                 150                 155                 160

Met Thr Cys Ile Asn Arg Ala His Val Trp Thr Asp Arg His Leu Glu
                165                 170                 175

Glu Ala Gln Gln Val Val His Trp Asp Arg Gln Leu Pro Gly Val Ser
            180                 185                 190

His Asp Arg Ala Asp Arg Leu Leu Asp Leu Tyr Ala Ser Gly Glu Arg
        195                 200                 205

Arg Ala Tyr Gly Pro Pro Phe Leu Arg Asp Arg Val Ser Val Asn Thr
    210                 215                 220

Asn Ala Phe Ala Arg Gly Asp Phe Ser Leu Arg Ile Asp Glu Leu Glu
225                 230                 235                 240

Arg Ala Asp Glu Gly Ile Tyr Ser Cys His Leu His His His Tyr Cys
                245                 250                 255

Gly Leu His Glu Arg Arg Val Phe His Leu Gln Val Thr Glu Pro Ala
            260                 265                 270

Phe Glu Pro Pro Ala Arg Ala Ser Pro Gly Asn Gly Ser Gly His Ser
        275                 280                 285

Ser Ala Pro Ser Pro Asp Pro Thr Leu Thr Arg Gly His Ser Ile Ile
    290                 295                 300

Asn Val Ile Val Pro Glu Asp
305                 310


<210> SEQ ID NO 71
<211> LENGTH: 311
<212> TYPE: PRT
<213> ORGANISM: Homo sapiens

<400> SEQUENCE: 71
```

Ser Gly Ser Ser Val Pro Ala Ala Ala Gly Ser Ser Val Val Ser Glu
1 5 10 15

Ser Ala Val Ser Trp Glu Ala Gly Ala Arg Ala Val Leu Arg Cys Gln
20 25 30

Ser Pro Arg Met Val Trp Thr Gln Asp Arg Leu His Asp Arg Gln Arg
35 40 45

Val Leu His Trp Asp Leu Arg Gly Pro Gly Gly Gly Pro Ala Arg Arg
50 55 60

Leu Leu Asp Leu Tyr Ser Ala Gly Glu Gln Arg Val Tyr Glu Ala Arg
65 70 75 80

Asp Arg Gly Arg Leu Glu Leu Ser Ala Ser Ala Phe Asp Asp Gly Asn
85 90 95

Phe Ser Leu Leu Ile Arg Ala Val Glu Glu Thr Asp Ala Gly Leu Tyr
100 105 110

Thr Cys Asn Leu His His His Tyr Cys His Leu Tyr Glu Ser Leu Ala
115 120 125

Val Arg Leu Glu Val Thr Asp Gly Pro Pro Ala Thr Pro Ala Tyr Trp
130 135 140

Asp Gly Glu Lys Glu Val Leu Ala Val Ala Arg Gly Ala Pro Ala Leu
145 150 155 160

Leu Thr Cys Val Asn Arg Gly His Val Trp Thr Asp Arg His Val Glu
165 170 175

Glu Ala Gln Gln Val Val His Trp Asp Arg Gln Pro Pro Gly Val Pro
180 185 190

His Asp Arg Ala Asp Arg Leu Leu Asp Leu Tyr Ala Ser Gly Glu Arg
195 200 205

Arg Ala Tyr Gly Pro Leu Phe Leu Arg Asp Arg Val Ala Val Gly Ala
210 215 220

Asp Ala Phe Glu Arg Gly Asp Phe Ser Leu Arg Ile Glu Pro Leu Glu
225 230 235 240

Val Ala Asp Glu Gly Thr Tyr Ser Cys His Leu His His His Tyr Cys
245 250 255

Gly Leu His Glu Arg Arg Val Phe His Leu Thr Val Ala Glu Pro His
260 265 270

Ala Glu Pro Pro Pro Arg Gly Ser Pro Gly Asn Gly Ser Ser His Ser
275 280 285

Gly Ala Pro Gly Pro Asp Pro Thr Leu Ala Arg Gly His Asn Val Ile
290 295 300

Asn Val Ile Val Pro Glu Ser
305 310

<210> SEQ ID NO 72
<211> LENGTH: 332
<212> TYPE: PRT
<213> ORGANISM: Bos taurus

<400> SEQUENCE: 72

Ser Gly Pro Ser Gly Pro Ala Thr Ser Asp Arg Ser Val Val Ser Glu
1 5 10 15

Ser Thr Val Ser Trp Ala Ala Gly Ala Arg Ala Val Leu Arg Cys Gln
20 25 30

Ser Pro Arg Met Val Trp Thr Gln Asp Arg Leu His Asp Arg Gln Arg
35 40 45

Val Val His Trp Asp Leu Ser Gly Ser Lys Ala Gly Gly Pro Ala Arg

```
    50                  55                  60

Arg Leu Val Asp Met Tyr Ser Thr Gly Glu Gln Arg Val Gly Glu Gln
65                  70                  75                  80

Arg Leu Gly Glu Gln Arg Val Gly Glu Gln Arg Val Tyr Glu Pro Arg
                85                  90                  95

Asp Arg Gly Arg Leu Leu Leu Pro Pro Ser Ala Phe His Asp Gly Asn
            100                 105                 110

Phe Ser Leu Phe Ile Arg Ala Val Glu Glu Thr Asp Glu Gly Leu Tyr
        115                 120                 125

Thr Cys Asn Leu His His His Tyr Cys His Leu Tyr Glu Ser Leu Ala
    130                 135                 140

Val Ser Leu Glu Val Thr Asp Asp Pro Arg Ala Ala Gly Ala His Trp
145                 150                 155                 160

Asp Gly Glu Lys Glu Val Leu Ala Val Glu Arg Gly Ala Pro Ala Leu
                165                 170                 175

Leu Thr Cys Val Asn Arg Ala His Val Trp Thr Asp Arg His Leu Glu
            180                 185                 190

Glu Ala Gln Gln Val Val His Trp Asp Arg Gln Pro Pro Gly Val Pro
        195                 200                 205

His Asp Arg Ala Asp Arg Leu Leu Asp Leu Tyr Ala Ser Gly Glu Arg
    210                 215                 220

Arg Ala Tyr Gly Pro Pro Phe Leu Arg Asp Arg Val Ala Val Glu Ala
225                 230                 235                 240

Asp Ala Phe Ala Arg Gly Asp Phe Ser Leu Leu Ile Asp Pro Val Glu
                245                 250                 255

Pro Ala Asp Glu Gly Thr Tyr Ser Cys His Leu His His His Tyr Cys
            260                 265                 270

Gly Leu His Glu Arg Arg Val Phe His Leu Arg Val Thr Glu Pro Ala
        275                 280                 285

Ala Arg Pro Pro Pro Pro Pro Arg Asp Ser Pro Gly Asn Gly Ser Ser
    290                 295                 300

His Ser Gly Ala Pro Gly Pro Gly Ala Arg Asp Pro Thr Leu Thr Arg
305                 310                 315                 320

Gly Arg Ser Val Ile Asn Val Ile Val Pro Glu Gly
                325                 330


<210> SEQ ID NO 73
<211> LENGTH: 439
<212> TYPE: PRT
<213> ORGANISM: Chikungunya virus

<400> SEQUENCE: 73

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Gln Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Ser Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95
```

```
Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Ala Ala Tyr Ala Asn Gly Asp His Ala Val Thr Val Lys Asp Ala Lys
145                 150                 155                 160

Phe Val Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Lys Asp Val Tyr Ala Asn Thr Gln Leu Val Leu Gln Arg Pro
    210                 215                 220

Ala Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
            260                 265                 270

Val Gly Asn Ile Pro Ile Ser Ile Asp Ile Pro Asp Ala Ala Phe Thr
        275                 280                 285

Arg Val Val Asp Ala Pro Ser Val Thr Asp Met Ser Cys Glu Val Pro
    290                 295                 300

Ala Cys Thr His Ser Ser Asp Phe Gly Gly Val Ala Ile Ile Lys Tyr
305                 310                 315                 320

Thr Ala Ser Lys Lys Gly Lys Cys Ala Val His Ser Met Thr Asn Ala
                325                 330                 335

Val Thr Ile Arg Glu Ala Asp Val Glu Val Glu Gly Asn Ser Gln Leu
            340                 345                 350

Gln Ile Ser Phe Ser Thr Ala Leu Ala Ser Ala Glu Phe Arg Val Gln
        355                 360                 365

Val Cys Ser Thr Gln Val His Cys Ala Ala Ala Cys His Pro Pro Lys
    370                 375                 380

Asp His Ile Val Asn Tyr Pro Ala Ser His Thr Thr Leu Gly Val Gln
385                 390                 395                 400

Asp Ile Ser Thr Thr Ala Met Ser Trp Val Gln Lys Ile Thr Gly Gly
                405                 410                 415

Val Gly Leu Ile Val Ala Val Ala Ala Leu Ile Leu Ile Val Val Leu
            420                 425                 430

Cys Val Ser Phe Ser Arg His
        435


<210> SEQ ID NO 74
<211> LENGTH: 436
<212> TYPE: PRT
<213> ORGANISM: Mayaro virus

<400> SEQUENCE: 74

Tyr Glu His Thr Ala Val Ile Pro Asn Gln Val Gly Phe Pro Tyr Lys
1               5                   10                  15

Ala His Val Ala Arg Glu Gly Tyr Ser Pro Leu Thr Leu Gln Met Gln
            20                  25                  30
```

-continued

```
Val Val Glu Thr Ser Leu Glu Pro Thr Leu Asn Leu Glu Tyr Ile Thr
        35                  40                  45

Cys Asp Tyr Lys Thr Lys Val Pro Ser Pro Tyr Val Lys Cys Cys Gly
    50                  55                  60

Thr Ala Glu Cys Arg Thr Gln Asp Lys Pro Glu Tyr Lys Cys Ala Val
65                  70                  75                  80

Phe Thr Gly Val Tyr Pro Phe Met Trp Gly Gly Ala Tyr Cys Phe Cys
                85                  90                  95

Asp Ser Glu Asn Thr Gln Met Ser Glu Ala Tyr Val Glu Arg Ala Asp
            100                 105                 110

Val Cys Lys His Asp Tyr Ala Ala Ala Tyr Arg Ala His Thr Ala Ser
        115                 120                 125

Leu Arg Ala Lys Ile Lys Val Thr Tyr Gly Thr Val Asn Gln Thr Val
    130                 135                 140

Glu Ala Tyr Val Asn Gly Asp His Ala Val Thr Ile Ala Gly Thr Lys
145                 150                 155                 160

Phe Ile Phe Gly Pro Val Ser Thr Ala Trp Thr Pro Phe Asp Thr Lys
                165                 170                 175

Ile Val Val Tyr Lys Gly Glu Val Tyr Asn Gln Asp Phe Pro Pro Tyr
            180                 185                 190

Gly Ala Gly Gln Pro Gly Arg Phe Gly Asp Ile Gln Ser Arg Thr Leu
        195                 200                 205

Asp Ser Lys Asp Leu Tyr Ala Asn Thr Gly Leu Lys Leu Ala Arg Pro
    210                 215                 220

Ala Ala Gly Asn Ile His Val Pro Tyr Thr Gln Thr Pro Ser Gly Phe
225                 230                 235                 240

Lys Thr Trp Gln Lys Asp Arg Asp Ser Pro Leu Asn Ala Lys Ala Pro
                245                 250                 255

Phe Gly Cys Thr Ile Gln Thr Asn Pro Val Arg Ala Met Asn Cys Ala
            260                 265                 270

Val Gly Asn Ile Pro Val Ser Met Asp Ile Ala Asp Ser Ala Phe Thr
        275                 280                 285

Arg Leu Thr Asp Ala Pro Ile Ile Ser Glu Leu Leu Cys Thr Val Ser
    290                 295                 300

Thr Cys Thr His Ser Ser Asp Phe Gly Gly Val Ala Val Leu Ser Tyr
305                 310                 315                 320

Lys Val Glu Lys Ala Gly Arg Cys Asp Val His Ser His Ser Asn Val
                325                 330                 335

Ala Val Leu Gln Glu Val Ser Ile Glu Ala Glu Gly Arg Ser Val Ile
            340                 345                 350

His Phe Ser Thr Ala Ser Ala Ala Pro Ser Phe Ile Val Ser Val Cys
        355                 360                 365

Ser Ser Arg Ala Thr Cys Thr Ala Lys Cys Glu Pro Pro Lys Asp His
    370                 375                 380

Val Val Thr Tyr Pro Ala Asn His Asn Gly Ile Thr Leu Pro Asp Leu
385                 390                 395                 400

Ser Ser Thr Ala Met Thr Trp Ala Gln His Leu Ala Gly Gly Val Gly
                405                 410                 415

Leu Leu Ile Ala Leu Ala Val Leu Ile Leu Val Ile Val Thr Cys Ile
            420                 425                 430

Thr Leu Arg Arg
        435
```

<210> SEQ ID NO 75
<211> LENGTH: 438
<212> TYPE: PRT
<213> ORGANISM: Ross River virus

<400> SEQUENCE: 75

Tyr Glu His Thr Ala Thr Ile Pro Asn Val Val Gly Phe Pro Tyr Lys
1 5 10 15

Ala His Ile Glu Arg Asn Gly Phe Ser Pro Met Thr Leu Gln Leu Glu
20 25 30

Val Val Glu Thr Ser Leu Glu Pro Thr Leu Asn Leu Glu Tyr Ile Thr
35 40 45

Cys Glu Tyr Lys Thr Val Val Pro Ser Pro Phe Ile Lys Cys Cys Gly
50 55 60

Thr Ser Glu Cys Ser Ser Lys Glu Gln Pro Asp Tyr Gln Cys Lys Val
65 70 75 80

Tyr Thr Gly Val Tyr Pro Phe Met Trp Gly Gly Ala Tyr Cys Phe Cys
85 90 95

Asp Ser Glu Asn Thr Gln Leu Ser Glu Ala Tyr Val Asp Arg Ser Asp
100 105 110

Val Cys Lys His Asp His Ala Ser Ala Tyr Lys Ala His Thr Ala Ser
115 120 125

Leu Lys Ala Thr Ile Arg Ile Ser Tyr Gly Thr Ile Asn Gln Thr Thr
130 135 140

Glu Ala Phe Val Asn Gly Glu His Ala Val Asn Val Gly Gly Ser Lys
145 150 155 160

Phe Ile Phe Gly Pro Ile Ser Thr Ala Trp Ser Pro Phe Asp Asn Lys
165 170 175

Ile Val Val Tyr Lys Asp Asp Val Tyr Asn Gln Asp Phe Pro Pro Tyr
180 185 190

Gly Ser Gly Gln Pro Gly Arg Phe Gly Asp Ile Gln Ser Arg Thr Val
195 200 205

Glu Ser Lys Asp Leu Tyr Ala Asn Thr Ala Leu Lys Leu Ser Arg Pro
210 215 220

Ser Pro Gly Val Val His Val Pro Tyr Thr Gln Thr Pro Ser Gly Phe
225 230 235 240

Lys Tyr Trp Leu Lys Glu Lys Gly Ser Ser Leu Asn Thr Lys Ala Pro
245 250 255

Phe Gly Cys Lys Ile Lys Thr Asn Pro Val Arg Ala Met Asp Cys Ala
260 265 270

Val Gly Ser Ile Pro Val Ser Met Asp Ile Pro Asp Ser Ala Phe Thr
275 280 285

Arg Val Val Asp Ala Pro Ala Val Thr Asp Leu Ser Cys Gln Val Val
290 295 300

Val Cys Thr His Ser Ser Asp Phe Gly Gly Val Ala Thr Leu Ser Tyr
305 310 315 320

Lys Thr Asp Lys Pro Gly Lys Cys Ala Val His Ser His Ser Asn Val
325 330 335

Ala Thr Leu Gln Glu Ala Thr Val Asp Val Lys Glu Asp Gly Lys Val
340 345 350

Thr Val His Phe Ser Thr Ala Ser Ala Ser Pro Ala Phe Lys Val Ser
355 360 365

Val Cys Asp Ala Lys Thr Thr Cys Thr Ala Ala Cys Glu Pro Pro Lys
370 375 380

Asp His Ile Val Pro Tyr Gly Ala Ser His Asn Asn Gln Val Phe Pro
385 390 395 400

Asp Met Ser Gly Thr Ala Met Thr Trp Val Gln Arg Leu Ala Ser Gly
405 410 415

Leu Gly Gly Leu Ala Leu Ile Ala Val Val Val Leu Val Leu Val Thr
420 425 430

Cys Ile Thr Met Arg Arg
435

<210> SEQ ID NO 76
<211> LENGTH: 439
<212> TYPE: PRT
<213> ORGANISM: Onyong-nyong virus

<400> SEQUENCE: 76

Tyr Glu His Ala Thr Val Ile Pro Asn Thr Val Gly Val Pro Tyr Lys
1 5 10 15

Thr Leu Val Ser Arg Pro Gly Tyr Ser Pro Met Val Leu Glu Met Glu
20 25 30

Leu Gln Ser Val Thr Leu Glu Pro Ala Leu Ser Leu Asp Tyr Ile Thr
35 40 45

Cys Glu Tyr Lys Thr Ile Thr Pro Ser Pro Tyr Val Lys Cys Cys Gly
50 55 60

Thr Ala Glu Cys Lys Ala Lys Asn Leu Pro Asp Tyr Asn Cys Lys Val
65 70 75 80

Phe Thr Gly Val Tyr Pro Phe Met Trp Gly Gly Ala Tyr Cys Phe Cys
85 90 95

Asp Ala Glu Asn Thr Gln Leu Ser Glu Ala His Val Glu Lys Ser Glu
100 105 110

Ser Cys Lys Thr Glu Phe Ala Ser Ala Tyr Arg Ala His Thr Ala Ser
115 120 125

Val Ser Ala Lys Leu Arg Val Phe Tyr Gln Gly Asn Asn Ile Thr Val
130 135 140

Ser Ala Tyr Ala Asn Gly Asp His Ala Val Thr Val Lys Asp Ala Lys
145 150 155 160

Phe Val Ile Gly Pro Leu Ser Ser Ala Trp Ser Pro Phe Asp Asn Lys
165 170 175

Ile Val Val Tyr Lys Gly Glu Val Tyr Asn Met Asp Tyr Pro Pro Phe
180 185 190

Gly Ala Gly Arg Pro Gly Gln Phe Gly Asp Ile Gln Ser Arg Thr Pro
195 200 205

Asp Ser Lys Asp Val Tyr Ala Asn Thr Gln Leu Ile Leu Gln Arg Pro
210 215 220

Ala Ala Gly Ala Ile His Val Pro Tyr Ser Gln Ala Pro Ser Gly Phe
225 230 235 240

Lys Tyr Trp Leu Lys Glu Lys Gly Ala Ser Leu Gln His Thr Ala Pro
245 250 255

Phe Gly Cys Gln Ile Ala Thr Asn Pro Val Arg Ala Val Asn Cys Ala
260 265 270

Val Gly Asn Ile Pro Val Ser Ile Asp Ile Pro Asp Ala Ala Phe Thr
275 280 285

Arg Val Thr Asp Ala Pro Ser Ile Thr Asp Met Ser Cys Glu Val Ala
290 295 300

Ser Cys Thr His Ser Ser Asp Phe Gly Gly Ala Ala Val Ile Lys Tyr

```
305                 310                 315                 320

Thr Ala Ser Lys Lys Gly Lys Cys Ala Val His Ser Val Thr Asn Ala
                325                 330                 335

Val Thr Ile Arg Glu Pro Asn Val Asp Val Glu Gly Thr Ala Gln Leu
            340                 345                 350

Gln Ile Ala Phe Ser Thr Ala Leu Ala Ser Ala Glu Phe Lys Val Gln
        355                 360                 365

Ile Cys Ser Thr Leu Val His Cys Ser Ala Thr Cys His Pro Pro Lys
    370                 375                 380

Asp His Ile Val Asn Tyr Pro Ser Pro His Thr Thr Leu Gly Val Gln
385                 390                 395                 400

Asp Ile Ser Thr Thr Ala Met Ser Trp Val Gln Lys Ile Thr Gly Gly
                405                 410                 415

Val Gly Leu Val Val Ala Ile Ala Ala Leu Ile Leu Ile Ile Val Leu
            420                 425                 430

Cys Val Ser Phe Ser Arg His
        435


<210> SEQ ID NO 77
<211> LENGTH: 438
<212> TYPE: PRT
<213> ORGANISM: Semliki Forest virus

<400> SEQUENCE: 77

Tyr Glu His Ser Thr Val Met Pro Asn Val Val Gly Phe Pro Tyr Lys
1               5                   10                  15

Ala His Ile Glu Arg Pro Gly Tyr Ser Pro Leu Thr Leu Gln Met Gln
            20                  25                  30

Val Val Glu Thr Ser Leu Glu Pro Thr Leu Asn Leu Glu Tyr Ile Thr
        35                  40                  45

Cys Glu Tyr Lys Thr Val Val Pro Ser Pro Tyr Val Lys Cys Cys Gly
    50                  55                  60

Ala Ser Glu Cys Ser Thr Lys Glu Lys Pro Asp Tyr Gln Cys Lys Val
65                  70                  75                  80

Tyr Thr Gly Val Tyr Pro Phe Met Trp Gly Gly Ala Tyr Cys Phe Cys
                85                  90                  95

Asp Ser Glu Asn Thr Gln Leu Ser Glu Ala Tyr Val Asp Arg Ser Asp
            100                 105                 110

Val Cys Arg His Asp His Ala Ser Ala Tyr Lys Ala His Thr Ala Ser
        115                 120                 125

Leu Lys Ala Lys Val Arg Val Met Tyr Gly Asn Val Asn Gln Thr Val
    130                 135                 140

Asp Val Tyr Val Asn Gly Asp His Ala Val Thr Ile Gly Gly Thr Gln
145                 150                 155                 160

Phe Ile Phe Gly Pro Leu Ser Ser Ala Trp Thr Pro Phe Asp Asn Lys
                165                 170                 175

Ile Val Val Tyr Lys Asp Glu Val Phe Asn Gln Asp Phe Pro Pro Tyr
            180                 185                 190

Gly Ser Gly Gln Pro Gly Arg Phe Gly Asp Ile Gln Ser Arg Thr Val
        195                 200                 205

Glu Ser Asn Asp Leu Tyr Ala Asn Thr Ala Leu Lys Leu Ala Arg Pro
    210                 215                 220

Ser Pro Gly Met Val His Val Pro Tyr Thr Gln Thr Pro Ser Gly Phe
225                 230                 235                 240
```

```
Lys Tyr Trp Leu Lys Glu Lys Gly Thr Ala Leu Asn Thr Lys Ala Pro
                245                 250                 255

Phe Gly Cys Gln Ile Lys Thr Asn Pro Val Arg Ala Met Asn Cys Ala
            260                 265                 270

Val Gly Asn Ile Pro Val Ser Met Asn Leu Pro Asp Ser Ala Phe Thr
        275                 280                 285

Arg Ile Val Glu Ala Pro Thr Ile Ile Asp Leu Thr Cys Thr Val Ala
    290                 295                 300

Thr Cys Thr His Ser Ser Asp Phe Gly Gly Val Leu Thr Leu Thr Tyr
305                 310                 315                 320

Lys Thr Asp Lys Asn Gly Asp Cys Ser Val His Ser His Ser Asn Val
                325                 330                 335

Ala Thr Leu Gln Glu Ala Thr Ala Lys Val Lys Thr Ala Gly Lys Val
            340                 345                 350

Thr Leu His Phe Ser Thr Ala Ser Ala Ser Pro Ser Phe Val Val Ser
        355                 360                 365

Leu Cys Ser Ala Arg Ala Thr Cys Ser Ala Ser Cys Glu Pro Pro Lys
    370                 375                 380

Asp His Ile Val Pro Tyr Ala Ala Ser His Ser Asn Val Val Phe Pro
385                 390                 395                 400

Asp Met Ser Gly Thr Ala Leu Ser Trp Val Gln Lys Ile Ser Gly Gly
                405                 410                 415

Leu Gly Ala Phe Ala Ile Gly Ala Ile Leu Val Leu Val Val Val Thr
            420                 425                 430

Cys Ile Gly Leu Arg Arg
        435


<210> SEQ ID NO 78
<211> LENGTH: 439
<212> TYPE: PRT
<213> ORGANISM: Sindbis virus

<400> SEQUENCE: 78

Tyr Glu His Ala Thr Thr Val Pro Asn Val Pro Gln Ile Pro Tyr Lys
1               5                   10                  15

Ala Leu Val Glu Arg Ala Gly Tyr Ala Pro Leu Asn Leu Glu Ile Thr
            20                  25                  30

Val Met Ser Ser Glu Val Leu Pro Ser Thr Asn Gln Glu Tyr Ile Thr
        35                  40                  45

Cys Lys Phe Thr Thr Val Val Pro Ser Pro Lys Val Lys Cys Cys Gly
    50                  55                  60

Ser Leu Glu Cys Gln Pro Ala Ala His Ala Asp Tyr Thr Cys Lys Val
65                  70                  75                  80

Phe Gly Gly Val Tyr Pro Phe Met Trp Gly Gly Ala Gln Cys Phe Cys
                85                  90                  95

Asp Ser Glu Asn Ser Gln Met Ser Glu Ala Tyr Val Glu Leu Ser Ala
            100                 105                 110

Asp Cys Ala Thr Asp His Ala Gln Ala Ile Lys Val His Thr Ala Ala
        115                 120                 125

Met Lys Val Gly Leu Arg Ile Val Tyr Gly Asn Thr Thr Ser Phe Leu
    130                 135                 140

Asp Val Tyr Val Asn Gly Val Thr Pro Gly Thr Ser Lys Asp Leu Lys
145                 150                 155                 160

Val Ile Ala Gly Pro Ile Ser Ala Ser Phe Thr Pro Phe Asp His Lys
                165                 170                 175
```

Val Val Ile His Arg Gly Leu Val Tyr Asn Tyr Asp Phe Pro Glu Tyr
180 185 190

Gly Ala Met Lys Pro Gly Ala Phe Gly Asp Ile Gln Ala Thr Ser Leu
195 200 205

Thr Ser Lys Asp Leu Ile Ala Ser Thr Asp Ile Arg Leu Leu Lys Pro
210 215 220

Ser Ala Lys Asn Val His Val Pro Tyr Thr Gln Ala Ala Ser Gly Phe
225 230 235 240

Glu Met Trp Lys Asn Asn Ser Gly Arg Pro Leu Gln Glu Thr Ala Pro
245 250 255

Phe Gly Cys Lys Ile Ala Val Asn Pro Leu Arg Ala Val Asp Cys Ser
260 265 270

Tyr Gly Asn Ile Pro Ile Ser Ile Asp Ile Pro Asn Ala Ala Phe Ile
275 280 285

Arg Thr Ser Asp Ala Pro Leu Val Ser Thr Val Lys Cys Asp Val Ser
290 295 300

Glu Cys Thr Tyr Ser Ala Asp Phe Gly Gly Met Ala Thr Leu Gln Tyr
305 310 315 320

Val Ser Asp Arg Glu Gly Gln Cys Pro Val His Ser His Ser Ser Thr
325 330 335

Ala Thr Leu Gln Glu Ser Thr Val His Val Leu Glu Lys Gly Ala Val
340 345 350

Thr Val His Phe Ser Thr Ala Ser Pro Gln Ala Asn Phe Ile Val Ser
355 360 365

Leu Cys Gly Lys Lys Thr Thr Cys Asn Ala Glu Cys Lys Pro Pro Ala
370 375 380

Asp His Ile Val Ser Thr Pro His Lys Asn Asp Gln Glu Phe Gln Ala
385 390 395 400

Ala Ile Ser Lys Thr Ser Trp Ser Trp Leu Phe Ala Leu Phe Gly Gly
405 410 415

Ala Ser Ser Leu Leu Ile Ile Gly Leu Met Ile Phe Ala Cys Ser Met
420 425 430

Met Leu Thr Ser Thr Arg Arg
435

<210> SEQ ID NO 79
<211> LENGTH: 438
<212> TYPE: PRT
<213> ORGANISM: Western equine encephalomyelitis virus

<400> SEQUENCE: 79

Phe Glu His Ala Thr Thr Val Pro Asn Val Pro Gly Ile Pro Tyr Lys
1 5 10 15

Ala Leu Val Glu Arg Ala Gly Tyr Ala Pro Leu Asn Leu Glu Ile Lys
20 25 30

Val Val Ser Ser Glu Leu Thr Pro Ser Thr Asn Lys Glu Tyr Val Thr
35 40 45

Cys Lys Phe His Thr Val Ile Pro Ser Pro Gln Val Lys Cys Cys Gly
50 55 60

Ser Leu Glu Cys Lys Ala Ser Ser Lys Ala Asp Tyr Thr Cys Arg Val
65 70 75 80

Phe Gly Gly Val Tyr Pro Phe Met Trp Gly Gly Ala Gln Cys Phe Cys
85 90 95

Asp Ser Glu Asn Thr Gln Leu Ser Glu Ala Tyr Val Glu Phe Ala Pro

```
            100                 105                 110

Asp Cys Thr Ile Asp His Ala Val Ala Leu Arg Val His Thr Ala Ala
        115                 120                 125

Leu Lys Val Gly Leu Arg Ile Val Tyr Gly Asn Thr Thr Ala Tyr Leu
    130                 135                 140

Asp Thr Phe Val Asn Gly Val Thr Pro Gly Ser Ser Arg Asp Leu Lys
145                 150                 155                 160

Val Ile Ala Gly Pro Ile Ser Ala Ala Phe Ser Pro Phe Asp His Lys
                165                 170                 175

Val Val Ile Arg Lys Gly Leu Val Tyr Asn Tyr Asp Phe Pro Glu Tyr
            180                 185                 190

Gly Ala Met Lys Pro Gly Ala Phe Gly Asp Ile Gln Ala Ser Ser Leu
        195                 200                 205

Asp Ala Thr Asp Ile Val Ala Arg Thr Asp Ile Arg Leu Leu Lys Pro
    210                 215                 220

Ser Val Lys Asn Ile His Val Pro Tyr Thr Gln Ala Val Ser Gly Tyr
225                 230                 235                 240

Glu Met Trp Lys Asn Asn Ser Gly Arg Pro Leu Gln Glu Thr Ala Pro
                245                 250                 255

Phe Gly Cys Lys Ile Glu Val Glu Pro Leu Arg Ala Ser Asn Cys Ala
            260                 265                 270

Tyr Gly His Ile Pro Ile Ser Ile Asp Ile Pro Asp Ala Ala Phe Val
        275                 280                 285

Arg Ser Ser Glu Ser Pro Thr Ile Leu Glu Val Ser Cys Thr Ala Asp
    290                 295                 300

Cys Ile Tyr Ser Ala Asp Phe Gly Gly Ser Leu Thr Leu Gln Tyr Lys
305                 310                 315                 320

Ala Asp Arg Glu Gly His Cys Pro Val His Ser His Ser Thr Thr Ala
                325                 330                 335

Val Leu Lys Glu Ala Thr Thr His Val Thr Ala Thr Gly Ser Ile Thr
            340                 345                 350

Leu His Phe Ser Thr Ser Ser Pro Gln Ala Asn Phe Ile Val Ser Leu
        355                 360                 365

Cys Gly Lys Lys Thr Thr Cys Asn Ala Glu Cys Lys Pro Pro Ala Asp
    370                 375                 380

His Ile Ile Gly Glu Pro His Lys Val Asp Gln Glu Phe Gln Ala Ala
385                 390                 395                 400

Val Ser Lys Thr Ser Trp Asn Trp Leu Leu Ala Leu Phe Gly Gly Ala
                405                 410                 415

Ser Ser Leu Ile Val Val Gly Leu Ile Val Leu Val Cys Ser Ser Met
            420                 425                 430

Leu Ile Asn Thr Arg Arg
        435


<210> SEQ ID NO 80
<211> LENGTH: 440
<212> TYPE: PRT
<213> ORGANISM: Eastern equine encephalomyelitis virus

<400> SEQUENCE: 80

Tyr Glu His Thr Ala Val Met Pro Asn Lys Val Gly Ile Pro Tyr Lys
1               5                   10                  15

Ala Leu Val Glu Arg Pro Gly Tyr Ala Pro Val His Leu Gln Ile Gln
            20                  25                  30
```

```
Leu Val Asn Thr Arg Ile Ile Pro Ser Thr Asn Leu Glu Tyr Ile Thr
        35                  40                  45

Cys Lys Tyr Lys Thr Lys Val Pro Ser Pro Val Val Lys Cys Cys Gly
    50                  55                  60

Ala Thr Gln Cys Ser Ser Lys Pro His Pro Asp Tyr Gln Cys Gln Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Met Ser Glu Ala Tyr Val Glu Arg Ser Glu
            100                 105                 110

Glu Cys Ser Ile Asp His Ala Lys Ala Tyr Lys Val His Thr Gly Thr
        115                 120                 125

Val Gln Ala Met Val Asn Ile Thr Tyr Gly Ser Val Ser Trp Arg Ser
    130                 135                 140

Ala Asp Val Tyr Val Asn Gly Glu Thr Pro Ala Lys Ile Gly Asp Ala
145                 150                 155                 160

Lys Leu Ile Ile Gly Pro Leu Ser Ser Ala Trp Ser Pro Phe Asp Asn
                165                 170                 175

Lys Val Val Val Tyr Gly His Glu Val Tyr Asn Tyr Asp Phe Pro Glu
            180                 185                 190

Tyr Gly Thr Gly Lys Ala Gly Ser Phe Gly Asp Leu Gln Ser Arg Thr
        195                 200                 205

Ser Thr Ser Asn Asp Leu Tyr Ala Asn Thr Asn Leu Lys Leu Gln Arg
    210                 215                 220

Pro Gln Ala Gly Ile Val His Thr Pro Phe Thr Gln Ala Pro Ser Gly
225                 230                 235                 240

Phe Glu Arg Trp Lys Arg Asp Lys Gly Ala Pro Leu Asn Asp Val Ala
                245                 250                 255

Pro Phe Gly Cys Ser Ile Ala Leu Glu Pro Leu Arg Ala Glu Asn Cys
            260                 265                 270

Ala Val Gly Ser Ile Pro Ile Ser Ile Asp Ile Pro Asp Ala Ala Phe
        275                 280                 285

Thr Arg Ile Ser Glu Thr Pro Thr Val Ser Asp Leu Glu Cys Lys Ile
    290                 295                 300

Thr Glu Cys Thr Tyr Ala Ser Asp Phe Gly Gly Ile Ala Thr Val Ala
305                 310                 315                 320

Tyr Lys Ser Ser Lys Ala Gly Asn Cys Pro Ile His Ser Pro Ser Gly
                325                 330                 335

Val Ala Val Ile Lys Glu Asn Asp Val Thr Leu Ala Glu Ser Gly Ser
            340                 345                 350

Phe Thr Phe His Phe Ser Thr Ala Asn Ile His Pro Ala Phe Lys Leu
        355                 360                 365

Gln Val Cys Thr Ser Ala Val Thr Cys Lys Gly Asp Cys Lys Pro Pro
    370                 375                 380

Lys Asp His Ile Val Asp Tyr Pro Ala Gln His Thr Asp Leu Leu Thr
385                 390                 395                 400

Ser Ala Ile Ser Ala Thr Ala Trp Ser Trp Leu Lys Val Leu Val Gly
                405                 410                 415

Gly Thr Ser Ala Phe Ile Val Leu Gly Leu Ile Ala Thr Ala Val Val
            420                 425                 430

Ala Leu Val Leu Phe Phe His Arg
        435                 440
```

<210> SEQ ID NO 81
<211> LENGTH: 439
<212> TYPE: PRT
<213> ORGANISM: Venezuelan equine encephalitis virus

<400> SEQUENCE: 81

Tyr Glu His Ala Thr Thr Met Pro Ser Gln Ala Gly Ile Ser Tyr Asn
1 5 10 15

Thr Ile Val Asn Arg Ala Gly Tyr Ala Pro Leu Pro Ile Ser Ile Thr
20 25 30

Pro Thr Lys Ile Lys Leu Ile Pro Thr Val Asn Leu Glu Tyr Val Thr
35 40 45

Cys His Tyr Lys Thr Gly Met Asp Ser Pro Ala Ile Lys Cys Cys Gly
50 55 60

Ser Gln Glu Cys Thr Pro Thr Tyr Arg Pro Asp Glu Gln Cys Lys Val
65 70 75 80

Phe Thr Gly Val Tyr Pro Phe Met Trp Gly Gly Ala Tyr Cys Phe Cys
85 90 95

Asp Thr Glu Asn Thr Gln Val Ser Lys Ala Tyr Val Met Lys Ser Asp
100 105 110

Asp Cys Leu Ala Asp His Ala Glu Ala Tyr Lys Ala His Thr Ala Ser
115 120 125

Val Gln Ala Phe Leu Asn Ile Thr Val Gly Glu His Ser Ile Val Thr
130 135 140

Thr Val Tyr Val Asn Gly Glu Thr Pro Val Asn Phe Asn Gly Val Lys
145 150 155 160

Ile Thr Ala Gly Pro Leu Ser Thr Ala Trp Thr Pro Phe Asp Arg Lys
165 170 175

Ile Val Gln Tyr Ala Gly Glu Ile Tyr Asn Tyr Asp Phe Pro Glu Tyr
180 185 190

Gly Ala Gly Gln Pro Gly Ala Phe Gly Asp Ile Gln Ser Arg Thr Val
195 200 205

Ser Ser Ser Asp Leu Tyr Ala Asn Thr Asn Leu Val Leu Gln Arg Pro
210 215 220

Lys Ala Gly Ala Ile His Val Pro Tyr Thr Gln Ala Pro Ser Gly Phe
225 230 235 240

Glu Gln Trp Lys Lys Asp Lys Ala Pro Ser Leu Lys Phe Thr Ala Pro
245 250 255

Phe Gly Cys Glu Ile Tyr Thr Asn Pro Ile Arg Ala Glu Asn Cys Ala
260 265 270

Val Gly Ser Ile Pro Leu Ala Phe Asp Ile Pro Asp Ala Leu Phe Thr
275 280 285

Arg Val Ser Glu Thr Pro Thr Leu Ser Ala Ala Glu Cys Thr Leu Asn
290 295 300

Glu Cys Val Tyr Ser Ser Asp Phe Gly Gly Ile Ala Thr Val Lys Tyr
305 310 315 320

Ser Ala Ser Lys Ser Gly Lys Cys Ala Val His Val Pro Ser Gly Thr
325 330 335

Ala Thr Leu Lys Glu Ala Ala Val Glu Leu Thr Glu Gln Gly Ser Ala
340 345 350

Thr Ile His Phe Ser Thr Ala Asn Ile His Pro Glu Phe Arg Leu Gln
355 360 365

Ile Cys Thr Ser Tyr Val Thr Cys Lys Gly Asp Cys His Pro Pro Lys
370 375 380

Asp His Ile Val Thr His Pro Gln Tyr His Ala Gln Thr Phe Thr Ala
385 390 395 400

Ala Val Ser Lys Thr Ala Trp Thr Trp Leu Thr Ser Leu Leu Gly Gly
405 410 415

Ser Ala Val Ile Ile Ile Ile Gly Leu Val Leu Ala Thr Ile Val Ala
420 425 430

Met Tyr Val Leu Thr Asn Gln
435

<210> SEQ ID NO 82
<211> LENGTH: 419
<212> TYPE: PRT
<213> ORGANISM: Chikungunya virus

<400> SEQUENCE: 82

Asn Phe Asn Val Tyr Lys Ala Thr Arg Pro Tyr Leu Ala His Cys Pro
1 5 10 15

Asp Cys Gly Glu Gly His Ser Cys His Ser Pro Ile Ala Leu Glu Arg
20 25 30

Ile Arg Asn Glu Ala Thr Asp Gly Thr Leu Lys Ile Gln Val Ser Leu
35 40 45

Gln Ile Gly Ile Lys Thr Asp Asp Ser His Asp Trp Thr Lys Leu Arg
50 55 60

Tyr Met Asp Ser His Thr Pro Ala Asp Ala Glu Arg Ala Gly Leu Leu
65 70 75 80

Val Arg Thr Ser Ala Pro Cys Thr Ile Thr Gly Thr Met Gly His Phe
85 90 95

Ile Leu Ala Arg Cys Pro Lys Gly Glu Thr Leu Thr Val Gly Phe Thr
100 105 110

Asp Ser Arg Lys Ile Ser His Thr Cys Thr His Pro Phe His His Glu
115 120 125

Pro Pro Val Ile Gly Arg Glu Arg Phe His Ser Arg Pro Gln His Gly
130 135 140

Lys Glu Leu Pro Cys Ser Thr Tyr Val Gln Ser Thr Ala Ala Thr Ala
145 150 155 160

Glu Glu Ile Glu Val His Met Pro Pro Asp Thr Pro Asp Arg Thr Leu
165 170 175

Met Thr Gln Gln Ser Gly Asn Val Lys Ile Thr Val Asn Gly Gln Thr
180 185 190

Val Arg Tyr Lys Cys Asn Cys Gly Gly Ser Asn Glu Gly Leu Thr Thr
195 200 205

Thr Asp Lys Val Ile Asn Asn Cys Lys Ile Asp Gln Cys His Ala Ala
210 215 220

Val Thr Asn His Lys Asn Trp Gln Tyr Asn Ser Pro Leu Val Pro Arg
225 230 235 240

Asn Ala Glu Leu Gly Asp Arg Lys Gly Lys Ile His Ile Pro Phe Pro
245 250 255

Leu Ala Asn Val Thr Cys Arg Val Pro Lys Ala Arg Asn Pro Thr Val
260 265 270

Thr Tyr Gly Lys Asn Gln Val Thr Met Leu Leu Tyr Pro Asp His Pro
275 280 285

Thr Leu Leu Ser Tyr Arg Asn Met Gly Gln Glu Pro Asn Tyr His Glu
290 295 300

Glu Trp Val Thr His Lys Lys Glu Val Thr Leu Thr Val Pro Thr Glu
305 310 315 320

Gly Leu Glu Val Thr Trp Gly Asn Asn Glu Pro Tyr Lys Tyr Trp Pro
325 330 335

Gln Met Ser Thr Asn Gly Thr Ala His Gly His Pro His Glu Ile Ile
340 345 350

Leu Tyr Tyr Tyr Glu Leu Tyr Pro Thr Met Thr Val Val Ile Val Ser
355 360 365

Val Ala Ser Phe Val Leu Leu Ser Met Val Gly Thr Ala Val Gly Met
370 375 380

Cys Val Cys Ala Arg Arg Arg Cys Ile Thr Pro Tyr Glu Leu Thr Pro
385 390 395 400

Gly Ala Thr Val Pro Phe Leu Leu Ser Leu Leu Cys Cys Val Arg Thr
405 410 415

Thr Lys Ala

<210> SEQ ID NO 83
<211> LENGTH: 418
<212> TYPE: PRT
<213> ORGANISM: Mayaro virus

<400> SEQUENCE: 83

His Phe Asn Ala Tyr Lys Leu Thr Arg Pro Tyr Val Ala Tyr Cys Ala
1 5 10 15

Asp Cys Gly Met Gly His Ser Cys His Ser Pro Ala Met Ile Glu Asn
20 25 30

Val Gln Ala Asp Ala Thr Asp Gly Thr Leu Lys Ile Gln Phe Ala Ser
35 40 45

Gln Ile Gly Leu Thr Lys Ala Asp Thr His Asp His Thr Lys Ile Arg
50 55 60

Tyr Ala Glu Gly His Asp Ile Ala Glu Ala Ala Arg Ser Thr Leu Lys
65 70 75 80

Val His Ser Ser Ser Glu Cys Ala Val Thr Gly Thr Met Gly His Phe
85 90 95

Ile Leu Ala Lys Cys Pro Pro Gly Glu Val Ile Ser Val Ser Phe Val
100 105 110

Asp Ser Lys Asn Glu Gln Arg Thr Cys Arg Ile Ala Tyr His His Glu
115 120 125

Gln Arg Leu Ile Gly Arg Glu Arg Phe Thr Val Arg Pro His His Gly
130 135 140

Ile Glu Leu Pro Cys Thr Thr Tyr Gln Leu Thr Thr Ala Glu Thr Ser
145 150 155 160

Glu Glu Ile Asp Met His Met Pro Pro Asp Ile Pro Asp Arg Thr Ile
165 170 175

Leu Ser Gln Gln Ser Gly Asn Val Lys Ile Thr Val Asn Gly Arg Thr
180 185 190

Val Lys Tyr Ser Cys Ser Cys Gly Ser Lys Pro Ser Gly Thr Thr Thr
195 200 205

Thr Asp Lys Thr Ile Asn Ser Cys Thr Val Asp Lys Cys Gln Ala Tyr
210 215 220

Val Thr Ser His Thr Lys Trp Gln Phe Asn Ser Pro Phe Val Pro Arg
225 230 235 240

Ala Glu Gln Ala Glu Arg Lys Gly Lys Val His Ile Pro Phe Pro Leu
245 250 255

Ile Asn Thr Thr Cys Arg Val Pro Leu Ala Pro Glu Ala Leu Val Arg
260 265 270

```
Ser Gly Lys Arg Glu Ala Thr Leu Ser Leu His Pro Ile His Pro Thr
        275                 280                 285

Leu Leu Ser Tyr Arg Thr Leu Gly Arg Glu Pro Val Phe Asp Glu Gln
    290                 295                 300

Trp Ile Thr Thr Gln Thr Glu Val Thr Ile Pro Val Pro Val Glu Gly
305                 310                 315                 320

Val Glu Tyr Arg Trp Gly Asn His Lys Pro Gln Arg Leu Trp Ser Gln
                325                 330                 335

Leu Thr Thr Asp Gly Arg Ala His Gly Trp Pro His Glu Ile Ile Glu
            340                 345                 350

Tyr Tyr Tyr Gly Leu His Pro Thr Thr Thr Ile Val Val Val Val Ala
        355                 360                 365

Val Ser Val Val Val Leu Leu Ser Val Ala Ala Ser Val Tyr Met Cys
    370                 375                 380

Val Val Ala Arg Asn Lys Cys Leu Thr Pro Tyr Ala Leu Thr Pro Gly
385                 390                 395                 400

Ala Val Val Pro Val Thr Ile Gly Val Leu Cys Cys Ala Pro Lys Ala
                405                 410                 415

His Ala


<210> SEQ ID NO 84
<211> LENGTH: 418
<212> TYPE: PRT
<213> ORGANISM: Ross River virus
<220> FEATURE:
<221> NAME/KEY: misc_feature
<222> LOCATION: (14)..(14)
<223> OTHER INFORMATION: Xaa can be any naturally occurring amino acid

<400> SEQUENCE: 84

His Phe Asn Val Tyr Lys Ala Thr Arg Pro Tyr Leu Ala Xaa Cys Ala
1               5                   10                  15

Asp Cys Gly Asp Gly Tyr Phe Cys Tyr Ser Pro Val Ala Ile Glu Lys
            20                  25                  30

Ile Arg Asp Glu Ala Ser Asp Gly Met Leu Lys Ile Gln Val Ser Ala
        35                  40                  45

Gln Ile Gly Leu Asp Lys Ala Gly Thr His Ala His Thr Lys Ile Arg
    50                  55                  60

Tyr Met Ala Gly His Asp Val Gln Glu Ser Lys Arg Asp Ser Leu Arg
65                  70                  75                  80

Val Tyr Thr Ser Ala Ala Cys Ser Ile His Gly Thr Met Gly His Phe
                85                  90                  95

Ile Val Ala His Cys Pro Pro Gly Asp Tyr Leu Lys Val Ser Phe Glu
            100                 105                 110

Asp Ala Asp Ser His Val Lys Ala Cys Lys Val Gln Tyr Lys His Asp
        115                 120                 125

Pro Leu Pro Val Gly Arg Glu Lys Phe Val Val Arg Pro His Phe Gly
    130                 135                 140

Val Glu Leu Pro Cys Thr Ser Tyr Gln Leu Thr Thr Ala Pro Thr Asp
145                 150                 155                 160

Glu Glu Ile Asp Met His Thr Pro Pro Asp Ile Pro Asp Arg Thr Leu
                165                 170                 175

Leu Ser Gln Thr Ala Gly Asn Val Lys Ile Thr Ala Gly Gly Arg Thr
            180                 185                 190

Ile Arg Tyr Asn Cys Thr Cys Gly Arg Asp Asn Val Gly Thr Thr Ser
```

```
        195                 200                 205

Thr Asp Lys Thr Ile Asn Thr Cys Lys Ile Asp Gln Cys His Ala Ala
    210                 215                 220

Val Thr Ser His Asp Lys Trp Gln Phe Thr Ser Pro Phe Val Pro Arg
225                 230                 235                 240

Ala Asp Gln Thr Ala Arg Arg Gly Lys Val His Val Pro Phe Pro Leu
                245                 250                 255

Thr Asn Val Thr Cys Arg Val Pro Leu Ala Arg Ala Pro Asp Val Thr
            260                 265                 270

Tyr Gly Lys Lys Glu Val Thr Leu Arg Leu His Pro Asp His Pro Thr
        275                 280                 285

Leu Phe Ser Tyr Arg Ser Leu Gly Ala Glu Pro His Pro Tyr Glu Glu
    290                 295                 300

Trp Val Asp Lys Phe Ser Glu Arg Ile Ile Pro Val Thr Glu Glu Gly
305                 310                 315                 320

Ile Glu Tyr Gln Trp Gly Asn Asn Pro Pro Val Arg Leu Trp Ala Gln
                325                 330                 335

Leu Thr Thr Glu Gly Lys Pro His Gly Trp Pro His Glu Ile Ile Gln
            340                 345                 350

Tyr Tyr Tyr Gly Leu Tyr Pro Ala Ala Thr Ile Ala Ala Val Ser Gly
        355                 360                 365

Ala Ser Leu Met Ala Leu Leu Thr Leu Ala Ala Thr Cys Cys Met Leu
    370                 375                 380

Ala Thr Ala Arg Arg Lys Cys Leu Thr Pro Tyr Ala Leu Thr Pro Gly
385                 390                 395                 400

Ala Val Val Pro Leu Thr Leu Gly Leu Leu Cys Cys Ala Pro Arg Ala
                405                 410                 415

Asn Ala


<210> SEQ ID NO 85
<211> LENGTH: 419
<212> TYPE: PRT
<213> ORGANISM: Onyong-nyong virus

<400> SEQUENCE: 85

Asn Phe Asn Val Tyr Lys Val Thr Arg Pro Tyr Leu Ala His Cys Pro
1               5                   10                  15

Asp Cys Gly Glu Gly His Ser Cys His Ser Pro Ile Ala Leu Glu Arg
            20                  25                  30

Ile Arg Ser Glu Ala Thr Asp Gly Thr Leu Lys Ile Gln Val Ser Leu
        35                  40                  45

Gln Ile Gly Ile Lys Thr Asp Asp Ser His Asp Trp Thr Lys Leu Arg
    50                  55                  60

Tyr Met Asp Ser His Thr Pro Val Asp Ala Ala Arg Ser Gly Leu Phe
65                  70                  75                  80

Val Arg Thr Ser Ala Pro Cys Thr Ile Thr Gly Thr Met Gly His Phe
                85                  90                  95

Ile Leu Ala Arg Cys Pro Lys Gly Glu Thr Leu Thr Val Gly Phe Val
            100                 105                 110

Asp Ser Arg Arg Ile Ser His Thr Cys Met His Pro Phe His His Glu
        115                 120                 125

Pro Pro Leu Ile Gly Arg Glu Lys Phe His Ser Arg Pro Gln His Gly
    130                 135                 140

Lys Glu Leu Pro Cys Ser Thr Tyr Val His Thr Thr Ala Ala Thr Ala
```

145 150 155 160

Glu Glu Ile Glu Val His Met Pro Pro Asp Thr Pro Asp Tyr Thr Leu
165 170 175

Met Thr Gln Gln Ala Gly Asn Val Lys Ile Thr Val Asx Gly Gln Thr
180 185 190

Val Arg Tyr Lys Cys Lys Cys Asp Gly Ser Asn Glu Gly Leu Ile Thr
195 200 205

Ala Asp Lys Val Ile Asn Asn Cys Lys Val Asp Gln Cys His Thr Ala
210 215 220

Val Thr Asn His Lys Lys Trp Gln Tyr Asn Ser Pro Leu Thr Pro Arg
225 230 235 240

Asn Ser Glu Gln Gly Asp Arg Lys Gly Lys Ile His Ile Pro Phe Pro
245 250 255

Leu Val Asn Thr Thr Cys Arg Val Pro Lys Ala Arg Asn Pro Thr Val
260 265 270

Thr Tyr Gly Lys Asn Arg Val Thr Leu Leu Leu Tyr Pro Asp His Pro
275 280 285

Thr Leu Leu Ser Tyr Arg Ala Met Gly Arg Ile Pro Asp Tyr His Glu
290 295 300

Glu Trp Ile Thr Asn Lys Lys Glu Ile Ser Ile Thr Val Pro Ala Glu
305 310 315 320

Gly Leu Glu Val Thr Trp Gly Asn Asn Asp Pro Tyr Lys Tyr Trp Pro
325 330 335

Gln Leu Ser Thr Asn Gly Thr Ala His Gly His Pro His Glu Ile Ile
340 345 350

Leu Tyr Tyr Tyr Glu Leu Tyr Pro Thr Thr Thr Ile Ala Val Leu Ala
355 360 365

Ala Ala Ser Ile Val Ile Thr Ser Leu Val Gly Leu Ser Leu Gly Met
370 375 380

Cys Ile Cys Ala Arg Arg Arg Cys Ile Thr Pro Tyr Glu Leu Thr Pro
385 390 395 400

Gly Ala Thr Ile Pro Phe Leu Leu Gly Val Leu Cys Cys Ala Arg Thr
405 410 415

Ala Lys Ala

<210> SEQ ID NO 86
<211> LENGTH: 418
<212> TYPE: PRT
<213> ORGANISM: Semliki Forest virus

<400> SEQUENCE: 86

His Phe Asn Val Tyr Lys Ala Thr Arg Pro Tyr Ile Ala Tyr Cys Ala
1 5 10 15

Asp Cys Gly Ala Gly His Ser Cys His Ser Pro Val Ala Ile Glu Ala
20 25 30

Ile Arg Ser Glu Ala Thr Asp Gly Met Leu Lys Ile Gln Phe Ser Ala
35 40 45

Gln Ile Gly Ile Asp Lys Ser Asp Asn His Asp Tyr Thr Lys Ile Arg
50 55 60

Tyr Ala Asp Gly His Ala Ile Glu Asn Ala Val Arg Ser Ser Leu Lys
65 70 75 80

Val Ala Thr Ser Gly Asp Cys Phe Val His Gly Thr Met Gly His Phe
85 90 95

Ile Leu Ala Thr Cys Pro Pro Gly Glu Phe Leu Gln Val Ser Ile Gln

```
            100                 105                 110

Asp Thr Arg Asn Ala Val Arg Ala Cys Arg Ile Gln Tyr His His Asp
        115                 120                 125

Pro Gln Pro Val Gly Arg Glu Lys Phe Thr Ile Arg Pro His Tyr Gly
    130                 135                 140

Lys Glu Ile Pro Cys Thr Thr Tyr Gln Gln Thr Thr Ala Glu Thr Val
145                 150                 155                 160

Glu Glu Ile Asp Met His Met Pro Pro Asp Thr Pro Asp Arg Thr Leu
                165                 170                 175

Leu Ser Gln Gln Ser Gly Asn Val Lys Ile Thr Val Gly Gly Lys Lys
            180                 185                 190

Val Lys Tyr Asn Cys Thr Cys Gly Thr Gly Asn Val Gly Thr Thr Asn
        195                 200                 205

Ser Asp Met Thr Ile Asn Thr Cys Leu Ile Glu Gln Cys His Val Ser
    210                 215                 220

Val Thr Asp His Lys Lys Trp Gln Phe Asn Ser Pro Phe Val Pro Arg
225                 230                 235                 240

Ala Asp Glu Pro Ala Arg Lys Gly Lys Val His Ile Pro Phe Pro Leu
                245                 250                 255

Asp Asn Ile Thr Cys Arg Val Pro Met Ala Arg Glu Pro Thr Val Ile
            260                 265                 270

His Gly Lys Arg Glu Val Thr Leu His Leu His Pro Asp His Pro Thr
        275                 280                 285

Leu Phe Ser Tyr Arg Thr Leu Gly Glu Asp Pro Gln Tyr His Glu Glu
    290                 295                 300

Trp Val Thr Ala Ala Val Glu Arg Thr Ile Pro Val Pro Val Asp Gly
305                 310                 315                 320

Met Glu Tyr His Trp Gly Asn Asn Asp Pro Val Arg Leu Trp Ser Gln
                325                 330                 335

Leu Thr Thr Glu Gly Lys Pro His Gly Trp Pro His Gln Ile Val Gln
            340                 345                 350

Tyr Tyr Tyr Gly Leu Tyr Pro Ala Ala Thr Val Ser Ala Val Val Gly
        355                 360                 365

Met Ser Leu Leu Ala Leu Ile Ser Ile Phe Ala Ser Cys Tyr Met Leu
    370                 375                 380

Val Ala Ala Arg Ser Lys Cys Leu Thr Pro Tyr Ala Leu Thr Pro Gly
385                 390                 395                 400

Ala Ala Val Pro Trp Thr Leu Gly Ile Leu Cys Cys Ala Pro Arg Ala
                405                 410                 415

His Ala


<210> SEQ ID NO 87
<211> LENGTH: 419
<212> TYPE: PRT
<213> ORGANISM: Sindbis virus

<400> SEQUENCE: 87

Asp Phe Thr Leu Thr Ser Pro Tyr Leu Gly Thr Cys Ser Tyr Cys His
1               5                   10                  15

His Thr Glu Pro Cys Phe Ser Pro Ile Lys Ile Glu Gln Val Trp Asp
            20                  25                  30

Glu Ala Asp Asp Asn Thr Ile Arg Ile Gln Thr Ser Ala Gln Phe Gly
        35                  40                  45

Tyr Asp Gln Ser Gly Ala Ala Ser Ser Asn Lys Tyr Arg Tyr Met Ser
```

50 55 60

Leu Glu Gln Asp His Thr Val Lys Glu Gly Thr Met Asp Asp Ile Lys
65 70 75 80

Ile Ser Thr Ser Gly Pro Cys Arg Arg Leu Ser Tyr Lys Gly Tyr Phe
85 90 95

Leu Leu Ala Lys Cys Pro Pro Gly Asp Ser Val Thr Val Ser Ile Ala
100 105 110

Ser Ser Asn Ser Ala Thr Ser Cys Thr Met Ala Arg Lys Ile Lys Pro
115 120 125

Lys Phe Val Gly Arg Glu Lys Tyr Asp Leu Pro Pro Val His Gly Lys
130 135 140

Lys Ile Pro Cys Thr Val Tyr Asp Arg Leu Lys Glu Thr Thr Ala Gly
145 150 155 160

Tyr Ile Thr Met His Arg Pro Gly Pro His Ala Tyr Thr Ser Tyr Leu
165 170 175

Glu Glu Ser Ser Gly Lys Val Tyr Ala Lys Pro Pro Ser Gly Lys Asn
180 185 190

Ile Thr Tyr Glu Cys Lys Cys Gly Asp Tyr Lys Thr Gly Thr Val Thr
195 200 205

Thr Arg Thr Glu Ile Thr Gly Cys Thr Ala Ile Lys Gln Cys Val Ala
210 215 220

Tyr Lys Ser Asp Gln Thr Lys Trp Val Phe Asn Ser Pro Asp Leu Ile
225 230 235 240

Arg His Ala Asp His Thr Ala Gln Gly Lys Leu His Leu Pro Phe Lys
245 250 255

Leu Ile Pro Ser Thr Cys Met Val Pro Val Ala His Ala Pro Asn Val
260 265 270

Val His Gly Phe Lys His Ile Ser Leu Gln Leu Asp Thr Asp His Leu
275 280 285

Thr Leu Leu Thr Thr Arg Arg Leu Gly Ala Asn Pro Glu Pro Thr Thr
290 295 300

Glu Trp Ile Ile Gly Lys Thr Val Arg Asn Phe Thr Val Asp Arg Asp
305 310 315 320

Gly Leu Glu Tyr Ile Trp Gly Asn His Glu Pro Val Arg Val Tyr Ala
325 330 335

Gln Glu Ser Ala Pro Gly Asp Pro His Gly Trp Pro His Glu Ile Val
340 345 350

Gln His Tyr Tyr His Arg His Pro Val Tyr Thr Ile Leu Ala Val Ala
355 360 365

Ser Ala Ala Val Ala Met Met Ile Gly Val Thr Val Ala Ala Leu Cys
370 375 380

Ala Cys Lys Ala Arg Arg Glu Cys Leu Thr Pro Tyr Ala Leu Ala Pro
385 390 395 400

Asn Ala Val Ile Pro Thr Ser Leu Ala Leu Leu Cys Cys Val Arg Ser
405 410 415

Ala Asn Ala

<210> SEQ ID NO 88
<211> LENGTH: 419
<212> TYPE: PRT
<213> ORGANISM: Western equine encephalomyelitis virus

<400> SEQUENCE: 88

Asp Phe Thr Leu Thr Ser Pro Tyr Leu Gly Phe Cys Pro Asn Cys Arg

```
1               5                   10                  15

His Ser Ala Pro Cys Phe Ser Pro Ile Lys Ile Glu Asn Val Trp Asp
            20                  25                  30

Glu Ser Asp Asp Gly Ser Ile Arg Ile Gln Val Ser Ala Gln Phe Gly
        35                  40                  45

Tyr Asn Gln Ala Gly Thr Ala Asp Val Thr Lys Phe Arg Tyr Met Ser
    50                  55                  60

Tyr Asp His Asp His Asp Ile Glu Glu Asp Ser Met Glu Lys Ile Ala
65                  70                  75                  80

Ile Ser Thr Ser Gly Pro Cys Arg Arg Leu Gly His Lys Gly Tyr Phe
                85                  90                  95

Leu Leu Ala Gln Cys Pro Pro Gly Asp Ser Val Thr Val Ser Ile Thr
            100                 105                 110

Ser Gly Ala Ser Glu Asn Ser Cys Thr Val Glu Phe Lys Ile Arg Arg
        115                 120                 125

Lys Phe Val Gly Arg Glu Glu Tyr Leu Phe Pro Pro Val His Gly Lys
    130                 135                 140

Arg Val Lys Cys His Val Tyr Asp His Leu Lys Glu Arg Ser Ala Gly
145                 150                 155                 160

Tyr Ile Thr Met His Arg Pro Ser Pro His Ala Tyr Lys Ser Tyr Leu
                165                 170                 175

Lys Glu Ala Ser Gly Glu Val Tyr Ile Lys Pro Pro Ser Gly Lys Asn
            180                 185                 190

Val Thr Tyr Glu Cys Lys Cys Gly Asp Tyr Ser Thr Gly Ile Val Ser
        195                 200                 205

Thr Pro Thr Lys Met Asn Gly Cys Thr Lys Ala Lys Gln Cys Ile Ala
    210                 215                 220

Tyr Lys Ser Asp Gln Thr Lys Trp Val Phe Asn Ser Pro Asp Leu Ile
225                 230                 235                 240

Arg His Thr Asp His Ser Val Gln Gly Lys Leu His Ile Pro Phe Arg
                245                 250                 255

Leu Ile Pro Thr Val Cys Pro Val Pro Leu Ala His Thr Pro Thr Val
            260                 265                 270

Thr Lys Trp Phe Lys Gly Ile Thr Leu His Leu Thr Ala Thr Arg Pro
        275                 280                 285

Thr Leu Leu Thr Thr Arg Lys Leu Gly Leu Arg Ala Asp Ala Thr Ala
    290                 295                 300

Glu Trp Ile Thr Gly Thr Thr Ser Arg Asn Phe Ser Val Gly Arg Glu
305                 310                 315                 320

Gly Leu Glu Tyr Val Trp Gly Asn His Glu Pro Val Arg Val Trp Ala
                325                 330                 335

Gln Glu Ser Ala Pro Ser Asp Pro His Gly Trp Pro His Glu Ile Ile
            340                 345                 350

Ile His Tyr Tyr His Arg His Pro Val Tyr Thr Val Ile Val Leu Cys
        355                 360                 365

Gly Val Ala Leu Ala Ile Leu Val Gly Thr Ala Ser Ser Ala Ala Cys
    370                 375                 380

Ile Thr Lys Ala Arg Arg Asp Cys Leu Thr Pro Tyr Ala Leu Ala Pro
385                 390                 395                 400

Asn Ala Thr Val Pro Thr Ala Leu Ala Val Leu Cys Cys Ile Arg Pro
                405                 410                 415

Thr Asn Ala
```

<210> SEQ ID NO 89
<211> LENGTH: 416
<212> TYPE: PRT
<213> ORGANISM: Eastern equine encephalomyelitis virus

<400> SEQUENCE: 89

His Phe Thr Arg Tyr Lys Leu Ala Arg Pro Tyr Ile Ala Asp Cys Pro
1 5 10 15

Asn Cys Gly His Ser Arg Cys Asp Ser Pro Ile Ala Ile Glu Glu Val
20 25 30

Arg Gly Asp Ala His Ala Gly Ala Ile Arg Ile Gln Thr Ser Ala Met
35 40 45

Phe Gly Leu Lys Thr Asp Gly Val Asp Leu Ala Tyr Met Ser Phe Met
50 55 60

Asn Gly Lys Thr Gln Lys Ser Ile Lys Ile Asp Asn Leu His Val Arg
65 70 75 80

Thr Ser Ala Pro Cys Ser Leu Val Ser His His Gly Tyr Tyr Ile Leu
85 90 95

Ala Gln Cys Pro Pro Gly Asp Thr Val Thr Val Gly Phe His Asp Gly
100 105 110

Pro Asn Arg His Thr Cys Thr Val Ala His Lys Val Glu Phe Arg Pro
115 120 125

Val Gly Arg Glu Glu Tyr Arg His Pro Pro Glu His Gly Val Glu Leu
130 135 140

Pro Cys Asn Arg Tyr Thr His Lys Arg Ala Asp Gln Gly His Tyr Val
145 150 155 160

Glu Met His Gln Pro Gly Leu Val Ala Asp His Ser Leu Leu Ser Ile
165 170 175

His Ser Ala Lys Val Lys Ile Thr Val Pro Ser Gly Ala Gln Val Lys
180 185 190

Tyr Tyr Cys Lys Cys Pro Asp Val Arg Glu Gly Ile Thr Ser Ser Asp
195 200 205

His Thr Thr Thr Cys Thr Asp Val Lys Gln Cys Arg Ala Tyr Leu Ile
210 215 220

Asp Asn Lys Lys Trp Val Tyr Asn Phe Gly Arg Leu Leu Arg Gly Glu
225 230 235 240

Gly Asp Thr Phe Lys Gly Lys Leu His Val Pro Phe Val Pro Val Lys
245 250 255

Ala Lys Cys Ile Ala Thr Leu Ala Pro Glu Leu Leu Val Glu His Lys
260 265 270

His Arg Thr Leu Ile Leu His Leu His Pro Asp His Pro Thr Leu Leu
275 280 285

Thr Thr Arg Ser Leu Gly Ser Asp Ala Asn Pro Ile Arg Gln Trp Ile
290 295 300

Glu Arg Pro Thr Thr Val Asn Phe Thr Val Thr Gly Glu Gly Leu Glu
305 310 315 320

Tyr Thr Trp Gly Asn His Pro Pro Lys Arg Val Trp Ala Gln Glu Ser
325 330 335

Gly Glu Gly Asn Pro His Gly Trp Pro His Glu Val Val Val Tyr Tyr
340 345 350

Tyr Asn Arg Tyr Pro Leu Thr Thr Ile Ile Gly Leu Cys Thr Cys Val
355 360 365

Ala Ile Ile Met Val Ser Cys Val Thr Ser Val Trp Leu Leu Cys Arg
370 375 380

Ala Arg Asn Leu Cys Ile Thr Pro Tyr Lys Leu Ala Pro Asn Ala Gln
385 390 395 400

Val Pro Ile Leu Leu Ala Leu Leu Cys Cys Ile Lys Pro Thr Lys Ala
405 410 415

<210> SEQ ID NO 90
<211> LENGTH: 419
<212> TYPE: PRT
<213> ORGANISM: Venezuelan equine encephalitis virus

<400> SEQUENCE: 90

Leu Phe Asn Glu Tyr Lys Leu Thr Arg Pro Tyr Met Ala Arg Cys Ile
1 5 10 15

Arg Cys Ala Val Gly Ser Cys His Ser Pro Ile Ala Ile Glu Ala Val
20 25 30

Lys Ser Asp Gly His Asp Gly Tyr Val Arg Leu Gln Thr Ser Ser Gln
35 40 45

Tyr Gly Leu Asp Ser Ser Gly Asn Leu Lys Gly Arg Thr Met Arg Tyr
50 55 60

Asp Met His Gly Thr Ile Lys Glu Ile Pro Leu His Gln Val Ser Leu
65 70 75 80

Tyr Thr Ser Arg Pro Cys His Ile Val Asp Gly His Gly Tyr Phe Leu
85 90 95

Leu Ala Arg Cys Pro Ala Gly Asp Ser Ile Thr Met Glu Phe Lys Lys
100 105 110

Asp Ser Val Arg His Ser Cys Ser Val Pro Tyr Glu Val Lys Phe Asn
115 120 125

Pro Val Gly Arg Glu Leu Tyr Thr His Pro Pro Glu His Gly Val Glu
130 135 140

Gln Ala Cys Gln Val Tyr Ala His Asp Ala Gln Asn Arg Gly Ala Tyr
145 150 155 160

Val Glu Met His Leu Pro Gly Ser Glu Val Asp Ser Ser Leu Val Ser
165 170 175

Leu Ser Gly Ser Ser Val Thr Val Thr Pro Pro Asp Gly Thr Ser Ala
180 185 190

Leu Val Glu Cys Glu Cys Gly Gly Thr Lys Ile Ser Glu Thr Ile Asn
195 200 205

Lys Thr Lys Gln Phe Ser Gln Cys Thr Lys Lys Glu Gln Cys Arg Ala
210 215 220

Tyr Arg Leu Gln Asn Asp Lys Trp Val Tyr Asn Ser Asp Lys Leu Pro
225 230 235 240

Lys Ala Ala Gly Ala Thr Leu Lys Gly Lys Leu His Val Pro Phe Leu
245 250 255

Leu Ala Asp Gly Lys Cys Thr Val Pro Leu Ala Pro Glu Pro Met Ile
260 265 270

Thr Phe Gly Phe Arg Ser Val Ser Leu Lys Leu His Pro Lys Asn Pro
275 280 285

Thr Tyr Leu Ile Thr Arg Gln Leu Ala Asp Glu Pro His Tyr Thr His
290 295 300

Glu Leu Ile Ser Glu Pro Ala Val Arg Asn Phe Thr Val Thr Glu Lys
305 310 315 320

Gly Trp Glu Phe Val Trp Gly Asn His Pro Pro Lys Arg Phe Trp Ala
325 330 335

Gln Glu Thr Ala Pro Gly Asn Pro His Gly Leu Pro His Glu Val Ile

-continued

```
            340                 345                 350

Thr His Tyr Tyr His Arg Tyr Pro Met Ser Thr Ile Leu Gly Leu Ser
        355                 360                 365

Ile Cys Ala Ala Ile Ala Thr Val Ser Val Ala Ala Ser Thr Trp Leu
    370                 375                 380

Phe Cys Arg Ser Arg Val Ala Cys Leu Thr Pro Tyr Arg Leu Thr Pro
385                 390                 395                 400

Asn Ala Arg Ile Pro Phe Cys Leu Ala Val Leu Cys Cys Ala Arg Thr
                405                 410                 415

Ala Arg Ala


<210> SEQ ID NO 91
<211> LENGTH: 15
<212> TYPE: PRT
<213> ORGANISM: Artificial Sequence
<220> FEATURE:
<223> OTHER INFORMATION: insertion sequence
<220> FEATURE:
<221> NAME/KEY: MISC_FEATURE
<223> OTHER INFORMATION: L or V

<400> SEQUENCE: 91

Gly Glu Gln Arg Leu Gly Glu Gln Arg Val Gly Glu Gln Arg Val
1               5                   10                  15


<210> SEQ ID NO 92
<211> LENGTH: 5
<212> TYPE: PRT
<213> ORGANISM: Artificial Sequence
<220> FEATURE:
<223> OTHER INFORMATION: insertion sequence
<220> FEATURE:
<221> NAME/KEY: MISC_FEATURE
<222> LOCATION: (5)..(5)
<223> OTHER INFORMATION: L or V

<400> SEQUENCE: 92

Gly Glu Gln Arg Xaa
1               5
```

COMPOSITIONS AND METHODS FOR INHIBITION OF ALPHAVIRUS INFECTION

CROSS-REFERENCE TO RELATED APPLICATIONS

This application claims the benefit of priority to PCT International Application No. PCT/US19/12435 filed on 4 Jan. 2019, which claims the benefit of U.S. Provisional Application Ser. No. 62/613,658 filed on 4 Jan. 2018; 62/671,680 filed on 15 May 2018; and 62/672,080 filed on 16 May 2018, which are incorporated herein by reference in their entireties.

STATEMENT REGARDING FEDERALLY SPONSORED RESEARCH OR DEVELOPMENT

This invention was made with government support under HHSN272201700060C and AI143673 awarded by the National Institutes of Health. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention (file name "017583-WO-US_Replacement_Sequence_Listing.txt" created on 9 Nov. 2023; 179,695 bytes). The subject matter of the Sequence Listing is incorporated herein by reference in its entirety.

FIELD OF THE INVENTION

The present disclosure generally relates to compositions and methods for inhibition of arthritogenic alphavirus infections.

SUMMARY OF THE INVENTION

Among the various aspects of the present disclosure is the provision of compositions and methods of treating arthritogenic alphavirus infection and screening methods.

An aspect of the present disclosure provides for a fusion protein comprising an Fc region and at least one Mxra8 region or functional fragment or functional variant thereof, wherein the Mxra8 region has Mxra8 activity or Mxra8 receptor activity.

In some embodiments, the Mxra8 region comprises a polypeptide, wherein the polypeptide is encoded by a polynucleotide comprising SEQ ID NO: 1 or functional fragment or functional variant thereof; or the polypeptide comprises SEQ ID NO: 2 or a functional fragment or functional variant thereof.

In some embodiments, the functional fragment or functional variant thereof has a nucleotide sequence or an amino acid sequence of at least 90-95% identity to SEQ ID NO: 1 or SEQ ID NO: 2; and Mxra8 activity or Mxra8 receptor activity.

In some embodiments, the Mxra8 region is a Mxra8 ectodomain region or functional fragment or variant thereof. In some embodiments, the Fc region is selected from human IgG1, human IgG1 with N297Q mutation, or mouse IgG2b.

In some embodiments, the fusion protein comprises a human rhinovirus 3C (HRV) protease site between the Mxra8 C-terminus and an Fc domain.

Another aspect of the present disclosure provides for a method of treating a Mxra8-associated alphavirus comprising: administering a therapeutically effective amount of a Mxra8 inhibiting agent.

In some embodiments, the Mxra8-associated alphavirus is an arthritogenic alphavirus having a Mxra8 entry receptor.

In some embodiments, the Mxra8 inhibiting agent comprises an anti-Mxra8 antibody or Mxra8 fusion protein.

In some embodiments, the Mxra8 inhibiting agent is selected from one or more of the group consisting of anti-Mxra8, Mxra8-Fc, MXRA8-2-Fc, or a fusion protein comprising an Fc antibody domain fused to an ectodomain of Mxra8 or ectodomain of MXRA8-2 or a functional fragment or variant thereof having Mxra8 or Mxra8 receptor activity.

In some embodiments, the Mxra8 inhibiting agent comprises a small molecule Mxra8 inhibitor, Mxra8 siRNA, Mxra8 sgRNA, or Mxra8 shRNA.

In some embodiments, the therapeutically effective amount of a Mxra8 inhibiting agent reduces or prevents infection by an arthritogenic alphavirus.

In some embodiments, the arthritogenic alphavirus is selected from the group consisting of: Chikungunya Virus (CHIKV), Mayaro Virus (MAYV), Ross River Virus (RRV), O'nyong nyong (ONNV), Barmah Forest Virus (BFV), Semliki Forest virus, and Getah virus.

In some embodiments, the arthritogenic alphavirus is selected from the group consisting of: Semliki Forest and Getah viruses.

Yet another aspect of the present disclosure provides for a method of treating an arthritogenic alphavirus infection comprising: genetically modifying Mxra8 in a subject or genetically modifying a subject to reduce or prevent expression of the Mxra8 gene, such as through the use of CRISPR-Cas9 or analogous technologies, wherein, such modification reduces or prevents infection of a host by an arthritogenic alphavirus.

In some embodiments, the subject is a mammal.

In some embodiments, the subject is selected from the group consisting of: a human, a fish (e.g., salmon, trout), a mouse, or a mosquito.

In some embodiments, the subject is selected from the group consisting of: a mammal, such as a horse, dog, cat, sheep, pig, mouse, rat, monkey, hamster, guinea pig, chicken, and human.

Yet another aspect of the present disclosure provides for a pharmaceutical composition comprising a Mxra8 inhibiting agent.

In some embodiments, the Mxra8 inhibiting agent reduces inflammation and infection by an arthritogenic alphavirus.

In some embodiments, the Mxra8 inhibiting agent is an anti-Mxra8 antibody.

In some embodiments, the Mxra8 inhibiting agent is selected from one or more of the group consisting of anti-Mxra8, Mxra8-Fc, MXRA8-2-Fc, or a fusion protein comprising an Fc antibody domain fused to an ectodomain of Mxra8 or an ectodomain of MXRA8-2.

In some embodiments, the Mxra8 inhibiting agent comprises a small molecule Mxra8 inhibitor, Mxra8 siRNA, Mxra8 sgRNA, or Mxra8 shRNA.

Yet another aspect of the present disclosure provides for a method of generating antibodies against Mxra8, the method comprising: (a) immunizing a subject (e.g., a mammal) with Mxra8 protein or analog; and/or (b) isolating Mxra8-specific antibodies.

Yet another aspect of the present disclosure provides for a method of screening for a Mxra8 inhibitor, which method comprises: (a) contacting a receptor having a Mxra8 function with a test compound; (b) measuring the ability of Mxra8 to bind a viral protein or to allow viral infection; and/or (c) determining whether the test compound is a Mxra8 inhibitor from the measurements taken in step (b).

Yet another aspect of the present disclosure provides for a method of binding a surface-displayed E2 protein in alphavirus-infected cells comprising: administering to an alphavirus infected cell a therapeutically effective amount of a fusion protein comprising SEQ ID NO: 2 and/or SEQ ID NO: 8 or a functional variant or functional fragment of SEQ ID NO: 2 and/or SEQ ID NO: 8.

Yet another aspect of the present disclosure provides for an in silico method of identifying a compound that binds to Mxra8 or Mxra8 entry receptor comprising: (i) providing or receiving an estimated three-dimensional structure of atomic coordinates of Mxra8 or atomic coordinates Mxra8 entry receptor, their complexes, or a portion thereof, the three-dimensional structure comprising a plurality of amino acids; (ii) selecting a chemical probe; or (iii) determining if the chemical probe binds to Mxra8, Mxra8 entry receptor, or a portion of Mxra8, or a portion of a Mxra8 entry receptor (e.g., E2).

Yet another aspect of the present disclosure provides for an in silico method comprising: identifying a set(s) of one or more protein conformations to which the chemical probe binds; testing the compound or chemical probe in an in vitro or in vivo assay to determine its efficacy; determining a toxicity of the compound or chemical probe; determining if the compound or chemical probe has an off-target effect; determining toxicity or the off-target effect in an in vitro, an in vivo, or an in silico assay; optimizing the compound or chemical probe; or optimizing the compound or chemical probe to reduce toxicity of the compound to reduce an off-target effect; to increase or decrease a binding affinity of the compound or chemical probe; or to increase or decrease an activity of an off-target protein.

Yet another aspect of the present disclosure provides for a the three-dimensional structure comprising cryo-EM atomic coordinates according to PDB code 6NK3, PDB code 6NK5, EMDB code EMD-9393, PDB code 6NK6, EMDB code EMD-9394, PDB code 6NK7, EMDB code EMD-9395, TABLE 5, FIG. 14C, FIG. 14D, FIG. 21, FIG. 23A-D, FIG. 24, FIG. 25, FIG. 26B, FIG. 31, or FIG. 32 or a portion thereof; or the Mxra8 is capable of wedging into a cleft created by adjacent alphavirus E2 proteins in one trimeric spike and engages E1 protein on an adjacent spike.

Yet another aspect of the present disclosure provides for a method of treating a Mxra8-associated alphavirus comprising: administering a therapeutically effective amount of a Mxra8 inhibiting agent identified using the in silico method.

Yet another aspect of the present disclosure provides for a method of measuring integrity of an alphavirus vaccine or alphavirus antigen comprising: capturing Mxra8, Mxra8 fusion protein, or functional fragment or variant thereof, on a substrate; incubating the alphavirus vaccine or alphavirus antigen and the substrate; and detecting with a monoclonal or polyclonal anti-vaccine/antigen antibody or Mxra8-Fc; capturing the alphavirus vaccine or alphavirus antigen in a solid phase (e.g., directly or via a bridging antibody); and/or incubating the captured alphavirus vaccine or alphavirus antigen with Mxra8, Mxra8 fusion protein, or functional fragment or functional variant thereof.

Yet another aspect of the present disclosure provides for a fusion protein selected from Mxra8-Fc; the substrate is selected from a microtiter well plate, chip, or pin; or a method comprising an assay selected from ELISA, biolayerinterferometry, or surface plasmon resonance.

Yet another aspect of the present disclosure provides for an alphavirus vaccine or antigen selected from a live-attenuated virus, a virus-like particle, a viral structural protein, or a nucleic acid or vector producing viral proteins or particles.

Yet another aspect of the present disclosure provides for a method of reducing or preventing alphavirus infection comprising gene editing of Mxra8.

Yet another aspect of the present disclosure provides for a gene editing selected from CRISPR-Cas9-based gene editing.

Yet another aspect of the present disclosure provides for the gene editing comprises insertion of at least one GEQRL/V in Domain 1 or the Mxra8 ectodomain; three or more GEQRL/V in Domain 1 or the Mxra8 ectodomain; or GEQRLGEQRVGEQRV in Domain 1 or the Mxra8 ectodomain, wherein the insertion disrupts interactions with the Mxra8 receptor on an alphavirus or wherein the insertion provides for a disordered extension of the Mxra8 C'-C" loop in Domain 1.

Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 6 shows the efficiency of targeting Mxra8 expression by CRISPR-Cas9 gene editing. (a) 3T3 cells were edited with a control or three different Mxra8 sgRNAs. After puromycin selection, bulk cells were inoculated with CHIKV-181/25-mKate2 and processed for marker gene expression by flow cytometry. Data are pooled from three experiments and expressed as mean±s.d. (n=6, one-way ANOVA with a Dunnett's multiple comparison test compared to control). (b) Western blotting of Mxra8 in control and ΔMxra8 3T3 or MEF cells using hamster mAb 3G2.F5. One representative of two is shown. (c) 3T3 and MEF cells (parent or ΔMxra8) were tested for Mxra8 surface expression by flow cytometry using anti-Mxra8 antibody (4E7.D10) and an isotype control mAb. One representative experiment of two is shown. (d) Sanger sequencing of Mxra8 in control and ΔMxra8 3T3 or MEF cells (SEQ ID NOs: 55-61). Sequencing data shows an alignment and individual out-of-frame deletions. (e) Viability of control and ΔMxra8 3T3 and MEF cells. Equal numbers of cells were plated and viability was assessed over a 24-h period using the Cell-Titer Glo assay. The results were normalized to control cells and pooled from two experiments (n=6). Error bars indicate s.d. ****P<0.0001.

FIG. 15A is a bar graph showing surface expression of Mxra8 as determined by flow cytometry and staining with cross-reactive anti-Mxra8 monoclonal antibodies.

FIG. 15B is a bar graph showing CHIKV infection in cells trans-complemented with Mxra8 from different species. Note, Cow Mxra8 was expressed strongly on the surface but did not support CHIKV infection as judged by staining for viral antigen. Results are representative of three independent experiments.

FIG. 16 shows a 15-amino acid insertion in cow Mxra8 prevents binding to CHIKV virions. A. Diagram of generation of recombinant mouse Mxra8-Fc fusion proteins that lacked or contained the additional 15 residues from cow (mouse Mxra8 and mouse Mxra8+moo) and reciprocally cow Mxra8-Fc fusion protein that lacked or contained the 15 residues (cow Mxra8 and cow Mxra8 Δmoo). B. Alignment of mouse Mxra8, mouse Mxra8+moo, cow Mxra8, and cow Mxra8 Δmoo proteins in the region of the 15-amino acid insertion. C. Binding data in an ELISA. CHIKV virions were captured with a human anti-CHIKV mAb and then tested for binding to increasing doses (0.1, 1, and 10 μg/ml) of mouse Mxra8-Fc, mouse Mxra8-Fc+moo, cow Mxra8-Fc, and cow Mxra8-Fc Δmoo. Signal was detected by Optical density. Results are representative of three independent experiments. Mxra8 mouse sequence (SEQ ID NO: 53) and bovine sequence (SEQ ID NO: 54).

FIG. 18 depicts the generation of $Mxra8^{mut/mut}$ mice by CRISPR-Cas9 gene targeting. A. Sequencing of Mxra8 gene of two different founder lines establishes 8 and 97 nucleotide deletions (SEQ ID NOs: 66-69). B. Western blotting of muscle tissue from $Mxra8^{+/+}$, $Mxra8^{\Delta 8/+}$ (HET), $Mxra8^{\Delta 8/\Delta 8}$ (KO) lines. Data are representative of two experiments.

FIG. 34(A-D) shows Table 1 listing binding reactivity (% WT (Range)) for Domain A mutations (FIGS. 34A, 34B, and 34C) and Domain B mutations (FIG. 34D).

DETAILED DESCRIPTION OF THE INVENTION

Figure 1:
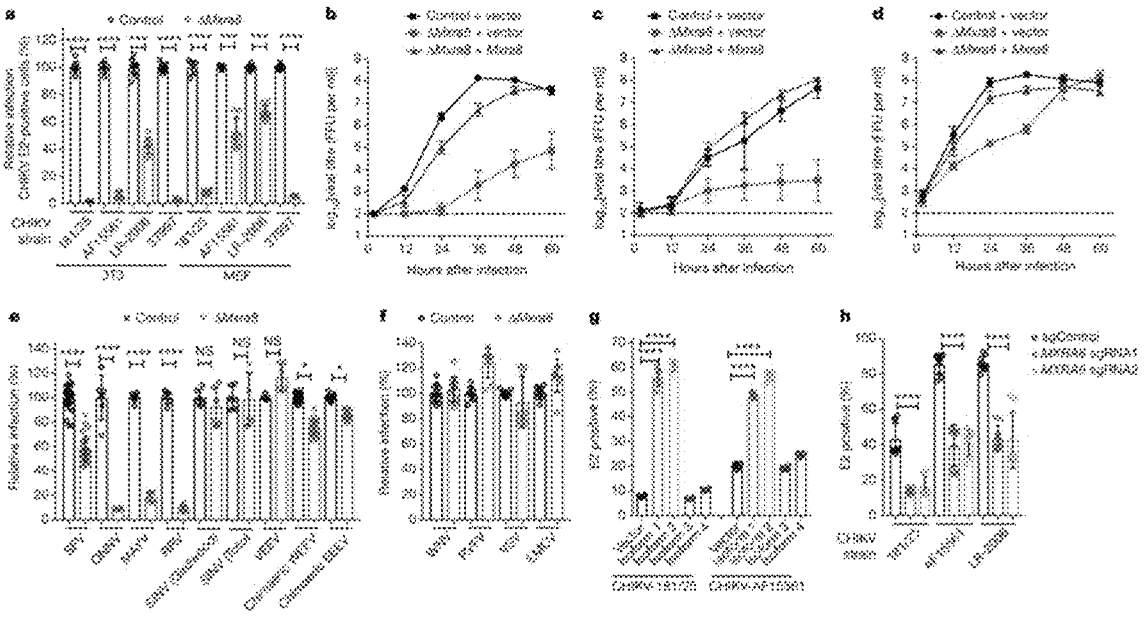
FIG. 1 is a series of graphs showing Mxra8 is required for optimal infection of CHIKV and other alphaviruses. (a) ΔMxra8 or control 3T3 or MEF cells were inoculated with CHIKV and stained for E2 protein (3 experiments, n=9; two-tailed t-test with Holm-Sidak correction; mean±s.d.). (b-d) Multi-step growth curves with CHIKV-181/25 (b), CHIKV-AF15561 (c) or CHIKV-LR-2006 (d) in control, ΔMxra8 or Mxra8 trans-complemented ΔMxra8 3T3 cells (3 experiments, n=9; mean±s.d.). FFU, focus forming units. (e) ΔMxra8 or control 3T3 cells were inoculated with alphaviruses and processed for E2 or reporter gene expression (3 or more experiments, n=6 except for Semliki Forest virus (SFV), Sindbis-Western equine encephalitis virus chimaera (WEEV) and Sindbis-Eastern equine encephalitis virus chimaera (EEEV) in which with Holm-Sidak correction; mean±s.d.). (f) ΔMxra8 or control 3T3 cells were inoculated with indicated viruses and processed for viral antigen or reporter gene expression (3 experiments, mean±s.d.). (g) Hela cells were transduced with control or MXRA8-1, MXRA8-2, MXRA8-3 or MXRA8-4 alleles, inoculated with CHIKV and processed for E2 staining (3 experiments, n=6; one-way ANOVA with Dunnett's test; mean±s.d.). (h) Human MRC-5 cells depleted of MXRA8 with two different sgRNA were inoculated with CHIKV, and E2 expression was analysed (3 experiments, n=9; one-way ANOVA with Dunnett's test; mean±s.d.). EMCV, encephalomyocarditis virus; MAYV; Mayaro virus; ONNV, O'nyong nyong virus; RRV, Ross River virus; RVFV, Rift Valley fever virus; VEEV, Venezuelan equine encephalitis virus; VSV, vesicular stomatitis virus; WNV, West Nile virus. *P<0.05; P<0.01; *P<0.001; ****P<0.0001; NS, not significant.

The present disclosure is based, at least in part, on the discovery that Mxra8 is a receptor for arthritogenic alphaviruses, including chikungunya (CHIKV), Ross River, Mayaro, and O'nyong nyong (ONNV) viruses.

Mxra8

One aspect of the present disclosure provides for targeting of Mxra8 (also called DICAM, ASP3, or limitrin). The present disclosure provides methods of treating alphaviruses based on the discovery that Mxra8 is critical for an entry step in the virus lifecycle.

As described herein, the mouse protein Mxra8 was identified in a whole genome CRISPR/Cas9 screen looking for host factors that were required for infection of chikungunya virus (CHIKV). Mxra8 was one of the top hits of the screen. Subsequent validation studies revealed that gene editing of mouse Mxra8 via CRISPR/Cas9 resulted in markedly reduced infection of chikungunya, Ross River, Mayaro, and O'nyong nyong viruses but did not directly impact distantly related alphaviruses (Sindbis, EEEV, WEEV) or unrelated flaviviruses. Transcomplementation of KO cells with mouse or human Mxra8 restored infectivity of CHIKV.

As described herein, mechanism of action studies using CHIKV pseudotyped viruses or transfection of genomic RNA revealed that Mxra8 was critical for an entry step in the virus lifecycle. Direct binding and entry assays showed Mxra8 was not an attachment receptor but rather functioned as an entry receptor critical for allowing the virus to gain access to the cytoplasm.

As described herein, using a genome-wide CRISPR/Cas9-based screen, cell adhesion molecule Mxra8 was identified as an entry mediator for multiple emerging arthritogenic alphaviruses including chikungunya (CHIKV), Ross River, Mayaro, and O'nyong nyong (ONNV) viruses.

As described herein, gene editing of mouse Mxra8 or human MXRA8 resulted in reduced viral infection of cells, and reciprocally, ectopic expression resulted in increased infection.

As described herein, Mxra8 bound directly to CHIKV particles and enhanced virus attachment and internalization into cells.

As described herein, Mxra8-Fc protein or anti-Mxra8 monoclonal antibodies blocked CHIKV infection in multiple cell types including primary human synovial fibroblasts, osteoblasts, chondrocytes, and skeletal muscle cells.

As described herein, mutagenesis experiments suggest that Mxra8 binds to a surface-exposed region across the A and B domains of CHIKV E2, a speculated site of attachment.

As described herein, administration of Mxr8a-Fc protein or anti-Mxra8 blocking antibodies reduced CHIKV or ONNV infection and associated foot swelling in mice.

As such, it has been shown that pharmacological targeting of Mxra8 can form a strategy for mitigating infection and disease by multiple arthritogenic alphaviruses.

Consistent with a role in attachment and entry, Mxra8-Fc protein or anti-Mxra8 antibody directly blocked CHIKV infection.

Mxra8 can be an isoform of Mxra8. For example, an isoform of Mxra8 can be selected from one or more of the group selected from MXRA8-1, MXRA8-2, MXRA8-3, and MXRA8-4.

Mxra8—Associated Viruses

As described herein, the Mxra8 receptor was discovered on cells as an entry receptor for viruses (e.g., arthritogenic alphaviruses) that expressed Mxra8 on its surface. A Mxra8-associated virus can be any virus expressing Mxra8 on the surface of the virus and using a Mxra8 receptor on cell as the entry point of infection. As described herein, arthritogenic alphaviruses comprise Mxra8 and cells comprise Mxra8 entry receptors. Inhibition of Mxra8, inhibition of Mxra8 receptors, or knock out of the Mxra8 receptors reduce arthritogenic alphavirus infection.

Arthritogenic alphaviruses comprise a group of enveloped RNA viruses that can be transmitted to humans by mosquitoes and cause debilitating acute and chronic musculoskeletal disease[1]. The host factors required for alphavirus entry remain poorly characterized[2].

As described herein, Mxra8 was discovered as an entry receptor for several arthritogenic alphaviruses. For example, a Mxra8-associated alphavirus can be any arthritogenic alphavirus. As another example, the Mxra8-associated alphavirus can be Chikungunya (e.g., CHIKV-181/25, 181/25-mKate2, CHIKV-AF15561, CHIKV-LR 2006, CHIKV-37997 (West African lineage)), Ross River (e.g., RRV (T48)), Mayaro (e.g., MAYV (BeH407)), Barmah Forest, or O'nyong nyong (e.g., ONNV (MP30)) viruses. Other Mxra8-associated alphaviruses can be Semliki Forest virus (SFV) (e.g., SFV (Kumba)) or Getah virus. Mxra8 can also be associated with or play an entry role in additional viruses or alphaviruses that have not yet been tested or discovered.

Alphaviruses that were discovered to not be Mxra8-associated alphaviruses were distantly related alphaviruses (e.g., Sindbis, Bebaru, Una, Middleburg, Eastern equine encephalitis, Western equine encephalitis or Venezuelan equine encephalitis viruses) or unrelated flaviviruses (e.g., West Nile virus), bunyaviruses (Rift Valley fever virus), rhabdoviruses (e.g., Vesicular stomatitis virus), or picornaviruses (encephalomyocarditis virus). It was also discovered that Mxra8 showed no effect for unrelated positive- or negative-sense RNA viruses.

Mxra8 Inhibiting Agent

As described herein, a Mxra8 inhibiting agent reduces, prevents, or aborts infection of many different alphaviruses (e.g., Mxra8-associated alphaviruses). For example, a Mxra8 inhibiting agent can be an agent that interrupts the interaction of Mxra8 expressed on the virus and the Mxra8 entry receptor on the cell surface. As another example, the Mxra8 inhibiting agent can bind to Mxra8 on the virus or can bind to the Mxra8 receptor on the cell. The Mxra8 inhibiting agent can be an agent that binds to the viral structural protein (e.g., E2) of the viron on the cell surface. As another example, a Mxra8 inhibiting agent can be an inhibitor of Mxra8 or an inhibitor of Mxra8 receptors (e.g., antibodies, fusion proteins, small molecules).

A Mxra8 inhibiting agent can be any agent that can inhibit Mxra8, inhibit a Mxra8 receptor (e.g., Mxra8 fusion proteins, Mxra8, Mxra8 dimers, and functional variants thereof), downregulate Mxra8, or knockdown Mxra8.

As another example, a Mxra8 inhibiting agent can be a mutated or genetically edited Mxra8 to render it unable to bind to the Mxra8 receptor on an alphavirus.

As another example, the Mxra8 inhibiting agent can be a fusion protein. For example, the Mxra8 fusion protein can comprise a fragment or variant of Mxra8 (e.g., Mxra8-Fc, MXRA8-2-Fc). As another example, the fusion protein can comprise a mouse or human Fc antibody domain fused to the ectodomain of Mxra8 or MXRA8-2. Fusion proteins as described herein can comprise a Mxra8 or functional variant thereof.

Mxra8 can comprise a Mxra8 ectodomain (see e.g., SEQ ID NOs: 1-4) or a Mxra8 isoform (see e.g., (SEQ ID NOs: 25-31)) or a functional variant or functional fragment thereof.

As an example, the following fusion proteins were developed: human Mxra8 on mouse Fc (see e.g., SEQ ID NOs: 17-18); mouse Mxra8 on mouse Fc (see e.g., SEQ ID NOs: 19-20); mouse Mxra8 on human Fc (see e.g., SEQ ID NOs: 21-22); and mouse Mxra8 on human Fc N297Q (see e.g., SEQ ID NOs: 23-24). As another example, the fusion proteins can comprise a signal peptide (e.g., an IL-2 signal peptide), a Mxra isoform fragment, or functional variant thereof (e.g., fragment of Mxra8 comprising the ectodomain of Mxra8); a linker (optionally) (e.g., GS linker), or an Fc region (e.g., mIgG2b Fc region).

```
Human Mxra8 iso form 1 ectodomain nucleotide sequence
                                                              (SEQ ID NO: 1)
GTCCTGTTGCATAGCGGCTCCTCTGTCCCGGCCGCAGCGGGATCAAGCGTAGTGAGCGAGTCAGCAGTTTCCT

GGGAAGCGGGGGCAAGGGCTGTTCTGAGGTGTCAGAGCCCAAGGATGGTGTGGACGCAAGACCGGCTCCACGA

CAGGCAAAGAGTGCTTCACTGGGACCTCAGGGGACCCGGTGGTGGCCCAGCACGCCGGCTCCTGGACCTCTAT

AGCGCGGGAGAACAACGAGTATACGAAGCTAGGGACAGAGGAAGACTGGAGCTTTCAGCCAGTGCGTTCGATG

ATGGAAATTTTTCACTTCTGATCCGGGCTGTGGAAGAAACTGATGCTGGACTGTATACTTGTAATCTCCACCA

TCACTACTGCCACCTCTATGAGTCATTGGCTGTCAGACTGGAAGTTACCGATGGCCCGCCCGCCACACCAGCT

TACTGGGATGGCGAAAAAGAAGTACTTGCTGTCGCGCGAGGTGCCCCTGCGCTCCTGACATGCGTCAACAGGG

GTCACGTTTGGACTGATCGGCACGTCGAAGAGGCTCAGCAAGTAGTTCACTGGGACCGCCAGCCGCCTGGCGT

ACCTCACGATAGGGCCGACCGCCTCTTGGACCTCTACGCCTCCGGTGAAAGGAGGGCCTATGGGCCTCTGTTC

CTCAGAGATAGGGTTGCGGTGGGCGCAGATGCCTTTGAACGAGGCGATTTCAGCCTCCGCATTGAGCCCCTGG

AGGTAGCCGATGAGGGCACCTACTCCTGTCATCTGCATCATCATTATTGCGGATTGCACGAGAGGAGGGTCTT

CCACTTGACTGTAGCTGAACCGCATGCTGAACCGCCACCTCGCGGATCACCCGGAAACGGTAGCAGTCATTCC

GGGGCTCCCGGGCCGGATCCGACATTGGCACGAGGGCATAACGTAATAAATGTCATCGTTCCCGAGTCACGCG

CTCAT

Human Mxra8 isoform 1 ectodomain polypeptide sequence
                                                              (SEQ ID NO: 2)
VLLHSGSSVPAAAGSSVVSESAVSWEAGARAVLRCQSPRMVWTQDRLHDRQRVLHQDLRGPGGGPARRLLDLY

SAGEQRVYEARDRGRLELSASAFDDGNFSLLIRAVEETDAGLYTCNLHHHYCHLYESLAVRLEVTDGPPATPA

YWDGEKEVLAVARGAPALLTCVNRGHVWTDRHVEEAQQVVHWDRQPPGVPHDRADRLLDLYASGERRAYGPLF

LRDRVAVGADAFERGDFSLRIEPLEVADEGTYSCHLHHHCGLHERRVFHLTVAEPHAEPPPRGSPGNGSSHSG

APGPDPTLARGHNVINVIVPESRAH
```

-continued

Mouse Mxra8 ectodomain nucleotide sequence (SEQ ID NO: 3)

TCTGGCCCGAGCGGTACTGCTGCCGCAAGCTCAAGCCTCGTCTCTGAATCAGTTGTGTCTCTCGCGGCCGGAA

CTCAGGCGGTCCTGAGGTGTCAAAGTCCAAGGATGGTTTGGACCCAAGATCGCTTGCATGATCGACAAAGAGT

TGTGCACTGGGACCTCAGCGGTGGTCCTGGATCACAACGAAGAAGGCTGGTGGACATGTACTCAGCCGGAGAA

CAGCGCGTTTACGAGCCACGAGACCGAGATCGACTCCTTTTGTCACCTTCTGCGTTCCATGACGGCAACTTTT

CTTTGTTGATAAGAGCCGTAGATCGCGGAGATGAAGGAGTTTATACGTGTAACCTTCACCACCATTACTGCCA

TCTCGATGAAAGTCTCGCCGTACGGCTGGAAGTTACGGAGGACCCACTTCTTTCACGGGCATATTGGGATGGC

GAGAAGGAGGTCCTGGTCGTTGCTCACGGCGCACCAGCCCTGATGACATGCATCAACAGAGCCCATGTTTGGA

CCGACAGGCACCTTGAAGAAGCACAACAAGTTGTCCATTGGGACCGACAGCTCCCAGGTGTTAGCCATGATCG

GGCCGATCGCTTGCTTGACTTGTATGCCAGCGGGGAACGGAGGGCATACGGCCCGCCTTTTCTTCGGGATCGA

GTTAGCGTAAACACTAACGCCTTTGCACGCGGTGACTTCAGCCTTCGCATAGATGAACTCGAACGAGCAGATG

AAGGAATATACTCCTGCCATTTGCATCATCATTATTGCGGCCTGCATGAGCGAAGGGTATTTCACCTCCAAGT

GACTGAACCTGCATTCGAGCCACCAGCGAGGGCCTCACCGGGAAACGGCTCCGGCCACAGCAGCGCACCGTCT

CCGGACCCGACTTTGACACGGGGCCATAGTATAATAAACGTAATAGTTCCTGAGGACCATACCCAC

Mouse Mxra8 ectodomain polypeptide sequence (SEQ ID NO: 4)

SGPSGTAAASSSLVSESVVSLAAGTQAVLRCQSPRMVWTQDRLHDRQRVVHWDLSGGPGSQRRRLVDMYSAGE

QRVYEPRDRDRLLLSPSAFHDGNFSLLIRAVDRGDEGVYTCNLHHHYCHLDESLAVRLEVTEDPLLSRAYWDG

EKEVLVVAHGAPALMTCINRAHVWTDRHLEEAQQVVHWDRQLPGVSHDRADRLLDLYASGERRAYGPPFLRDR

VSVNTNAFARGDFSLRIDELERADEGIYSCHLHHHYCGLHERRVFHLQVTEPAFEPPARASPGNGSGHSSAPS

PDPTLTRGHSIINVIVPEDHTH mIgG2b Fc nucleotide sequence (SEQ ID NO: 5)

CCCAGCGGGCCCATTTCAACAATCAACCCCTGTCCTCCATGCAAGGAGTGTCACAAATGCCCAGGTAAGTCAC

TACCAGAGCTCCACTCCCAGGAGAATGGTAAGTGCTGTAAAAATCCCTGTAATGGAGGATAAGCCATGTACAA

ATCCATTTCCATCTCTCCTCATCAGCTCCTAACCTCGAGGGTGGACCATCCGTCTTCATCTTCCCTCCAAATA

TCAAGGATGTACTCATGATCTCCCTGACACCCAAGGTCACGTGTGTGGTGGTGGATGTGAGCGAGGATGACCC

AGACGTCCAGATCAGCTGGTTTGTGAACAACGTGGAAGTACACACAGCTCAGACACAAACCCATAGAGAGGAT

TACAACAGTACTATCCGGGTGGTCAGCACCCTCCCCATCCAGCACCAGGACTGGATGAGTGGCAAGGAGTTCA

AATGCAAGGTCAACAACAAAGACCTCCCATCACCCATCGAGAGAACCATCTCAAAAATTAAAGGTGGGACCTG

CAGGACAACTGCATGGGGGCTGGGATGGGCATAAGAATAAATGTCTATGTGGACAGCCTTCCACTTCAGCCAT

GACCTCTATGTATGTTTCTAACCCCACAGGGCTAGTCAGAGCTCCACAAGTATACATCTTGCCGCCACCAGCA

GAGCAGTTGTCCAGGAAAGATGTCAGTCTCACTTGCCTGGTCGTGGGCTTCAACCCTGGAGACATCAGTGTGG

AGTGGACCAGCAATGGGCATACAGAGGAGAACTACAAGGACACCGCACCAGTCCTGGACTCTGACGGTTCTTA

CTTCATATATAGCAAGCTCAATATGAAAACAAGCAAGTGGGAGAAAACAGATTCCTTCTCATGCAACGTGAGA

CACGAGGGTCTGAAAAATTACTACCTGAAGAAGACCATCTCCCGGTCTCCGGGTAAA mIgG2b Fc polypeptide sequence (SEQ ID NO: 6)

PSGPISTINPCPPCKECHKCPAPNLEGGPSVFIFPPNIKDVLMISLTPKVTCVVVDVSEDDPDVQTISWFVNN

VEVHTAQTQTHREDYNSTIRVVSTLPIQHQDWMSGKEFKCKVNNKDLPSPEIPTISKIKGLRAPQVYILPPPA

EQLSRKDVSLTCLVVGFNPGDISVEWTSNGHTEENYKDTAPVLDSDGSYFIYSKLNMKTSKWEKTDSFSCNVR

HEGLKNYYLKKTISRSPGK

-continued

Human IgG1 Fc nucleotide sequence (SEQ ID NO: 7)

GACAAAACCCATACATGCCCACCTTGTCCAGCACCAGAGCTGCTGGGAGGACCAAGCGTGTTCCTGTTTCCAC

CCAAGCCCAAAGATACCCTGATGATCTCCCGGACTCCCGAAGTCACCTGCGTGGTCGTGGACGTGTCTCACGA

GGACCCCGAAGTCAAGTTCAACTGGTACGTGGACGGGGTCGAGGTGCATAATGCCAAGACAAAACCCAGAGAG

GAACAGTACAACAGTACCTATAGAGTCGTGTCAGTCCTGACAGTGCTGCATCAGGATTGGCTGAACGGGAAAG

AGTATAAGTGCAAAGTGAGTAATAAGGCTCTGCCTGCACCAATCGAGAAAACTATTTCCAAGGCCAAAGGACA

GCCCAGGGAACCTCAGGTGTACACCCTGCCTCCATCACGCGAGGAAATGACAAAGAACCAGGTCAGCCTGACT

TGTCTGGTGAAAGGCTTCTATCCTTCTGACATCGCTGTGGAGTGGGAAAGTAATGGGCAGCCAGAGAACAATT

ACAAGACAACTCCCCCTGTCCTGGACTCTGATGGAAGTTTCTTTCTGTATAGCAAGCTGACCGTGGATAAATC

CCGGTGGCAGCAGGGCAATGTCTTTAGCTGTTCCGTGATGCACGAAGCCCTGCACAACCACTACACCCAGAAG

AGCCTGAGCCTGTCACCCGGCAAA

Human IgG1 Fc polypeptide sequence (SEQ ID NO: 8)

DKTHTCPPCPAPELLGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLPPSREEMTKNQVSLT

CLVKGFYPSDIAVEWESNGQPENNYKTTPPVLDSDGSFFLYSKLTVDKSRWQQGNVFSCSVMHEALHNHYTQK

SLSLSPGK

Human IgG1 Fc with N297Q mutation nucleotide sequence (SEQ ID NO: 9)

GACAAAACCCATACATGCCCACCTTGTCCAGCACCAGAGCTGCTGGGAGGACCAAGCGTGTTCCTGTTTCCAC

CCAAGCCCAAAGATACCCTGATGATCTCCCGGACTCCCGAAGTCACCTGCGTGGTCGTGGACGTGTCTCACGA

GGACCCCGAAGTCAAGTTCAACTGGTACGTGGACGGGGTCGAGGTGCATAATGCCAAGACAAAACCCAGAGAG

GAACAGTACCAGAGTACCTATAGAGTCGTGTCAGTCCTGACAGTGCTGCATCAGGATTGGCTGAACGGGAAAG

AGTATAAGTGCAAAGTGAGTAATAAGGCTCTGCCTGCACCAATCGAGAAAACTATTTCCAAGGCCAAAGGACA

GCCCAGGGAACCTCAGGTGTACACCCTGCCTCCATCACGCGAGGAAATGACAAAGAACCAGGTCAGCCTGACT

TGTCTGGTGAAAGGCTTCTATCCTTCTGACATCGCTGTGGAGTGGGAAAGTAATGGGCAGCCAGAGAACAATT

ACAAGACAACTCCCCCTGTCCTGGACTCTGATGGAAGTTTCTTTCTGTATAGCAAGCTGACCGTGGATAAATC

CCGGTGGCAGCAGGGCAATGTCTTTAGCTGTTCCGTGATGCACGAAGCCCTGCACAACCACTACACCCAGAAG

AGCCTGAGCCTGTCACCCGGCAAA

Human IgG1 Fc with N297Q mutation polypeptide sequence (SEQ ID NO: 10)

DKTHTCPPCPAPELLGGPSVFLFPPKPKDTLMISRTPEVTCVVVDVSHEDPEVKFNWYVDGVEVHNAKTKPRE

EQYQSTYRVVSVLTVLHQDWLNGKEYKCKVSNAKLPAPIEKTISKAKGQPREPQVYTLPPSREEMTKNQVSLT

CLVKGFYPSDIAVEWESNGQPENNYKTTPPVLDSDGSFFLYSKLTVDKSRWQQGNVFSCSVMHEALHNHYTQK

SLSLSPGK

IL-2 signal peptide nucleic acid sequence (SEQ ID NO: 11)

ATGTACAGGATGCAACTCCTGTCTTGCATTGCACTAAGTCTTGCACTTGTCACGAATTCG

IL-2 signal peptide polypeptide sequence (SEQ ID NO: 12)

MYRMQLLSCIALSLALVTNS

GS linker nucleotide sequence (SEQ ID NO: 13)

TCAAGCGCCAGCAGCGGGAGTTCAGGG

GS linker polypeptide sequence (SEQ ID NO: 14)

SSGSSGSSG

-continued

Signal peptide nucleic acid sequence (SEQ ID NO: 15)

ATGGGGATCCTTCCCAGCCCTGGGATGCCTGCGCTGCTCTCCCTCGTGAGCCTTCTCTCCGTGCTGCTGATGG

GTTGCGTAGCT

Signal peptide polypeptide sequence (SEQ ID NO: 16)

MGILPSPGMPALLSLVSLLSVLLMGCVA mIgG2b_human_Mxra8_iso1 nucleotide sequence (SEQ ID NO: 17)

ATGTACAGGATGCAACTCCTGTCTTGCATTGCACTAAGTCTTGCACTTGTCACGAATTCGATATCGGTCCTGT

TGCATAGCGGCTCCTCTGTCCCGGCCGCAGCGGGATCAAGCGTAGTGAGCGAGTCAGCAGTTTCCTGGGAAGC

GGGGGCAAGGGCTGTTCTGAGGTGTCAGAGCCCAAGGATGGTGTGGACGCAAGACCGGCTCCACGACAGGCAA

AGAGTGCTTCACTGGGACCTCAGGGGACCCGGTGGTGGCCCAGCACGCCGGCTCCTGGACCTCTATAGCGCGG

GAGAACAACGAGTATACGAAGCTAGGGACAGAGGAAGACTGGAGCTTTCAGCCAGTGCGTTCGATGATGGAAA

TTTTTCACTTCTGATCCGGGCTGTGGAAGAAACTGATGCTGGACTGTATACTTGTAATCTCCACCATCACTAC

TGCCACCTCTATGAGTCATTGGCTGTCAGACTGGAAGTTACCGATGGCCCGCCCGCCACACCAGCTTACTGGG

ATGGCGAAAAAGAAGTACTTGCTGTCGCGCGAGGTGCCCCTGCGCTCCTGACATGCGTCAACAGGGGTCACGT

TTGGACTGATCGGCACGTCGAAGAGGCTCAGCAAGTAGTTCACTGGGACCGCCAGCCGCCTGGCGTACCTCAC

GATAGGGCCGACCGCCTCTTGGACCTCTACGCCTCCGGTGAAAGGAGGGCCTATGGGCCTCTGTTCCTCAGAG

ATAGGGTTGCGGTGGGCGCAGATGCCTTTGAACGAGGCGATTTCAGCCTCCGCATTGAGCCCCTGGAGGTAGC

CGATGAGGGCACCTACTCCTGTCATCTGCATCATCATTATTGCGGATTGCACGAGAGGAGGGTCTTCCACTTG

ACTGTAGCTGAACCGCATGCTGAACCGCCACCTCGCGGATCACCCGGAAACGGTAGCAGTCATTCCGGGGCTC

CCGGGCCGGATCCGACATTGGCACGAGGGCATAACGTAATAAATGTCATCGTTCCCGAGTCACGCGCTCATGC

TAGCGTTAGATCTCCCAGCGGGCCCATTTCAACAATCAACCCCTGTCCTCCATGCAAGGAGTGTCACAAATGC

CCAGGTAAGTCACTACCAGAGCTCCACTCCCAGGAGAATGGTAAGTGCTGTAAAAATCCCTGTAATGGAGGAT

AAGCCATGTACAAATCCATTTCCATCTCTCCTCATCAGCTCCTAACCTCGAGGGTGGACCATCCGTCTTCATC

TTCCCTCCAAATATCAAGGATGTACTCATGATCTCCCTGACACCCAAGGTCACGTGTGTGGTGGTGGATGTGA

GCGAGGATGACCCAGACGTCCAGATCAGCTGGTTTGTGAACAACGTGGAAGTACACACAGCTCAGACACAAAC

CCATAGAGAGGATTACAACAGTACTATCCGGGTGGTCAGCACCCTCCCCATCCAGCACCAGGACTGGATGAGT

GGCAAGGAGTTCAAATGCAAGGTCAACAACAAAGACCTCCCATCACCCATCGAGAGAACCATCTCAAAAATTA

AAGGTGGGACCTGCAGGACAACTGCATGGGGGCTGGGATGGGCATAAGAATAAATGTCTATGTGGACAGCCTT

CCACTTCAGCCATGACCTCTATGTATGTTTCTAACCCCACAGGGCTAGTCAGAGCTCCACAAGTATACATCTT

GCCGCCACCAGCAGAGCAGTTGTCCAGGAAAGATGTCAGTCTCACTTGCCTGGTCGTGGGCTTCAACCCTGGA

GACATCAGTGTGGAGTGGACCAGCAATGGGCATACAGAGGAGAACTACAAGGACACCGCACCAGTCCTGGACT

CTGACGGTTCTTACTTCATATATAGCAAGCTCAATATGAAAACAAGCAAGTGGGAGAAAACAGATTCCTTCTC

ATGCAACGTGAGACACGAGGGTCTGAAAAATTACTACCTGAAGAAGACCATCTCCCGGTCTCCGGGTAAA

Orange: IL-2 signal peptide

Blue: Human Mxra8 isoform 1 ectodomain

Red: mIgG2b Fc region mIgG2b_human_Mxra8_iso1 polypeptide sequence (SEQ ID NO: 18)

MYRMQLLSCIALSLALVTNNISVLLHSGSSVPAAAGSSVVSESAVSWEAGARAVLRQSPRMVWTQDRLHDRQR

VLHWDLGPGGGPARRLLDLYSAGEQRVYEARDRGRLELSASAFDDGNFSLLIRAVEETDAGLYTCNLHHHYCH

LYESLAVRLEVTDGPPATPAYWDGEKEVLAVARGAPALLTCVNRGHVWTDRHVEEAQQVVHWDRQPPGVPHDR

ADRLLDLYASGERRAYGPLFLRDRVAVGADAFERGDFSLRIEPLEVADEGTYSCHLHHHYCGLHERRVFHLTV

-continued

AEPHAEPPPRGSPGNGSSHSGAPGPDPTLARGHNVINVIVPESRAHASVRSPSGPISTINPCPPCKECHKCPA

PNLEGGPSVFIFPPNIKDVLMISLTPKVTCVVVDVSEDDPDVQISWFVNNVEVHTAQTQTHREDYNSLTIRVV

STLPIQHQDWMSGKEFKCKVNNKDLPSPIERTISKIKGLVRAPQVYILPPPAEQLSRKDVSLTCLVVGFNPGD

ISVEWTSNGHTEENYKDTAPVLDSDGSYFIYSKLNMKTSKWEKTDSFSCNVRHEGLKNYYLKKTISRSPGK

Orange: IL-2 signal peptide

Blue: Human Mxra8 isoform 1 ectodomain

Red: mIgG2b Fc region mIgG2b_mouse_Mxra8 nucleotide sequence (SEQ ID NO: 19)

ATGTACAGGATGCAACTCCTGTCTTGCATTGCACTAAGTCTTGCACTTGTCACGAATTCGATATCGTCTGGCC

CGAGCGGTACTGCTGCCGCAAGCTCAAGCCTCGTCTCTGAATCAGTTGTGTCTCTCGCGGCCGGAACTCAGGC

GGTCCTGAGGTGTCAAAGTCCAAGGATGGTTTGGACCCAAGATCGCTTGCATGATCGACAAAGAGTTGTGCAC

TGGGACCTCAGCGGTGGTCCTGGATCACAACGAAGAAGGCTGGTGGACATGTACTCAGCCGGAGAACAGCGCG

TTTACGAGCCACGAGACCGAGATCGACTCCTTTTGTCACCTTCTGCGTTCCATGACGGCAACTTTTCTTTGTT

GATAAGAGCCGTAGATCGCGGAGATGAAGGAGTTTATACGTGTAACCTTCACCACCATTACTGCCATCTCGAT

GAAAGTCTCGCCGTACGGCTGGAAGTTACGGAGGACCCACTTCTTTCACGGGCATATTGGGATGGCGAGAAGG

AGGTCCTGGTCGTTGCTCACGGCGCACCAGCCCTGATGACATGCATCAACAGAGCCCATGTTTGGACCGACAG

GCACCTTGAAGAAGCACAACAAGTTGTCCATTGGGACCGACAGCTCCCAGGTGTTAGCCATGATCGGGCCGAT

CGCTTGCTTGACTTGTATGCCAGCGGGGAACGGAGGGCATACGGCCCGCCTTTTCTTCGGGATCGAGTTAGCG

TAAACACTAACGCCTTTGCACGCGGTGACTTCAGCCTTCGCATAGATGAACTCGAACGAGCAGATGAAGGAAT

ATACTCCTGCCATTTGCATCATCATTATTGCGGCCTGCATGAGCGAAGGGTATTTCACCTCCAAGTGACTGAA

CCTGCATTCGAGCCACCAGCGAGGGCCTCACCGGGAAACGGCTCCGGCCACAGCAGCGCACCGTCTCCGGACC

CGACTTTGACACGGGGCCATAGTATAATAAACGTAATAGTTCCTGAGGACCATACCCACGCTAGCGTTAGATC

TCCCAGCGGGCCCATTTCAACAATCAACCCCTGTCCTCCATGCAAGGAGTGTCACAAATGCCCAGGTAAGTCA

CTACCAGAGCTCCACTCCCAGGAGAATGGTAAGTGCTGTAAAAATCCCTGTAATGGAGGATAAGCCATGTACA

AATCCATTTCCATCTCTCCTCATCAGCTCCTAACCTCGAGGGTGGACCATCCGTCTTCATCTTCCCTCCAAAT

ATCAAGGATGTACTCATGATCTCCCTGACACCCAAGGTCACGTGTGTGGTGGTGGATGTGAGCGAGGATGACC

CAGACGTCCAGATCAGCTGGTTTGTGAACAACGTGGAAGTACACACAGCTCAGACACAAACCCATAGAGAGGA

TTACAACAGTACTATCCGGGTGGTCAGCACCCTCCCCATCCAGCACCAGGACTGGATGAGTGGCAAGGAGTTC

AAATGCAAGGTCAACAACAAAGACCTCCCATCACCCATCGAGAGAACCATCTCAAAAATTAAAGGTGGGACCT

GCAGGACAACTGCATGGGGGCTGGGATGGGCATAAGAATAAATGTCTATGTGGACAGCCTTCCACTTCAGCCA

TGACCTCTATGTATGTTTCTAACCCCACAGGGCTAGTCAGAGCTCCACAAGTATACATCTTGCCGCCACCAGC

AGAGCAGTTGTCCAGGAAAGATGTCAGTCTCACTTGCCTGGTCGTGGGCTTCAACCCTGGAGACATCAGTGTG

GAGTGGACCAGCAATGGGCATACAGAGGAGAACTACAAGGACACCGCACCAGTCCTGGACTCTGACGGTTCTT

ACTTCATATATAGCAAGCTCAATATGAAAACAAGCAAGTGGGAGAAAACAGATTCCTTCTCATGCAACGTGAG

ACACGAGGGTCTGAAAAATTACTACCTGAAGAAGACCATCTCCCGGTCTCCGGGTAAA

Orange: IL-2 signal peptide

Blue: Mouse Mxra8 ectodomain

Red: mIgG2b Fc region

-continued mIgG2b_mouse_Mxra8 polypeptide sequence (SEQ ID NO: 20)

MYRMQLLSCIALSLALVTNSISSGPSGTAAASSSLVSESVVSLAAGTQAVLRCQSPRMVWTQDRLHDRQRVVH

WDLSGGPGSQRRRLVDMYSAGEQRVYEPRDRDRLLLSPSAFHDGNFSLLIRAVDRGDEGVYTCNLHHHYCHLD

ESLAVRLEVTEDPLLSRAYWDGEKEVLVVAHGAPALMTCINRAHVWTDRHLEEAQQVVHWDRQLPGVSHDRAD

RLLDLYASGERRAYGPPFLRDRVSVNTNAFARGDFSLRIDELERADEGIYSCHLHHHYCGLHERRVFHLQVTE

PAFEPPARASPGNGSGHSSAPSPDPTLTRGHSIINVIVPEDHTHASVRSPSGPISTINPCPPCKECHKCPAPN

LEGGPSVFIFPPNIKDVLMISLTPKVTCVVVDVSEDDPDVQISWFVNNVEVHTAQTQTHREDYNSTIRVVSTL

PIQHQDWMSGKEFKCKVNNKDLPSPIERTISKIKGLVRAPQVYILPPPAEQLSRKDVSLTCLVVGFNPGDISV

EWTSNGHTEENYKDTAPVLDSDGSYFIYSKLNMKTSKWEKTDSFSCNVRHEGLKNYYLKKTISRSPGK

Orange: IL-2 signal peptide

Blue: Mouse Mxra8 ectodomain

Red: mIgG2b Fc region hIgG1_9L_mouse_Mxra8 nucleotide sequence (SEQ ID NO: 21)

ATGGGGATCCTTCCCAGCCCTGGGATGCCTGCGCTGCTCTCCCTCGTGAGCCTTCTCTCCGTGCTGCTGATGG

GTTGCGTAGCTGAAACCGGTTCTGGCCCGAGCGGTACTGCTGCCGCAAGCTCAAGCCTCGTCTCTGAATCAGT

TGTGTCTCTCGCGGCCGGAACTCAGGCGGTCCTGAGGTGTCAAAGTCCAAGGATGGTTTGGACCCAAGATCGC

TTGCATGATCGACAAAGAGTTGTGCACTGGGACCTCAGCGGTGGTCCTGGATCACAACGAAGAAGGCTGGTGG

ACATGTACTCAGCCGGAGAACAGCGCGTTTACGAGCCACGAGACCGAGATCGACTCCTTTTGTCACCTTCTGC

GTTCCATGACGGCAACTTTTCTTTGTTGATAAGAGCCGTAGATCGCGGAGATGAAGGAGTTTATACGTGTAAC

CTTCACCACCATTACTGCCATCTCGATGAAAGTCTCGCCGTACGGCTGGAAGTTACGGAGGACCCACTTCTTT

CACGGGCATATTGGGATGGCGAGAAGGAGGTCCTGGTCGTTGCTCACGGCGCACCAGCCCTGATGACATGCAT

CAACAGAGCCCATGTTTGGACCGACAGGCACCTTGAAGAAGCACAACAAGTTGTCCATTGGGACCGACAGCTC

CCAGGTGTTAGCCATGATCGGGCCGATCGCTTGCTTGACTTGTATGCCAGCGGGGAACGGAGGGCATACGGCC

CGCCTTTTCTTCGGGATCGAGTTAGCGTAAACACTAACGCCTTTGCACGCGGTGACTTCAGCCTTCGCATAGA

TGAACTCGAACGAGCAGATGAAGGAATATACTCCTGCCATTTGCATCATCATTATTGCGGCCTGCATGAGCGA

AGGGTATTTCACCTCCAAGTGACTGAACCTGCATTCGAGCCACCAGCGAGGGCCTCACCGGGAAACGGCTCCG

GCCACAGCAGCGCACCGTCTCCGGACCCGACTTTGACACGGGGCCATAGTATAATAAACGTAATAGTTCCTGA

GGACCATACCCAGTCAAGCGGCAGCAGCGGCAGTTCAGGGGACAAAACCCATACATGCCCACCTTGTCCAGCA

CCAGAGCTGCTGGGAGGACCAAGCGTGTTCCTGTTTCCACCCAAGCCCAAAGATACCCTGATGATCTCCCGGA

CTCCCGAAGTCACCTGCGTGGTCGTGGACGTGTCTCACGAGGACCCCGAAGTCAAGTTCAACTGGTACGTGGA

CGGGGTCGAGGTGCATAATGCCAAGACAAAACCCAGAGAGGAACAGTACAACAGTACCTATAGAGTCGTGTCA

GTCCTGACAGTGCTGCATCAGGATTGGCTGAACGGGAAAGAGTATAAGTGCAAAGTGAGTAATAAGGCTCTGC

CTGCACCAATCGAGAAACTATTTCCAAGGCCAAAGGACAGCCCAGGGAACCTCAGGTGTACACCCTGCCTCCA

TCACGCGAGGAAATGACAAAGAACCAGGTCAGCCTGACTTGTCTGGTGAAAGGCTTCTATCCTTCTGACATCG

CTGTGGAGTGGGAAAGTAATGGGCAGCCAGAGAACAATTACAAGACAACTCCCCCTGTCCTGGACTCTGATGG

AAGTTTCTTTCTGTATAGCAAGCTGACCGTGGATAAATCCCGGTGGCAGCAGGGCAATGTCTTTAGCTGTTCC

GTGATGCACGAAGCCCTGCACAACCACTACACCCAGAAGAGCCTGAGCCTGTCACCCGGCAAA

Orange: Signal peptide

Blue: Mouse Mxra8 ectodomain

-continued

Green: GS linker

Red: Human IgG1 Fc region hIgG1_9L_mouse_Mxra8 polypeptide sequence (SEQ ID NO: 22)

MGILPSPGMPALLSLVSLLSVLLMGCVAETGSGPSGTAAASSSLVSESVVSLAAGTQAVLRCQSPRMVWTQDR

LHDRQRVVHWDLSGGPGSQRRRLVDMYSAGEQRVYEPRDRDRLLLSPSAFHDGNFSLLIRAVDRGDEGVYTCN

LHHHYCHLDESLAVRLEVTEDPLLSRAYWDGEKEVLVVAHGAPALMTCINRAHVWTDRHLEEAQQVVHDRQLP

GVSHDRADRLLDLYASGERRAYGPPFLRDRVSVNTNAFARGDFSLRIDELERADEGIYSCHLHHHYCGLHERR

VFHLQVTEP[AFEPPARASPGNGSGHSSAPSPDPTLTRGHSIINVIVPEDHTHSSGSSGSSGDKTHTCPPSPA

PELLGGPSVFLFPPKPKDTLMISRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSVMHEALHNHYTQKSLSLSPGK

Orange: Signal peptide

Blue: Mouse Mxra8 ectodomain

Green: GS linker

Red: Human IgG1 Fc region hIgG1_N297Q_9L_mouse_Mxra8 nucleotide sequence (SEQ ID NO: 23)

ATGGGGATCCTTCCCAGCCCTGGGATGCCTGCGCTGCTCTCCCTCGTGAGCCTTCTCTCCGTGCTGCTGATGG

GTTGCGTAGCTGAAACCGGTTCTGGCCCGAGCGGTACTGCTGCCGCAAGCTCAAGCCTCGTCTCTGAATCAGT

TGTGTCTCTCGCGGCCGGAACTCAGGCGGTCCTGAGGTGTCAAAGTCCAAGGATGGTTTGGACCCAAGATCGC

TTGCATGATCGACAAAGAGTTGTGCACTGGGACCTCAGCGGTGGTCCTGGATCACAACGAAGAAGGCTGGTGG

ACATGTACTCAGCCGGAGAACAGCGCGTTTACGAGCCACGAGACCGAGATCGACTCCTTTTGTCACCTTCTGC

GTTCCATGACGGCAACTTTTCTTTGTTGATAAGAGCCGTAGATCGCGGAGATGAAGGAGTTTATACGTGTAAC

CTTCACCACCATTACTGCCATCTCGATGAAAGTCTCGCCGTACGGCTGGAAGTTACGGAGGACCCACTTCTTT

CACGGGCATATTGGGATGGCGAGAAGGAGGTCCTGGTCGTTGCTCACGGCGCACCAGCCCTGATGACATGCAT

CAACAGAGCCCATGTTTGGACCGACAGGCACCTTGAAGAAGCACAACAAGTTGTCCATTGGGACCGACAGCTC

CCAGGTGTTAGCCATGATCGGGCCGATCGCTTGCTTGACTTGTATGCCAGCGGGGAACGGAGGGCATACGGCC

CGCCTTTTCTTCGGGATCGAGTTAGCGTAAACACTAACGCCTTTGCACGCGGTGACTTCAGCCTTCGCATAGA

TGAACTCGAACGAGCAGATGAAGGAATATACTCCTGCCATTTGCATCATCATTATTGCGGCCTGCATGAGCGA

AGGGTATTTCACCTCCAAGTGACTGAACCTGCATTCGAGCCACCAGCGAGGGCCTCACCGGGAAACGGCTCCG

GCCACAGCAGCGCACCGTCTCCGGACCCGACTTTGACACGGGGCCATAGTATAATAAACGTAATAGTTCCTGA

GGACCATACCCACTCAAGCCGCAGCAGGGGCAGTTCAGGGGACAAAACCCATACATGCCCACCTTGTCCAGCA

CCAGAGCTGCTGGGAGGACCAAGCGTGTTCCTGTTCCACCCAAGCCCAAAGATACCCTGATGATCTCCCGGAC

TCCCGAAGTCACCTGCGTGGTCGTGGACGTGTCTCACGAGGACCCCGAAGTCAAGTTCAACTGGTACGTGGAC

GGGGTCGAGGTGCATAATGCCAAGACAAAACCCAGAGAGGAACAGTACCAGAGTACCTATAGAGTCGTGTCAG

TCCTGACAGTGCTGCATCAGGATTGGCTGAACGGGAAAGAGTATAAGTGCAAAGTGAGTAATAAGGCTCTGCC

TGCACCAATCGAGAAAACTATTTCCAAGGCCAAAGGACAGCCCAGGGAACCTCAGGTGTACACCCTGCCTCCA

TCACGCGAGGAAATGACAAAGAACCAGGTCAGCCTGACTTGTCTGGTGAAAGGCTTCTATCCTTCTGACATCG

CTGTGGAGTGGGAAAGTAATGGGCAGCCAGAGAACAATTACAAGACAACTCCCCCTGTCCTGGACTCTGATGG

AAGTTTCTTTCTGTATAGCAAGCTGACCGTGGATAAATCCCGGTGGCAGCAGGGCAATGTCTTTAGCTGTTCC

GTGATGCACGAAGCCCTGCACAACCACTACACCCAGAAGAGCCTGAGCCTGTCACCCGGCAAA

-continued

Orange: Signal peptide

Blue: Mouse Mxra8 ectodomain

Green: GS linker

Red: Human IgG1 Fc region

Cyan: N297Q mutation hIgG1_N297Q_9L_mouse_Mxra8 polypeptide sequence (SEQ ID NO: 24)

MGILPSPGMPALLSLVSLLSVLLMGCVAETGSGPSGTAAASSSLVSESVVSLAAGTQAVLRCQSPRMVWTQDR

LHDRQRVVHWDLSGGPGSQRRRLVDMYSAGEQRVYEPRDRDRLLLSPSAFHDGNFSLLIRAVDRGDEGVYTCN

LHHHYCHLDESLAVRLEVTEDPLLSRAYWDGEKEVLVVAHGAPALMTCINRAHVWTDRHLEEAQQVVHWDRQL

PGVSHDRADRLLDLYASGERRAYGPPFLRDRVSVNTNAFARGDFSLRIDELERADEGIYSCHLHHHYCGLHER

RVFHLQVTEPAFEPPARASPGNGSGHSSAPSPDPTLTRGHSIINVIVPEDHTHSSGSGSSGDKTHTCPPCPAP

ELLGGPSVFLFPPKPKDTLMISRTPEVTCVVVDVSHEDPEVKFNWYVDGVEVHNAKTKPREEQYQSTYRVVSV

LTVLHQDWLNGKEYKCKVSNKALPAPIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVMHEALHNHYTQKSLSLSPGK

Orange: Signal peptide

Blue: Mouse Mxra8 ectodomain

Green: GS linker

Red: Human IgG1 Fc region

Cyan: N297Q mutation

As another example, the Mxra8 inhibiting agent can comprise an ectodomain of Mxra8 or any of Mxra8 isoforms SEQ ID NOs: 25-31 (e.g., XP_016857006.1; XP_016857005.1; NP_001269511.1; NP_001269512.1; NP_001269513.1; NP_001269514.1; NP_115724.1) or functional fragments or variants thereof with Mxra8 activity or Mxra8 receptor activity.

As described herein, the Mxra8 inhibiting agent can comprise an Fc region. The Fc region can be chosen from any Fc region known in the art. For example, the Fc region can comprise human IgG1, human IgG1 Fc with N297Q mutation, or mouse mIgG2b (see e.g., Saxena et al. 2016 Front Immunol. 7:580).

As an example, a Mxra8 inhibiting agent can be an anti-Mxra8 antibody. The anti-Mxra8 antibody can be an anti-Mxra8 antibody that has Mxra8 inhibitory activity. As an example, the anti-Mxra8 antibody can be anti-Mxra8 (mouse) armenian hamster serum, anti-Mxra8 (mouse) hamster monoclonal antibodies, or anti-MXRA8 (human) monoclonal antibodies. As another example, the anti-Mxra8 purified hamster monoclonal antibody clones can be 1G11.E6, 1H1.F5, 3G2.F5, 4E7.D10, 7F1.D8, 8F7.E1, 9G2.D6 or any combination of the aforementioned clones (e.g., 1G11.E6+7F1.D8, or 4E7.D10+8F7.E1).

As another example, Mxra8 inhibiting agent can be SYKi, which can be used to downregulate Mxra8.A Mxra8 inhibiting agent can be a short hairpin RNA (shRNA) or a short interfering RNA (siRNA). A Mxra8 inhibiting agent can be an sgRNA targeting Mxra8 (e.g., SEQ ID NOs: 34-40).

Measuring Vaccine or Diagnostic Antigen Integrity

As described herein, Mxra8 can be used to assess an alphavirus vaccine or a diagnostic antigen integrity.

Because Mxra8 is a receptor for multiple arthritogenic alphaviruses, it can be used to physically assess the integrity of alphavirus vaccine or diagnostic antigens. As such, Mxra8 can be used to define lot-to-lot integrity or variation, for example, in the context of commercial production. Alphavirus vaccine or diagnostic antigens can include, but are not limited to, live-attenuated viruses, virus-like particles, viral structural proteins, or nucleic acids or vectors producing these viral proteins or particles.

The integrity assay can include capturing Mxra8 or Mxra8 fusion proteins (e.g., Mxra8-Fc) on a substrate (e.g., microtiter well plate, chip, or pin) and then incubating the alphavirus vaccine or diagnostic antigen and detection with a monoclonal or polyclonal anti-vaccine/diagnostic antigen antibody or even Mxra8-Fc itself. Alternatively, the alphavirus vaccine or diagnostic antigen can be captured in the solid phase (directly or via a bridging antibody) and then incubated with Mxra8 or Mxra8-Fc fusion proteins for binding. The assay could be performed by ELISA, biolayerinterferometry, surface plasmon resonance, or any other detection based system for binding.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10:0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5 (9), 680-688; Sanger et al. (1991) Gene 97 (1), 119-123; Ghadessy et al. (2001) Proc Natl Acad Sci USA 98 (8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature (Tm) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6 ($\log_{10}[Na^+]$)+0.41 (fraction G/C content)−0.63 (% formamide)−(600/l). Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10:0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Conservative Substitutions I

| SIDE CHAIN CHARACTERISTIC | AMINO ACID |
|---|---|
| Non-polar | G A P I L V |
| Polar-uncharged | C S T M N Q |
| Polar-charged | D E K R |
| Aromatic | H F W Y |
| Other | N Q D E |

Conservative Substitutions II

| SIDE CHAIN CHARACTERISTIC | AMINO ACID |
|---|---|
| Non-polar (hydrophobic) | A L I V P |
| A, Aliphatic: | F W |
| B, Ammatic: | M |
| C, Sulfur-containing: | G |
| D, Borderline: | |
| Uncharged-polar | |
| A, Hydroxyl: | S T Y |
| B, Amides: | N Q |
| C, Sulfhydryl: | C |
| D, Borderline: | G |
| Positively Charged (Basic): | K R H |
| Negatively Charged (Acidic): | D E |

Conservative Substitutions III

| Original Residue | Exemplary Substitution |
|---|---|
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |

-continued

| Conservative Substitutions III | |
|---|---|
| Original Residue | Exemplary Substitution |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Thr (T) |
| Tyr (Y) | Trp (W), Phe (F), Thr (T), Ser (S) |
| Val (V) | Ile (I), Leu (L), Met (M), Phe (F), Ala (A) |

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41 (1), 207-234; Gellissen, ed. (2005) Production of Recombinant Proteins: Novel Microbial and Eukaryotic Expression Systems, Wiley-VCH, ISBN-10:3527310363; Baneyx (2004) Protein Expression Technologies, Taylor & Francis, ISBN-10:0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14 (12): 807-15, describing targeting deoxyribonucleotide sequences; Lee et al. (2006) Curr Opin Chem Biol. 10, 1-8, describing aptamers; Reynolds et al. (2004) Nature Biotechnology 22 (3), 326-330, describing RNAi; Pushparaj and Melendez (2006) Clinical and Experimental Pharmacology and Physiology 33 (5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-IT™ RNAi Designer, Invitrogen; siRNA Whitehead Institute Design Tools, Bioinofrmatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a Mxra8-associated alphavirus in a subject in need administration of a therapeutically effective amount a Mxra8 inhibiting agent, so as to reduce infection, prevent or block infection, reduce viral load, shorten the duration of the infection, or reduce the symptoms of the infection, including joint or tissue swelling or joint or tissue inflammation.

Methods described herein are generally performed on a subject in need thereof. A subject in need of the therapeutic methods described herein can be a subject having, diagnosed with, suspected of having, or at risk for developing a Mxra8-associated alphavirus. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject. The subject can be an insect subject, such as a mosquito.

Generally, a safe and effective amount of a Mxra8 inhibiting agent is, for example, that amount that would cause the desired therapeutic effect in a subject while minimizing undesired side effects. In various embodiments, an effective amount of a Mxra8 inhibiting agent described herein can substantially inhibit a Mxra8-associated alphavirus infection, slow the progress of a Mxra8-associated alphavirus infection, limit the development of a Mxra8-associated alphavirus infection, reduce infection, prevent or block infection, reduce viral load, shorten the duration of the infection, or reduce the symptoms of the infection, including joint or tissue swelling or joint or tissue inflammation.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a Mxra8 inhibiting agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to inhibit a Mxra8-associated alphavirus infection, slow the progress of a Mxra8-associated alphavirus infection, limit the development of a Mxra8-associated alphavirus infection, reduce infection, prevent or block infection, reduce viral load, shorten the duration of the infection, or reduce the symptoms of the infection, including joint or tissue swelling or joint or tissue inflammation.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a Mxra8 inhibiting agent can occur as a single event or over a time course of treatment. For example, a Mxra8 inhibiting agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for viral infections (e.g., a Mxra8-associated alphavirus infection).

A Mxra8 inhibiting agent can be administered simultaneously or sequentially with another agent, such as an antiviral, an antibiotic, an anti-inflammatory, or another agent. For example, a Mxra8 inhibiting agent can be administered simultaneously with another agent, such as an antiviral, an antibiotic or an anti-inflammatory. Simultaneous administration can occur through administration of separate compositions, each containing one or more of a Mxra8 inhibiting agent, an antiviral, an antibiotic, an anti-inflammatory, or another agent. Simultaneous administration can occur through administration of one composition containing two or more of a Mxra8 inhibiting agent, an antiviral, an antibiotic, an anti-inflammatory, or another agent. A Mxra8 inhibiting agent can be administered sequentially with an antiviral, an antibiotic, an anti-inflammatory, or another agent. For example, a Mxra8 inhibiting agent can be administered before or after administration of an antiviral, an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10:0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Screening

Also provided are methods for screening candidate molecules.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlogP of about-2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlogP of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

In Silico Screening

As described herein, the atomic coordinates for Mxra8 alone has been discovered by x-ray crystallography and its complexes with the Mxra8 entry receptor have been discovered by single particle cryo-EM. These coordinates can be used in any in silico screening method known in the art (e.g., Miteva (2011) In silico Lead Discovery; Kortagere (2013) In Silico Models for Drug Discovery).

As used herein, three-dimensional (3D) structure refers to the Cartesian coordinates corresponding to an atom's spatial relationship to other atoms in a macromolecule, for example a protein macromolecule. In the methods provided herein, an estimated three-dimensional (3D) structure can be determined by computer modeling, nuclear magnetic resonance (MR), X-ray crystallography, electron microscopy, or homology modeling.

Many in-silico methods for structure prediction and modeling can be used in connection with the methods described herein, including, without limitation, comparative protein modeling methods (e.g., homology modeling methods such as those described in Marti-Renom et al. 2000. Annu Rev Biophys Biomol Struct 29:291-325), protein threading modeling methods (such as those described in Bowie et al. 1991. Science 253:164-170; Jones et al. 1992. Nature 358:86-89), ab initio or de novo protein modeling methods (Simons et al. 1999. Genetics 37: 171-176; Baker 2000, Nature 405:39-42; Wu et al. 2007. BMC Biol 5:17), physics-based prediction (Duan and Kollman 1998, Science 282:740-744; Oldziej et al. 2005, Proc Natl Acad Sci USA 102:7547-7552); or any combination thereof. Comparative modeling methods can be performed using a number of modeling programs, including, but not limited to, Modeller (Fiser and Sali 2003, Methods Enzymol 374:461-91) or Swiss-Model (Arnold et al. 2006, Bioinformatics 22:195-201). Protein threading modeling methods can be performed using a number of modeling programs, including, but not limited to, HHsearch (Soding 2005, Bioinformatics 21:951-960), Phyre (Kelley and Sternberg. 2009, Nature Protocols 4:363-371), or Raptor (Xu et al. 2003, J Bioinform Comput Biol 1:95-117). Ab initio or de novo protein modeling methods can be performed using a number of modeling programs including, but not limited to, Rosetta (Simons et al. 1999. Genetics 37:171-176; Baker 2000, Nature 405:39-42; Bradley et al. 2003, Proteins 53:457-468; Rohl 2004, Methods in Enzymology 383:66-93) and I-TASSER (Wu et al. 2007. BMC Biol 5:17).

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10:0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41 (1), 207-234; Gellissen, ed. (2005) Production of Recombinant Proteins: Novel Microbial and Eukaryotic Expression Systems, Wiley-VCH, ISBN-10:3527310363; Baneyx (2004) Protein Expression Technologies, Taylor & Francis, ISBN-10:0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Mxra8 is an Entry Receptor for Arthritogenic Alphaviruses

The following example describes the discovery that a receptor for Mxra8 on the surface of arthritogenic alphaviruses is an entry receptor. Furthermore, this example describes inhibition of Mxra8 on the alpha virus or inhibition of the Mxra8 receptor on a cell mitigates infection by alphaviruses.

Arthritogenic alphaviruses comprise a group of enveloped RNA viruses that are transmitted to humans by mosquitoes and cause debilitating acute and chronic musculoskeletal disease[1]. The host factors required for alphavirus entry remain poorly characterized[2]. This example describes the use of a genome-wide CRISPR-Cas9-based screen to identify the cell adhesion molecule Mxra8 as an entry mediator for multiple emerging arthritogenic alphaviruses, including chikungunya, Ross River, Mayaro and O'nyong nyong viruses. Gene editing of mouse Mxra8 or human MXRA8 resulted in reduced levels of viral infection of cells and, reciprocally, ectopic expression of these genes resulted in increased infection. Mxra8 bound directly to chikungunya virus particles and enhanced virus attachment and internalization into cells. Consistent with these findings, Mxra8-Fc fusion protein or anti-Mxra8 monoclonal antibodies blocked chikungunya virus infection in multiple cell types, including primary human synovial fibroblasts, osteoblasts, chondrocytes and skeletal muscle cells. Mutagenesis experiments suggest that Mxra8 binds to a surface-exposed region across the A and B domains of chikungunya virus E2 protein, which are a speculated site of attachment. Finally, administration of the Mxra8-Fc protein or anti-Mxra8 blocking antibodies to mice reduced chikungunya and O'nyong nyong virus infection as well as associated foot swelling. Pharmacological targeting of Mxra8 could form a strategy for mitigating infection and disease by multiple arthritogenic alphaviruses.

Figure 5:
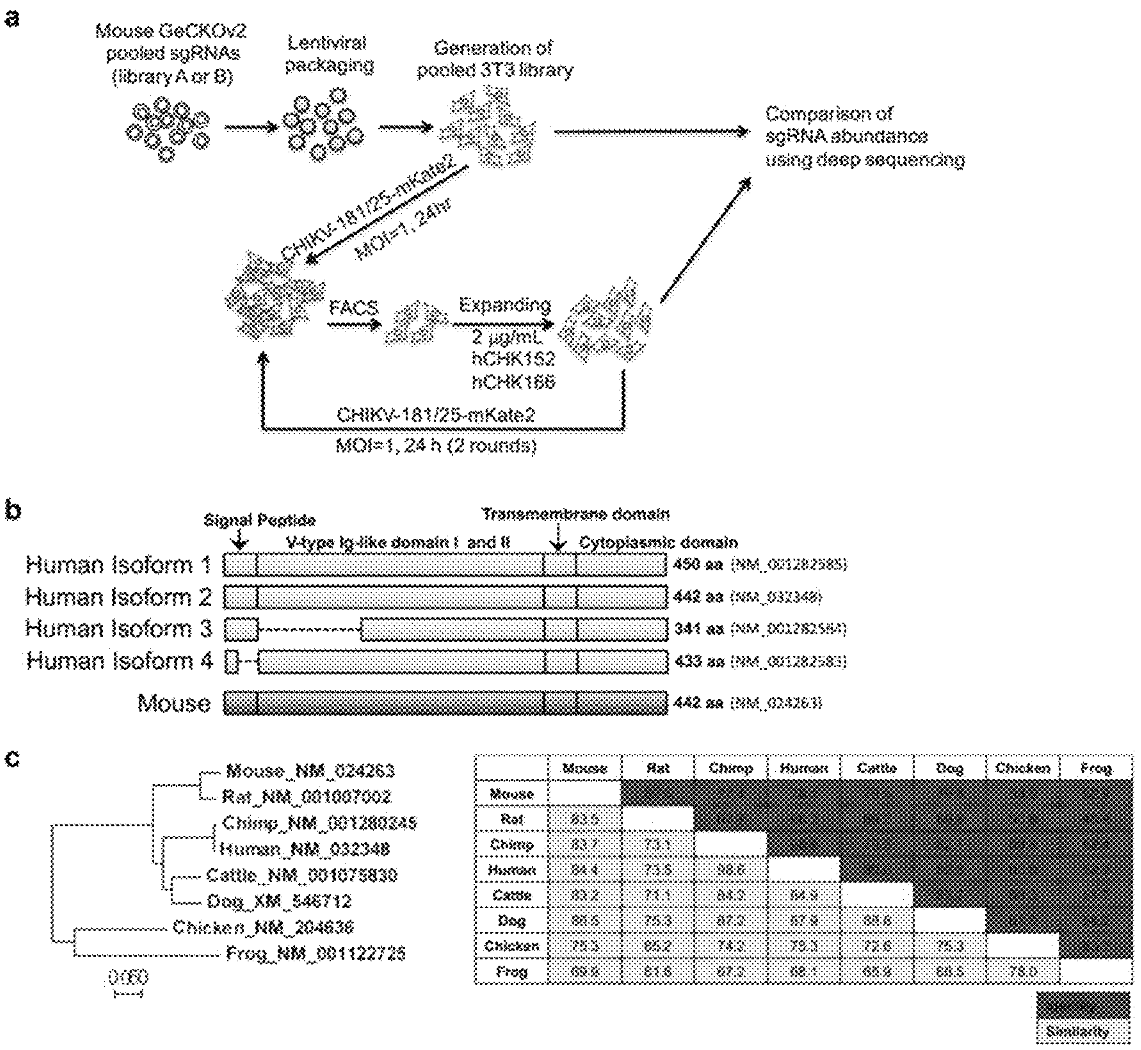
FIG. 5 is a series of illustrations and diagrams showing CRISPR-Cas9-based gene editing screen. (a) Mouse 3T3 cells were transduced separately with two half libraries (A+B) comprising 130,209 sgRNAs, selected with puromycin and then inoculated with CHIKV-181/25-mKate2 (MOI of 1). One day later, mKate2-negative cells were sorted and then expanded in the presence of 2 μg mi-1 each of CHK-152 and CHK-166 neutralizing mAbs. Several days later, cells were re-inoculated with CHIKV-181/25-mKate2 without neutralizing mAbs and re-sorted for mKate2-negative cells. This procedure was repeated one additional time. Afterwards, genomic DNA was collected for sgRNA sequencing and compared to the parent library for abundance (see e.g., Tables 1A, 1B, 2A, and 2B in provisional application Nos. 62/671,680 and 62/672,080, incorporated herein by reference). (b) Diagram of the mouse Mxra8 and human MXRA8 orthologues. The transcript identification numbers and length of proteins are indicated to the right. Partial deletions in the isoforms 3 and 4 are shown as dashed lines. (c) Phylogenetic tree of Mxra8 indicating genetic relationships. The neighbour-joining tree was constructed using MEGA 7. Scale bar shows the branch length. Right, identity (red) and similarity (yellow) matrix indicating the conservation of Mxra8 between species. The matrix was generated using MagGat 1.8.
Figure 7:
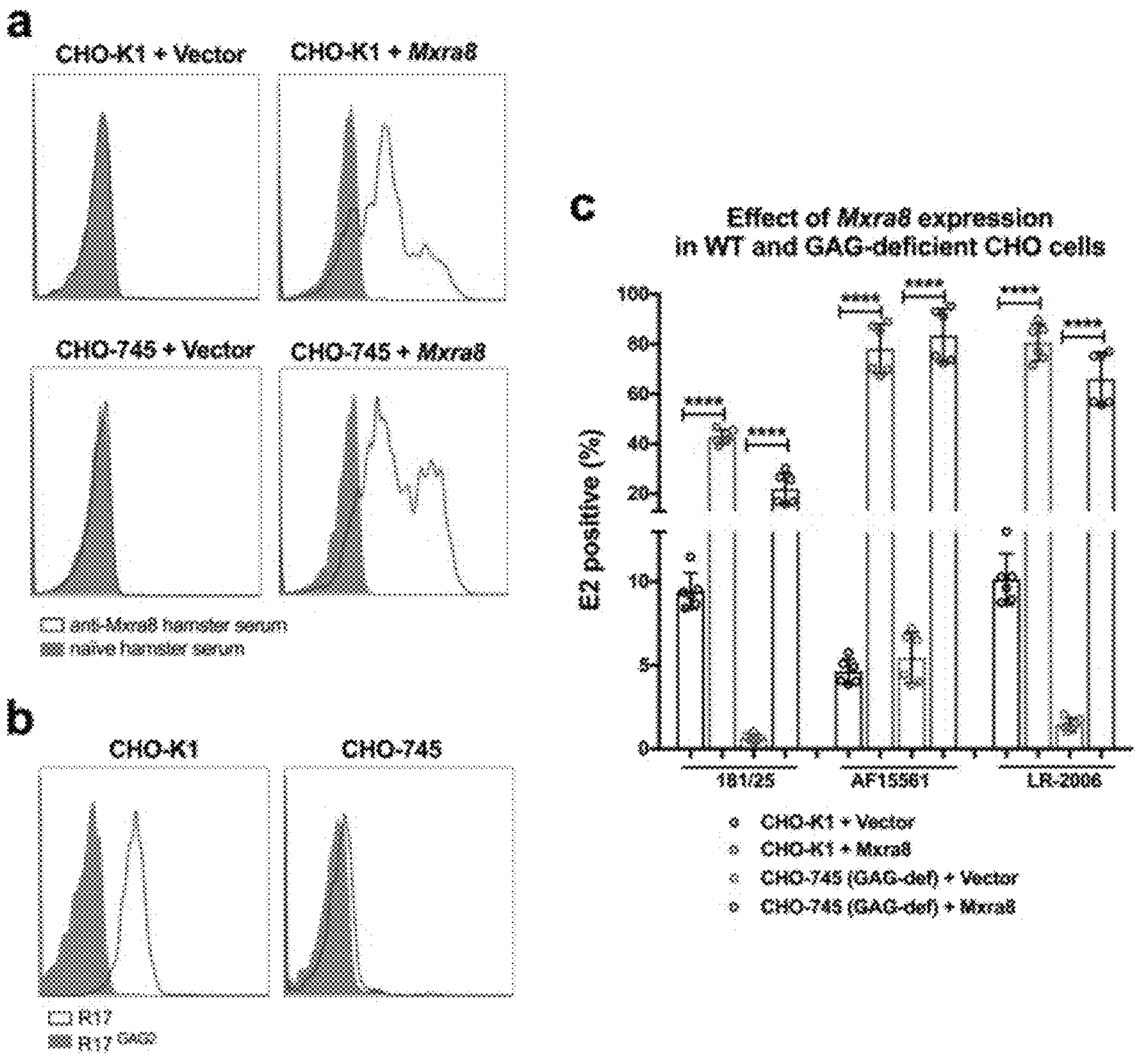
FIG. 7 shows CHIKV infectivity in CHO-K1 and CHO-745 cells in the presence or absence of ectopic Mxra8 expression. (a) Surface expression of Mxra8 on CHO-K1 (wild type) and CHO-745 (glycosaminoglycan deficient[15]) cells stably transduced with control (vector-only) or mouse Mxra8 as judged by flow cytometry. (b) Confirmation of heparan sulfate expression on the surface of CHO-K1 (wild type) and CHO-745 cells. Surface expression of heparan sulfate was evaluated using the R17 protein of rodent herpesvirus Peru, which binds to glycosaminoglycans on the surface of cells[39]. $R17^{GAG2}$ is a mutant form of the protein that lacks binding to glycosaminoglycans and served as a negative control. In a and b, data are representative of two experiments. (c) CHO-K1 (wild type) and CHO-745 cells were transduced stably with control (vector) or mouse Mxra8 and inoculated with CHIKV (strains 181/25, AF15561 or LR-2006) and processed for intracellular E2 protein staining by flow cytometry. Data are from three experiments: mean±s.d. (n=6, one-way ANOVA with a Dunnett's multiple comparison test). ****P<0.001.

A genome-wide screen was performed for host factors required for chikungunya virus (CHIKV) infection, using the CRISPR-Cas9 system[3,4] and lentiviruses delivering single-guide RNAs (sgRNA) targeting 20,611 mouse genes (see e.g., FIG. 5). We inoculated lentivirus-transduced 3T3 mouse fibroblasts with CHIKV strain 181/25 that contained the mKate2 reporter (CHIKV-181/25-mKate2), such that almost all cells expressed the reporter gene by 24 h. The few cells that lacked mKate2 expression were sorted, propagated in the presence of neutralizing anti-CHIKV monoclonal antibodies (mAbs)[5] and then re-inoculated with CHIKV-181/25-mKate2. After two rounds of infection and sorting, genomic DNA from mKate2-negative cells was collected, sgRNAs were sequenced and then analysed using MAGeCK[6] (see e.g., TABLES 1A, 1B, 2A, and 2B in provisional application Nos. 62/671,680 and 62/672,080, incorporated herein by reference describe the frequency of sgRNA deep-sequencing reads). Data was obtained by deep-sequencing of sgRNAs from uninfected or sorted CHIKV-181/25-mKate2-negative cells. The two half libraries (A+B) were used for independent screens. The top candidate was Mxra8 (also known as DICAM, ASP3 or limitrin), an adhesion molecule found in mammals, birds and amphibians (see e.g., FIG. 5*b*, FIG. 5*c*) that is expressed on epithelial, myeloid and mesenchymal cells[7,8,9,10] and shares homology with junctional adhesion molecule[9], a reovirus entry receptor[11]. Mxra8 was validated using three different sgRNAs in bulk 3T3 cells, by generating ΔMxra8 single-cell clones in 3T3 and MEF cells, and by confirming gene deletion and cell viability (see e.g., FIG. 6*a*-FIG. 6*e*). Infection of CHIKV-181/25 was reduced in ΔMxra8 cells, and trans-complementation of Mxra8 in ΔMxra8 3T3 cells restored infectivity (see e.g., FIG. a, FIG. 1*b*). As CHIKV-181/25 is a cell-culture-adapted vaccine strain[12] that has acquired heparan sulfate binding activity[13], Mxra8 was evaluated with other CHIKV strains. Infection of CHIKV-AF15561—the parental Asian strain of CHIKV-181/25, which binds poorly to heparan sulfate[14]—and CHIKV-37997, a West African genotype strain, was abolished in ΔMxra8 3T3 cells, reduced in ΔMxra8 MEF cells (see e.g., FIG. 1*a*) and restored in trans-complemented ΔMxra8 3T3 cells (see e.g., FIG. 1*b*, FIG. 1*c*). However, the dependence on Mxra8 was less with CHIKV-LR 2006, a strain of the East/Central/South African genotype (see e.g., FIG. 1*a*, FIG. 1*d*). To confirm that CHIKV required Mxra8 independently of heparan sulfate binding, murine Mxra8 was expressed in parental or glycosaminoglycan-deficient Chinese hamster ovary cells[15] (see e.g., FIG. 7*a*). Expression of Mxra8 enhanced infectivity of CHIKV regardless of whether Chinese hamster ovary cells expressed heparan sulfate or other glycosaminoglycans (see e.g., FIG. 7*b*, FIG. 7*c*).

Figure 8:
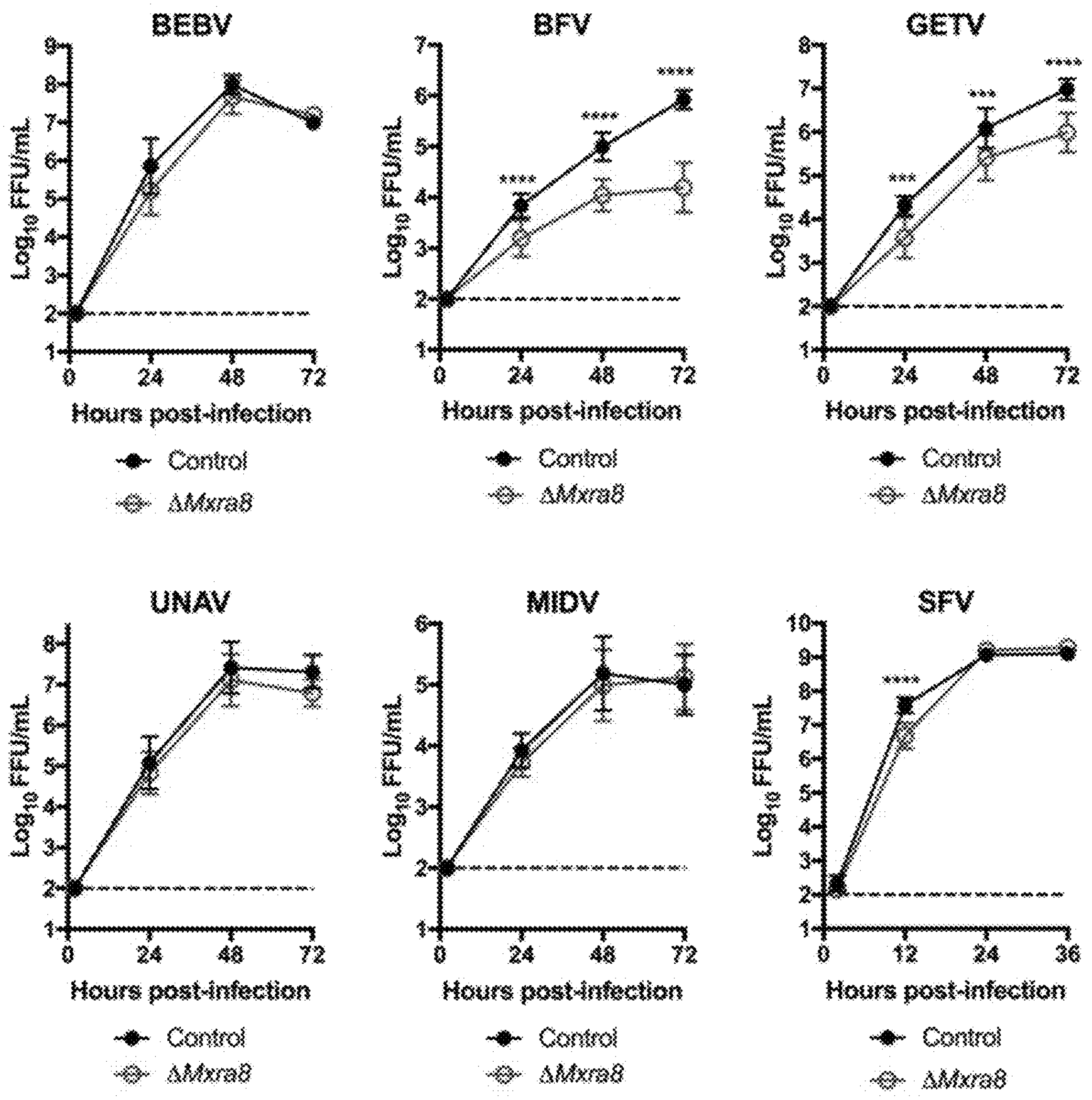
FIG. 8 shows growth curves of related alphaviruses in ΔMxra8 3T3 cells. Control and ΔMxra8 3T3 cells were inoculated with BEBV, BFV, GETV, UNAV, MIDV or SFV at an MOI of 0.01 (except for BEBV, which was at 0.001), and supernatants were collected at the indicated times for focus forming assay. Data are pooled from two (BEBV) or three (all others) experiments and expressed as mean±s.d. (n=6, BEBV; n=9, BFV, GETV, UNAV and MIDV; n=12, SFV; two-way ANOVA with Sidak's multiple comparisons test). *P<0.001; **P<0.0001.
Figure 9:
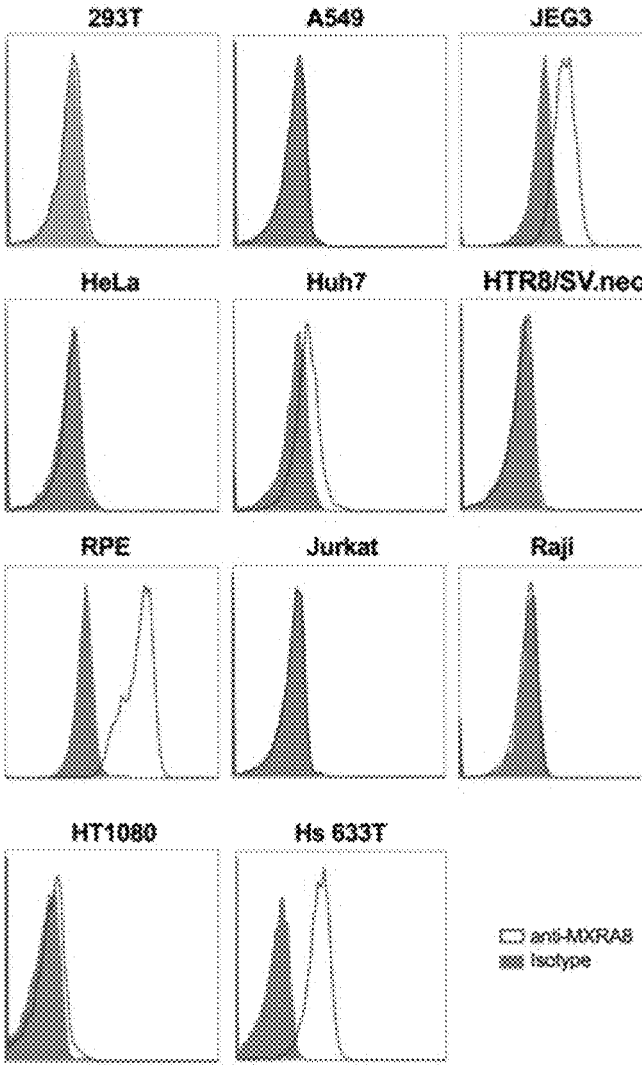
FIG. 9 shows surface expression of MXRA8 in different human cell lines. Human cell lines were tested for MXRA8 surface expression by flow cytometry: 293T (embryonic kidney), A549 (lung adenocarcinoma), JEG3 (placental choriocarcinoma), U2OS (osteosarcoma), HFF-1 (foreskin fibroblasts), HeLa (cervical carcinoma), Huh7 (hepatocarcinoma), HTR8/SVneo (trophoblast progenitor), MRC-5 (lung carcinoma), hCMEC/D3 (cerebral microvascular endothelial cells), RPE (retinal pigment epithelial cell), Jurkat (T cell lymphoma), Raji (B cell lymphoma), K562 (eryrtholeukaemia), HT1080 (fibrosarcoma) and Hs 633T (fibrosarcoma) cells. Representative data are shown of two independent experiments. Grey histograms, isotype control mAb; red histograms, anti-MXRA8 mAb.
Figure 10:
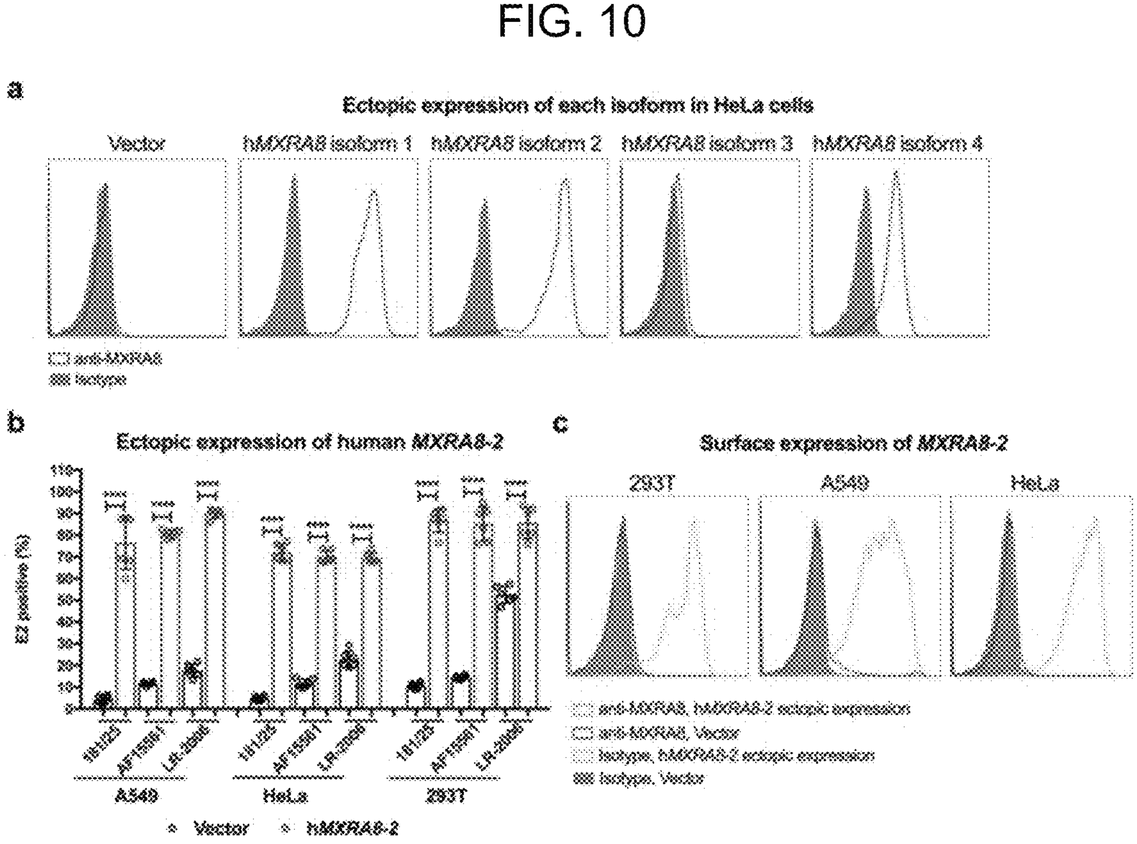
FIG. 10 shows MXRA8 supports enhanced infection of different CHIKV strains. (a) Transduction and expression of different MXRA8 (MXRA8-1, MXRA8-2, MXRA8-3 and MXRA8-4) isoforms in Hela cells. Representative data are shown from two experiments. Grey histograms, isotype control mAb; red histograms, anti-MXRA8 mAb. (b) Effect of ectopic expression of MXRA8-2 on CHIKV (strains 181/25, AF15561, and LR-2006) infection of A549, HeLa or 293T cells. Cells were collected and stained for CHIKV antigen with an anti-E2 antibody. Data are pooled from three experiments and expressed as mean±s.d. (n=6; two-tailed t-test with Holm-Sidak multiple comparison correction). (c) Transduction and expression of MXRA8-2 in 293T, A549, and HeLa cells. Representative data are shown from two experiments. *P<0.001; **P<0.0001.
Figure 11:
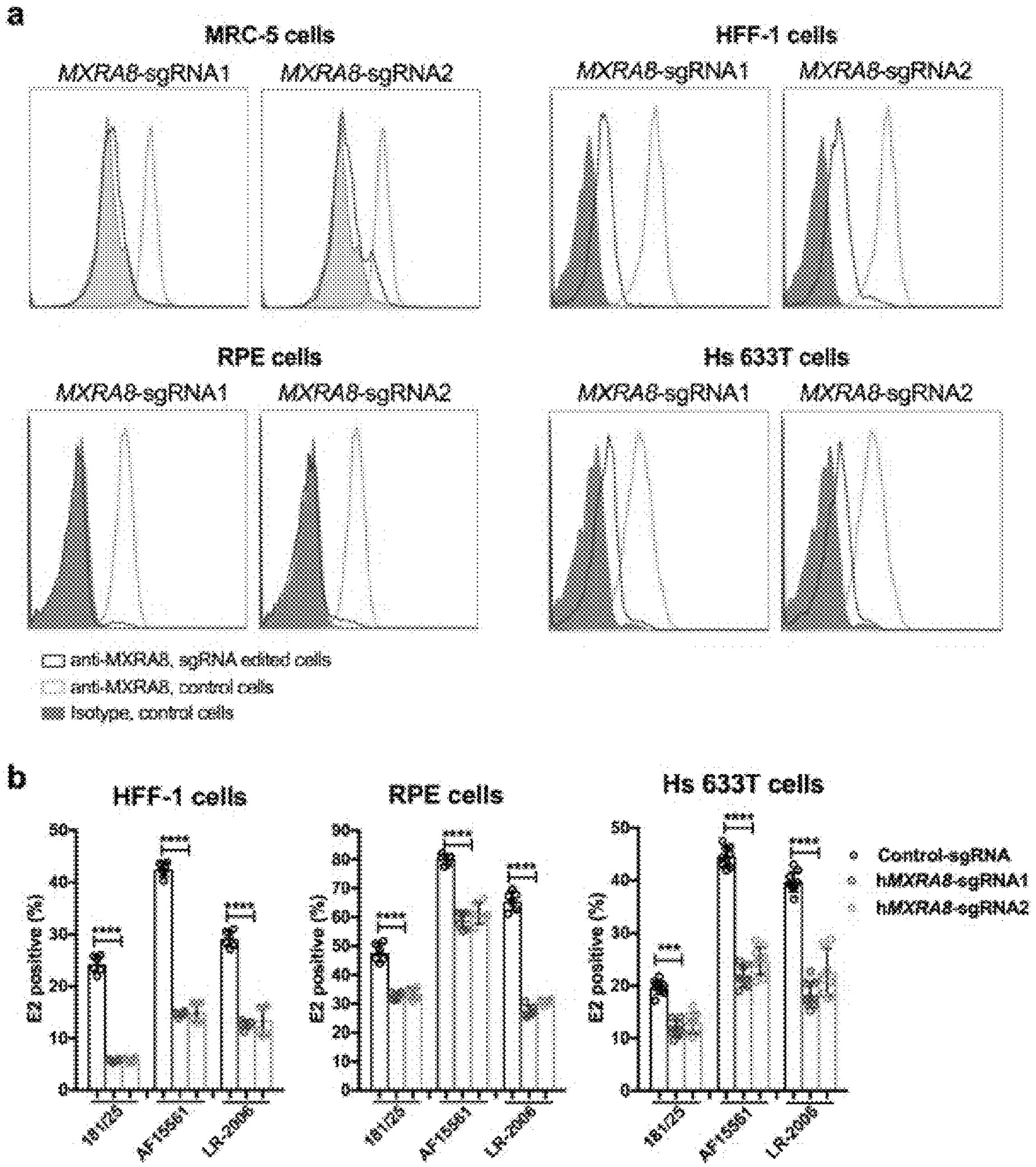
FIG. 11 shows gene-editing of MXRA8 in human cell lines. (a) Flow cytometry analysis of MXRA8 expression in human MRC-5, HFF-1, RPE and Hs 633T cells expressing control or two different MXRA8 sgRNAs. Data are representative of two experiments. (b) Gene-edited cells were inoculated with CHIKV (strains 181/25, AF15561 or LR-2006) in HFF-1, RPE, and Hs 633T cells. Cells were stained for viral antigen with an anti-E2 antibody. Data are pooled from two (HFF-1 and Hs 633T) or three (RPE) independent experiments and expressed as mean values±s.d. (n=6; one-way ANOVA with a Dunnett's multiple comparison test compared to the control). ****P<0.0001.

The requirement of Mxra8 for infection by other alphaviruses was tested. Whereas Mayaro, Ross River, O'nyong nyong and Barmah Forest arthritogenic alphaviruses showed reduced infection in ΔMxra8 3T3 cells, Semliki Forest and Getah viruses had partial phenotypes, and other related alphaviruses (Sindbis, Bebaru, Una and Middleburg viruses) showed little dependence on Mxra8 (see e.g., FIG. 1*e* and FIG. 8). Minimal differences in infection were observed between control and ΔMxra8 3T3 cells with chimaeric Sindbis viruses expressing the structural genes of the Eastern or Western equine encephalitis alphaviruses, or a Venezuelan equine encephalitis virus that expressed GFP (see e.g., FIG. 1*e*). No effect of Mxra8 was seen on infection of unrelated positive- or negative-sense RNA viruses (see e.g., FIG. 1*f*). It was next assessed whether any of the four isoforms of the human MXRA8 orthologue (see e.g., FIG. 5*b*) served a similar function. As Hela cells did not express MXRA8 (see e.g., FIG. 9), these cells were used for ectopic expression (see e.g., FIG. 10*a*). MXRA8-1, MXRA8-2, and MXRA8-4—but not MXRA8-3—were detected on the cell surface, and MXRA8-1 and MXRA8-2 enhanced CHIKV infectivity (see e.g., FIG. 1*g*). Similarly, expression of MXRA8-2 in A549 or 293T cells resulted in greater CHIKV infection (see e.g., FIG. 10*b*, FIG. 10*c*). Consistent with this observation, expression of different sgRNAs targeting all isoforms of MXRA8 in MRC-5 human lung fibroblasts, HFF-1 foreskin fibroblasts, RPE retinal pigment epithelial cells and Hs 633T fibrosarcoma cells resulted in less CHIKV infection than in control gene-edited cells (see e.g., FIG. 1*h* and FIG. 11*a*, FIG. 11*b*).

Figure 2:
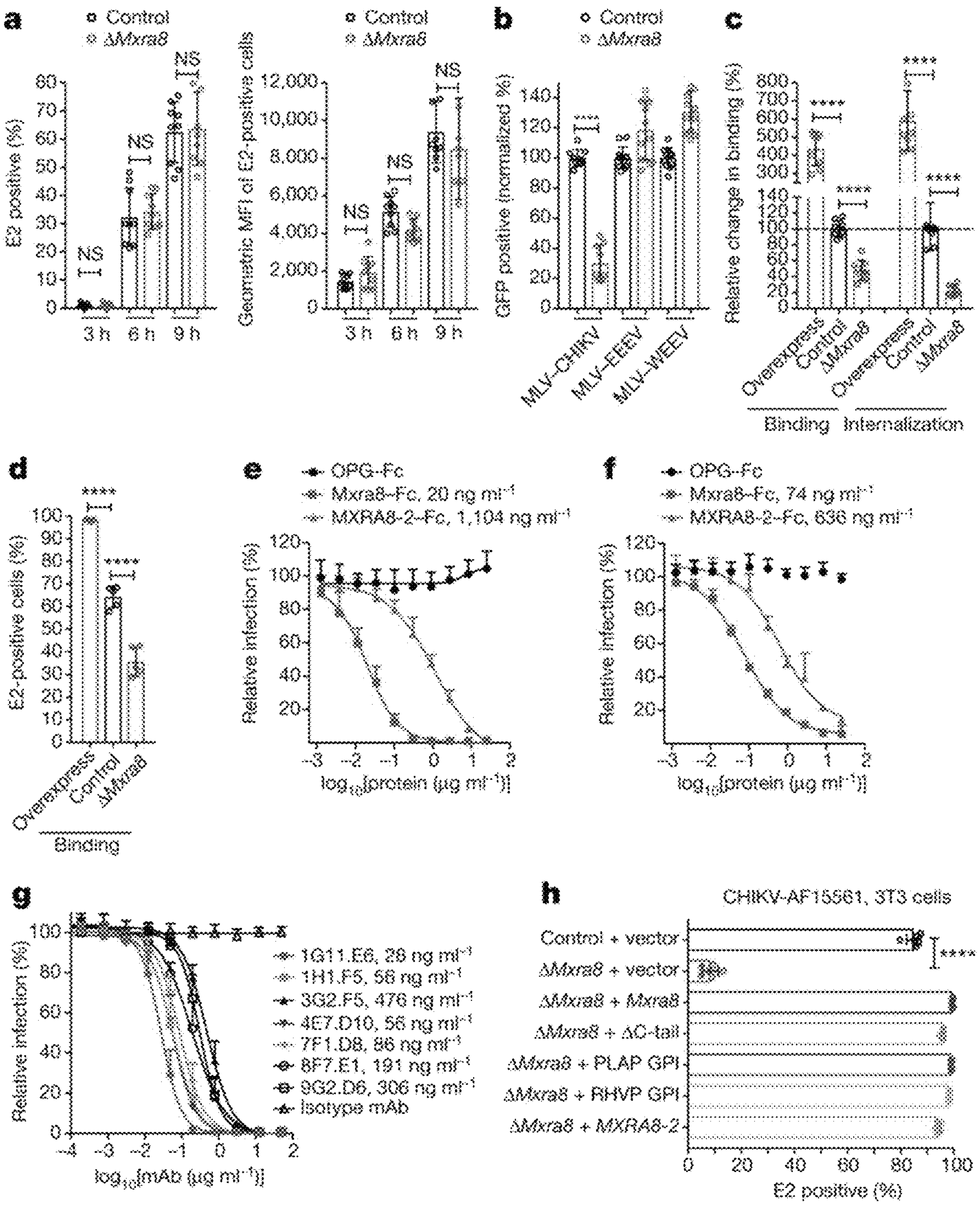
FIG. 2 is a series of graphs showing Mxra8 modulates CHIKV attachment and internalization. (a) Transfection of CHIKV RNA into control or ΔMxra8 cells. Cells were analysed for E2 expression: left, percent positive; right, mean fluorescence intensity (MFI) (3 experiments, n=9; two-tailed t-test with Holm-Sidak correction, mean±s.d.). b. Murine leukaemia virus (MLV) RNAs encoding GFP and pseudotyped with alphavirus structural genes were added to control or ΔMxra8 cells. Data are from three (MLV-CHIKV, n=9) or four (MLV-WEEV and MLV-EEEV, n=12) experiments (two-tailed t-test with Holm-Sidak correction; mean±s.d.). (c, d) CHIKV-AF15561 was incubated with control, ΔMxra8 and Mxra8-overexpressing MEF cells at 4° C. (c left, d) or 37° C. (c right) as described in Methods section of Example 1. Cells were collected, and RNA (CHIKV and Gapdh) was measured by qRT-PCR (c) or surface E2 protein was analysed by flow cytometry (d) (3 experiments; c, n=9; d, n=5; one-way ANOVA with Dunnett's test; mean±s.d.). (e, f) Mxra8-Fc, MXRA8-2-Fc or OPG-Fc were mixed with CHIKV-181/25 before infection of 3T3 (e) or MRC-5 (f) cells. Data are from two (MRC-5, n=6) or three (3T3, n=8-12) experiments; mean±s.d.; 50% inhibitory concentrations (EC50) are indicated to the right of each protein. (g) Blockade of CHIKV-181/25 infection in 3T3 cells with hamster anti-Mxra8 or isotype control mAbs (2 experiments, n=6; mean±s.d., EC50 values are indicated to the right of each mAb). h, Trans-complementation of ΔMxra8 cells with vector, Mxra8, Mxra8 AC-tail, Mxra8 with GPI anchors (derived from placental alkaline phosphatase (PLAP) or the rodent herpesvirus Peru (RHVP) open reading frame R1 gene[26]) or human MXRA8-2 (3 experiments; n=6; one-way ANOVA with Dunnett's test; mean±s.d.). ****P<0.0001; NS, not significant.

To determine whether Mxra8 is required for replication, CHIKV genomic RNA was transfected into control and ΔMxra8 MEF cells in the presence of $NH_4Cl$ to inhibit virus maturation and further rounds of infection. As no difference in CHIKV gene expression was detected (see e.g., FIG. 2*a*), Mxra8 does not appear to affect translation or replication. An Mxra8-dependence of the structural proteins using pseudotyped viruses was demonstrated. Whereas infection of CHIKV pseudotyped virions that encapsidated a murine leukaemia virus GFP-reporter RNA was reduced in ΔMxra8 compared to control MEF cells, infection of Eastern or Western equine encephalitis virus pseudotyped virions was not (see e.g., FIG. 2*b*). Consistent with a role for Mxra8 in the entry pathway, at 4° C. CHIKV-AF15561 showed reduced binding to ΔMxra8 compared to control MEF cells, and increased binding to cells overexpressing Mxra8 (see e.g., FIG. 2*c*, FIG. 2*d*). When virus internalization assays were performed at 37° C., less CHIKV RNA was measured within ΔMxra8 MEF cells, and more CHIKV RNA was detected in cells overexpressing Mxra8 (see e.g., FIG. 2*c*).

Figure 12:
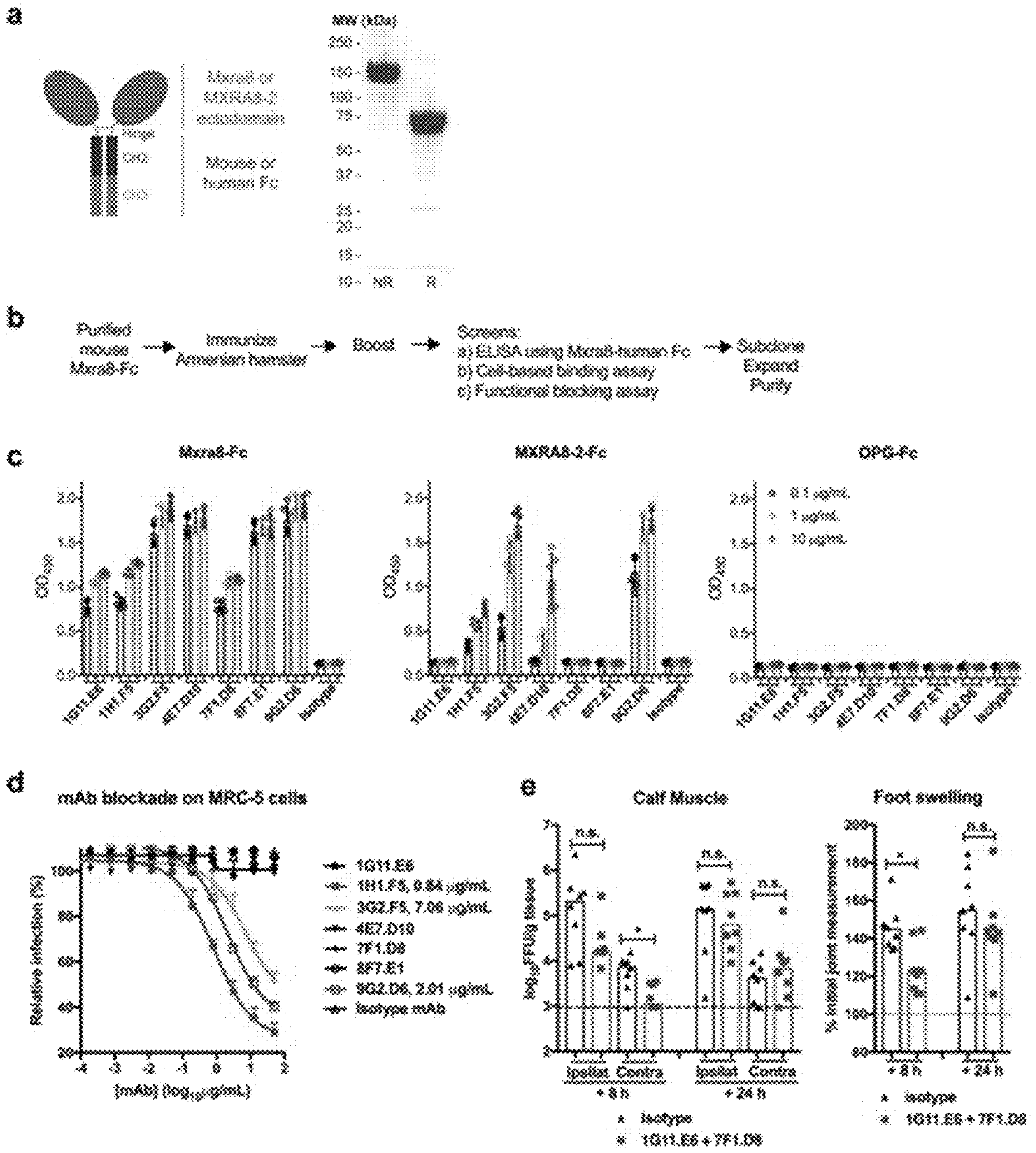
FIG. 12 shows Mxra8-Fc and anti-Mxra8 generation and function. (a) Diagram of Mxra8-Fc (left) and SDS-PAGE (non-reducing (NR) and reducing (R) conditions) of purified material (right). Data are representative of three experiments. (b) Scheme of anti-Mxra8 generation in Armenian hamsters. (c) ELISA reactivity of anti-Mxra8 mAbs against Mxra8-Fc, MXRA8-2-Fc or OPG-Fc. Purified proteins (50 µl, 5 µg $ml^{-1}$) were immobilized overnight at 4° C. on ELISA plates. Anti-Mxra8 and isotype control mAbs were incubated for 1 h at room temperature. Signal was detected at 450 nm after incubation with horseradish peroxide conjugated goat anti-Armenian hamster IgG (H+L) and development with 3,3'-5,5' tetramethylbenzidine substrate. (d) Blockade of CHIKV-181/25 infection in MRC-5 cells with seven different hamster anti-Mxra8 or isotype control mAbs. mAbs were pre-incubated with cells for 1 h at 37° C. before addition of virus. After infection, cells were processed for E2 staining by flow cytometry. Relative infection was compared to a no mAb condition using flow cytometry and anti-E2 staining. Data in c and d are pooled from two experiments (n=6) and expressed as mean±s.d. (e) Anti-Mxra8 mAbs (1G11+7F1) or isotype control hamster mAbs (300 µg total) were administered via intraperitoneal route 8 or 24 h after inoculation of CHIKV-AF15561 in the footpad. Left, at 72 h after initial infection, CHIKV titres were measured in the ipsilateral and contralateral gastrocnemius (calf) muscles. Right, at 72 h, ipsilateral foot swelling was measured and compared to measurements taken immediately before infection. Data are pooled from two experiments (n=8; two-tailed Mann-Whitney test) and expressed as median values. *P<0.05, n.s., not significant.
Figure 13:
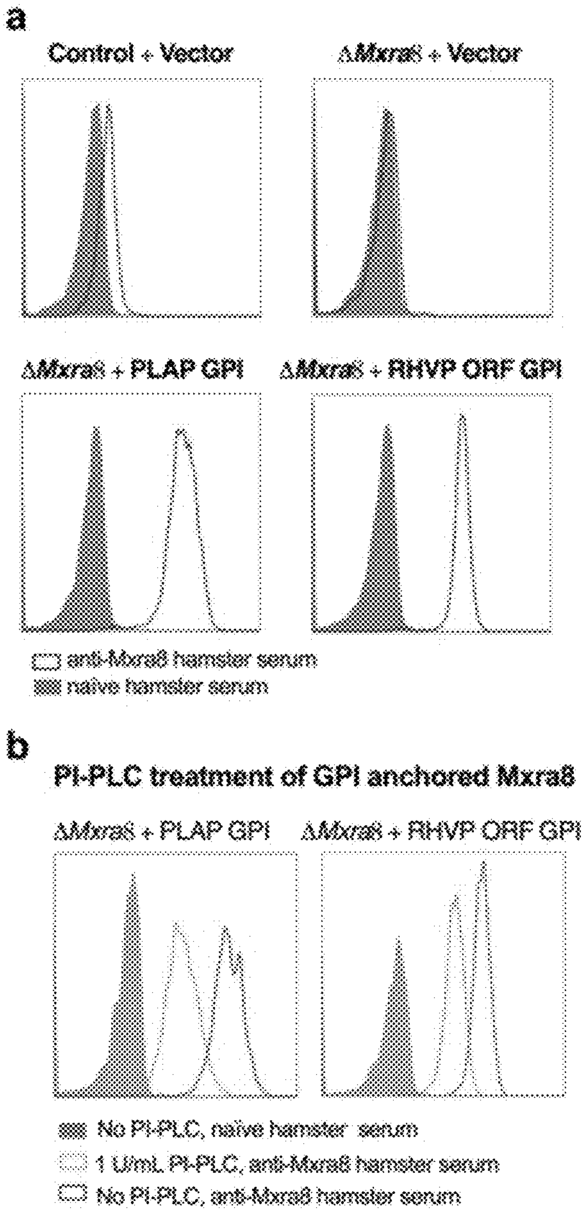
FIG. 13 shows expression of truncated forms of Mxra8 mutants. (a) Cell-surface expression of Mxra8 in ΔMxra8 3T3 cells trans-complemented with vector, Mxra8, Mxra8 ΔC-tail, Mxra8 with GPI anchors (derived from PLAP or RHVP open reading frame R1) or MXRA8-2. Data are representative of two independent experiments. (b) Effect of PI-PLC treatment on expression of different GPI-anchored forms or Mxra8. Data are representative of two independent experiments.

To corroborate an effect of Mxra8 on binding and entry, Fc fusion proteins with the extracellular domains of mouse Mxra8 (Mxra8-Fc) or human MXRA8-2 (MXRA8-2-Fc) were generated, along with a control osteoprotegerin protein (OPG-Fc) (see e.g., FIG. 12*a*). Pre-incubation with Mxra8-Fc or MXRA8-2-Fc, but not the control OPG-Fc, reduced CHIKV-181/25 infection in 3T3 (see e.g., FIG. 2*e*) and MRC-5 (see e.g., FIG. 2*f*) cells. A panel of hamster mAbs were tested against mouse Mxra8 (see e.g., FIG. 12*b*) for their capacity to inhibit. CHIKV infection. Seven mAbs bound to mouse Mxra8-Fc, with four also recognizing human MXRA8-2-Fc (see e.g., FIG. 12*c*). Pre-treatment of 3T3 cells with anti-Mxra8 mAbs reduced CHIKV infection (see e.g., FIG. 2*g*). Three of the mAbs that bound human MXRA8-2-Fc also reduced infection in MRC-5 cells (see e.g., FIG. 12*d*). To establish the importance of the Mxra8 ectodomain, forms with glycophosphatidylinositol anchors (Mxra8-GPI) or lacking a cytoplasmic domain (Mxra8-AC-tail) for trans-complementation were engineered (see e.g., FIG. 13). Notably, Mxra8-GPI and Mxra8-AC-tail restored CHIKV infection (see e.g., FIG. 2*h*). Interaction with the Mxra8 ectodomain may facilitate viral glycoprotein conformational changes that are required for internalization or fusion[16] or potentiate interactions with other host factors that bridge membrane penetration and entry[17]. Finally, heterologous expression of human MXRA8-2 in ΔMxra8 mouse cells also restored CHIKV infection (see e.g., FIG. 2*h*).

Figure 3:
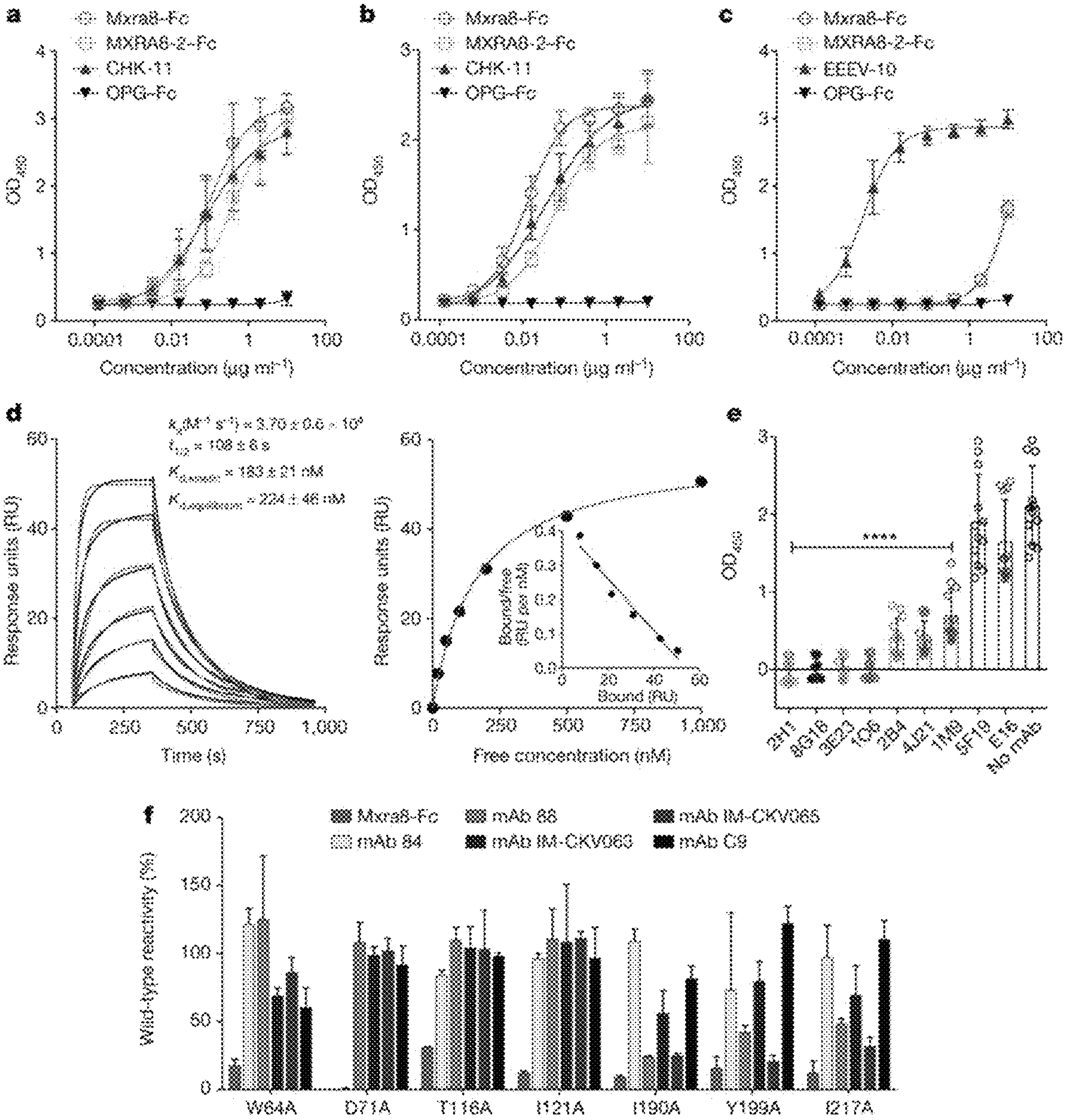
FIG. 3 is a series of graphs showing direct binding of Mxra8 to CHIKV. (a-c) Purified CHIKV-181/25 (a), CHIKV virus-like particles (b) or chimaeric EEEV virions (c) were captured with anti-CHIKV or anti-EEEV human mAbs. Mxra8-Fc, MXRA8-2-Fc or OPG-Fc, and positive-control mAbs (CHK-11 or EEEV-10), were added. Data are from two (b, c) or three (a) experiments (a, n=8; b, n=4; c, n=6); mean±s.d. d, Left, sensograms of Mxra8 binding to CHIKV virus-like particles. Experimental curves (black traces) were fit using a 1:1 binding model (red traces). Right, representative response curve for steady-state analysis, in which binding is plotted versus Mxra8 concentration. Inset, linear Scatchard plot (4 experiments; mean and s.e.m.). (e) Antibody blockade of Mxra8-Fc binding to CHIKV. Virus was incubated with indicated human mAbs against CHIKV, a mAb against WNV (E16) or no mAb before the addition of Mxra8-Fc (4 experiments, n=12; one-way ANOVA with Dunnett's test; mean±s.d.). (f) Residues that result in loss of Mxra8-Fc binding to cell-surface-displayed CHIKV E2-E1. Residues are considered involved in the epitope if there is diminished binding without loss of protein integrity as judged by retention of interaction with mAbs (except for those previously mapped to a specific residue) Data are from two experiments. ****P<0.0001.
Figure 14:
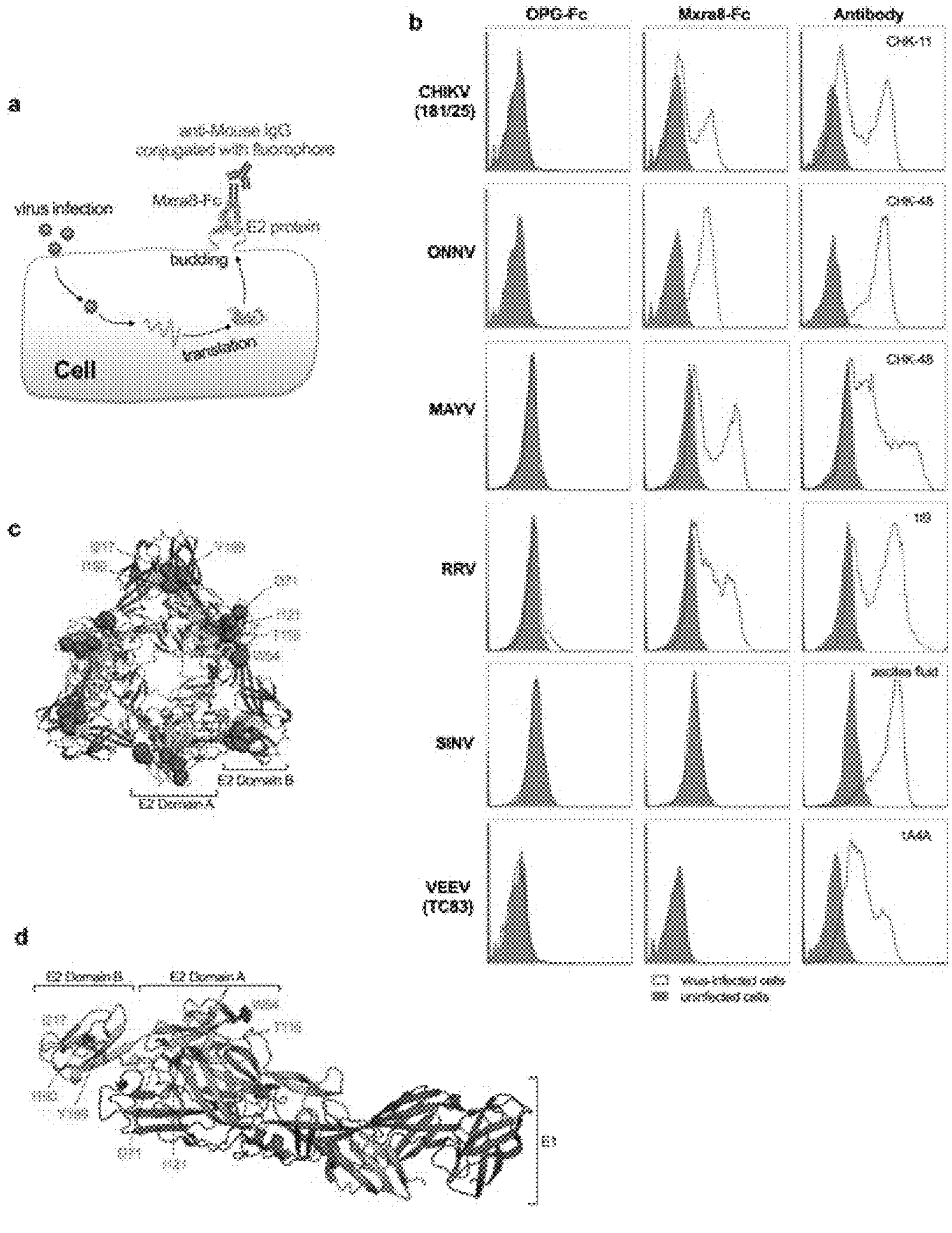
FIG. 14 shows binding of Mxra8-Fc to surface-displayed E2 protein in virus-infected cells and mapping of Mxra8 binding site on E2. (a) Diagram of the cell-based binding assay. After infection, viral structural proteins (for example, E2) traffic to the cell plasma membrane where progeny virion assembles and buds. E2 protein is displayed on the cell surface and is accessible to the binding of Mxra8-Fc and detection with a goat anti-mouse IgG secondary antibody by flow cytometry. (b) Binding of Mxra8-Fc to virus-infected wild-type 3T3 cells. Cell were infected with the indicated viruses and processed for Mxra8-Fc binding by flow cytometry. Virus-specific anti-E2 antibodies were used as positive controls. Data are representative of two independent experiments. (c, d) Mapped residues are shown as magenta spheres (c) or sticks (d) on the CHIKV p62-E1 structure (c, trimer of dimers, top view; d, heterodimer, side view) using PyMOL (Protein Data Bank code: 3N41). The E1 and E2 proteins are coloured in grey and cyan, respectively.

To determine whether Mxra8 directly binds to CHIKV, virions or virus-like particles[18] were captured with a human anti-CHIKV mAb[19], and added Mxra8-Fc or MXRA8-2-Fc in an enzyme-linked immunosorbent assay. Both Mxra8-Fc and MXRA8-2-Fc, but not OPG-Fc, bound to CHIKV virions and virus-like particles (see e.g., FIG. 3*a*, FIG. 3*b*). By comparison, Mxra8-Fc and MXRA8-2-Fc did not bind efficiently to Eastern equine encephalitis virus particles derived from a chimaera with Sindbis virus (see e.g., FIG. 3*c*). In a complementary assay, binding of Mxra8-Fc protein to cell-surface-displayed alphavirus proteins on infected cells[19,20] was assessed. Mxra8-Fc bound cells infected with CHIKV, O'nyong nyong virus, Mayaro virus and Ross River virus, but not cells infected with Sindbis virus or Venezuelan equine encephalitis virus (see e.g., FIG. 14*a*, FIG. 14*b*). Binding of Mxra8 to CHIKV virus-like particles by surface plasmon resonance was analyzed, and a slow association rate, a long half-life and an affinity of about 200 nM was found (see e.g., FIG. 3*d*).

It was evaluated whether human anti-CHIKV mAbs that bound epitopes within the E2 protein[19] altered Mxra8-Fc binding to CHIKV. Several mAbs recognizing epitopes in the A domain (2H1, 8G18, 3E23 and 1O6) and mAbs recognizing shared epitopes in the A and B domains (1H12 and 4J14) inhibited binding, whereas other mAbs that localize to distinct sites had less effect (see e.g., FIG. 3*e*). The binding of Mxra8-Fc to an alanine scanning mutagenesis library of E2 A and B domains in the context of display on the surface of 293T cells[19,20] was then tested. Residues W64, D71, T116 and 1121 in the A domain, and I190, Y199 and I217 in the B domain, of E2 emerged as essential for optimal Mxra8-Fc binding (see e.g., FIG. 3*f* and TABLE 1 shown in FIGS. 34(A-D)) and overlap the binding sites of the blocking mAbs that were tested[19]. Mapping of these residues onto the p62 (E2 precursor)—E1 heterodimer or the trimer of heterodimers (see e.g., FIG. 14*c*, FIG. 14*d*) on the virion surface[21] revealed a solvent-accessible epitope across the top of the A and B domains, which is a proposed site of alphavirus receptor engagement[22,23].

TABLE 1, as shown in FIG. 34(A-D), lists Mxra8-Fc binding to 293T cells transfected with alanine scanning mutants of C-E3-E2-6K-E1. Alanine mutations of E2 are indicated in the first column, and binding to Mxra-Fc and several CHIKV mAbs (84, 88, IM-CKV063, IM-CKV065, and C9) was tested in 293T cells and processed by flow cytometry. Percent binding of Mxra-Fc or mAbs to the respective mutant was normalized to cells transfected with wild-type C-E3-E2-6K-E1 plasmid. Data are representative of two independent experiments and parentheses indicate range. Yellow highlighting indicates mutants with loss-of-binding to Mxra-Fc that retain expression and folding. Green highlighting indicates mutations that affect overall domain/protein folding and expression, and cannot be evaluated with certainty.

Figure 4:
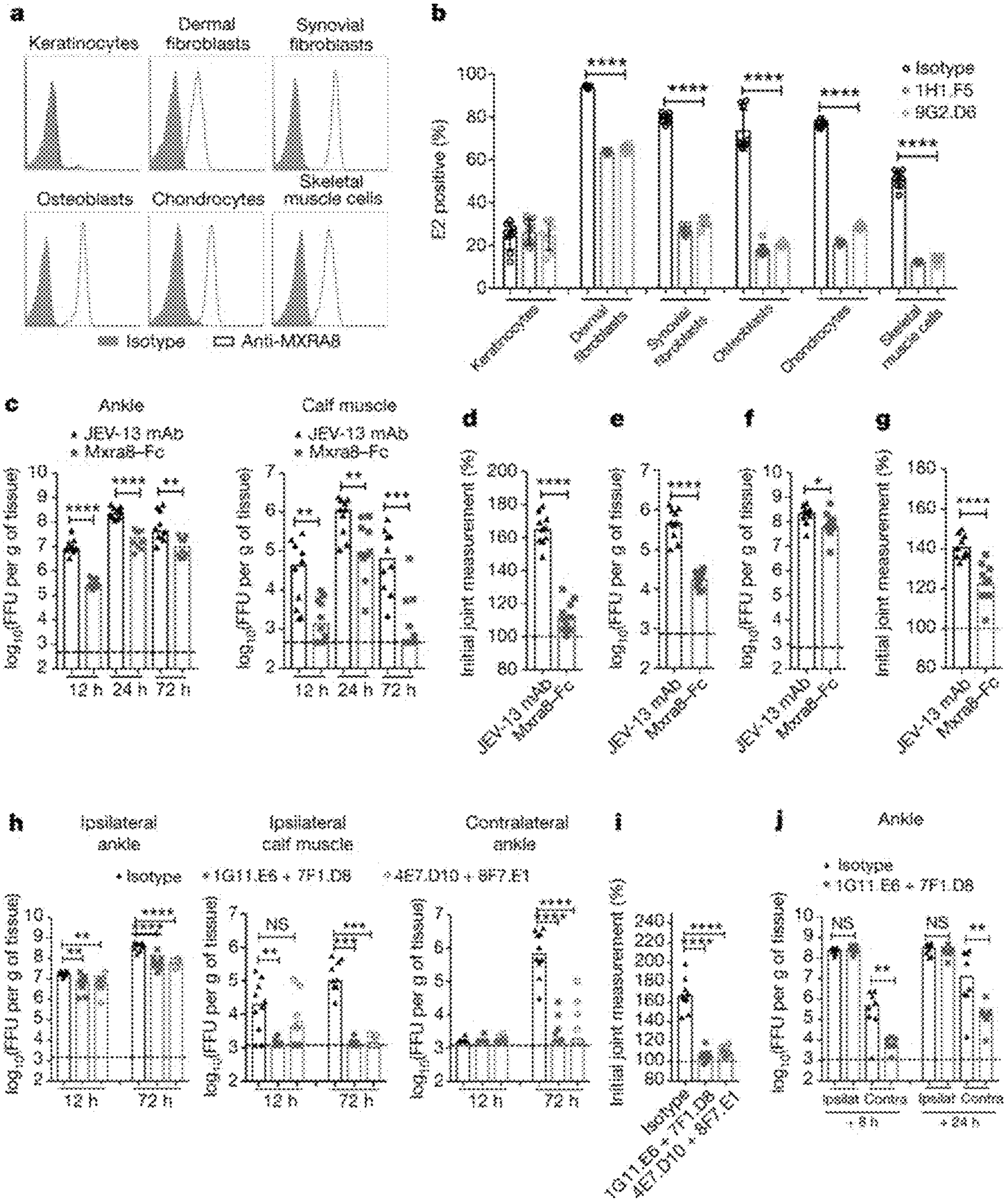
FIG. 4 is a series of graphs showing Mxra8 contributes to alphavirus pathogenesis. (a) Surface expression of MXRA8 on primary human keratinocytes, dermal fibroblasts, synovial fibroblasts, osteoblasts, chondrocytes and skeletal muscle cells. One experiment of three is shown. (b) Primary human cells were pre-incubated with anti-MXRA8 blocking mAbs before addition of CHIKV-AF15561 and processed for E2 staining (3 experiments, n=9; one-way ANOVA with Dunnett's test). (c, d) Mxra8-Fc or JEV-13 mAb were incubated with CHIKV-AF15561 for 30 min before subcutaneous inoculation. (c) At 12, 24 and 72 h, CHIKV was measured in the ipsilateral ankle and calf muscle. (d) At 72 h, foot swelling was measured (2 experiments, n=10; median viral titres: two-tailed Mann-Whitney test; mean foot swelling: two-tailed unpaired t-test). (e), Mxra8-Fc or JEV-13 mAb was mixed with O'nyong nyong virus immediately before subcutaneous inoculation. At 12 h, O'nyong nyong virus was measured in the ipsilateral ankle (2 experiments, n=10; two-tailed unpaired t-test; median values). (f, g) Mxra8-Fc or JEV-13 mAb was administered via an intraperitoneal route 6 h before CHIKV-AF15561 inoculation in the footpad. At 24 h, CHIKV was measured in the ipsilateral ankle (f). At 72 h, foot swelling was measured (g) (2 experiments, n=10; median viral titres: two-tailed Mann-Whitney test; mean foot swelling: two-tailed unpaired t-test). (h-j) Pairs of anti-Mxra8 mAbs or isotype control hamster mAbs were administered via an intraperitoneal route 12 h before (h, i) or 8 or 24 h after (j) inoculation of CHIKV-AF15561. At 12 (h) and 72 (h, j) h, CHIKV was measured. At 72 h, foot swelling (i) was measured (2 experiments; h left, i: n=10; one-way ANOVA with Dunnett's test; h middle and right: n=10; Kruskal-Wallis with Dunn's test; j: n=8; two-tailed Mann-Whitney test). Ipsilat, ipsilateral; contra, contralateral. *P<0.05; P<0.01; *, P<0.001; ****P<0.0001.

To begin to assess the physiological importance of MXRA8 interaction with CHIKV, surface expression of MXRA8 on primary human keratinocytes, dermal fibroblasts, synovial fibroblasts, osteoblasts, chondrocytes and skeletal muscle cells were tested (see e.g., FIG. 4*a*), all of which are targets of infection by alphaviruses[24]. Pretreatment with anti-MXRA8 blocking mAbs inhibited infection of CHIKV-AF15561 in all cells but keratinocytes, which lack MXRA8 expression (see e.g., FIG. 4*a, b*). It was next evaluated whether co-injection of Mxra8-Fc with CHIKV-AF15561 would diminish infection in C57BL/6 mice. The addition of Mxra8-Fc diminished CHIKV infection in the ipsilateral ankle and muscle (see e.g., FIG. 4*c*) and reduced foot swelling (see e.g., FIG. 4*d*) compared to a control mAb. Treatment with Mxra8-Fc also inhibited O'nyong nyong virus infection in the ipsilateral ankle of mice (see e.g., FIG. 4*e*). Mxra8-Fc was next administered via an intraperitoneal route, and 6 h later CHIKV was inoculated in the footpad. Mxra8-Fc treatment reduced foot swelling and viral burden in the ipsilateral ankle (see e.g., FIG. 4*f*, FIG. 4*g*), although the phenotype was less pronounced than in co-injection experiments. To extend these findings, hamster anti-Mxra8 blocking or control mAbs were transferred to mice via an intraperitoneal route 12 h before CHIKV inoculation. Reduced CHIKV titres were observed in the ipsilateral ankle and calf muscle, and contralateral ankle at 12 and 72 h after infection in anti-Mxra8 compared to control mAb-treated mice (see e.g., FIG. 4*h*). Treatment with anti-Mxra8 mAbs also reduced foot swelling (see e.g., FIG. 4*i*). In post-exposure therapeutic experiments, reduced CHIKV infection in the contralateral ankle and muscle when anti-Mxra8 mAbs were administered at 8 or 24 h after virus inoculation was observed (see e.g., FIG. 4*j* and FIG. 12*e*). These in vivo experiments establish a function for Mxra8 in the pathogenesis of infection of arthritogenic alphaviruses.

These studies establish that mouse Mxra8 contributes to CHIKV entry and is required for infection and disease. Human MXRA8 also bound CHIKV and supported infection, and MXRA8 expression in primary human cells overlapped with the tropism of CHIKV in vivo. Infection of several arthritogenic alphaviruses—including CHIKV, O'nyong nyong virus, Mayaro virus and Ross River virus—was reduced in ΔMxra8 cells, which suggests that Mxra8 may serve as a shared receptor. The disclosed data contrasts with those relating to natural resistance-associated macrophage protein (NRAMP2), which is an entry receptor for Sindbis virus but not for CHIKV or Ross River virus[25]. Nonetheless, residual CHIKV infection in the absence of Mxra8 in cells and in mice, and the absence of an apparent mosquito orthologue, suggests that additional unidentified host factors contribute to cell binding and entry.

The mutagenesis mapping studies suggest that amino acids in the E2 A and B domains contribute to the interaction of CHIKV with Mxra8. Higher-resolution structural experiments are needed to define the complete footprint of binding between Mxra8 and CHIKV E2 protein. Such studies could facilitate the development of small molecules or biological agents that disrupt Mxra8 interaction with E2 protein, which could form the basis of therapeutic strategies for the amelioration of diseases caused by multiple emerging alphaviruses.

Methods

Cells and Viruses.

Vero, NIH-3T3, MEF, HEK 293T, A549, HeLa (ATCC #CCL-2), MRC-5 (provided by D. Wang, Washington University), HFF-1 (ATCC #SCRC-1041), Hs 633T (Sigma-Aldrich #89050201), Huh7, RPE (provided by M. Mahjoub, Washington University), JEG3 (provided by I. Mysorekar, Washington University), U2OS (provided by S. Cherry, University of Pennsylvania), HT1080 (provided by J. Cooper, Washington University), Raji and K562 cells all were cultured at 37° C. in Dulbecco's Modified Eagle medium supplemented with 10% fetal bovine serum (FBS), 10 mM HEPES, 1 mM sodium pyruvate, 1× non-essential amino acids, and 100 U/ml of penicillin-streptomycin. HTR8/SV.neo cells (provided by I. Mysorekar, Washington University) were cultured in RPMI 1640 supplemented with 5% FBS and 1% penicillin and streptomycin. Jurkat cells were cultured at 37° C. in RPMI 1640 supplemented with 10% FBS and 10 mM HEPES. hCMEC/D3 cells (provided by R. Klein, Washington University) were cultured in EBM-2 medium (Lonza, 00190860) supplemented with 5% FBS, 5 μg/ml ascorbic acid, 10 mM HEPES, 1% lipid concentrate (Gibco, 11905-031) in plates pre-coated with collagen. All cell lines were tested and found to be free of *mycoplasma* contamination using a commercial kit. Cell lines were not authenticated.

Primary human keratinocytes (#102-05n), synovial fibroblasts (#408-05a), osteoblasts (#406-05f), chondrocytes (#402-05f) and skeletal muscle cells (#S150-05f) were purchased from Cell Applications. Primary human dermal fibroblasts (#CC-2509) were obtained from Lonza. Cells were thawed and cultured in specified medium according to the instructions of the manufacturers, and used within one week.

The following alphaviruses were used: CHIKV (strains 2006 La Reunion OPY1, 37997, AF15561, 181/25, and 181/25-mKate2 (rescued from pJM6 CHIKV-181/25 mKate2 cDNA clone, provided by T. Morrison and M. Heise), RRV (T48), MAYV (BeH407), ONNV (MP30), SFV (Kumba), SINV (Toto1101, Girdwood), Bebaru virus (BEBV, MM 2354), Middleburg virus (MIDV, 30037), Getah virus (GETV, AMM-2021), Una virus (UNAV, CoAr2380) and Barmah Forest virus (BRV, K10521). Additional viruses tested included chimaeric encephalitic alphaviruses (SINV-EEEV and SINV-WEEV), VEEV-GFP (TC-83)), a flavivirus (WNV, New York 2000), a bunyavirus (RVFV-GFP, MP-12), a rhabdovirus (VSV-GFP, Indiana) and a picornavirus (encephalomyocarditis virus, EMCV). Replication-competent SINV chimaeric viruses were constructed by replacing the SINV TR339 structural protein genes with EEEV FL93-939 or WEEV Fleming structural protein genes under control of the SINV subgenomic promoter in the TR339 cDNA clone[27]. All viruses were propagated in Vero cells and titrated by standard plaque or focus-forming assays[28].

Pooled sgRNA Screen and Data Analysis.

A GeCKOv2 CRISPR knockout pooled library encompassing 130,209 different sgRNAs against 20,611 mouse genes[29] was made available by F. Zhang (Addgene #1000000053), and amplified in Endura cells (Lucigen #60242) as previously described[29,30]. The sgRNA library was divided in half (A+B), packaged into lentiviruses and used for independent screening. The sgRNA plasmid library was packaged in 293 FT cells after co-transfection with psPAX2 (Addgene #12260) and pMD2.G (Addgene #12259) at a ratio of 2:2:1 using FugeneHD (Promega). Approximately 48 h after transfection, supernatants were collected, clarified by centrifugation (3,500 r.p.m.×20 min) and aliquotted for storage at −80° C.

For the CRISPR screen, a clonal 3T3-Cas9 cell line was generated by transduction with a packaged lentivirus (lentiCas9-Blast, Addgene #52962), blasticidin selection and limiting dilution. 3T3-Cas9 cells were expanded and transduced with CRISPR sgRNA lentivirus library at a multiplicity of infection (MOI) of 0.3 by spinoculation (1,000 g) at 32° C. for 30 min in 12-well plates. After selection with puromycin for 7 days, ~$1\times10^8$ cells were inoculated with CHIKV-181/25-mKate2 (MOI of 1) and then incubated for 24 h to allow nearly all cells to become infected. Cells were sorted for an absence of mKate2 expression using a Sony Biotechnology Synergy SY3200 Cell sorter (Siteman Flow Cytometry Core, Washington University). To enrich for the cell population that was resistant to CHIKV infection and increase the signal-to-noise ratio, the mKate2-negative cells were expanded in culture. Given the rapid replication rate and cytopathic effect of CHIKV, two humanized neutralizing mAbs[5], CHK-152 and CHK-166 (2 μg/ml of each), were added to block infection by any residual virus. The expanded cells were re-infected with CHIKV-181/25-mKate2 in the absence of mAbs, sorted for mKate2 negative cells and the procedure was repeated for one additional round.

Genomic DNA was extracted from the uninfected cells ($5\times10^7$) or the mKate2-negative sorted cells ($1\times10^7$), and sgRNA sequences were amplified[31] and subjected to next generation sequencing using an Illumina HiSeq 2500 platform (Genome Technology Access Center, Washington University). The sgRNA sequences against specific genes were determined after removal of the tag sequences using the FASTX-Toolkit and cutadapt 1.8.1. sgRNA sequences were analyzed using a published computational tool (MAGeCK)[6] (see e.g., TABLES 1A, 1B, 2A, and 2B in provisional application Nos. 62/671,680 and 62/672,080, incorporated herein by reference).

Gene Validation.

Mxra8 was validated by using three independent sgRNAs as follows: Mxra8 sgRNA1, 5'-CTTGTGGATATGTAT-TCGGC-3' (SEQ ID NO: 34); Mxra8 sgRNA2, 5'-TGTGCGCCTCGAGGTTACAG-3' (SEQ ID NO: 35); Mxra8 sgRNA3, 5'-GCTGCATGATCGCCAGCGCG-3' (SEQ ID NO: 36). The sgRNAs were cloned into the plasmid lentiCRISPR v.2 (Addgene #52961) and packaged with a lentivirus express system. 3T3 or MEF cells were transduced with lentiviruses expressing individual sgRNA and selected with puromycin for seven days before infection with different viruses. For some validation experiments, clonal cells edited by sgRNA1 were isolated by limiting dilution. To validate the human orthologue MXRA8, two different sgRNAs targeting all four isoforms were used: MXRA8 sgRNA1, 5'-GGCGCGGATGCCTTTGAGCG-3' (SEQ ID NO: 37); MXRA8 sgRNA2, 5'-GTCCGCCTG-GAGGTCACCGA-3' (SEQ ID NO: 38). The sgRNAs were cloned similarly as above, and the gene-edited bulk cells were used for validation studies.

For flow cytometric analyses, gene-edited 3T3 cells were inoculated with different viruses as follows: CHIKV-181/25 (MOI of 3, 9.5 h), CHIKV-AF15561 (MOI of 10, 24 h), CHIKV-37997 (MOI of 3, 10 h), CHIKV-LR 2006 (MOI of 1, 9.5 h), ONNV (MOI of 3, 12 h), RRV (MOI of 3, 32 h), MAYV (MOI of 3, 24 h), SFV (MOI of 1, 9 h), SINV (MOI of 10, 6 h), SIN-WEEV (MOI of 10, 10 h), SIN-EEEV (MOI of 10, 10 h), VEEV-GFP (MOI of 3, 6.5 h), RVFV-GFP (MOI of 10, 8 h), VSV-GFP (MOI of 3, 6 h), WNV (MOI of 10, 25 h) and EMCV (MOI of 3, 6 h). Gene-edited MEF cells were inoculated with CHIKV-181/25 (MOI of 3, 8 h), CHIKV-AF15561 (MOI of 10, 10 h), CHIKV-37997 (MOI of 1, 10 h) and CHIKV-LR 2006 (MOI of 1, 8 h). Gene-edited MRC-5, RPE and HFF-1 cells were inoculated with CHIKV-181/25 (MOI of 10, 10 h), CHIKV-AF15561 (MOI of 10, 10 h) and CHIKV-LR 2006 (MOI of 1, 10 h). Gene-edited Hs 633 T cells were inoculated with CHIKV-181/25 (MOI of 15), CHIKV-AF15561 (MOI of 15) and CHIKV-LR 2006 (MOI of 3) for 11.5 h. At the indicated times, cells were collected with trypsin, and fixed with 1% paraformaldehyde (PFA) diluted in PBS for 15 min at room temperature and permeabilized with Perm buffer (Hank's Balanced Salt Solution (HBSS) supplemented with 10 mM HEPES, 0.1% (w/v) saponin, and 2% FBS) for 10 min at room temperature. Cells were then incubated for 30 min at room temperature with 1 μg/ml of the following virus-specific antibodies: CHIKV (mouse CHK-11[5]), ONNV and MAYV (mouse CHK-48), RRV (human 119); SINV (ascites fluid, ATCC VR-1248AF), SFV (mouse CHK-124), VEEV (mouse 1A4A), WEEV (mouse 11A1), EEEV (mouse EEEV-10), WNV (human E16[32]) and EMCV (mouse serum). After washing, cells were incubated with 2 μg/ml of Alexa Fluor 647-conjugated goat anti-mouse or anti-human IgG (Invitrogen) for 30 min at room temperature. Cells were processed on a MACSQuant Analyzer 10 (Miltenyi Biotec), and analyzed using FlowJo software (Tree Star).

Validation also was performed by an infectious virus yield assay. Gene-edited 3T3 cells were plated 12 h before infection. Cells were inoculated with CHIKV-181/25, CHIKV AF15561, CHIKV-LR 2006 at an MOI of 0.01 or other alphaviruses (BEBV, MOI 0.001; BFV, GETV, UNAV, MIDV, and SFV, all at MOI of 0.01) for 1 h, then washed once and maintained in reduced 2% FBS culture medium. Supernatants were collected at specific times after infection for titration on Vero cells by focus-forming assay (CHIKV) or standard plaque assay (all other viruses).

Genomic RNA Transfection and Analysis.

To assess for effects of Mxra8 on CHIKV replication, capped viral genomic RNA was transfected into MEF cells. Capped genomic RNA was generated using an mMESSAGE mMACHINE SP6 Transcription Kit according to the manufacturer's instructions (Thermo Fisher #AM1340) from the Notl-linearized CHIKV-181/25 cDNA clone. One microgram of purified RNA was transfected into control or ΔMxra8 cells using the Neon transfection system according to the manufacturer's instructions (Thermo Fisher Scientific). Cells were then incubated in 15 mM $NH_4Cl$ to prevent subsequent rounds of infection. At specified times, cells were collected with trypsin and processed for E2 expression levels by flow cytometry.

Pseudotyped Virus Experiments.

MLV-GFP pseudoviruses were made as described[33,34] except plasmids encoding structural proteins of CHIKV (strain 37997), VEEV (strain TrD) and EEEV (strain FL91-4697) were used. Pseudovirus entry in 3T3 cells expressing or lacking Mxra8 was assessed 36 h later by measuring GFP expression by flow cytometry.

Plasmid Construction.

The C-terminal Flag-tagged mouse Mxra8 corresponding to the transcript (NM_024263) was synthesized (Integrated DNA Technologies) and cloned into the lentivirus vector pCSII-EF1-IRES-Venus with restriction sties Notl/BamHI. The Mxra8 sgRNA target sequences were mutated (cttgtggatatgtattcggcg (SEQ ID NO: 39) to ctGgtCgaCatgtaCAGCgcg (SEQ ID NO: 40)) to avoid re-cutting by Cas9 protein for the trans-complementation. Based on this plasmid, a truncation lacking the cytoplasmic domain was constructed by PCR-mediated mutagenesis, the ΔC-tail (378-442). To express the GPI-anchored Mxra8, the N-terminal 336 amino acids missing the transmembrane and cytoplasmic domains were fused with PLAP (ctggcgccccc cgccggcaccaccgacgccgcgcacccggggcggtccgtggtcc ccgcg ttgcttcctctg ctggccgggaccctgctgctgctggagacggccactgctccc) (SEQ ID NO: 41) or the rodent herpesvirus Peru (RHVP) open reading frame R1 gene (tacccatacgatgttccagattacgctacgtcctcaccatccattggcggcccaaacatgactttactattggcca tgatcatgtttgcgttaaagatagggtcg, HA tag is underlined) (SEQ ID NO: 42) GPI anchor sequences. To assess the function of different human MXRA8 isoforms, the cDNA of isoform 2 (NM_032348.3; SEQ ID NO: 43) containing C-terminal Myc and Flag tags was purchased from OriGene (Cat. No. RC200955), and cloned into the lentivirus vector pCSII-EF1-IRES-Venus. Isoform 1 (NM_001282585.1; SEQ ID NO: 44), isoform 3 (NM_001282584.1; SEQ ID NO: 45) and isoform 4 (NM_001282583.1; SEQ ID NO: 46) were created by either mutagenesis of isoform 2 or gene synthesis (Integrated DNA Technologies), and cloned into the lentivirus vector pCSII-EF1-IRES-Venus containing C terminus Myc and Flag tags. Trans-complementation and ectopic expression experiments.

The plasmids constructed above were packaged using the lentivirus expression system. Cells transduced with these lentiviruses were sorted for Venus-positive cells by flow cytometry. 3T3 cells were inoculated with CHIKV-181/25 (MOI 3) for 9.5 h or CHIKV-AF15561 (MOI 10) for 20 h. HeLa and A549 cells were inoculated with CHIKV-181/25 (MOI. 3), CHIKV-AF15561 (MOI 10) or CHIKV-LR 2006 (MOI 1) for 14 h. 293T cells were inoculated with CHIKV-181/25 (MOI 1), CHIKV-AF15561 (MOI 3) or CHIKV-LR 2006 (MOI 0.5) for 11.5 h. CHO cells (K1 and 745) were inoculated with CHIKV-181/25 (MOI 0.3), CHIKV-AF15561 (MOI 10) or CHIKV-LR 2006 (MOI 0.3) for 12 h. Cells were then collected and processed for E2 expression by flow cytometry.

Generation and Production of Mxra8-Fc and MXRA8-2-Fc.

A cDNA fragment encoding the mouse Mxra8 extracellular domain (residues 22-336, GenBank accession number NM_024263 (SEQ ID NO: 32)) or the human MXRA8-2 extracellular domain (residues 20-337, GenBank accession number NM_032348.3 (SEQ ID NO: 33)) and the mouse IgG2b-Fc were synthesized (Integrated DNA Technologies) and inserted into the pCDNA3.4 vector (Thermo Fisher) downstream of an IL-2 signal peptide sequence. After confirmation by Sanger sequencing, Mxra8-Fc and MXRA8-2-Fc were expressed into Expi293 cells (Thermo Fisher). Cells were seeded at $5\times10^6$ cells per ml one day before transfection. Two hundred micrograms of plasmid was diluted in Opti-MEM (Thermo Fisher) and complexed with HYPE-5 transfection reagent before addition to cells. Transfected cells were supplemented daily with Expi293 medium and 2% (w/v) Hyclone Cell Boost. Four days after transfection, supernatant was collected, centrifuged at 3,000 g for 15 min, and purified by protein A sepharose 4B (Thermo Fisher) chromatography. After elution and buffer neutralization, the purified protein was dialysed into 20 mM HEPES, 150 mM NaCl (pH 7.5), filtered through a 0.20-μm filter, and stored at −80° C. Mxra8 that was cleaved from the IgG backbone was generated by inserting an HRV cleavage sequence (LEVLFQGP) (SEQ ID NO: 52) into Mxra8-Fc downstream of the Mxra8 coding sequence and before the mouse IgG sequence. Mxra8-HRV-Fc was expressed in Expi293 cells as described above. After purification, Mxra8-HRV-Fc was cleaved using HRV 3C protease (Thermo Fisher) at a 1:10 ratio overnight at 4° C. Cleaved Fc fragments were depleted using protein A sepharose chromatography, and the purity of Mxra8 was confirmed using SDS-PAGE analysis.

Expression of CHIKV virus-like particles.

The CHIKV virus-like particles plasmid (strain 37997) was provided by G. Nabel (via the Vaccine Research Center, NIH) and expressed in Expi293 cells as previously described[18]. The supernatant was collected four days after transfection, 0.2-μm filtered and stored at 4° C.

ELISA-Based Mxra8-Fc Binding Assays.

Anti-CHIKV human mAb 4N1219 or anti-EEEV human mAb 53 (J.E.C., unpublished data) were immobilized (50 μl, 2 μg/ml) onto Maxisorp ELISA plates (Thermo Fisher) overnight in sodium bicarbonate buffer, pH 9.3. Plates were washed four times with PBS and blocked with PBS supplemented with 4% BSA for 1 h at room temperature. CHIKV-181/25 or SINV-EEEV was diluted to $1.5\times10^7$ FFU per ml in PBS and 50 μl per well was added for 1 h at room temperature. Mxra8-Fc and respective positive (CHK-11[5] and EEEV-10 (A.S.K. and M.S.D., unpublished results) and negative OPC-Fc (D.H.F., unpublished results) controls were diluted in PBS supplemented with 2% BSA and incubated for 1 h at room temperature. After serial washes with PBS, plates were incubated with horseradish peroxide conjugated goat anti-mouse IgG (H+L) (1:2000 dilution, Jackson ImmunoResearch) for 1 h at room temperature. After washing with PBS, plates were developed with 3,3'-5,5' tetramethylbenzidine substrate (Dako) and 2N $H_2SO_4$. Absorbance was read at 450 nm with a TriStar Microplate Reader (Berthold). The mAb competition binding assay was performed by incubating 10 μg/ml of indicated anti-CHIKV human mAbs[19] for 30 min before the addition of mMxra8-Fc, as described above; the anti-CHIKV human mAbs were mapped previously to different epitopes by alanine scanning mutagenesis and evaluated for neutralizing activity[19]. Humanized anti-WNV mAb E16[32] was included as a negative control in competition binding assays.

Surface Plasmon Resonance Based Mxra8 Binding Assay.

Surface plasmon resonance binding experiments were performed on a Biacore T200 system (GE Healthcare) to measure the kinetics and affinity of Mxra8 binding to CHIKV virus-like particles. Experiments were performed at 30 μl/min and 25° C. using 0.01 M HEPES PH 7.4, 0.15 M NaCl, 3 mM EDTA, 0.005% v/v surfactant P20 as running buffer. CHK-265 mAb[5] was immobilized onto a CM5 sensor chip (GE Healthcare) using standard amine coupling chemistry, and CHIKV virus-like particles were captured. Recombinant Mxra8 was injected over a range of concentrations (1 μM to 20 nM) for 5 min followed by a 10 min dissociation period. As a negative control, murine norovirus was captured with mAb A6.2, as previously described[35]. Real-time data were analysed using BIAevaluation 3.1 (GE Healthcare). Kinetic profiles and steady-state equilibrium concentration curves were fitted using a global 1:1 binding algorithm with drifting baseline.

Cell-Based Mxra8-Fc Binding Assay.

3T3 cells were inoculated with different viruses at the following MOI: CHIKV-181/25 (MOI of 3, 9.5 h), ONNV (MOI of 5, 12 h), MAYV (MOI of 3, 24 h), RRV (MOI of 3, 32 h), SINV (MOI of 10, 9 h) and VEEV (MOI of 3, 6.5 h). Cells were detached using TrypLE (Thermo Fisher #12605010), washed twice with cold HBSS supplemented with 15 mM HEPES and 2% FBS. Cells were incubated with 1 g/ml of Mxra8-Fc, OPG-Fc or viral E2-specific antibodies at 4° C. for 25 min. After washing, cells were stained with goat anti-mouse IgG (H+L) conjugated with Alexa Fluor 647 for 25 min at 4° C. After washing twice, cells were fixed with 2% PFA for 10 min at room temperature. After two additional washes, cells were subjected to flow cytometry analysis.

Virus Binding and Internalization Assays.

The assays were conducted in suspension. MEF cells were collected using TrypLE and washed twice with ice-cold medium supplemented with 2% FBS. CHIKV-AF15561 virions were purified through a 25% glycerol cushion at 25,000 r.p.m. for 2 h. For the binding assay, cells ($5\times10^5$) and virions (MOI of 20) were mixed in a 1.5-ml microcentrifuge tube and incubated on ice for 45 min. After five cycles of centrifugation and washing, cells were lysed in RLT buffer for RNA extraction using an RNeasy Mini Kit (QIAGEN #74104). For the internalization assay, after 5 cycles of centrifugation and washing, cells were resuspended into medium supplemented with 2% FBS and 15 mM $NH_4Cl$ and then incubated at 37° C. for 1 h. Cells were chilled on ice and treated with 500 ng/ml proteinase K on ice for 1 h. After three additional washes, cells were lysed in RLT buffer for RNA extraction. qRT-PCR was conducted with Gapdh as an internal control using a TaqMan RNA-to-CT 1-Step Kit (Thermo Fisher #4392938). Primers and probes used are as follows: Fwd CHK181/AF: 5'-TCGACGCGCCATCTTTAA-3' (SEQ ID NO: 47); rev CHK181/AF: 5'-ATCGAATGCACCGCACACT-3' (SEQ ID NO: 48); probe CHK181/AF: 5' 6-FAM/ACCAGCCTG/ZEN/CACCCACTCCTCAGAC/3' IABKFQ (SEQ ID NO: 49); fwd Gapdh: 5'-GTGGAGTCATACTGGAA-CATGTAG-3' (SEQ ID NO: 50); rev Gapdh: 5'-AATGGT-GAAGGTCGGTGTG-3' (SEQ ID NO: 51); and probe Gapdh: 5' 6-FAM/TGCAAATGG/ZEN/CAGCCCTGGTG/3' IABKFQ (SEQ ID NO: 52).

For the flow cytometry-based binding assay, experiments were conducted as above but with $5\times10^4$ cells and an MOI of 200. After binding and washing, cells were fixed and stained with a mixture of mAbs (CHK-11, CHK-84, CHK-124 and CHK-1665) (1 μg/ml) at room temperature for 25 min. Cells were washed once and stained with 2 μg/ml of goat anti-mouse IgG (H+L) conjugated with Alexa Fluor 647 (Thermo Fisher #A21235) for 25 min. After two additional washes, cells were subjected to flow cytometry analysis.

Surface Staining of Mouse Mxra8 and Human MXRA8.

Mouse or human cells were collected with TrypLE and washed twice with cold HBSS supplemented with 15 mM HEPES and 2% FBS. Cells were incubated with anti-Mxra8 (mouse) Armenian hamster serum (1:300), anti-Mxra8 (mouse) hamster mAbs (1 μg/ml) or anti-MXRA8 (human) mAb (1 μg/ml) (MBL International #W040-3) at 4° C. for 25 min. After washing, cells were stained with 2 μg/ml goat anti-Armenian hamster IgG (H+L) conjugated with Alexa Fluor 647 (Abcam #ab173004) or goat anti-mouse IgG (H+L) conjugated with Alexa Fluor 647 (Thermo Fisher #A21235) for 25 min at 4° C. After two additional washes, cells were fixed with 2% PFA for 10 min at room temperature. Cells were then washed twice and subjected to flow cytometry analysis.

Cell Viability Assay.

A CellTiter-Glo Luminescent Cell Viability Assay (Promega) was performed according to the manufacturer's instructions. In brief, $2\times10^4$ 3T3 or MEF cells in 100 μl culture medium were seeded into opaque-walled 96-well plates. 24 h later, 100 μl of CellTiter-Glo reagent was added to each well and allowed to shake for 2 min. After a 10-min incubation at room temperature, luminescence was recorded by using a Synergy H1 Hybrid Plate Reader (Biotek) with an integration time of 0.5 s per well.

Western Blotting.

Cells seeded in 6-well plates were washed once with PBS, chilled on ice in PBS and detached with a cell scraper. After spinning at 300 g for 5 min, cell pellets were lysed in 45 μl RIPA buffer (Cell Signaling #9806S) with a cocktail of protease inhibitors (Sigma-Aldrich #S8830). Samples were prepared in LDS buffer (Life Technologies) under reducing (+dithiothreitol) conditions. After heating (70° C., 10 min), samples were electrophoresed using 10% Bis-Tris gels (Life Technologies) and proteins were transferred to PVDF membranes using an iBlot2 Dry Blotting System (Life Technologies). Membranes were blocked with 5% non-fat dry powdered milk and probed with hamster mAb 3G2.F5 (0.5 g/ml) against mouse Mxra8. Western blots were developed using SuperSignal West Pico Chemiluminescent Substrate or SuperSignal West Femto Maximum Sensitivity Substrate (Life Technologies).

Alanine Scanning Mutagenesis for Mapping.

A CHIKV E2, 6K and E1 envelope protein expression construct (strain S27, Uniprot Reference #Q8JUX5) with a C-terminal V5 tag was subjected to alanine scanning mutagenesis to generate a comprehensive mutation library[36]. Each residue of the envelope proteins was mutated to alanine, with alanine codons mutated to serine. One hundred and forty-one mutations within the E2 A and B domains were screened for binding by Mxra8-Fc. Binding of Mxra8-Fc to each mutant expressed in HEK-293T cells was determined by immunofluorescence detected with a high-throughput flow cytometer (Intellicyt), as previously described[36]. Residues of domains A or B were identified as contributing to the binding site if their mutation eliminated Mxra8-Fc binding, but supported binding of CHIKV mAbs that bind to the appropriate domain (control mAbs were CHKV-84, CHKV-88, IM-CKV063, IM-CKV065 and C9[5,36,37]).

Mapping of Mutations onto the CHIKV p62-E1 Crystal Structure.

Figures were prepared using the atomic coordinates of CHIKV p62-E1 (RCSB accession number 3N41) using the program PyMOL (The PyMOL Molecular Graphics System, Version 1.7.4 Schrödinger, LLC).

Mab Generation.

Four-week-old male Armenian hamsters were immunized intravenously with 100 μg of purified Mxra8-Fc. After two boosts (~7 months of age), spleens were collected for hybridoma fusion and mAb production. Hybridoma supernatants were initially screened by ELISA using Mxra8-human Fc (mouse Fc was replaced by human Fc). As a second assay, the binding of hybridoma supernatants to Mxra8 on the surface of 3T3 cells was examined by flow cytometry. Finally, a tertiary screen evaluating blockade of CHIKV-181/25 infection by hybridoma supernatants was performed in 3T3 cells. After limiting dilution subcloning, the seven clones with the strongest blocking activities were selected and expanded. Antibodies were purified using protein A sepharose 4B (Invitrogen #101042), dialysed in PBS, concentrated and filtered for in vitro and in vivo experiments.

Blocking Assays with Mxra8-Fc, MXRA8-2-Fc or Anti-Mxra8 mAbs.

Twenty-five thousand 3T3 or MRC-5 cells were seeded into 96-well plates 12 h before treatment. CHIKV-181/25 virions were purified through a 25% glycerol cushion at 25,000 r.p.m. for 2 h. Serially diluted Mxra8-Fc or MXRA8-2-Fc protein was incubated with purified virions (MOI of 3) for 1 h at 37° C. in a volume of 100 μl. The mixture was added to 3T3 or MRC-5 cells for 9.5 h or 11.5 h, respectively. Cells were then collected for intracellular E2 expression as measured by flow cytometry. For hamster mAb blocking experiments, 3T3 or MRC-5 cells were pre-incubated with serially diluted mAbs for 1 h at 37° C. in a volume of 50 μl, and then purified virions (MOI of 3) in 50 μl were added and incubated for 9.5 or 11.5 h, respectively. Cells were collected and intracellular E2 expression was analysed by flow cytometry. For hamster mAb blocking experiments on primary human cells (keratinocytes, dermal fibroblasts, synovial fibroblasts, osteoblasts, chondrocytes and skeletal muscle cells), $2\times10^4$ cells were seeded into 96-well plates 12 h before treatment. Cells were pre-incubated with Armenian hamster isotype control (Bio X Cell #BE0260), 1H1.F5 or 9G2.D6 mAb for 1 h at 37° C. in a volume of 50 μl (50 g/ml) and, subsequently, purified CHIKV-AF15561 virions (MOI of 15) in 50 μl were added and incubated for 10.5 h. Cells were collected and intracellular E2 expression was analysed by flow cytometry.

Phosphatidylinositol-Specific Phospholipase C Treatment.

3T3 cells ($10^5$) expressing GPI-anchored Mxra8 were collected using TrypLE and washed twice with PBS. Cells were then treated with 1 U/ml of phosphatidylinositol-specific phospholipase C (PI-PLC) (Sigma-Aldrich #P8804) in 50 μl PBS at 37° C. for 1 h. After two more cycles of washing, cells were stained for Mxra8 expression and processed by flow cytometry analysis as described above.

Mouse Experiments.

Experiments were carried out in accordance with the recommendations in the Guide for the Care and Use of Laboratory Animals of the National Institutes of Health after approval by the Institutional Animal Care and Use Committee at the Washington University School of Medicine (Assurance number A3381-01). Mxra8-Fc or an IgG control (JEV-13 mAb) (250 μg per mouse in PBS) was administered via an intraperitoneal route to four week-old wild-type male C57BL/6J mice 6 h before subcutaneous inoculation in the footpad with $10^3$ FFU of CHIKV-AF15561. Alternatively, in co-injection experiments, CHIKV or ONNV was mixed directly with Mxra8-Fc or JEV-13 (25 μg per mouse in PBS), and incubated at 37° C. for 30 min before inoculation. At 12 h, 24 h and 72 h post-infection, animals were euthanized, and after perfusion with PBS, indicated tissues were collected. For antibody pre- or post-treatment experiments, 300 μg of purified hamster mAbs 1G11.E6+7F1.D8 or 4E7.D10+8F7.E1, and isotype control PIP (Bio X cell #BE0260) in PBS were administered via an intraperitoneal route to four week-old wild-type male C57BL/6 mice 12 h prior to, or 8 or 24 h after, subcutaneous inoculation in the footpad with $10^3$ FFU of CHIKV-AF15561. Virus was titrated by focus forming assay as described[5] using mouse CHK-11[5] for CHIKV or mouse CHK-48 for ONNV as the detection antibody. Joint swelling was monitored at 72 h post-infection via left foot measurements (width×height) using digital calipers as previously described[38]. Samples sizes were estimated to determine a difference of three- to fivefold, depending on data distribution. Blinding and randomization were not performed.

Statistical Analysis.

Statistical significance was assigned when P values were <0.05 using Prism Version 7 (GraphPad). Cell culture experiments were analysed by multiple t-tests with a Holm-Sidak correction or ANOVA with a multiple comparison correction. Analysis of levels of joint swelling or viral burden in vivo was determined by a Mann-Whitney, ANOVA, Kruskal-Wallis or unpaired t-test depending on data distribution and the number of comparison groups.

REFERENCES

1. Weaver, S. C., Charlier, C., Vasilakis, N. & Lecuit, M. Zika, Chikungunya, and other emerging vector-borne viral diseases. *Annu. Rev. Med.* 69, 395-408 (2018).
2. Vancini, R., Hernandez, R. & Brown, D. Alphavirus entry into host cells. *Prog. Mol. Biol. Transl. Sci.* 129, 33-62 (2015).
3. Cong, L. et al. Multiplex genome engineering using CRISPR/Cas systems. *Science* 339, 819-823 (2013).
4. Jinek, M. et al. RNA-programmed genome editing in human cells. *eLife* 2, e00471 (2013).
5. Pal, P. et al. Development of a highly protective combination monoclonal antibody therapy against Chikungunya virus. *PLoS Pathog.* 9, e1003312 (2013).
6. Li, W. et al. MAGeCK enables robust identification of essential genes from genome-scale CRISPR/Cas9 knockout screens. *Genome Biol.* 15, 554 (2014).
7. Han, S. W. et al. DICAM inhibits angiogenesis via suppression of AKT and p38 MAP kinase signalling. *Cardiovasc. Res.* 98, 73-82 (2013).
8. Jung, Y. K. et al. DICAM inhibits osteoclast differentiation through attenuation of the integrin αVβ3 pathway. *J. Bone Miner. Res.* 27, 2024-2034 (2012).
9. Jung, Y. K. et al. DICAM, a novel dual immunoglobulin domain containing cell adhesion molecule interacts with αvβ3 integrin. *J. Cell. Physiol.* 216, 603-614 (2008).
10. Yonezawa, T. et al. Limitrin, a novel immunoglobulin superfamily protein localized to glia limitans formed by astrocyte endfeet. *Glia* 44, 190-204 (2003).

11. Barton, E. S. et al. Junction adhesion molecule is a receptor for reovirus. *Cell* 104, 441-451 (2001).
12. Levitt, N. H. et al. Development of an attenuated strain of chikungunya virus for use in vaccine production. *Vaccine* 4, 157-162 (1986).
13. Gardner, C. L., Burke, C. W., Higgs, S. T., Klimstra, W. B. & Ryman, K. D. Interferon-alpha/beta deficiency greatly exacerbates arthritogenic disease in mice infected with wild-type chikungunya virus but not with the cell culture-adapted live-attenuated 181/25 vaccine candidate. *Virology* 425, 103-112 (2012).
14. Ashbrook, A. W. et al. Residue 82 of the Chikungunya virus E2 attachment protein modulates viral dissemination and arthritis in mice. *J. Virol.* 88, 12180-12192 (2014).
15. Esko, J. D., Stewart, T. E. & Taylor, W. H. Animal cell mutants defective in glycosaminoglycan biosynthesis. *Proc. Natl Acad. Sci. USA* 82, 3197-3201 (1985).
16. Lee, J. et al. Structure of the Ebola virus envelope protein MPER/TM domain and its interaction with the fusion loop explains their fusion activity. *Proc. Natl Acad. Sci. USA* 114, E7987-E7996 (2017).
17. Doranz, B. J., Berson, J. F., Rucker, J. & Doms, R. W. Chemokine receptors as fusion cofactors for human immunodeficiency virus type 1 (HIV-1). *Immunol. Res.* 16, 15-28 (1997).
18. Akahata, W. et al. A virus-like particle vaccine for epidemic Chikungunya virus protects nonhuman primates against infection. *Nat. Med.* 16, 334-338 (2010).
19. Smith, S. A. et al. Isolation and characterization of broad and ultrapotent human monoclonal antibodies with therapeutic activity against Chikungunya virus. *Cell Host Microbe* 18, 86-95 (2015).
20. Fox, J. M. et al. Broadly neutralizing alphavirus antibodies bind an epitope on E2 and inhibit entry and egress. *Cell* 163, 1095-1107 (2015).
21. Sun, S. et al. Structural analyses at pseudo atomic resolution of Chikungunya virus and antibodies show mechanisms of neutralization. *eLife* 2, e00435 (2013).
22. Li, L., Jose, J., Xiang, Y., Kuhn, R. J. & Rossmann, M. G. Structural changes of envelope proteins during alphavirus fusion. *Nature* 468, 705-708 (2010).
23. Voss, J. E. et al. Glycoprotein organization of Chikungunya virus particles revealed by X-ray crystallography. *Nature* 468, 709-712 (2010).
24. Couderc, T. & Lecuit, M. Chikungunya virus pathogenesis: From bedside to bench. *Antiviral Res.* 121, 120-131 (2015).
25. Rose, P. P. et al. Natural resistance-associated macrophage protein is a cellular receptor for sindbis virus in both insect and mammalian hosts. *Cell Host Microbe* 10, 97-104 (2011).
26. Loh, J. et al. Identification and sequencing of a novel rodent gammaherpesvirus that establishes acute and latent infection in laboratory mice. *J. Virol.* 85, 2642-2656 (2011).
27. Klimstra, W. B., Ryman, K. D. & Johnston, R. E. Adaptation of Sindbis virus to BHK cells selects for use of heparan sulfate as an attachment receptor. *J. Virol.* 72, 7357-7366 (1998).
28. Brien, J. D., Lazear, H. M. & Diamond, M. S. Propagation, quantification, detection, and storage of West Nile virus. *Curr. Protoc. Microbiol.* 31, 15D.3.1-15D.3.18 (2013).
29. Sanjana, N. E., Shalem, O. & Zhang, F. Improved vectors and genome-wide libraries for CRISPR screening. *Nat Methods* 11, 783-784 (2014).
30. Joung, J. et al. Genome-scale CRISPR-Cas9 knockout and transcriptional activation screening. *Nat. Protocols* 12, 828-863 (2017).
31. Shalem, O. et al. Genome-scale CRISPR-Cas9 knockout screening in human cells. *Science* 343, 84-87 (2014).
32. Oliphant, T. et al. Development of a humanized monoclonal antibody with therapeutic potential against West Nile virus. *Nat. Med.* 11, 522-530 (2005).
33. Huang, I. C. et al. SARS coronavirus, but not human coronavirus NL63, utilizes cathepsin L to infect ACE2-expressing cells. *J. Biol. Chem.* 281, 3198-3203 (2006).
34. Jemielity, S. et al. TIM-family proteins promote infection of multiple enveloped viruses through virion-associated phosphatidylserine. *PLoS Pathog.* 9, e1003232 (2013).
35. Taube, S. et al. High-resolution x-ray structure and functional analysis of the murine norovirus 1 capsid protein protruding domain. *J. Virol.* 84, 5695-5705 (2010).
36. Selvarajah, S. et al. A neutralizing monoclonal antibody targeting the acid-sensitive region in chikungunya virus E2 protects from disease. *PLoS Negl. Trop. Dis.* 7, e2423 (2013).
37. Jin, J. et al. Neutralizing monoclonal antibodies block chikungunya virus entry and release by targeting an epitope critical to viral pathogenesis. *Cell Reports* 13, 2553-2564 (2015).
38. Hawman, D. W. et al. Chronic joint disease caused by persistent chikungunya virus infection is controlled by the adaptive immune response. *J. Virol.* 87, 13878-13888 (2013).
39. Lubman, O. Y. et al. Rodent herpesvirus Peru encodes a secreted chemokine decoy receptor. *J. Virol.* 88, 538-546 (2014).

Example 2: Using Mxra8 to Assess Alphavirus Vaccine or Diagnostic Antigen Integrity The following example shows that Mxra8 can be used to assess an alphavirus vaccine or a diagnostic antigen integrity.

Because Mxra8 is a receptor for multiple arthritogenic alphaviruses, it can be used to physically assess the integrity of alphavirus vaccine or diagnostic antigens, which is important to define lot-to-lot integrity or variation in the context of commercial production. Alphavirus vaccine or diagnostic antigens can include, but are not limited to, live-attenuated viruses, virus-like particles, viral structural proteins, or nucleic acids or vectors producing these viral proteins or particles.

The format of the integrity assay can include capturing Mxra8 or Mxra8 fusion proteins (e.g., Mxra8-Fc) on a substrate (e.g., microtiter well plate, chip, or pin) and then incubation of the alphavirus vaccine or diagnostic antigen and detection with a monoclonal or polyclonal anti-vaccine/diagnostic antigen antibody or even Mxra8-Fc itself. Alternatively, the alphavirus vaccine or diagnostic antigen can be captured in the solid phase (directly or via a bridging antibody) and then incubated with Mxra8 or Mxra8-Fc fusion proteins for binding. The assay could be performed by ELISA, biolayerinterferometry, surface plasmon resonance, or any other detection based system for binding.

Example 3: A 15-Amino Acid Insertion in Domain 1 of Mxra8 Abolishes Infection by Alphaviruses The following example describes a small insertion in Mxra8 renders it resistant to infection by alphaviruses. Thus, it is possible to make Mxra8 resistant to infection.

Figure 15A:
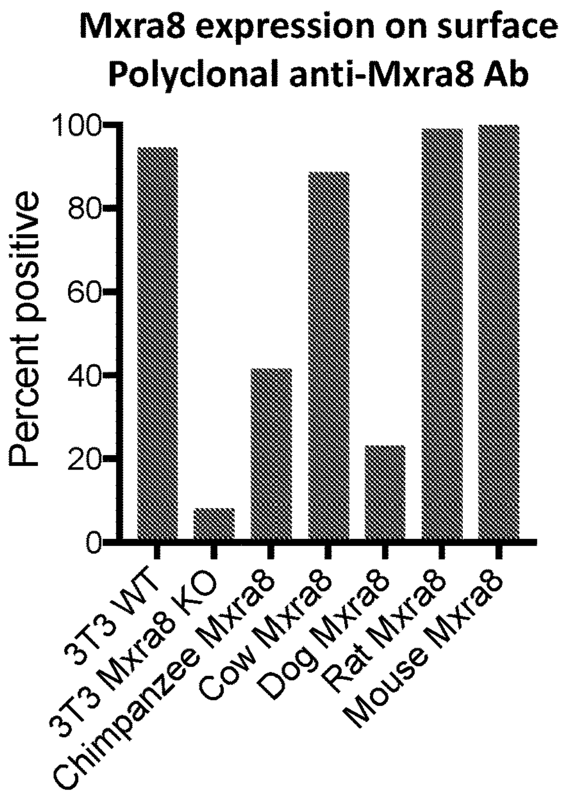
FIG. 15A-FIG. 15B is a series of bar graphs showing most animal orthologs of Mxra8 (with the exception of cow Mxra8) support infection of CHIKV in 3T3 trans-complemented cells.
Figure 15B:
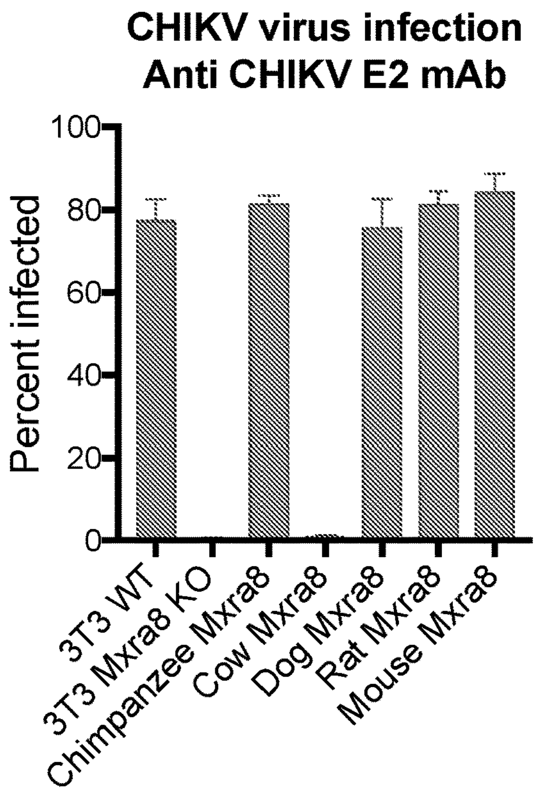

CRISPR-Cas9 based gene editing of Mxra8 resulted in markedly diminished alphavirus infection in vitro and in vivo, and viral infectivity was restored after trans-complementation with either mouse Mxra8 or human MXRA8. Because some alphaviruses can infect a range of vertebrate hosts in epizootic cycles, we explored whether Mxra8 orthologs from different mammalian species could support infection by arthritogenic alphaviruses. 3T3 cells lacking Mxra8 expression (ΔMxra8) were trans-complemented via lentivirus transduction with Mxra8 genes from mouse (*Mus musculus*, positive control), rat (*Rattus norvegicus* dog (*Canis lupus familiaris*), cow (*Bos taurus*), goat (*Capra hircus*), sheep (*Ovis aries*), horse (*Equus caballus*), chimpanzee (*Pan troglodytes*). Surface expression of the different Mxra8 orthologs was confirmed with an oligoclonal pool of species cross-reactive monoclonal antibodies (mAbs) against Mxra8 (see e.g., FIG. 15A). Trans-complemented cells were inoculated with CHIKV and evaluated for infection 9.5 h later by assessing intracellular viral E2 protein expression by flow cytometry. Consistent with published results, CHIKV E2 antigen was absent in ΔMxra8 cells but present at high levels in ΔMxra8 cells trans-complemented with mouse Mxra8 (see e.g., FIG. 15B). Analogously, trans-complementation of ΔMxra8 cells with rat, dog, goat, sheep, horse, and chimpanzee Mxra8 orthologs restored CHIKV infectivity. Notably, Mxra8 from cow (*Bos taurus*) failed to restore infectivity even though it was expressed on the cell surface. Similar results were observed with related arthritogenic alphaviruses including MAYV, RRV, and ONNV.

Figure 22:
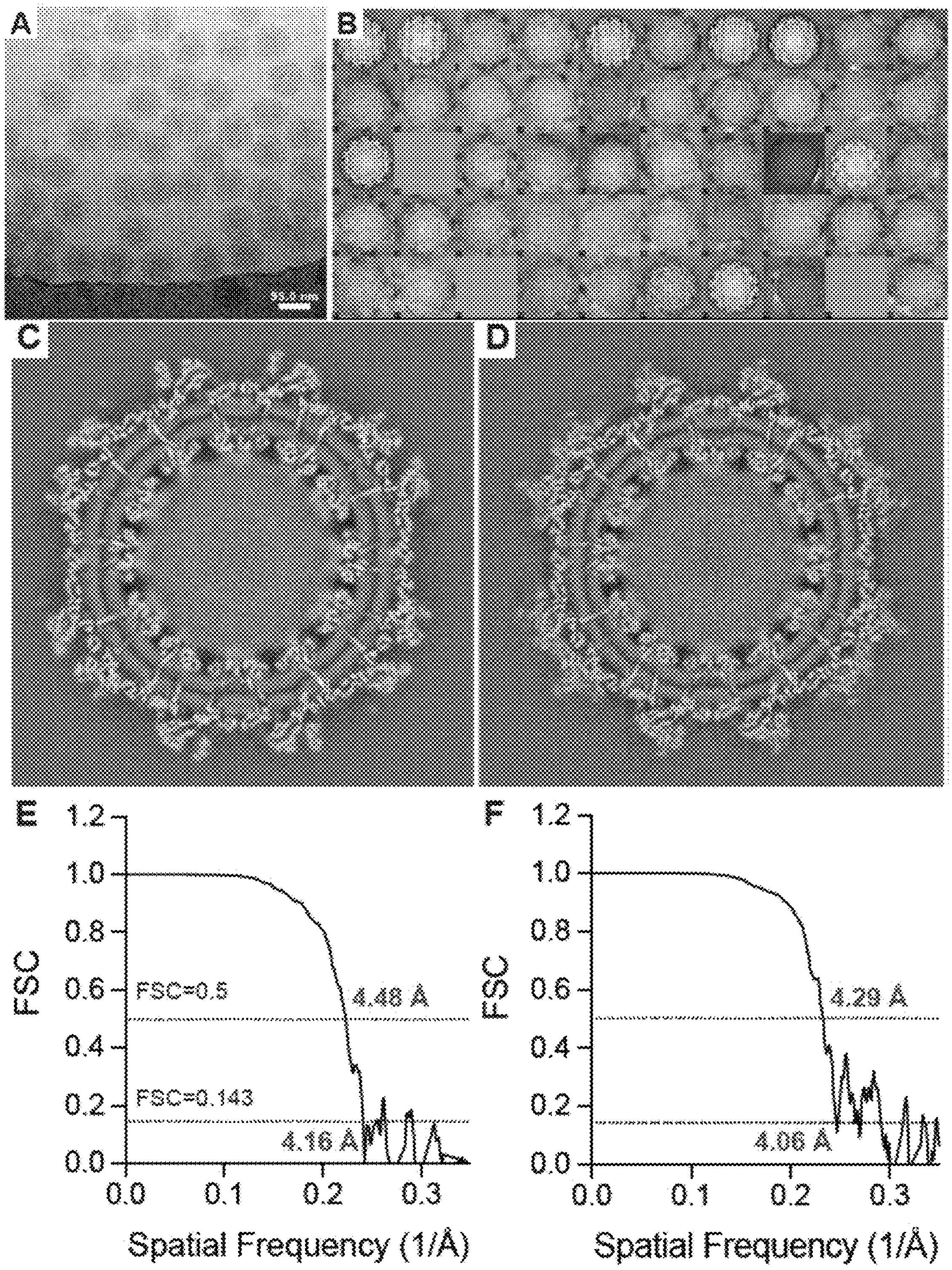
FIG. 22 shows two-dimensional cisTEM analysis of CHIKV particles with or without Mxra8 bound. A. Raw electron micrographs of CHIKV VLPs. B. Two-dimensional classification scheme for binning of CHIKV VLPs. C-D. Two-dimensional equatorial slices of CHIKV VLP alone (C) or CHIKV VLP in complex with Mxra8 (D). Dimensions: the outer radius of the nucleocapsid shell (~180 Å), lipid bilayer (~240 Å), E1 protein glycoprotein shell (~280 Å), E2 protein spike (~340 Å), and bound Mxra8 (~350 Å) from the viral center. E-F. Fourier shell correlation (FSC) plot versus resolution for CHIKV VLP alone (E) or CHIKV VLP with bound Mxra8 (F).

To begin to investigate why cow Mxra8 in particular failed to restore alphavirus infectivity, we aligned its protein sequence with other Mxra8 gene sequences (see e.g., FIG. 22 and FIG. 16B). Remarkably, cow Mxra8, but not any of the other species we had tested, contained a unique 15-amino acid insertion ($^{78}$GEQRLGEQRVGEQRV$^{92}$; SEQ ID NO: 91) composed of three quasi-identical (GEQRL/V; SEQ ID NO: 92) 5-residue repeats that likely were derived from the immediate upstream GEQRV gene sequence; the 45 nucleotides of the insertion correspond highly to upstream sequence. To gain insight into the significance of the 15-amino acid insertion we performed comparative structural analysis. The 15-amino acid insertion of cow Mxra8 was located as a disordered extension of the C'-C" loop in Domain 1.

The structural analysis suggested that the 15-amino acid insertion in Mxra8 of cows might disrupt interactions with the CHIKV virion. To begin to evaluate this hypothesis, we generated mouse Mxra8-Fc fusion proteins that lacked or contained the additional 15 residues from cow (mouse Mxra8 and mouse Mxra8+moo) and reciprocally cow Mxra8-Fc fusion protein that lacked or contained the 15 residues (cow Mxra8 and cow Mxra8 Δmoo) (see e.g., FIG. 16A). We tested the wild-type and chimeric Mxra8 proteins for their ability to bind CHIKV VLPs in a capture ELISA. Mouse Mxra8 and cow Mxra8 Δmoo bound avidly in a dose-dependent manner to CHIKV VLPs whereas mouse Mxra8+moo and cow Mxra8 did not (see e.g., FIG. 16C). These data suggest strongly that the 15-amino acid insertion in Mxra8 directly inhibits binding to CHIKV particles.

Figure 17:
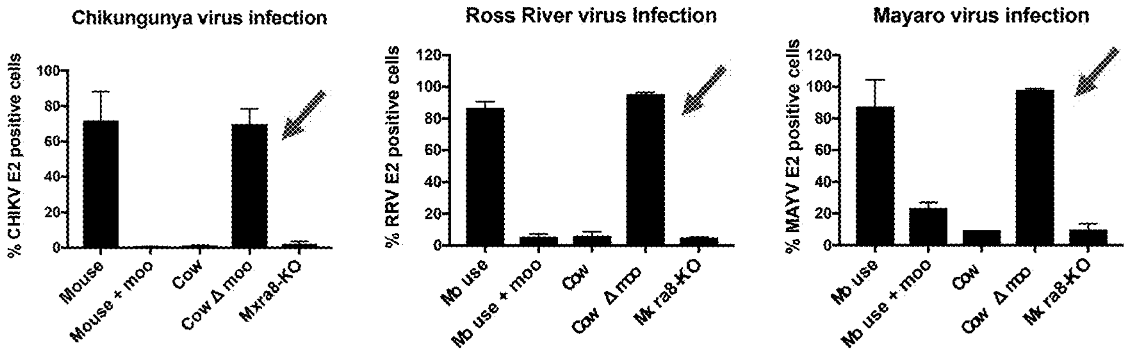
FIG. 17 shows a 15-amino acid insertion in cow Mxra8 prevents alphavirus infection. 3T3 cells were trans-complemented with mouse Mxra8, mouse Mxra8+moo, cow Mxra8, or cow Mxra8 Δmoo. Subsequently, cells were inoculated with CHIKV, Ross River virus, or Mayaro virus. One day later, cells were harvested and infection was determined by flow cytometry after staining with monoclonal antibodies against CHIKV, Ross River virus, and Mayaro virus E2 protein. Results are representative of three independent experiments. Red arrows show gain of infection when the 15-amino acid insertion is deleted in cow Mxra8. Note that addition of the 15-amino acid insertion to mouse Mxra8 renders it unable to support alphavirus infection.

To further evaluate the significance of the 15-amino acid insertion to alphavirus infectivity, we transduced ΔMxra8 3T3 cells with lentiviruses encoding mouse Mxra8, mouse Mxra8+moo, cow Mxra8, and cow Mxra8 Δmoo. The addition of the 15 residues to mouse Mxra8 abolished infectivity by CHIKV, MAYV, and RRV, whereas deletion of the 15 residues from cow Mxra8 facilitated infection by these viruses (see e.g., FIG. 17). Thus, a 15-amino acid insertion in Domain 1 of Mxra8 can determine the infectivity of multiple alphaviruses.

Example 4: Mxra8 Knockout Demonstrates Diminished Alphavirus Infection and Swelling The following example describes the generation of Mxra8 knockout mice and reduction of alphavirus infection in the KO mice.

Figure 19:
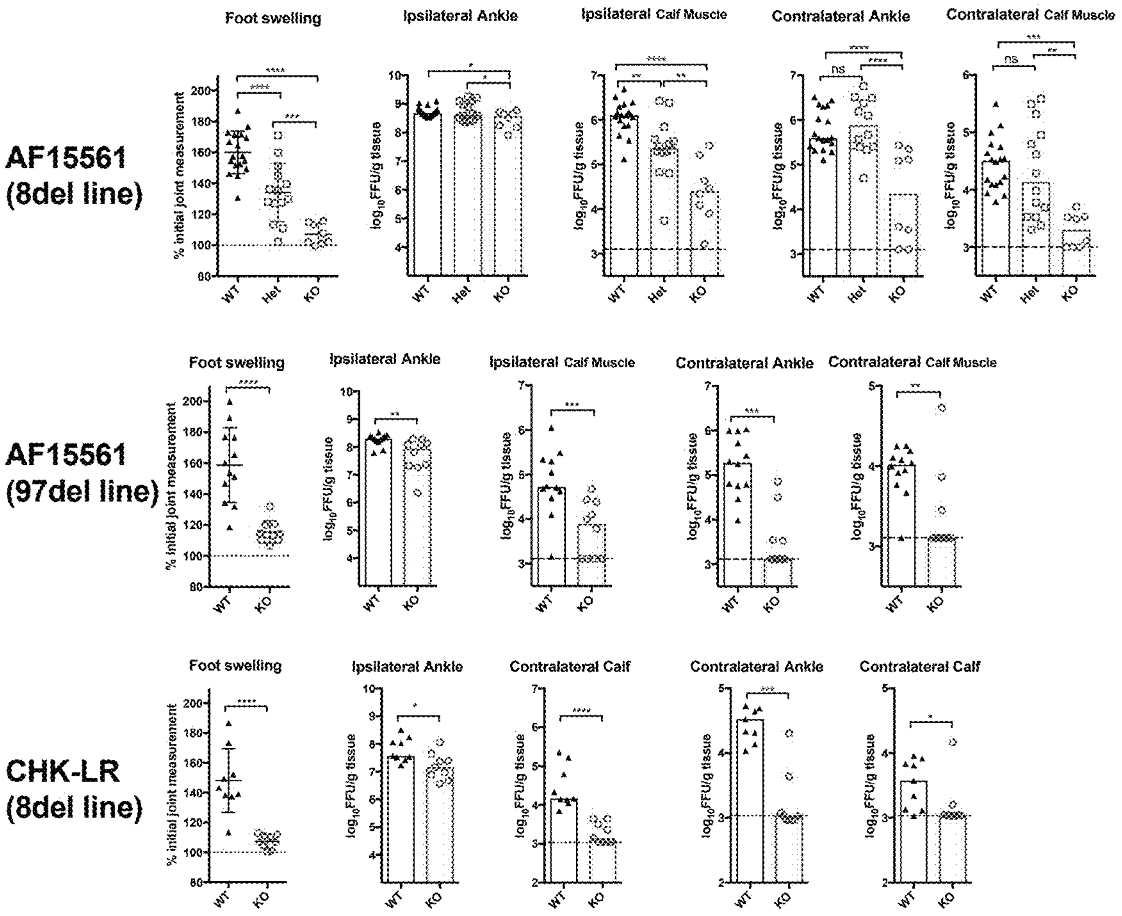
FIG. 19 is a series of graphs depicting diminished CHIKV infection and swelling in Mxra8-deficient mice during the acute phase. $Mxra8^{\Delta 8/\Delta 8}$, $Mxra8^{\Delta 8/+}$, $Mxra8^{\Delta 97/\Delta 97}$, or $Mxra8^{+/+}$ (WT) mice were inoculated subcutaneously in the foot with $10^3$ FFU of CHIKV-AF15561 (top two rows) or CHIKV-LR2006 (bottom row). At 3 dpi, foot swelling (left panels) was measured (2 experiments, n=10, Mann-Whitney test, *, P<0.001; **, P<0.0001), and ipsilateral and contralateral ankles and calf muscles (right panels) were harvested for infectious virus titration by FFU assay (2 experiments, n=10, ANOVA (top row) or Mann-Whitney (bottom two rows) tests, *, P<0.05; , P<0.01; *, P<0.001; ****, P<0.0001).
Figure 20:
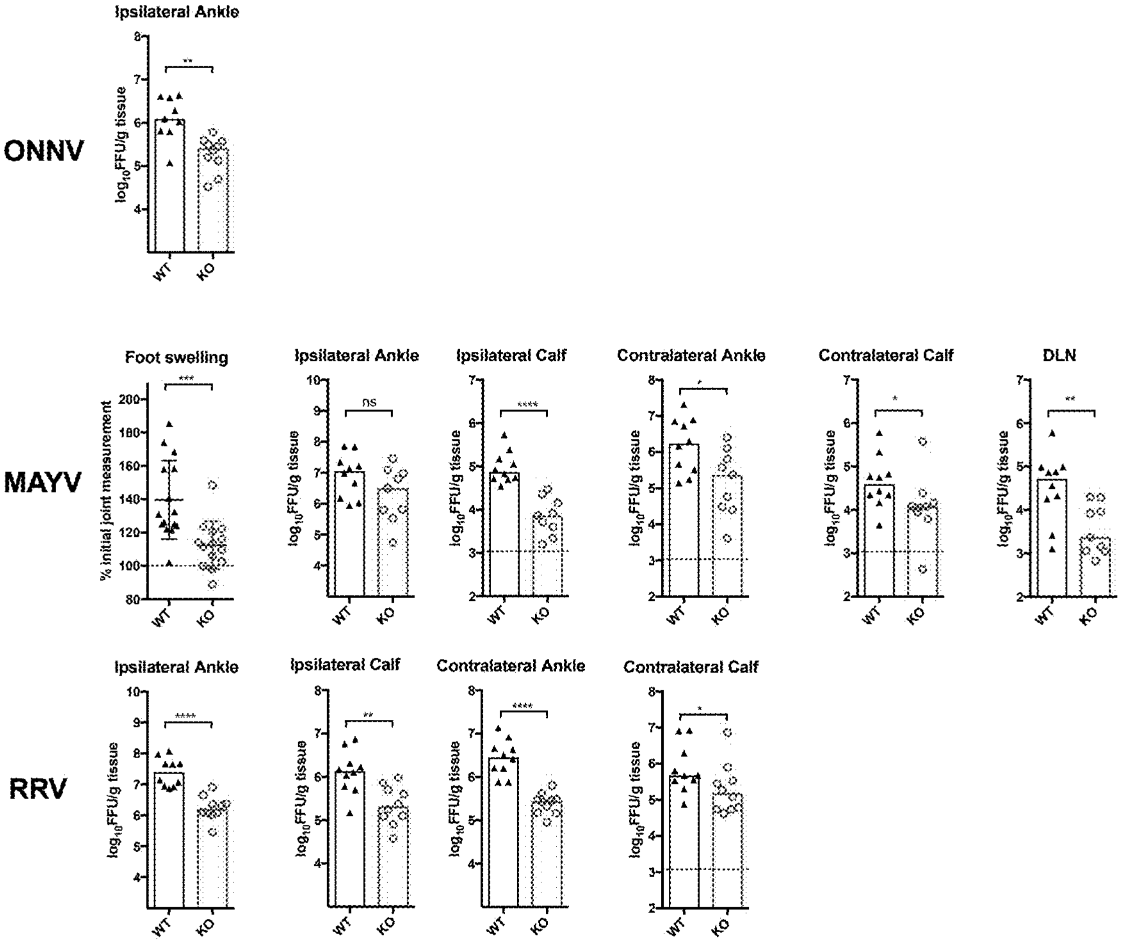
FIG. 20 is a series of graphs depicting diminished infection of other arthritiogenic alphaviruses (ONNV, MAYV, and RRV) in $Mxra8^{\Delta 8/\Delta 8}$ mice. $Mxra8^{\Delta 8/\Delta 8}$ and $Mxra8^{+/+}$ mice were inoculated subcutaneously in the foot with $10^3$ FFU of ONNV (top row), MAYV (middle row), or RRV (bottom row). Ipsilateral and contralateral musculoskeletal tissues at 3 dpi were harvested for infectious virus titration by FFU assay (2 experiments, n=10, Mann-Whitney test, *, P<0.05; , P<0.01; *, P<0.001; ****, P<0.0001).

Generation of Mxra8$^{mut/mut}$ mice by CRISPR-Cas9 gene targeting has been demonstrated (see e.g., FIG. 18). It was shown that CHIKV infection and swelling was diminished in Mxra8-deficient mice during the acute phase (see e.g., FIG. 19). Furthermore, it was demonstrated that infection of other arthritiogenic alphaviruses (ONNV, MAYV, and RRV) was also diminished in Mxra8$^{\Delta8/\Delta8}$ mice (see e.g., FIG. 20).

Example 5: Cryo-EM Structure of Chikungunya Virus in Complex with the Mxra8 Receptor Mxra8 is a receptor for multiple arthritogenic alphaviruses that cause debilitating acute and chronic musculoskeletal disease in humans. Here, we present a 2 Å X-ray crystallographic structure of Mxra8 and 4 to 5 Å resolution cryo-electron microscopy reconstructions of Mxra8 bound to chikungunya (CHIKV) virus-like particles (VLPs) and infectious virus. Mxra8 wedges into a cleft created by adjacent CHIKV E2 proteins in one trimeric spike and engages E1 protein on an adjacent spike. Two binding modes are observed with the fully mature VLP, with one of the Mxra8 binding sites having unique E1 contacts. Only this high-affinity binding mode was observed in the complex with infectious CHIKV, as viral maturation and E3 occupancy appear to influence receptor binding site usage. Our studies provide structural insight into how Mxra8 binds CHIKV and creates a path for developing alphavirus entry inhibitors.

INTRODUCTION

Alphaviruses are positive-sense, single-stranded RNA, enveloped viruses and are among the most important arthropod-borne viruses causing disease in humans (Powers et al., 2001). This genus includes chikungunya (CHIKV), Mayaro (MAYV), O'nyong'nyong (ONNV), and Ross River (RRV) viruses, which are emerging beyond their historical boundaries and now cause debilitating acute and chronic polyarthritis affecting millions of people in Africa, Asia, Europe, and the Americas. Despite their epidemic potential, there are no specific therapies or licensed vaccines for any alphavirus infection.

Alphavirus genomes encode four non-structural and five structural proteins. The non-structural proteins are required for virus replication, protein modification, and immune evasion. The structural proteins (capsid (C)-envelope (E) 3-E2-6K-E1) are synthesized from a subgenomic promoter and cleaved co- and post-translationally. The E1 envelope glycoprotein participates in cell fusion (Lescar et al., 2001), whereas the E2 envelope glycoprotein binds to entry factors (Smith et al., 1995; Zhang et al., 2005) and initiates clathrin-dependent endocytosis (DeTulleo and Kirchhausen, 1998; Lee et al., 2013; Ooi et al., 2013). The E3 protein is essential for the proper folding of p62 (precursor to E2) and the formation of the p62-E1 heterodimer (Carleton et al., 1997; Mulvey and Brown, 1995) but is cleaved by furin-like proteases during the maturation process in the trans-Golgi network (Heidner et al., 1996). Mature alphaviruses are ~700 Å icosahedral particles that assemble at the plasma membrane and contain a lipid bilayer with 240 embedded E2-E1 heterodimers assembled into 80 trimeric spikes with T=4 icosahedral symmetry (Cheng et al., 1995; Kostyuchenko et al., 2011; Paredes et al., 1993), and a nucleocapsid containing a single copy of genomic RNA.

Crystallographic studies of the precursor p62-E1, the mature E2-E1 glycoprotein complex, and the E1 protein (Lescar et al., 2001; Li et al., 2010; Roussel et al., 2006; Voss et al., 2010) have elucidated the glycoprotein structures. Several alphavirus virions structures also have been elucidated by cryo-electron microscopy (cryo-EM) (Cheng et al., 1995; Kostyuchenko et al., 2011; Lee et al., 1998; Li et al., 2010; Pletnev et al., 2001; Zhang et al., 2011; Zhang et al., 2002). The E1 ectodomain consists of three β-barrel domains termed Domain I (DI), DII, and DIII. The fusion peptide is located at the distal end of DII. E1 monomers lie at the base of the surface spikes and form trimers surrounding the icosahedral axes. E2 localizes to a long, thin, leaf-like structure on the top of the spike. The mature E2 protein contains three domains with immunoglobulin (Ig)-like folds: the N-terminal domain A, located at the center; domain B at the lateral tip; and the C-terminal domain C, located close to E1 and the viral membrane.

We recently used a genome-wide CRISPR/Cas9-based screen to identify the two immunoglobulin (Ig)-like domain containing cell adhesion molecule, Mxra8 as a receptor for multiple arthritogenic alphaviruses including CHIKV, RRV, MAYV, and ONNV (Zhang et al., 2018). Importantly, the human gene ortholog, MXRA8, also bound to CHIKV and other alphaviruses, and its cell surface expression facilitated infection of primary human target cells including fibroblasts, skeletal muscle cells, and chondrocytes. Mxra8 bound directly to CHIKV particles and enhanced attachment and internalization into cells, and Mxra8-Fc fusion protein or anti-Mxra8 monoclonal antibodies (mAbs) blocked CHIKV infection of several cell types. Administration of Mxr8a-Fc protein or anti-Mxra8 blocking mAbs to mice reduced CHIKV or ONNV infection and associated joint swelling. Despite defining several biological characteristics of CHIKV interaction with this receptor, structural insight as to how Mxra8 engages the spike proteins on the virion is lacking.

Here, we describe the X-ray crystallographic structure of Mxra8 and cryo-EM reconstructions of CHIKV virus-like particles (VLPs) (produced as capsid-E3-E2-6K-E1 but lacking viral RNA) and fully infectious CHIKV in complex with Mxra8. These are the first structures of alphavirus virions with their cognate host cell binding partner. Mxra8 has an unusual architecture, as its two Ig-like domains are oriented in a disulfide-linked head-to-head arrangement, with domain 2 emanating from the loops of domain 1 and the N- and C-terminal residues proximal to each other. Mxra8 binds into a cleft formed between two E2-E1 heterodimers within a trimeric spike, making dominant contacts with E2 domain A residues. Mxra8 also engages a determinant in E1 domain II on an adjacent glycoprotein spike. Two binding modes for Mxra8 were observed with mature CHIKV VLPs, which was consistent with a high and low affinity binding site model supported by surface plasmon resonance measurements. The low affinity binding sites, however, were sterically obscured by the retention of E3 on partially mature infectious CHIKV. Overall, this structural analysis defines how CHIKV engages its receptor Mxra8 to facilitate attachment and infection of cells. This information may inform the basis of therapies and improved vaccine designs that mitigate disease of multiple emerging alphaviruses.

RESULTS

Figure 24:
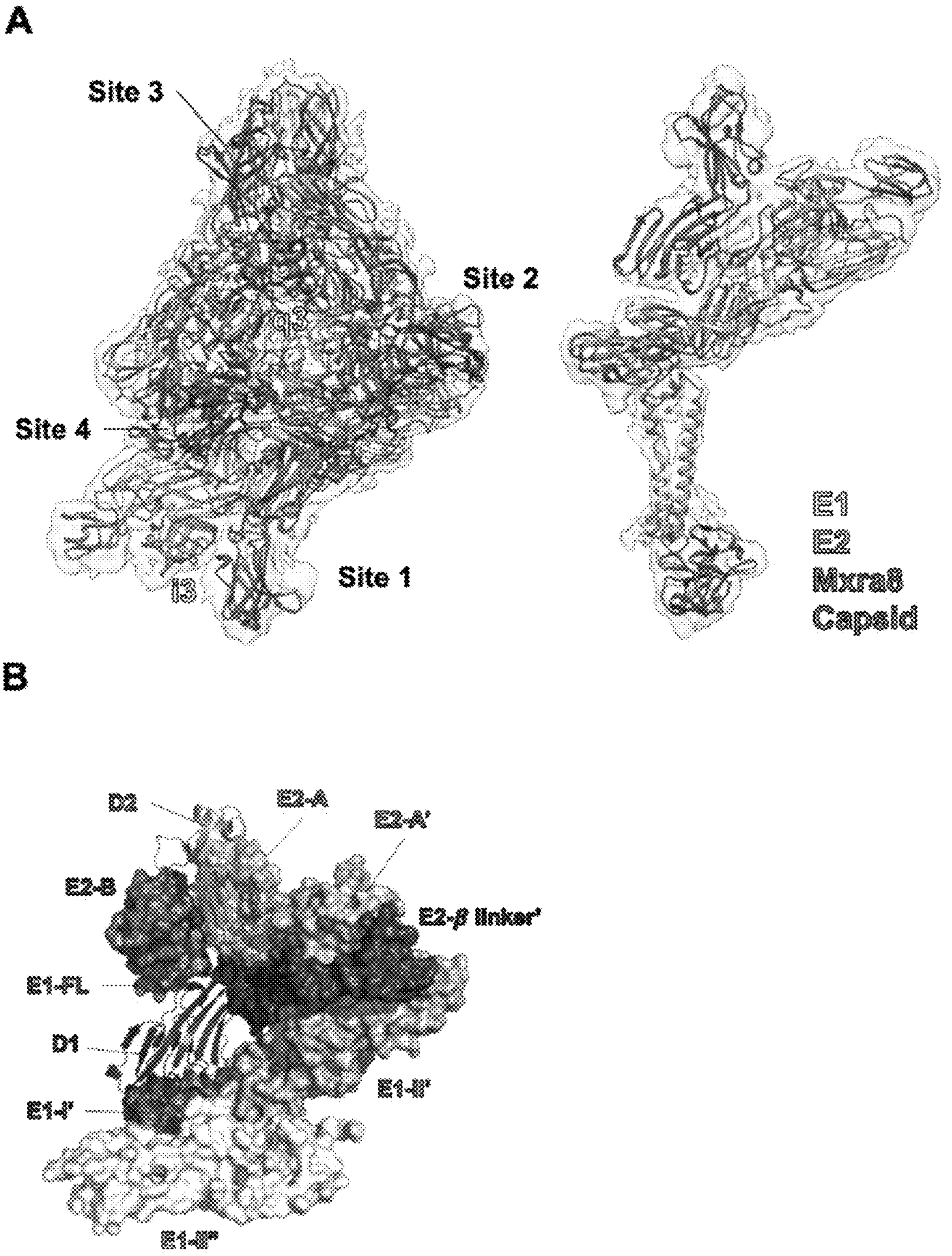
FIG. 24 shows the atomic model of Mxra8 interaction with CHIKV. A. The refined model of Mxra8 and CHIKV structural proteins (E1, E2, transmembrane (TM) helices, and Capsid) in the electron density map from CHIKV VLP with Mxra8 reconstruction, viewed from the top of the asymmetric unit (left panel) and from the side of a subunit (right panel). Color scheme: grey, E1; cyan, E2; green, capsid; and magenta, Mxra8. B. Surface representation of all E1 and E2 proteins in contact with a molecule of Mxra8 (shown as ribbon diagram), labeled and colored by domain. Prime denotes domains from adjacent intraspike E2-E1 heterodimer. Double prime denotes domains from the neighboring interspike E2-E1 heterodimer. D1 and D2 refer to the Ig-like domains of Mxra8.
Figure 27:
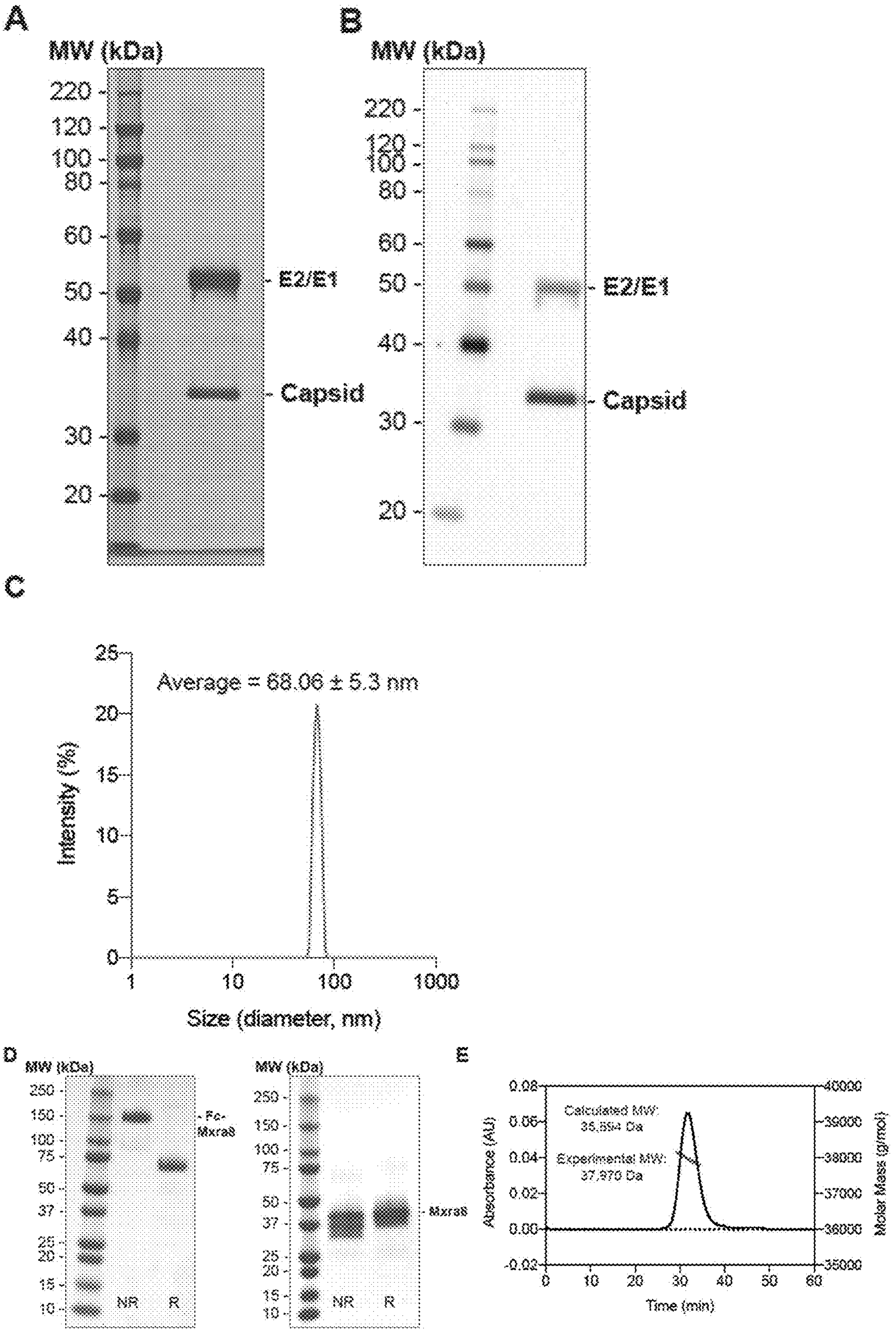
FIG. 27 shows the biochemical characterization of CHIKV VLPs and soluble Mxra8 protein. Related to FIG. 21 and FIG. 22. A-B. Mxra8 characterization. Mxra8-Fc was produced in Expi-293 cells, purified by protein A affinity chromatography, and digested with HRV protease to release the monomeric form of Mxra8 from the Fc region. A. Coomassie-stained SDS-PAGE under non-reducing and reducing conditions of 5 μg of undigested (left panel) and HRV-digested (right panel) Mxra8. One representative experiment of three is shown. B. SEC-MALS of soluble Mxra8 showing a monomeric form at ~38 kDa.C-E. VLP characterization. After transfection of HEK-293 cells with plasmid DNA encoding CHIKV C-E3-E2-6K-E1 (strain 37997), VLPs were harvested from the supernatant and purified by anion exchange chromatography. C. Coomassie-stained 4-12% SDS-PAGE of 2 μg of purified VLPs. E2 and E1 co-migrate at ~52-53 kDa. Capsid migrates at ~35 kDa. One representative experiment of two is shown. D. Immunoblotting of 0.25 μg of VLPs with a rabbit anti-CHIKV polyclonal antibody. One representative experiment of two is shown. E. Dynamic light scattering analysis of CHIKV VLPs. A single homogeneous peak of 68 nm (680 Å)±5.3 is shown. Data are representative of six experiments from two different VLP preparations.
Figure 28:
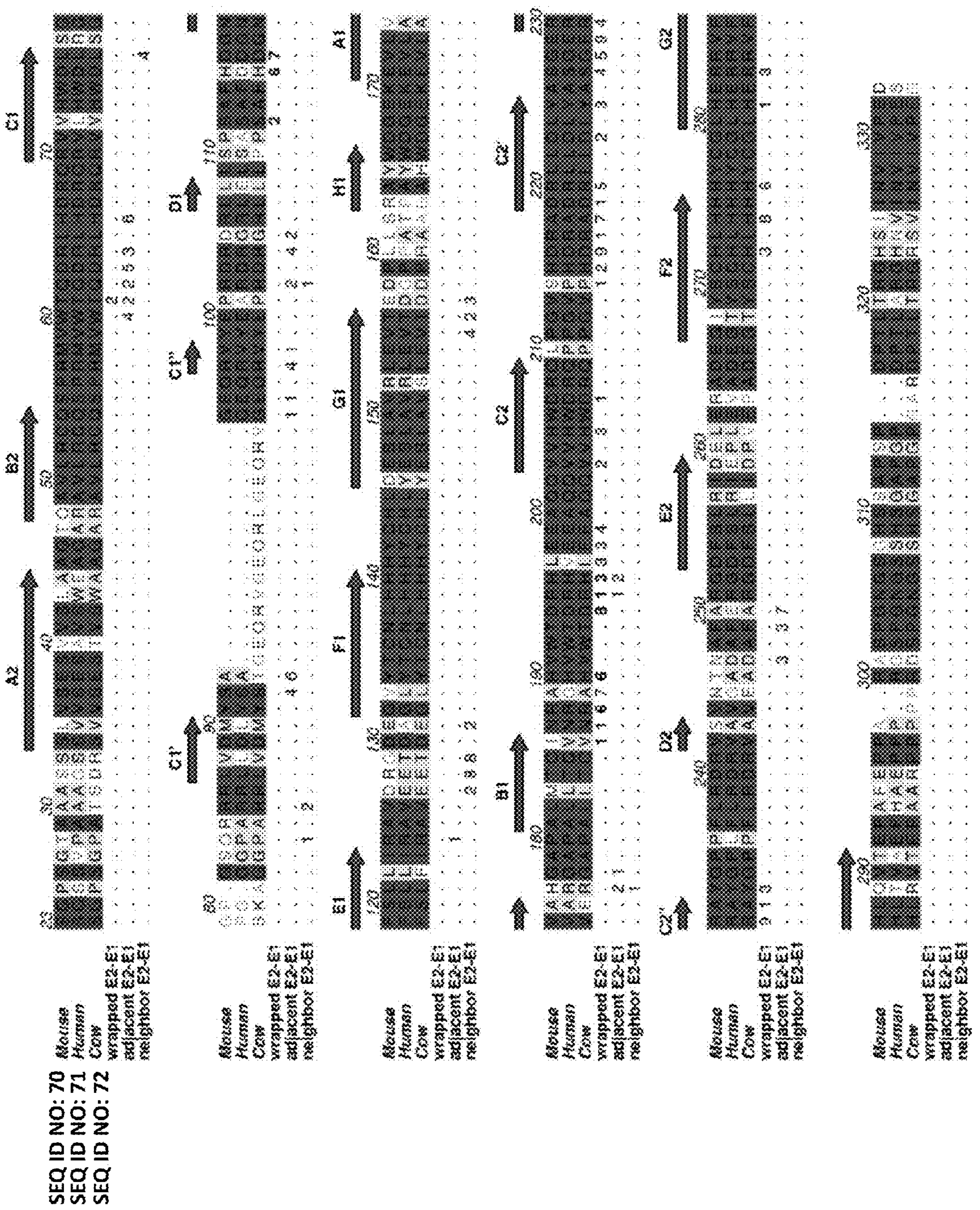
FIG. 28 shows the sequence alignment of Mxra8 orthologs (SEQ ID NOs: 70-72). Related to FIG. 21. The β-strand secondary structure from the mouse model is shown by arrows above the alignment. Numbering above the alignment corresponds to the sequence positions within the mouse protein. Aligned residues are colored by amino acid type with background boxes colored by conservation. Numbers under the alignment indicate contacts between the Mxra8 and individual E2-E1 heterodimers on the VLP, given as percentage buried surface area as defined by PDBePISA server: 1 represents 10% buried surface area, 2 represents 20% buried surface area, and so on. Wrapped E2-E1 represent the contacts to the E2-E1 heterodimer making the primary contacts to Mxra8. Adjacent E2-E1 denote the contacts to the E2-E1 heterodimer adjacent to the primary E2-E1 dimer but within the same trimeric spike. Neighbor E2-E1 denotes contacts against the E2-E1 pair in the neighboring spike.

CHIKV VLPs and Mxra8 protein. Previous studies have obtained high-resolution structural information that elucidated how neutralizing antibodies engage CHIKV using VLPs, which contain the structural proteins but lack infectious viral RNA and can be imaged under lower biosafety conditions (Long et al., 2015; Sun et al., 2013). To begin to define the structural basis for interaction between Mxra8 and arthritogenic alphaviruses (Zhang et al., 2018), we produced CHIKV VLPs (strain 37997) after transient transfection of HEK-293 cells with a plasmid encoding C-E3-E2-6K-E1 (Akahata et al., 2010); equivalent preparation of VLPs were used in a phase 1 or are being used in phase 2 human clinical trials for vaccine protection against CHIKV disease ((Chang et al., 2014), NCT02562482 and NCT03483961). Soluble VLPs were collected, buffer exchanged, and monitored for purity by SDS-PAGE and antigenicity by Western blotting with anti-capsid and anti-E2/E1 antibodies (see e.g., FIGS. 27A and B). Dynamic light scattering experiments revealed a particle size of ~680 Å (see e.g., FIG. 27C), which is close to the expected external diameter of 700 Å for a CHIKV virion (Cheng et al., 1995). To produce soluble Mxra8, we engineered Mxra8-Fc fusion proteins with a human rhinovirus 3C (HRV) protease site between the C-terminus of Mxra8 and the Fc domain. After production of Mxra8-Fc fusion protein in HEK-293F cells and purification by protein A affinity chromatography, we cleaved the Fc domain with HRV, and isolated Mxra8 in the flow-through of a second round of protein A agarose affinity chromatography (see e.g., FIG. 24D). Size exclusion chromatography coupled with multi-angle light scattering analysis revealed that cleaved mammalian cell-generated Mxra8 was monomeric with a molecular weight of 38 kDa (see e.g., FIG. 24E).

Figure 21:
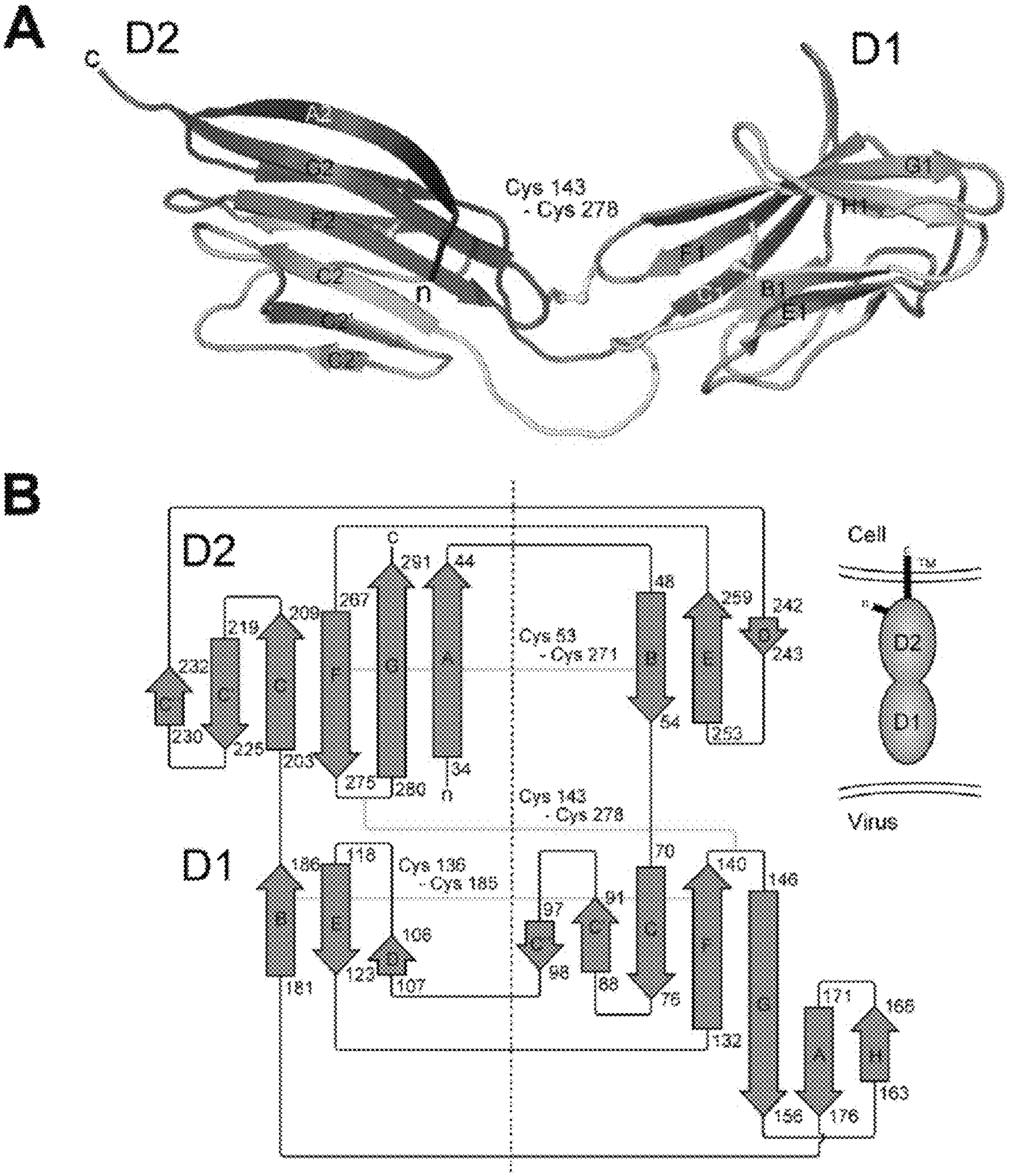
FIG. 21 shows Mxra8 crystal structure and topology diagram. A. Ribbon model of the mouse Mxra8 protein structure. The β-strands are labeled with a letter for each element followed by a number for the domain. The two Ig-like domains are colored from the N- to C-terminus in a rainbow spectrum of blue to red. The disulfides are shown as ball and stick bonds colored yellow. The cysteine positions forming the interdomain disulfide bond is given. The N- and C-termini are labeled in lowercase. B. Secondary structure diagram of Mxra8. Numbering corresponds to the sequence positions in the x-ray structure. The placement and orientation of β-strands are indicated by magenta arrows. The disulfide bonds are shown as yellow connecting lines with cysteine positions labeled. The dashed line divides the two halves of the Ig-like domain β-sandwich. The strand swaps are visible as connections between the D1 and D2 domains.

X-ray crystallographic structure of Mxra8. The ectodomain residues of Mxra8, corresponding to positions 23 through 295 of NCBI reference sequence: NP_077225, were crystallized and the structure solved by molecular replacement. The resulting protein consists of two Ig-like domains arranged in a head to head β-strand-swapped dimer that is connected by an interchain disulfide bond (see e.g., FIG. 21A-B).

Cryo-EM reconstruction of Mxra8 bound to CHIKV VLPs. Electron micrographs of CHIKV VLPs with or without bound Mxra8 were recorded using a 300 KV Titan Krios cryo-electron microscope with Gatan K2 detector at the Washington University Center for Cellular Imaging (WUCCI) (see e.g., FIG. 22A and TABLE 3). The images were corrected for beam-induced motion using MotionCor2 (Zheng et al., 2017). Particles were auto-picked from the micrographs and subjected to two-dimensional classification to remove ice contamination and debris (see e.g., FIG. 22B). The remaining particles underwent ab initio three-dimensional reconstruction and refinement in cisTEM (Grant et al., 2018). The reconstructions of CHIKV VLP alone and with Mxra8 were determined at overall resolutions of 4.16 Å and 4.06 Å (see e.g., FIGS. 22C and D), respectively, based on Fourier Shell Correlation (FCS) analysis (see e.g., FIGS. 22E and F).

Figure 23:
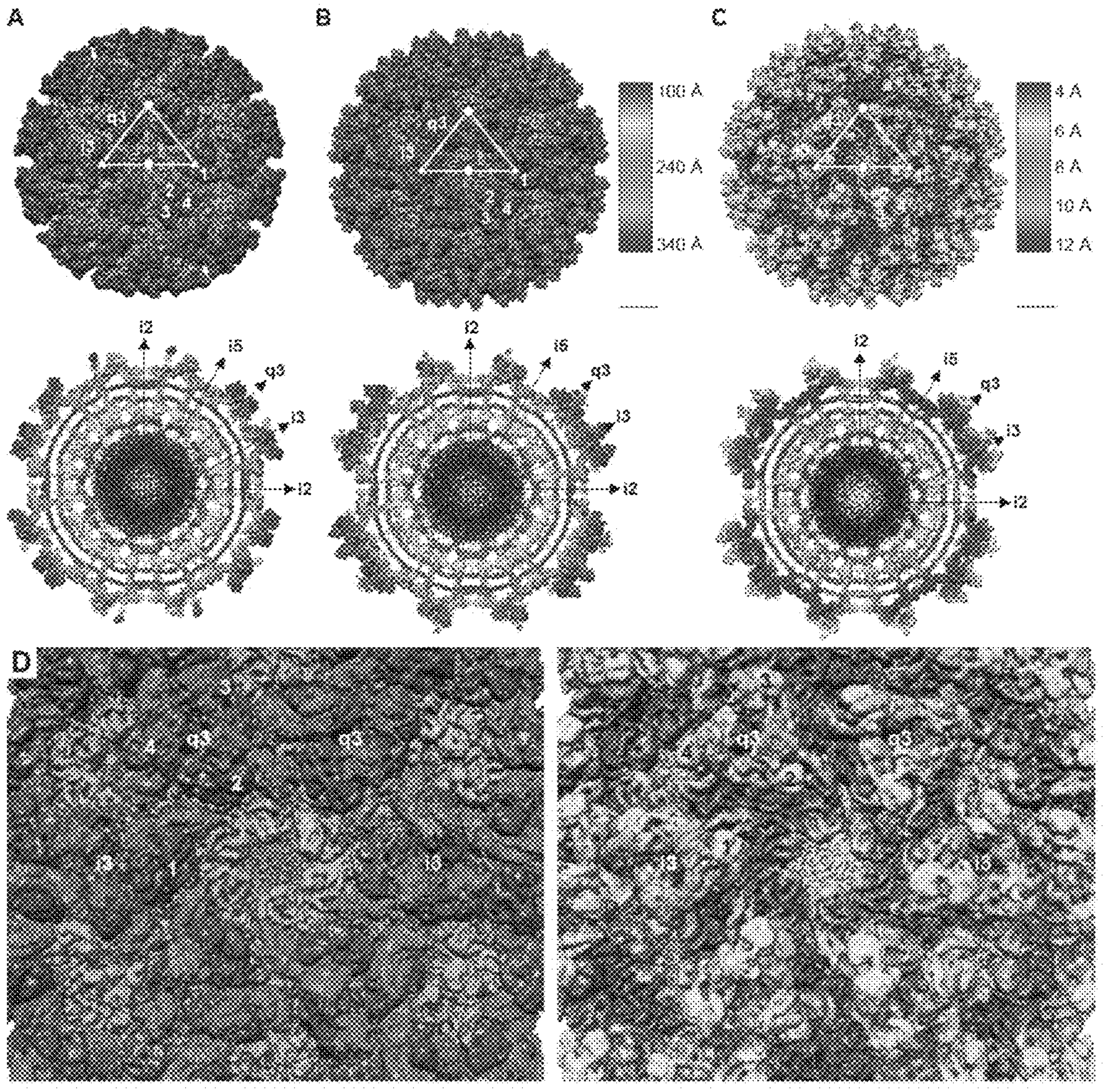
FIG. 23 shows Cryo-EM reconstruction of CHIKV particles with or without Mxra8 binding. A-C. Paired, colored surface representations (top panel) and equatorial cross-sections (bottom panel) of CHIKV VLP (A), CHIKV VLP+Mxra8 (B), and local resolution of CHIKV VLP+Mxra8. The white triangle indicates one icosahedral asymmetric unit. The 5-fold (15), 3-fold (13), and 2-fold (i2) icosahedral axes of symmetry are indicated with a pentagon, triangles, and oval, respectively. Trimeric spikes are labeled "i3" if coincident with the i3 axes, and "q3" if on a quasi 3-fold axes. Black arrows: directions of icosahedral symmetry axes (i2, i3, q3, and i5). C-D. Zoomed-in views of the geometry of Mxra8 binding to CHIKV E2-E1 proteins in different chemical environments, colored by radial distance (C) and local resolution (D). Radial distance color scheme in Figure: red, electron dense core and RNA; yellow, capsid; green, membrane lipid; cyan, E1; dark blue, E2 spike; and magenta, Mxra8.

The three-dimensional reconstructions showed no large conformational changes in the structure of the CHIKV VLP when Mxra8 is bound (see e.g., FIGS. 23A and B). Despite the different chemical environments of the structural glycoproteins within the asymmetric unit of the particle, Mxra8 bound E2-E1 heterodimers in a 1:1 ratio, with 240 Mxra8 molecules per virion. The local resolution of the reconstruction of CHIKV VLP-Mxra8 complex revealed that the viral E2-E1 proteins were the best resolved (see e.g., FIGS. 23C and D). The Mxra8 regions distal to the viral envelope were the least resolved, suggesting a greater degree of flexibility. The local resolution does not vary between the copies of Mxra8 and envelope proteins within the asymmetric unit.

Refinement of the model. We iteratively built an atomic model of the CHIKV VLP structural proteins and Mxra8 using a combination of published CHIKV crystal structures and de novo modelling. As a starting point, we used the structures of the CHIKV capsid (PDB: 5H23), CHIKV p62-E1 (PDB: 3N42), Venezuelan equine encephalitis virus (VEEV) transmembrane domains of E1 and E2 (PDB: 3J0C), and our structure of Mxra8 (see e.g., FIG. 21) to build one subunit. We then built one asymmetric unit surrounded by the adjacent subunits in neighboring asymmetric units. This process was essential to ensure accurate modeling of all interaction interfaces and prevent steric clashes. This model underwent manual and computational real-space refinement using the 4.06 Å cryo-EM map of CHIKV VLP bound to Mxra8 and employing programs COOT (Emsley et al., 2010) and PHENIX.REFINE (Afonine et al., 2012) (see e.g., FIGS. 24A and B, TABLE 4).

Figure 29:
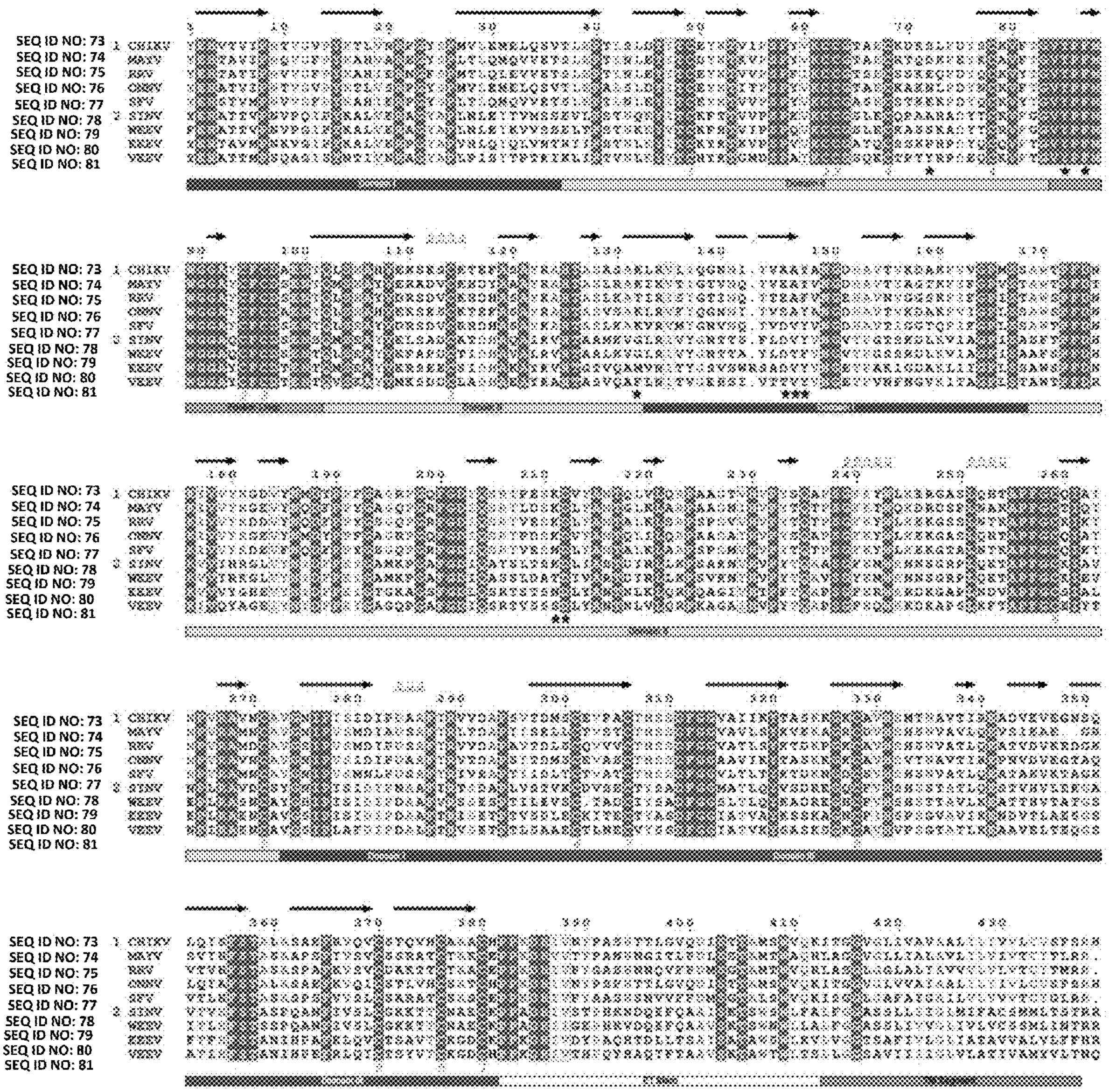
FIG. 29 shows the sequence alignment of E1 proteins of arthritogenic and encephalitic alphaviruses. Related to FIG. 25. Amino acid sequence alignment of E1 proteins of arthritogenic (CHIKV, ABX40011, SEQ ID NO: 73; MAYV, AAY45742, SEQ ID NO: 74; RRV, ACV67002, SEQ ID NO: 75; ONNV, AOS52786, SEQ ID NO: 76; SFV, AAM64227, SEQ ID NO: 77; and SINV, AUV65223, SEQ ID NO: 78) and encephalitic alphaviruses (WEEV, AAF60166, SEQ ID NO: 79; EEEV, AAF04796, SEQ ID NO: 80; and VEEV, AAB02517, SEQ ID NO: 81). Alignments were performed between alphaviruses that do (group 1, left margin) or do not (group 2, left margin) require Mxra8 for infection using Cobalt (Papadopoulos and Agarwala, 2007) and the Figure was prepared using ESPript 3.0 (Robert and Gouet, 2014). Domains I (red), II (yellow), III (blue), stem (clear), transmembrane (grey), and the fusion loop (orange) are indicated below the sequence. Red boxes, 100% conserved; White boxes and red letters; homologous residues; White boxes and black letters, non-conserved residues. Green numbers indicate disulfide bonds. Stars indicate contact residues for Mxra8 (see TABLE 4).
Figure 30:
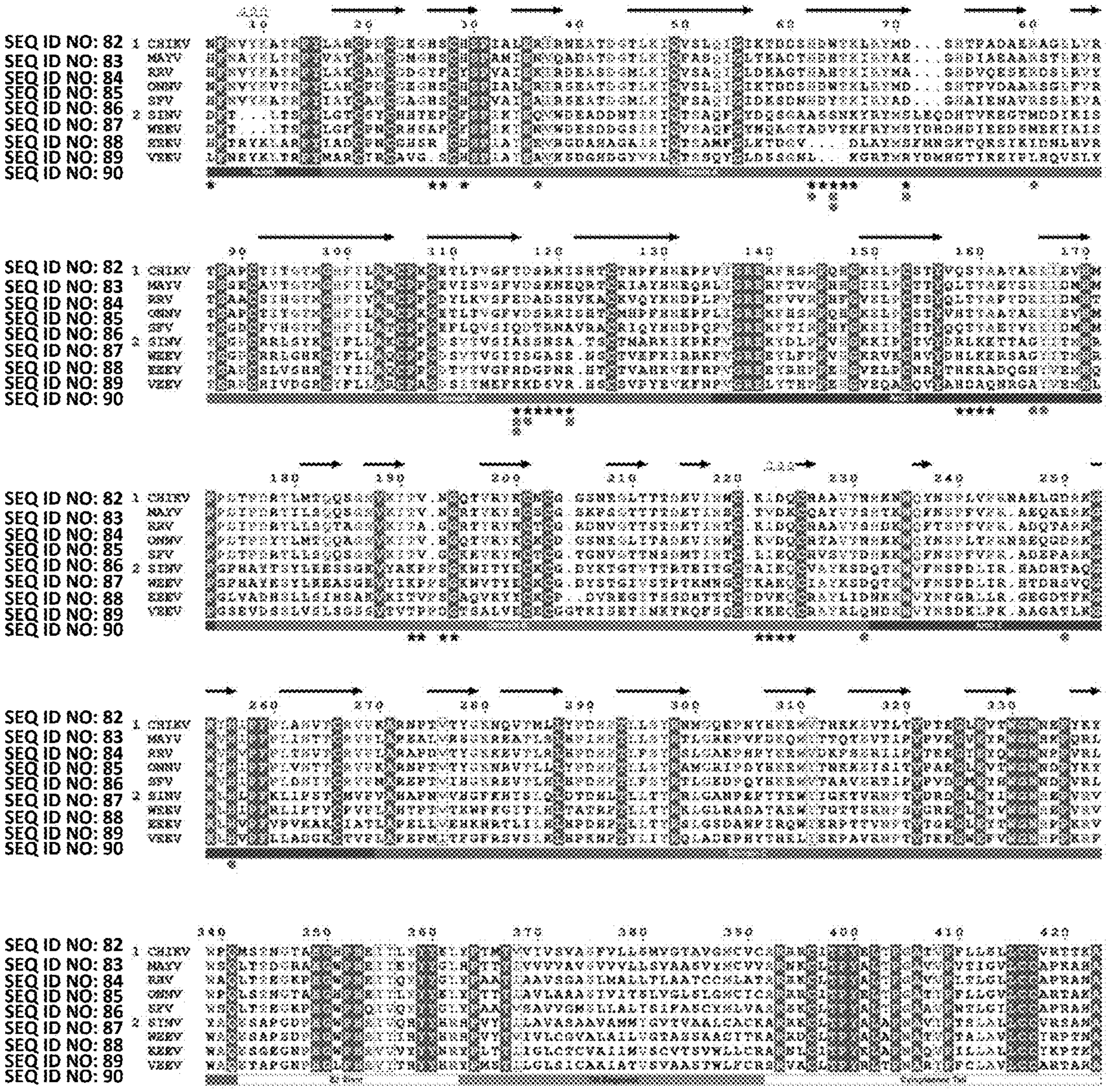
FIG. 30 shows the sequence alignment of E2 proteins of arthritogenic and encephalitic alphaviruses. Related to FIG. 25. Amino acid sequence alignment of E2 proteins of arthritogenic (CHIKV, ABX40011, SEQ ID NO: 82; MAYV, AAY45742, SEQ ID NO: 83; RRV, ACV67002, SEQ ID NO: 84; ONNV, AOS52786, SEQ ID NO: 85; SFV, AAM64227, SEQ ID NO: 86; and SINV, AUV65223, SEQ ID NO: 87) and encephalitic alphaviruses (WEEV, AAF60166, SEQ ID NO: 88; EEEV, AAF04796, SEQ ID NO: 89; and VEEV, AAB02517, SEQ ID NO: 90). Alignments were performed between alphaviruses that do (group 1, left margin) or do not (group 2, left margin) require Mxra8 for infection using Cobalt (Papadopoulos and Agarwala, 2007) and the Figure was prepared using ESPript 3.0 (Robert and Gouet, 2014). Domains A (aqua), B (green), C (red), N-terminal linker and arches (purple), stem (clear), transmembrane (grey), and cytoplasmic tail (clear) are indicated below the sequence. Red boxes, 100% conserved; White boxes and red letters; homologous residues; White boxes and black letters, non-conserved residues. Stars indicate contact residues for Mxra8 (see TABLE 4). Green squares indicate key E2 residues that result in loss of Mxra8 binding identified by alanine-scanning mutagenesis (Zhang et al., 2018). Salmon circles represent residues of epitopes of human anti-CHIKV mAbs that block Mxra8 binding (Smith et al., 2015).
Figure 31:
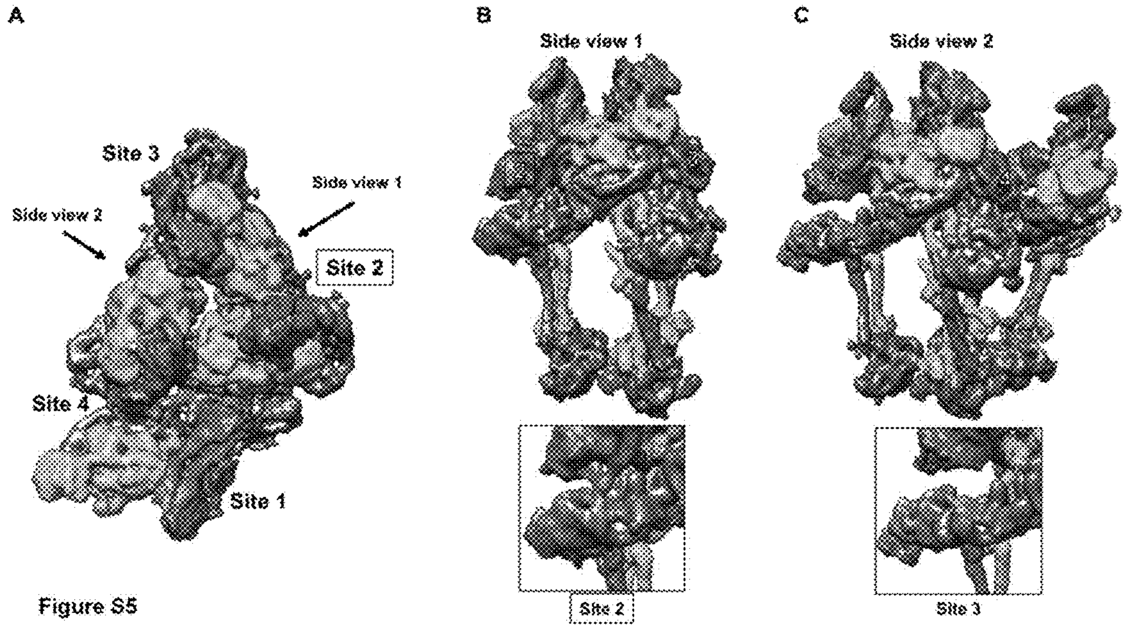
FIG. 31shows the unique E1 contacts by site 2 Mxra8. Related to FIG. 25A. Top view of the asymmetric unit of CHIKV VLP with labeled Mxra8 binding sites. Site 2 is the Mxra8 (magenta) site that makes additional contacts to domain I of E1 directly beneath it (grey). E2, yellow; capsid, green. B-C. Side views (top panels) and zoomed-in views (bottom panels) of site 2 (B) and site 3 (C), highlighting the unique residues of E1 (orange) that contact site 2 of Mxra8 binding. Contacts were identified from the atomic model using PDBePISA.

Our model details the residues of the CHIKV E2-E1 heterodimers at the Mxra8 binding interface. At all four sites of the icosahedral asymmetric unit, Mxra8 engages the A and B domains of the E2 protein (residues 26-29, 116-121, 191-194, 221-224), as well as the A domain and β-linker of the counter-clockwise, adjacent E2 neighbor within the same trimeric spike (residues 5, 62-66, 158-161). Mxra8 is also positioned near the fusion loop of E1 (residues 85 and 87) as well as E1 domain II of an adjacent spike (residues 72, 211, 212) (see e.g., FIGS. 25A and B, FIGS. 29 and 30, TABLE 5). We note that Mxra8 binding at site 2 is associated with unique E1 contacts (residues 132 and 145-147) in the primary engaged spike; these interactions were not observed at sites 1, 3, and 4 (see e.g., FIGS. 29 and 31).

Figure 25:
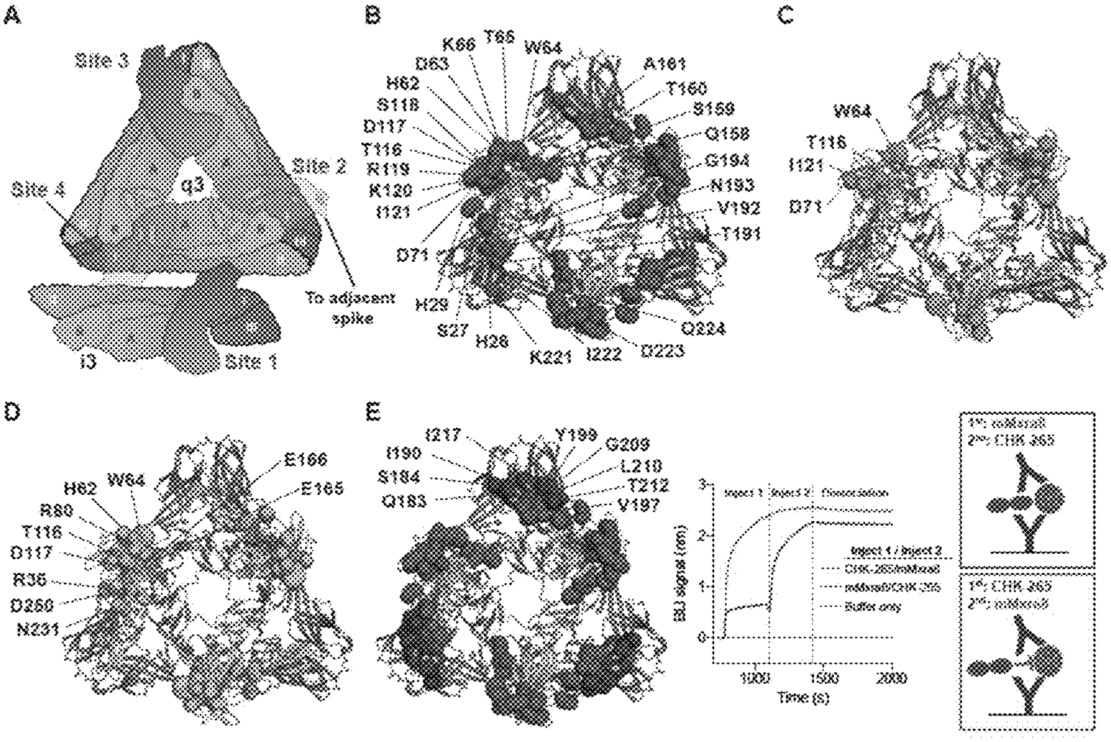
FIG. 25 shows the mutagenesis and antibody mapping data supporting the Mxra8-CHIKV model. A. Cartoon of the quaternary determinants of Mxra8 (magenta) binding to the asymmetric unit of CHIKV. Key Mxra8 contact regions (orange) on domains of E1 (grey) and E2 (cyan) were identified from the electron density map using COOT. B. CHIKV E2 residues at the binding interface as determined from the electron density map are labeled and shown as magenta spheres on the CHIKV E2-E1 heterotrimer (PDB 5ANY). C. CHIKV E2 residues at the CHIKV-Mxra8 interface as defined by previous alanine scanning mutagenesis data (Zhang et al., 2018). Mapped CHIKV E2 residues are labeled and shown as green spheres on the CHIKV E2-E1 heterotrimer. D. CHIKV E2 residues identified as epitopes for neutralizing human anti-CHIKV mAbs (Long et al., 2015; Smith et al., 2015) that also block binding to Mxra8 (Zhang et al., 2018). Antibody binding residues are labeled and shown as salmon spheres on the CHIKV E2-E1 heterotrimer. E. CHIKV E2 residues identified as the epitope for CHK-265 mAb (Fox et al., 2015) are labeled and shown as deep blue spheres on the CHIKV E2-E1 heterotrimer (left panel) and order-of-addition BLI assay traces (right panel). CHIKV VLP was captured on the biosensor with mAb and then incubated sequentially with CHK-265 and Mxra8 (red line and box) or Mxra8 and CHK-265 (blue line and box). Similar binding traces were seen using CHK-265 Fab fragments. Color scheme in figure: gray, E1; cyan, E2; and magenta, Mxra8.

Many of the structurally identified contact residues are coincident with previous alanine scanning mutagenesis mapping data, which identified W64, D71, T116, and I121 in the A domain and Y199 and I217 in the B domain of E2 as important for optimal Mxra8 binding (Zhang et al., 2018) (see e.g., FIG. 25C). Furthermore, several neutralizing human mAbs against CHIKV that disrupt Mxra8 binding (Zhang et al. 2018) map to epitopes in the A and B domains of E2 (Long et al., 2015; Smith et al., 2015) that are shared with the Mxra8 binding site (see e.g., FIG. 25D).

This finding prompted us to evaluate the effect on CHIKV-Mxra8 interactions of CHK-265, a murine mAb that cross-neutralizes infection of CHIKV, MAYV, RRV, and ONNV (Fox et al., 2015), all of which can use Mxra8 as an entry receptor (Zhang et al., 2018). CHK-265 cross-links trimeric spikes via bridging residues in the A and B domains of adjacent E2 proteins (Fox et al., 2015). Although the epitope of CHK-265 does not overlap directly the Mxra8 binding site, we hypothesized that it might still hinder interaction since the Mxra8 binding groove lies beneath the antibody epitope. Order-of-addition binding experiments showed that CHK-265 can bind CHIKV VLPs when Mxra8 is pre-bound, but that Mxra8 cannot bind when CHK-265 is bound (see e.g., FIG. 25E).

Figure 26:
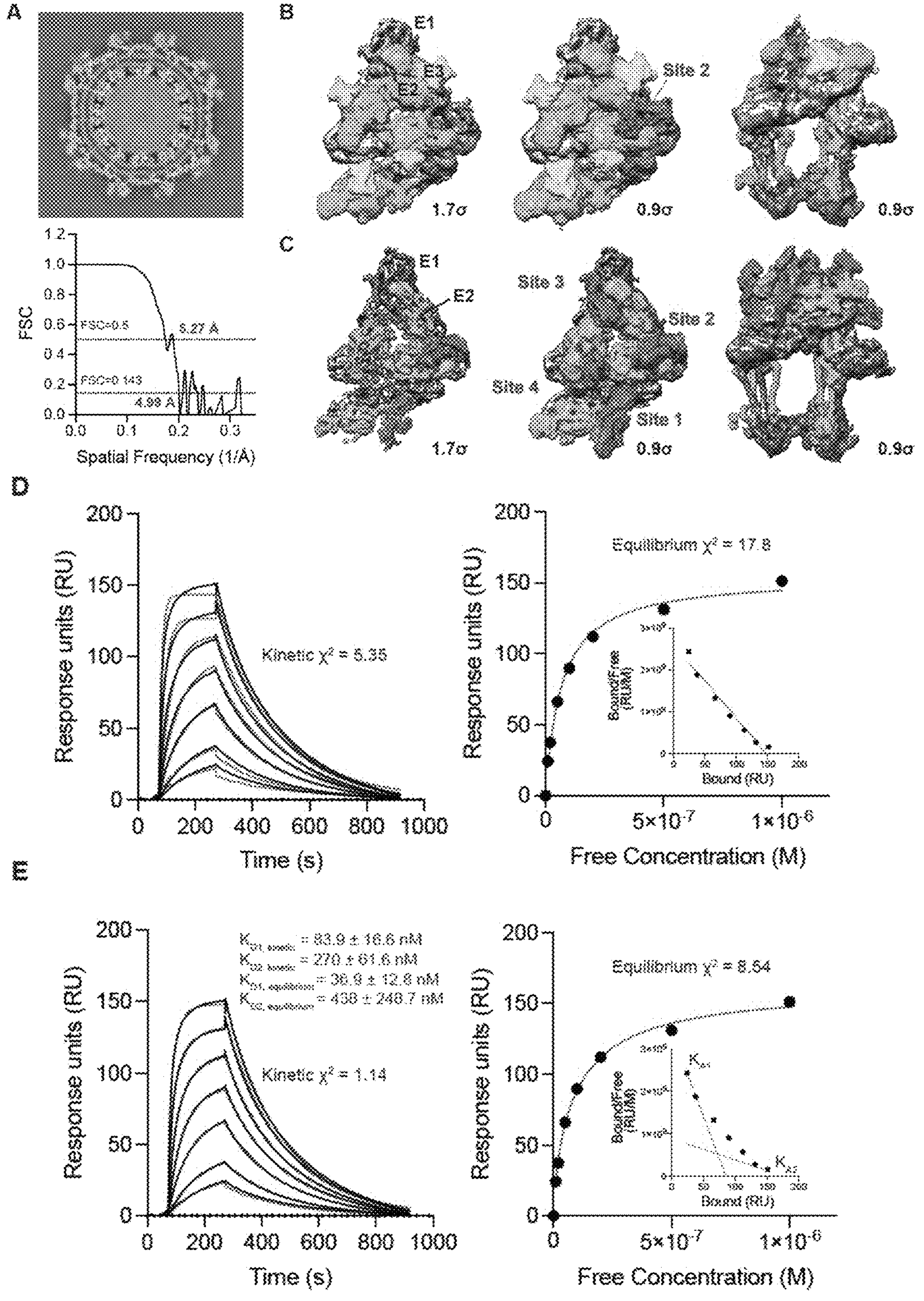
FIG. 26 shows the modes of Mxra8 engagement by CHIKV. A. Two-dimensional equatorial slice (top panel) and Fourier shell correlation (FSC) plot (bottom panel) of CHIKV infectious particles in complex with Mxra8. B-C. Views of asymmetric units of CHIKV infectious particles (B) or CHIKV VLP (C) with bound Mxra8 electron density at high contour (left panel) and low contour (middle and right panels), colored by structural proteins if within 6 Å of docked model coordinates. Mxra8 coordinates were removed from the model, and E3 was docked in for (B). The σ value is the standard deviation of density values above the mean. Color scheme: grey, E1; cyan, E2; yellow, E3; capsid, green; Mxra8 and other unexplained density, magenta. D-E. Kinetic sensograms and steady-state analysis of murine Mxra8 binding to CHIKV VLPs fit to a 1:1 binding model (D) or two-site model (one high affinity site and three low but equal affinity sites) (E). Raw experimental traces are in black, fit traces are in red. Inset, Scatchard plot (4 experiments; mean, standard error of the mean (SEM), and $\chi^2$ values).
Figure 32:
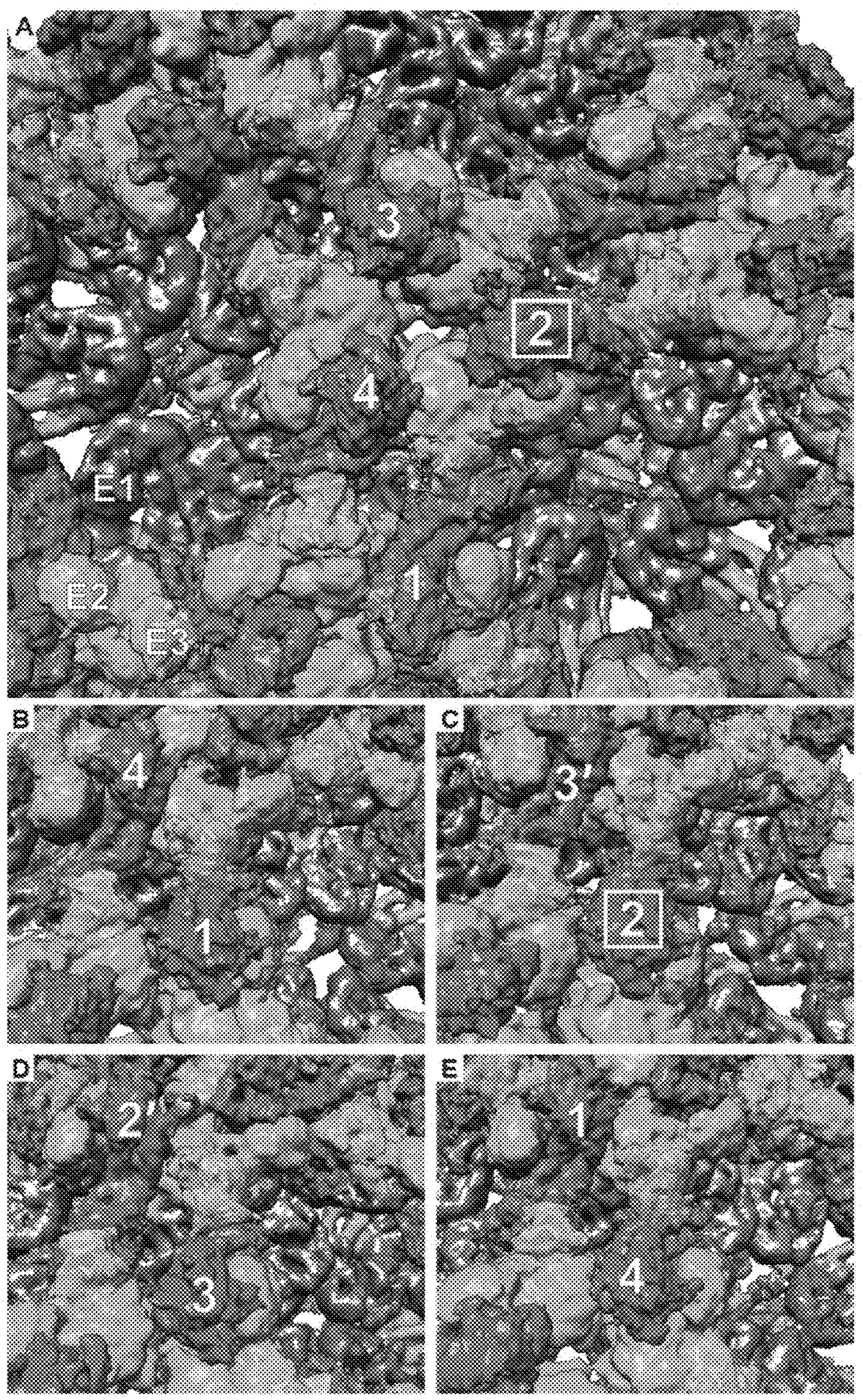
FIG. 32 shows the presence of E3 can sterically hinder Mxra8 binding. Related to FIG. 26. A. View of asymmetric unit of CHIKV infectious particles with difference map of Mxra8 docked on. E1, E2, E3, and Mxra8 sites are labeled, with the high affinity site 2 labeled with a square. B-D. Zoomed-in views highlight the amount of steric clashing of Mxra8 at site with E3 from the adjacent spike. We calculated the surface area of occluded Mxra8 density (zoned within 2 Å of E3 coordinates) as follows: site 1 (B), 400.3 $Å^2$; site 2 (C), 19.6 $Å^2$; site 3 (D), 218.4 $Å^2$; and site 4 (E), 421.4 $Å^2$. F. Cartoon schematic summarizing results. Color scheme: grey, E1; cyan, E2; transparent yellow, E3; capsid, green; Mxra8, magenta. Prime labels refer to Mxra8 sites on adjacent spikes.
Figure 33:
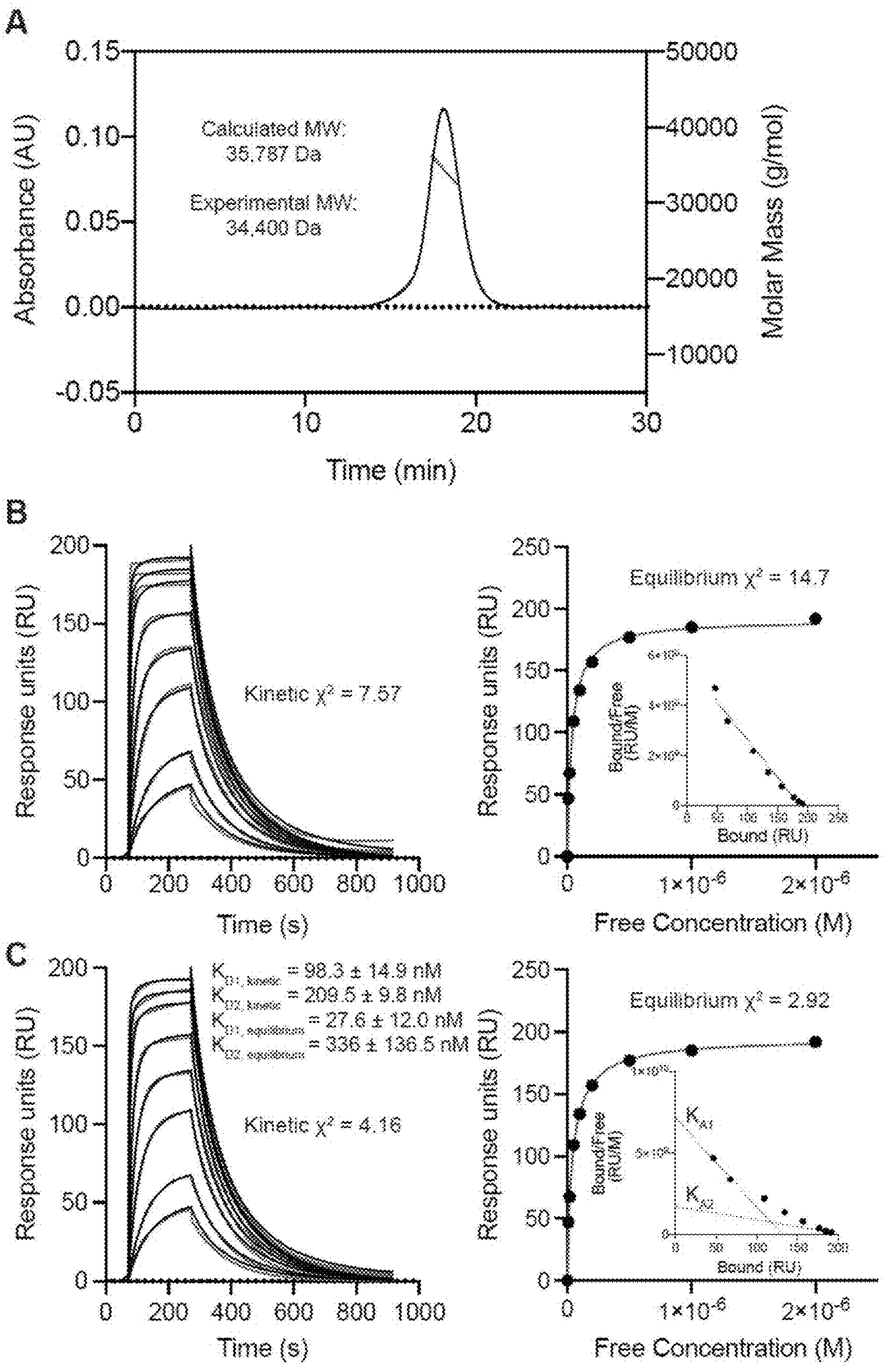
FIG. 33 shows human Mxra8 binding to CHIKV VLPs. Related to FIG. 26. A. SEC-MALS of cleaved human Mxra8 showing a monomeric form at ~34 kDa. B-C. Kinetic sensograms and steady-state analysis of human Mxra8 binding to CHIKV VLPs fit to a 1:1 binding model (B) or a two-site binding model (C) (one high affinity site and three low but equal affinity sites). Raw experimental traces are in black, fit traces are in red. Inset, Scatchard plot (2 experiments; mean, standard error of the mean (SEM), and $\chi^2$ values).

Modes of Mxra8 binding to CHIKV VLPs and infectious virus. We also generated a 4.99 Å cryo-EM reconstruction of CHIKV infectious particles with Mxra8 and built an atomic model (see e.g., FIG. 26A, TABLE 4). In contrast to the CHIKV VLP, strong electron density was seen for the E3 protein in all four chemical environments of the infectious CHIKV (see e.g., FIG. 26B-C), which similarly was observed in other infectious and non-infections alphavirus particle preparations (Yap et al., 2017; Zhang et al., 2011). In the CHIKV infectious particles, weaker electron density was seen for Mxra8 compared to the CHIKV VLP reconstruction. Only one of the four potential binding sites in the asymmetric unit showed interpretable Mxra8 density (see e.g., FIG. 26B). This suggested there might be a lower occupancy of Mxra8 binding on the infectious particle compared to the fully mature VLP, potentially due to steric hindrance by the residual E3 protein in three of four chemical environments. To test this hypothesis, we docked in the difference map of Mxra8 from the mature Mxra8-VLP complex onto our Mxra8-bound CHIKV infectious virus reconstruction and assessed for clashes. E3 appears to sterically obstruct Mxra8 binding at the i3 (site 1) and two of three of the q3 binding sites (sites 3 and 4), allowing for 60 binding sites per virion at site 2 (see e.g., FIG. 32). We note that electron density for Mxra8 on the CHIKV VLP is strongest at site 2, which corresponds to the Mxra8 binding site on the infectious virion (see e.g., FIG. 26C). This finding is consistent with our binding analysis of Mxra8 to CHIKV VLPs by surface plasmon resonance, where the raw traces did not fit well to kinetic and equilibrium 1:1 binding models (see e.g., FIG. 26D). One explanation for the higher occupancy of Mxra8 at one site in an asymmetric unit is a site-specific higher binding affinity, due to the slightly different chemical environments of each of the four E2-E1 heterodimers. We generated a model assuming one high affinity site and three lower but equal affinity sites (see Methods); this model produced a substantially better fit to our binding data (see e.g., FIG. 26E). Mxra8 binds the high affinity site with a kinetically derived $K_D$ of ~84 nM and the lower affinity sites with a $K_D$ of ~270 nM. Similar SPR measurements and two-site binding analysis were observed for human monomeric MXRA8 (as determined by SEC-MALS), which is 78% identical to the murine protein (see e.g., FIG. 33).

DISCUSSION

Cell culture infection experiments with mouse and human cells and in vivo pathogenesis studies in mice defined Mxra8 as a cell surface receptor required for optimal infectivity and induction of musculoskeletal disease by multiple arthritogenic alphaviruses (Zhang et al., 2018). Here, our single particle cryo-EM analysis of CHIKV VLPs and infectious virus provides structural insight into how CHIKV engages Mxra8 to facilitate interactions with target cells. Our study adds to the limited structural knowledge of how receptors bind to enveloped icosahedral virions. Only one other structure of an enveloped, icosahedral virus complexed with its receptor exists. In a 25 Å resolution cryo-EM structure, Dengue virus (DENV) was complexed with the carbohydrate recognition domain of DC-SIGN; the only contacts were with protruding N-linked glycans in domain II of the E protein (Pokidysheva et al., 2006). In contrast, we observed a complex network of quaternary protein-protein interactions involving Mxra8 engaging two E2-E1 heterodimers within one trimeric spike and E1 on an adjacent spike. These sites are coincident with alanine scanning mutagenesis analysis of E2 protein interactions with Mxra8 and epitope maps of neutralizing human mAbs against CHIKV that directly block engagement of Mxra8. Our structures indicate that Mxra8 can bind at four distinct sites in the icosahedral asymmetric unit of the CHIKV VLP but only one site in the infectious virus, which retains E3.

The quaternary interactions formed between Mxra8 and multiple envelope proteins would effectively cross-link CHIKV spikes in a manner analogous to a previously defined broadly neutralizing mAb (CHK-265) that binds domain B on one trimer and domain A on an adjacent spike (Fox et al., 2015). The cross-linking of the viral structural proteins by Mxra8, while facilitating attachment and entry, might create a conundrum for viral fusion in the endosome, which requires domain B on E2 to undergo a substantive conformational shift to expose the underlying hydrophobic fusion loop in domain II of E1 (Li et al., 2010; Voss et al., 2010). After clathrin-mediated endocytosis, fusion of CHIKV occurs within the acidic environment of early endosomes (Hoornweg et al., 2016). Although further studies are required, we speculate that some of the Mxra8 binding interactions with CHIKV E1 and E2 may be sensitive to acidic pH, such that upon transiting to the early endosome the cross-linked trimers can separate and allow the structural transitions required for fusion to occur. In preliminary experiments, we have observed deceased affinity of binding of Mxra8 to recombinant pE2-E1 under conditions of mildly acidic pH (K. Basore, unpublished results). It is plausible that the strength of Mxra8 interactions with viral proteins may regulate the stage of endocytosis and pH of fusion of some arthritogenic alphaviruses.

The alphavirus structural polyprotein is processed In the endoplasmic reticulum to yield E3-E2 (p62) and E1, which form heterodimers and oligomerize as trimers to generate the immature spike (Uchime et al., 2013). In the Golgi network, furin-like proteases cleave E3 from E2 (yielding E2-E1) to render the spikes optimally fusogenic. However, this cleavage event can be variable in a cell-type and virus type-specific manner, as E3 remains associated with the mature virus in some alphaviruses, including Sindbis virus, Semliki Forest virus, and VEEV (Heidner et al., 1996; Zhang et al., 2011; Ziemiecki and Garoff, 1978). The comparison of our cryo-EM structures of Mxra8 bound to CHIKV VLPs and infectious virus revealed a difference in stoichiometry of binding, with 240 Mxra8 proteins bound to CHIKV VLP and only 60 bound to our partially mature, infectious CHIKV particles. One reason for the decreased occupancy on the infectious CHIKV was the retention of the E3 protein, which appears to occlude Mxra8 binding at three of four chemical environments in the asymmetric unit. Biochemical and structural analysis confirmed that E3 was absent from our CHIKV VLP preparation, possibly because of the mildly alkaline buffers used in the chromatography purification steps. Our binding studies with soluble mouse or human Mxra8 and CHIKV VLPs defined two classes of sites, one of high affinity (~60 nM) and a second of lower affinity (~300 nM). In comparison, infectious CHIKV had only the high-affinity binding site. These data suggest that while Mxra8 can bind mature CHIKV virions in two binding modes with full occupancy, regions of partial maturity which retain E3 will bind in only a single mode. At present, the contribution of the low affinity site for Mxra8 to infectivity remains unclear although these same infectious virus preparations still showed a strong Mxra8-dependence (Zhang et al., 2018). It is plausible that E3 retention on some arthritogenic (e.g., SINV) alphaviruses could result in a lack of contribution of Mxra8 to entry and infection. Future studies with fully mature, infectious alphaviruses propagated in Vero cells over-expressing furin (Mukherjee et al., 2016) and lack E3 might address this hypothesis directly.

Our cryo-EM map of Mxra8 bound to CHIKV was corroborated by mutational analysis and coincidence mapping of neutralizing antibodies that blocked Mxra8 binding. We previously identified residues W64, D71, T116, and 1121 in the A domain and Y199 and 1217 in the B domain of E2 as essential for optimal Mxra8 engagement using an E2 alanine scanning mutagenesis library (Fox et al., 2015; Smith et al., 2015; Zhang et al., 2018). Our cryo-EM analysis identified all of these A domain amino acids as contact residues and several B domain residues in close proximity. In the original study, mutations in E1 were not evaluated for binding to Mxra8 because it was expected that E2 and not E1 contributed to receptor engagement (Strauss et al., 1994; Tucker and Griffin, 1991). In further support of the structurally determined Mxra8 binding site on CHIKV, neutralizing human mAbs recognizing epitopes in the A domain or shared epitopes in the A and B domains inhibited Mxra8 binding, whereas others localizing to distinct sites had less effect (Zhang et al., 2018). The epitopes of the mAbs that blocked Mxra8 binding, as determined by alanine scanning mutagenesis (Smith et al., 2015), directly overlap the structural binding sites of Mxra8 and CHIKV E2.

Mxra8 is a receptor for multiple arthritogenic but not encephalitic alphaviruses (Zhang et al., 2018). An alignment of amino acid sequences corresponding to residues comprising the Mxra8 binding site revealed that contact residues generally are conserved among arthritogenic alphaviruses but are located in regions containing or proximal to insertions in encephalitic alphaviruses, which likely explains the negligible interaction or binding requirement for infectivity of Mxra8 with VEEV or related encephalitic alphaviruses (Zhang et al., 2018). Cryo-EM structures with other alphaviruses including ONNV, MAYV, and RRV should provide further insight into the critical contacts on E2, E1, and Mxra8 that facilitate attachment, entry, and infection. Such analysis could identity targets on either the viral structural proteins or Mxra8 to facilitate the development of agents capable of disrupting these interactions. This approach could form the basis of a therapy that mitigates infection caused by multiple arthritogenic alphaviruses.

Experimental Models

Viruses. CHIKV strain 181/25 was obtained from the World Reference Center for Emerging Viruses and Arboviruses (S. Weaver and K. Plante, Galveston, TX). The virus was propagated in Vero cells (ATCC) in DMEM supplemented with 10% FBS, concentrated by sucrose gradient ultracentrifugation, and titrated by standard focus-forming assays (Brien et al., 2013; Pal et al., 2013).

VLP production and purification. CHIKV VLPs were produced via transient transfection of C-E3-E2-6K-E1 (CHIKV strain 37997) plasmid DNA (Akahata et al., 2010) into HEK293 cells (obtained from Vaccine Research Center, NIH), and purified via Q Sepharose XL (GE Healthcare, GE17-5072-01) anion chromatography. The peak of interest was diafiltered into a buffer containing 218 mM sucrose, 10 mM potassium phosphate, and 25 mM citrate, pH 7.2. The material was sterile-filtered using a 0.2 μM filter, 500 μL aliquots were made and stored at −80° C. The final material was analyzed by BCA assay for protein concentration, Coomassie-stained SDS-PAGE gel with densitometry, and Western blotting with rabbit polyclonal anti-CHIKV 181/25 (04-0008, IBT Bioservices) and a secondary horseradish peroxidase conjugated goat anti-rabbit antibody (65-6120, ThermoFisher Scientific).

SPR-based Mxra8 binding assay. SPR binding experiments were performed on a Biacore T200 system (GE Healthcare) to measure the kinetics and affinity of Mxra8 binding to CHIKV VLPs. Experiments were performed at 30 μl/min and 25° C. using HBS-EP (0.01 M HEPES PH 7.4, 0.15 M NaCl, 3 mM EDTA, 0.005% v/v Surfactant P20) as running buffer. CHK-265 mAb (Pal et al., 2013) was immobilized onto a CM5 sensor chip (GE Healthcare) using standard amine coupling chemistry, and CHIKV VLPs were captured. Recombinant Mxra8 was injected over a range of concentrations (2 μM to 20 nM) for 200 sec, followed by a 600 sec dissociation period. As a negative control, murine norovirus was captured with mAb A6.2, as described previously (Taube et al., 2010). Real-time data was analyzed using BIAevaluation 3.1 (GE Healthcare). For the equal affinity binding sites model, kinetic profiles and steady-state equilibrium concentration curves were fitted using a global 1:1 binding algorithm with drifting baseline.

For the model of Mxra8 binding to 1 of 4 sites with higher affinity, the following fits were used:

Equilibrium Analysis:

$$RU = \frac{k_1[A]}{1 + k_1[A]} + \frac{3k_2[A]}{1 + k_2[A]}$$

where $k_1$ corresponds to the high affinity site and $k_2$ denotes the low affinity sites.

Kinetic Analysis:

$$\text{Reaction equations: } A + B1 \underset{k_{d1}}{\overset{k_{a1}}{\rightleftharpoons}} AB1 \quad A + B2 \underset{3k_{d2}}{\overset{3k_{a2}}{\rightleftharpoons}} AB2$$

where A=analyte (Mxra8), B1=high affinity sites of ligand (CHIKV VLP), and B2=low affinity sites of ligand (CHIKV VLP)

Differential Equations:

$$\frac{d[B1]}{dt} = -(k_{a1}[A][B1] - k_{a1}[AB1])$$

$$\frac{d[B2]}{dt} = -3(k_{a2}[A][B2] - k_{a2}[AB2])$$

$$\frac{d[AB1]}{dt} = (k_{a1}[A][B1] - k_{a1}[AB1])$$

$$\frac{d[AB2]}{dt} = 3(k_{a2}[A][B2] - k_{a2}[AB2])$$

BLI-based binding Assay. Binding of CHK-265 and Mxra8 to mAb-captured CHIKV VLP was monitored in real-time at 25° C. using an Octet-Red96 device (Pall ForteBio). CHK-265 (100 μg) was mixed with biotin (EZ-Link-NHS-PEG4-Biotin, Thermo Fisher) at a molar ratio of 20:1 biotin: mAb, incubated at room temperature for 30 min, then unreacted biotin was removed by passage through a desalting column (5 mL Zeba Spin 7K MWCO, Thermo Fisher). Biotinylated-CHK-265 was loaded onto streptavidin biosensors (ForteBio) until saturation, typically 10 μg/ml for 2 min, in 10 mM HEPES (pH 7.4), 150 mM NaCl, 3 mM EDTA, and 0.005% P20 surfactant with 1% BSA. CHIKV VLP was then added for 5 min. The biosensors were dipped sequentially into saturating concentrations of Mxra8 and CHK-265 (2 μM and 100 nM, respectively) for 5 min or vice-versa, with 30 sec baseline measurements in between associations, followed by a final 10 min dissociation.

Cryo-EM sample preparation, data collection, and single particle reconstruction. CHIKV VLP with and without cleaved Mxra8 and CHIKV infectious virus (181/25 strain) with cleaved Mxra8 in molar excess were flash frozen on holey carbon EM grids in liquid ethane under BSL-2 containment conditions using an FEI Vitrobot (ThermoFisher). Movies of the samples were recorded with the software EPU (Thermo Fisher) using a K2 Summit electron detector (Gatan) mounted on a Bioquantum 968 GIF Energy Filter (Gatan) attached to a Titan Krios microscope operating at 300 keV with an electron dose of 50 $e^-/Å^2$ and a magnification of 18,000×. The movies (30 frames, 300 msec exposure per frame) were corrected for beam-induced motion using MotionCor2 (Zheng et al., 2017). Contrast transfer function parameters of the electron micrographs were estimated using CTFFIND4 (Rohou and Grigorieff, 2015) in cisTEM (Grant et al., 2018). Particles were auto-picked, and underwent reference-free 2D classification, ab initio 3D reconstruction, and 3D refinement in cisTEM. Local resolution was estimated using RELION-3 (Zivanov et al., 2018). Additional information regarding the number of images and particles is listed in TABLE 2. All structural analyses of the 3D reconstructions were performed using the programs Chimera and PyMOL (Bramucci et al., 2012).

Model building. The initial models of the CHIKV structural proteins (E1, E2, TM regions, and Capsid) with or without Mxra8 were built into the density of a subunit by docking the components from the crystal structures of CHIKV p62-E1 (PDB: 3N42), the CHIKV capsid (PDB: 5J23), and the modeled TM regions of VEEV (PDB: 3J0C) using the fitmap command in Chimera. Amino acid substitutions and connections were added manually in COOT to reflect the strain of CHIKV used for VLP production (CHIKV-37997) and infectious virus (CHIKV-181/25) for cryo-EM studies. The subunit models then underwent real-space refinement using PHENIX with default parameters plus rigid body refinement. Rigid bodies for E1 were divided into domains I and II (residues 1-292), domain III (293-381), stem (382-412), and transmembrane region (413-442). E2 was divided into the N-linker region (residues 5-15), domain A (residues 16-134), domain B (residues 173-231), domain C (residues 269-341), β-linker (residues 135-172, 232-268), and the stem, transmembrane region, and cytoplasmic tail (residues 342-423). The capsid protein was divided into two rigid bodies (residues 111-176 and residues 177-261), and Mxra8 was divided into D1 (residues 44-174) and D2 (10-43; 175-269). The refined subunits were used to build the asymmetric unit with adjacent subunits to prevent clashes and optimize interactions. These models underwent further real-space refinement. COOT was used to fix regions manually with poor geometry. After optimization, coordinates of the asymmetric units were checked by MolProbity (TABLE 4). Contact residues were identified, and buried surface areas were calculated using PDBePISA.

Mapping of antibody or Mxra8 contact residues onto the CHIKV p62-E1 crystal structure. Figures were prepared using the atomic coordinates of CHIKV pE2-E1 (RCSB accession number 3N42) using the program PyMOL (The PyMOL Molecular Graphics System, Version 1.7.4 Schrödinger, LLC). Amino acid contact residues for neutralizing anti-human or anti-mouse mAbs that block Mxra8 binding were derived from published studies (Fox et al., 2015; Smith et al., 2015).

Data Availability. All structures described below are deposited in the PDB and EMDB databases and are incorporated by reference in their entireties: Crystal structure of murine Mxra8 ectodomain (PDB code for this deposition is 6NK3); electron Cryo-Microscopy Of Chikungunya VLP alone (PDB code for this deposition is 6NK5; EMDB code for this deposition is EMD-9393); Electron Cryo-Microscopy of Chikungunya VLP in complex with mouse Mxra8 receptor (PDB code for this deposition is 6NK6; EMDB code for this deposition is EMD-9394); Electron Cryo-Microscopy of Chikungunya in complex with mouse Mxra8 receptor (PDB code for this deposition is 6NK7; EMDB code for this deposition is EMD-9395).

TABLE 2

Data collection and refinement statistics-mouse Mxra8.

| Mouse Mxra8 | |
|---|---|
| Resolution range | 36.88-2.0 (2.072-2.0) |
| Space group | I 2 2 2 |
| Unit cell | 72.588 142.847 195.585 90 90 90 |
| Unique reflections | 64594 (4630) |
| Completeness (%) | 93.65 (67.72) |
| Wilson B-factor | 37.68 |
| Reflections used in refinement | 64595 (4631) |
| Reflections used for R-free | 1989 (142) |
| R-work | 0.2238 (0.5262) |
| R-free | 0.2414 (0.5724) |
| macromolecules | 4258 |
| solvent | 193 |
| Protein residues | 528 |
| RMS(bonds) | 0.004 |
| RMS(angles) | 1.00 |
| Ramachandran favored (%) | 95.42 |
| Ramachandran allowed (%) | 4.20 |
| Ramachandran outliers (%) | 0.38 |
| Rotamer outliers (%) | 3.74 |

TABLE 2-continued

Data collection and refinement statistics-mouse Mxra8.

| Mouse Mxra8 | |
|---|---|
| Clashscore | 6.25 |
| Average B-factor | 63.01 |
| macromolecules | 63.22 |
| solvent | 58.19 |

Statistics for the highest-resolution shell are shown in parentheses.

TABLE 3

Summary of Cryo-EM data collection.

| Sample | VLP alone | VLP + Mxra8 | CHIKV + Mxra8 |
|---|---|---|---|
| # of Micrographs | 1332 | 7294 | 5318 |
| # of particles picked | 8888 | 26790 | 9547 |
| # of particles after 2D classification | 8113 | 22486 | 8357 |
| $Resolution_{FSC=0.5}$ (Å) | 4.48 | 4.32 | 5.27 |
| $Resolution_{FCS=0.143}$ (Å) | 4.16 | 4.06 | 4.99 |

The microscope settings for image collection were: Dose: 50 $e^{-}/Å^{2}$; Magnification: 18,000×; Pixel size: 1.4; and Voltage: 300 keV. Micrographs were corrected for the contrast transfer function using CTFFIND4 (Rohou and Grigorieff, 2015) in the program cisTEM (Grant et al., 2018).

TABLE 4

Refinement and model statistics.

| Asymmetric Unit Model | | VLP alone | VLP + Mxra8 | CHIKV + Mxra8 |
|---|---|---|---|---|
| CHIKV strain | | CHIKV-37997 | CHIKV-37997 | CHIKV-181/25 |
| Number of chains | | 12 | 16 | 17 |
| Resolution (Å) | | 4.5 | 4.4 | 5.5 |
| MolProbity score | | 2.26 | 2.30 | 2.26 |
| all-atom clashscore | | 13.77 | 15.20 | 12.86 |
| Rotamer outliers (%) | | 0.53 | 0.63 | 0.54 |
| Ramachandran Plot values | Favored (%) | 87.19 | 87.36 | 85.9 |
| | Allowed (%) | 12.66 | 12.38 | 13.95 |
| | Outliers (%) | 0.15 | 0.26 | 0.16 |
| R.M.S. Deviations | Bond lengths (Å) | 0.007 | 0.006 | 0.005 |
| | Bond angles | 1.128 | 1.097 | 1.151 |

TABLE 5

List of contact residues of CHIKV E2-E1 at Mxra8 binding interface.

| E2-E1 heterodimer | E2-E1 domain | E2-E1 residues | Mxra8 residues | Mxra8 domain |
|---|---|---|---|---|
| wrapped | Domain A of E2 | E24, H26, S27, C28, H29, D71, S72 | R64, H196, L197, E198, E199, D223, Y225, S227, G228, E229, R230, R231, A232, Y233 | D2 |
| | Domain B of E2 | T179, K189, I190, T191, N193, G194, D214, K215, K221, I222, D223 | N187, R188, A189, H190 | D1 |
| | | | V203, H205, D207, S214, H215, D216, R217, A218, D219, R220, H272, H274, H276, H281, R283 | D2 |
| | Fusion loop of E1 | Y85, F87, W89. G90, D97, A226 | S112, H115, D116, I186, R188, H190, D194, R195, H196 | D1 |

TABLE 5-continued

List of contact residues of CHIKV E2-E1 at Mxra8 binding interface.

| E2-E1 heterodimer | E2-E1 domain | E2-E1 residues | Mxra8 residues | Mxra8 domain |
|---|---|---|---|---|
| Adjacent intraspike | Domain A of E2 | N5, H62, D63, W64, T65 | W60, T61, Q62, D63, N247, F249, A250 | D2 |
| | β-linker of E2 | E150, V157, Q158, S159, N263, V264, T265, R267 | Q62, D63, R64, H66, S92, A93, G94, R195, H196 | D1 |
| | Domain I of E1 | T143, A145, A146, K157 | R102, R104, D105, R124, H177, G178 | D1 |
| | Domain II of E1 | K132, T263, N264, P265, R267 | E95, R97, V98, R124 | D1 |
| Neighboring imerspike | Domain II of E1 | D70, K71, S72, L73, P74, E209, K211, D212 | L76, Q83, R85, R102, D127, R128, G129, E131, V155, T156, E157, H177 | D1 |

Contact residues were identified using PDBePISA. Mxra8 is numbered according to NCBI reference sequence NP_077225.4. In bold are contacts unique to Mxra8 at binding site 2, and in italics are contacts at each Mxra8 position except binding site 2.

REFERENCES

Afonine, P. V., Grosse-Kunstleve, R. W., Echols, N., Headd, J. J., Moriarty, N. W., Mustyakimov, M., Terwilliger, T. C., Urzhumtsev, A., Zwart, P. H., and Adams, P. D. (2012). Towards automated crystallographic structure refinement with phenix.refine. Acta Crystallogr D Biol Crystallogr 68, 352-367.

Akahata, W., Yang, Z. Y., Andersen, H., Sun, S., Holdaway, H. A., Kong, W. P., Lewis, M. G., Higgs, S., Rossmann, M. G., Rao, S., et al. (2010). A virus-like particle vaccine for epidemic Chikungunya virus protects nonhuman primates against infection. Nat Med 16, 334-338.

Bramucci, E., Paiardini, A., Bossa, F., and Pascarella, S. (2012). PyMod: sequence similarity searches, multiple sequence-structure alignments, and homology modeling within PyMOL. BMC Bioinformatics 13 *Suppl* 4, S2.

Brien, J. D., Lazear, H. M., and Diamond, M. S. (2013). Propagation, quantification, detection, and storage of West Nile virus. Curr Protoc Microbiol 31, 15D 13 11-15D 13 18.

Carleton, M., Lee, H., Mulvey, M., and Brown, D. T. (1997). Role of glycoprotein PE2 in formation and maturation of the Sindbis virus spike. J Virol 71, 1558-1566.

Chang, L. J., Dowd, K. A., Mendoza, F. H., Saunders, J. G., Sitar, S., Plummer, S. H., Yamshchikov, G., Sarwar, U. N., Hu, Z., Enama, M. E., et al. (2014). Safety and tolerability of chikungunya virus-like particle vaccine in healthy adults: a phase 1 dose-escalation trial. Lancet 384, 2046-2052.

Cheng, R. H., Kuhn, R. J., Olson, N. H., Rossmann, M. G., Choi, H. K., Smith, T. J., and Baker, T. S. (1995). Nucleocapsid and glycoprotein organization in an enveloped virus. Cell 80, 621-630.

DeTulleo, L., and Kirchhausen, T. (1998). The clathrin endocytic pathway in viral infection. Embo j 17, 4585-4593.

Emsley, P., Lohkamp, B., Scott, W. G., and Cowtan, K. (2010). Features and development of Coot. Acta Crystallogr D Biol Crystallogr 66, 486-501.

Fox, J. M., Long, F., Edeling, M. A., Lin, H., van Duijl-Richter, M. K., Fong, R. H., Kahle, K. M., Smit, J. M., Jin, J., Simmons, G., et al. (2015). Broadly Neutralizing Alphavirus Antibodies Bind an Epitope on E2 and Inhibit Entry and Egress. Cell 163, 1095-1107.

Grant, T., Rohou, A., and Grigorieff, N. (2018). cisTEM, user-friendly software for single-particle image processing. Elife 7.

Heidner, H. W., Knott, T. A., and Johnston, R. E. (1996). Differential processing of sindbis virus glycoprotein PE2 in cultured vertebrate and arthropod cells. J Virol 70, 2069-2073.

Hoornweg, T. E., van Duijl-Richter, M. K. S., Ayala Nunez, N. V., Albulescu, I. C., van Hemert, M. J., and Smit, J. M. (2016). Dynamics of Chikungunya Virus Cell Entry Unraveled by Single-Virus Tracking in Living Cells. J Virol 90, 4745-4756.

Kostyuchenko, V. A., Jakana, J., Liu, X., Haddow, A. D., Aung, M., Weaver, S. C., Chiu, W., and Lok, S. M. (2011). The structure of barmah forest virus as revealed by cryo-electron microscopy at a 6-angstrom resolution has detailed transmembrane protein architecture and interactions. J Virol 85, 9327-9333.

Lee, R. C., Hapuarachchi, H. C., Chen, K. C., Hussain, K. M., Chen, H., Low, S. L., Ng, L. C., Lin, R., Ng, M. M., and Chu, J. J. (2013). Mosquito cellular factors and functions in mediating the infectious entry of chikungunya virus. PLoS neglected tropical diseases 7, e2050.

Lee, S., Kuhn, R. J., and Rossmann, M. G. (1998). Probing the potential glycoprotein binding site of sindbis virus capsid protein with dioxane and model building. Proteins 33, 311-317.

Lescar, J., Roussel, A., Wien, M. W., Navaza, J., Fuller, S. D., Wengler, G., and Rey, F. A. (2001). The Fusion glycoprotein shell of Semliki Forest virus: an icosahedral assembly primed for fusogenic activation at endosomal pH. Cell 105, 137-148.

Li, L., Jose, J., Xiang, Y., Kuhn, R. J., and Rossmann, M. G. (2010). Structural changes of envelope proteins during alphavirus fusion. Nature 468, 705-708.

Long, F., Fong, R. H., Austin, S. K., Chen, Z., Klose, T., Fokine, A., Liu, Y., Porta, J., Sapparapu, G., Akahata, W., et al. (2015). Cryo-EM structures elucidate neutralizing mechanisms of anti-chikungunya human monoclonal antibodies with therapeutic activity. Proc Natl Acad Sci USA 112, 13898-13903.

Mukherjee, S., Sirohi, D., Dowd, K. A., Chen, Z., Diamond, M. S., Kuhn, R. J., and Pierson, T. C. (2016). Enhancing dengue virus maturation using a stable furin over-expressing cell line. Virology 497, 33-40.

Mulvey, M., and Brown, D. T. (1995). Involvement of the molecular chaperone BiP in maturation of Sindbis virus envelope glycoproteins. J Virol 69, 1621-1627.

Ooi, Y. S., Stiles, K. M., Liu, C. Y., Taylor, G. M., and Kielian, M. (2013). Genome-wide RNAi screen identifies novel host proteins required for alphavirus entry. PLoS Pathog 9, e1003835.

Pal, P., Dowd, K. A., Brien, J. D., Edeling, M. A., Gorlatov, S., Johnson, S., Lee, I., Akahata, W., Nabel, G. J., Richter, M. K. S., et al. (2013). Development of a highly protective combination monoclonal antibody therapy against Chikungunya virus PLoS Pathog 9, e1003312.

Papadopoulos, J. S., and Agarwala, R. (2007). COBALT: constraint-based alignment tool for multiple protein sequences. Bioinformatics 23, 1073-1079.

Paredes, A. M., Brown, D. T., Rothnagel, R., Chiu, W., Schoepp, R. J., Johnston, R. E., and Prasad, B. V. (1993). Three-dimensional structure of a membrane-containing virus. Proc Natl Acad Sci USA 90, 9095-9099.

Pletnev, S. V., Zhang, W., Mukhopadhyay, S., Fisher, B. R., Hernandez, R., Brown, D. T., Baker, T. S., Rossmann, M. G., and Kuhn, R. J. (2001). Locations of carbohydrate sites on alphavirus glycoproteins show that E1 forms an icosahedral scaffold. Cell 105, 127-136.

Pokidysheva, E., Zhang, Y., Battisti, A. J., Bator-Kelly, C. M., Chipman, P. R., Xiao, C., Gregorio, G. G., Hendrickson, W. A., Kuhn, R. J., and Rossmann, M. G. (2006). Cryo-EM reconstruction of dengue virus in complex with the carbohydrate recognition domain of DC-SIGN. Cell 124, 485-493.

Powers, A. M., Brault, A. C., Shirako, Y., Strauss, E. G., Kang, W., Strauss, J. H., and Weaver, S. C. (2001). Evolutionary relationships and systematics of the alphaviruses. J Virol 75, 10118-10131.

Robert, X., and Gouet, P. (2014). Deciphering key features in protein structures with the new ENDscript server. Nucleic Acids Res 42, W320-324.

Rohou, A., and Grigorieff, N. (2015). CTFFIND4: Fast and accurate defocus estimation from electron micrographs. J Struct Biol 192, 216-221.

Roussel, A., Lescar, J., Vaney, M. C., Wengler, G., Wengler, G., and Rey, F. A. (2006). Structure and interactions at the viral surface of the envelope protein E1 of Semliki Forest virus. Structure 14, 75-86.

Smith, S. A., Silva, L. A., Fox, J. M., Flyak, A. I., Kose, N., Sapparapu, G., Khomadiak, S., Ashbrook, A. W., Kahle, K. M., Fong, R. H., et al. (2015). Isolation and Characterization of Broad and Ultrapotent Human Monoclonal Antibodies with Therapeutic Activity against Chikungunya Virus. Cell Host Microbe 18, 86-95.

Smith, T. J., Cheng, R. H., Olson, N. H., Peterson, P., Chase, E., Kuhn, R. J., and Baker, T. S. (1995). Putative receptor binding sites on alphaviruses as visualized by cryoelectron microscopy. Proc Natl Acad Sci USA 92, 10648-10652.

Strauss, J. H., Wang, K. S., Schmaljohn, A. L., Kuhn, R. J., and Strauss, E. G. (1994). Host-cell receptors for Sindbis virus. Arch Virol Suppl 9, 473-484.

Sun, S., Xiang, Y., Wataru, A., Holdaway, H. A., Pal, P., Zheng, X., Diamond, M. S., Nabel, G. J., and Rossmann, M. G. (2013). Structural analyses at pseudo atomic resolution of Chikungunya virus antibody neutralization mechanisms. eLife 2, e00435.

Taube, S., Rubin, J. R., Katpally, U., Smith, T. J., Kendall, A., Stuckey, J. A., and Wobus, C. E. (2010). High-resolution x-ray structure and functional analysis of the murine norovirus 1 capsid protein protruding domain. J Virol 84, 5695-5705.

Tucker, P. C., and Griffin, D. E. (1991). Mechanism of altered Sindbis virus neurovirulence associated with a single-amino-acid change in the E2 Glycoprotein. J Virol 65, 1551-1557.

Uchime, O., Fields, W., and Kielian, M. (2013). The role of E3 in pH protection during alphavirus assembly and exit. J Virol 87, 10255-10262.

Voss, J. E., Vaney, M. C., Duquerroy, S., Vonrhein, C., Girard-Blanc, C., Crublet, E., Thompson, A., Bricogne, G., and Rey, F. A. (2010). Glycoprotein organization of Chikungunya virus particles revealed by X-ray crystallography. Nature 468, 709-712.

Yap, M. L., Klose, T., Urakami, A., Hasan, S. S., Akahata, W., and Rossmann, M. G. (2017). Structural studies of Chikungunya virus maturation. Proc Natl Acad Sci USA 114, 13703-13707.

Zhang, R., Hryc, C. F., Cong, Y., Liu, X., Jakana, J., Gorchakov, R., Baker, M. L., Weaver, S. C., and Chiu, W. (2011). 4.4 A cryo-EM structure of an enveloped alphavirus Venezuelan equine encephalitis virus. Embo j 30, 3854-3863.

Zhang, R., Kim, A. S., Fox, J. M., Nair, S., Basore, K., Klimstra, W. B., Rimkunas, R., Fong, R. H., Lin, H., Poddar, S., et al. (2018). Mxra8 is a receptor for multiple arthritogenic alphaviruses. Nature 557, 570-574.

Zhang, W., Heil, M., Kuhn, R. J., and Baker, T. S. (2005). Heparin binding sites on Ross River virus revealed by electron cryo-microscopy. Virology 332, 511-518.

Zhang, W., Mukhopadhyay, S., Pletnev, S. V., Baker, T. S., Kuhn, R. J., and Rossmann, M. G. (2002). Placement of the structural proteins in Sindbis virus. J Virol 76, 11645-11658.

Zheng, S. Q., Palovcak, E., Armache, J. P., Verba, K. A., Cheng, Y., and Agard, D. A. (2017). MotionCor2: anisotropic correction of beam-induced motion for improved cryo-electron microscopy. Nat Methods 14, 331-332.

Ziemiecki, A., and Garoff, H. (1978). Subunit composition of the membrane glycoprotein complex of Semliki Forest virus. J Mol Biol 122, 259-269.

Zivanov, J., Nakane, T., Forsberg, B. O., Kimanius, D., Hagen, W. J., Lindahl, E., and Scheres, S. H. (2018). New tools for automated high-resolution cryo-EM structure determination in RELION-3. Elife 7.

What is claimed is:

1. A fusion protein comprising:
an Mxra8 region; and
an Fc region downstream from the Mxra8 region;
wherein:
the Mxra8 region comprises one of a mouse Mxra8 extracellular domain and a human Mxra8 extracellular domain;
the Fc region comprises one of mouse IgG2b, human IgG1, and human IgG1 with N297Q mutation; and
the fusion protein reduces inflammation and infection by an arthritogenic alphavirus.

2. The fusion protein of claim 1, wherein:
the mouse Mxra8 extracellular domain is selected from
SEQ ID NO: 4,
a polypeptide encoded by polynucleotide SEQ ID NO: 3,
a polypeptide encoded by polynucleotide SEQ ID NO: 32, and
SEQ ID NO: 53; and
the human Mxra8 extracellular domain is selected from
SEQ ID NO: 2,
a polypeptide encoded by polynucleotide SEQ ID NO: 1,
SEQ ID NO: 25,
SEQ ID NO: 26,
SEQ ID NO: 27,
SEQ ID NO: 28,
SEQ ID NO: 29,
SEQ ID NO: 30,
SEQ ID NO: 31,
a polypeptide encoded by polynucleotide SEQ ID NO: 33,
a polypeptide encoded by polynucleotide SEQ ID NO: 44,
a polypeptide encoded by polynucleotide SEQ ID NO: 45, and
a polypeptide encoded by polynucleotide SEQ ID NO: 46.

3. The fusion protein of claim 1, wherein:
the mouse IgG2b is selected from SEQ ID NO: 6 and a polypeptide encoded by polynucleotide SEQ ID NO: 5;
the human IgG1 is selected from SEQ ID NO: 8 and a polypeptide encoded by polynucleotide SEQ ID NO: 7; and
the human IgG1 with N297Q mutation is selected from SEQ ID NO: 10 and a polypeptide encoded by polynucleotide SEQ ID NO: 9.

4. The fusion protein of claim 1, further comprising a linker between the Mxra8 region and the Fc region, wherein the linker is selected from SEQ ID NO: 14 and a polypeptide encoded by polynucleotide SEQ ID NO: 13.

5. The fusion protein of claim 1, further comprising a human rhinovirus 3C (HRV) protease site between the Mxra8 region and the Fc region.

6. The fusion protein of claim 1, wherein the fusion protein is selected from:
- a polypeptide comprising SEQ ID NO: 2 and SEQ ID NO: 6;
- a polypeptide comprising SEQ ID NO: 4 and SEQ ID NO: 6;
- a polypeptide comprising SEQ ID NO: 4, SEQ ID NO: 14, and SEQ ID NO: 8;
- a polypeptide comprising SEQ ID NO: 4, SEQ ID NO: 14, and SEQ ID NO: 10;
- a polypeptide encoded by polynucleotide comprising SEQ ID NO: 1 and SEQ ID NO: 5;
- a polypeptide encoded by polynucleotide comprising SEQ ID NO: 3 and SEQ ID NO: 5;
- a polypeptide encoded by polynucleotide comprising SEQ ID NO: 3, SEQ ID NO: 13, and SEQ ID NO: 7; and
- a polypeptide encoded by polynucleotide comprising SEQ ID NO: 3, SEQ ID NO: 13, and SEQ ID NO: 9.

7. A method of treating an arthritogenic alphavirus infection in a subject in need thereof, the method comprising:
- administering to the subject a therapeutically effective amount of a fusion protein comprising:
  - an Mxra8 region; and
  - an Fc region downstream from the Mxra8 region;
  - wherein:
    - the Mxra8 region comprises one of a mouse Mxra8 extracellular domain and a human Mxra8 extracellular domain;
    - the Fc region comprises one of mouse IgG2b, human IgG1, human IgG1 with N297Q mutation; and
    - the fusion protein reduces inflammation and infection by the arthritogenic alphavirus.

8. The method of claim 7, wherein:
- the mouse Mxra8 extracellular domain is selected from SEQ ID NO: 4,
  - a polypeptide encoded by polynucleotide SEQ ID NO: 3,
  - a polypeptide encoded by polynucleotide SEQ ID NO: 32, and
  - SEQ ID NO: 53; and
- the human Mxra8 extracellular domain is selected from SEQ ID NO: 2,
  - a polypeptide encoded by polynucleotide SEQ ID NO: 1,
  - SEQ ID NO: 25,
  - SEQ ID NO: 26,
  - SEQ ID NO: 27,
  - SEQ ID NO: 28,
  - SEQ ID NO: 29,
  - SEQ ID NO: 30,
  - SEQ ID NO: 31,
  - a polypeptide encoded by polynucleotide SEQ ID NO: 33,
  - a polypeptide encoded by polynucleotide SEQ ID NO: 44,
  - a polypeptide encoded by polynucleotide SEQ ID NO: 45, and
  - a polypeptide encoded by polynucleotide SEQ ID NO: 46.

9. The method of claim 7, wherein:
- the mouse IgG2b is selected from SEQ ID NO: 6 and a polypeptide encoded by polynucleotide SEQ ID NO: 5;
- the human IgG1 is selected from SEQ ID NO: 8 and a polypeptide encoded by polynucleotide SEQ ID NO: 7; and
- the human IgG1 with N297Q mutation is selected from SEQ ID NO: 10 and a polypeptide encoded by polynucleotide SEQ ID NO: 9.

10. The method of claim 7, wherein the fusion protein further comprises a linker between the Mxra8 region and the Fc region, wherein the linker is selected from SEQ ID NO: 14 and a polypeptide encoded by polynucleotide SEQ ID NO: 13.

11. The method of claim 7, wherein the fusion protein further comprises a human rhinovirus 3C (HRV) protease site between the Mxra8 region and the Fc region.

12. The method of claim 7, wherein the arthritogenic alphavirus is selected from the group consisting of: Chikungunya Virus (CHIKV), Mayaro Virus (MAYV), Ross River Virus (RRV), O'nyong nyong (ONNV), Barmah Forest Virus (BFV), Semliki Forest virus, and Getah virus.

13. The method of claim 7, wherein the subject is a mammal.

14. The method of claim 7, wherein the fusion protein is selected from:
- a polypeptide comprising SEQ ID NO: 2 and SEQ ID NO: 6;
- a polypeptide comprising SEQ ID NO: 4 and SEQ ID NO: 6;
- a polypeptide comprising SEQ ID NO: 4, SEQ ID NO: 14, and SEQ ID NO: 8;
- a polypeptide comprising SEQ ID NO: 4, SEQ ID NO: 14, and SEQ ID NO: 10;
- a polypeptide encoded by polynucleotide comprising SEQ ID NO: 1 and SEQ ID NO: 5;
- a polypeptide encoded by polynucleotide comprising SEQ ID NO: 3 and SEQ ID NO: 5;
- a polypeptide encoded by polynucleotide comprising SEQ ID NO: 3, SEQ ID NO: 13, and SEQ ID NO: 7; and
- a polypeptide encoded by polynucleotide comprising SEQ ID NO: 3, SEQ ID NO: 13, and SEQ ID NO: 9.

15. A pharmaceutical composition comprising a fusion protein and at least one pharmaceutically acceptable carrier, wherein the fusion protein comprises:
- an Mxra8 region; and
- an Fc region downstream from the Mxra8 region;
- wherein:
  - the Mxra8 region comprises one of a mouse Mxra8 extracellular domain and a human Mxra8 extracellular domain;
  - the Fc region comprises one of mouse IgG2b, human IgG1, human IgG1 with N297Q mutation; and
  - the fusion protein reduces inflammation and infection by an arthritogenic alphavirus.

16. The pharmaceutical composition of claim 15, wherein:
- the mouse Mxra8 extracellular domain is selected from SEQ ID NO: 4,
  - a polypeptide encoded by polynucleotide SEQ ID NO: 3,
  - a polypeptide encoded by polynucleotide SEQ ID NO: 32, and
  - SEQ ID NO: 53; and
- the human Mxra8 extracellular domain is selected from SEQ ID NO: 2, a polypeptide encoded by polynucleotide SEQ ID NO: 1,
SEQ ID NO: 25,
SEQ ID NO: 26,
SEQ ID NO: 27,
SEQ ID NO: 28,
SEQ ID NO: 29,
SEQ ID NO: 30,
SEQ ID NO: 31,
a polypeptide encoded by polynucleotide SEQ ID NO: 33,
a polypeptide encoded by polynucleotide SEQ ID NO: 44,
a polypeptide encoded by polynucleotide SEQ ID NO: 45, and
a polypeptide encoded by polynucleotide SEQ ID NO: 46.

17. The pharmaceutical composition of claim 15, wherein:
the mouse IgG2b is selected from SEQ ID NO: 6 and a polypeptide encoded by polynucleotide SEQ ID NO: 5;
the human IgG1 is selected from SEQ ID NO: 8 and a polypeptide encoded by polynucleotide SEQ ID NO: 7; and
the human IgG1 with N297Q mutation is selected from SEQ ID NO: 10 and a polypeptide encoded by polynucleotide SEQ ID NO: 9.

18. The pharmaceutical composition of claim 15, wherein the fusion protein further comprises a linker between the Mxra8 region and the Fc region, wherein the linker is selected from SEQ ID NO: 14 and a polypeptide encoded by polynucleotide SEQ ID NO: 13.

19. The pharmaceutical composition of claim 15, wherein the fusion protein further comprises a human rhinovirus 3C (HRV) protease site between the Mxra8 region and the Fc region.

20. The pharmaceutical composition of claim 15, wherein the fusion protein is selected from:
a polypeptide comprising SEQ ID NO: 2 and SEQ ID NO: 6;
a polypeptide comprising SEQ ID NO: 4 and SEQ ID NO: 6;
a polypeptide comprising SEQ ID NO: 4, SEQ ID NO: 14, and SEQ ID NO: 8;
a polypeptide comprising SEQ ID NO: 4, SEQ ID NO: 14, and SEQ ID NO: 10;
a polypeptide encoded by polynucleotide comprising SEQ ID NO: 1 and SEQ ID NO: 5;
a polypeptide encoded by polynucleotide comprising SEQ ID NO: 3 and SEQ ID NO: 5;
a polypeptide encoded by polynucleotide comprising SEQ ID NO: 3, SEQ ID NO: 13, and SEQ ID NO: 7; and
a polypeptide encoded by polynucleotide comprising SEQ ID NO: 3, SEQ ID NO: 13, and SEQ ID NO: 9.

* * * * *